(12) United States Patent
Bremel et al.

(10) Patent No.: US 6,852,510 B2
(45) Date of Patent: Feb. 8, 2005

(54) HOST CELLS CONTAINING MULTIPLE INTEGRATING VECTORS

(75) Inventors: Robert D. Bremel, Hillpoint, WI (US); Linda U. Miller, Lodi, WI (US); Gregory T. Bleck, Baraboo, WI (US)

(73) Assignee: Gala Design Inc, Middleton, WI (US)

( * ) Notice: Subject to any disclaimer, the term of this patent is extended or adjusted under 35 U.S.C. 154(b) by 0 days.

(21) Appl. No.: 09/897,511

(22) Filed: Jun. 29, 2001

(65) Prior Publication Data

US 2003/0092882 A1 May 15, 2003

Related U.S. Application Data

(60) Provisional application No. 60/215,925, filed on Jul. 3, 2000.

(51) Int. Cl.[7] .................... C12N 15/09; C12N 5/10; C12N 15/63; C12N 15/867
(52) U.S. Cl. ............. 435/69.1; 435/325; 435/352; 435/358; 435/455; 435/456; 435/465; 435/473
(58) Field of Search ..................... 435/325, 358, 435/455, 456, 465, 473, 69.1, 352

(56) References Cited

U.S. PATENT DOCUMENTS

| | | | |
|---|---|---|---|
| 4,560,655 A | 12/1985 | Baker | 435/241 |
| 4,657,866 A | 4/1987 | Kumar | 435/240 |
| 4,677,066 A | 6/1987 | Takahashi et al. | 435/172.2 |
| 4,767,704 A | 8/1988 | Cleveland et al. | 435/68 |
| 4,816,567 A | 3/1989 | Cabilly et al. | 530/387 |
| 4,927,762 A | 5/1990 | Darfler | 435/240.31 |
| 4,937,190 A | 6/1990 | Palmenberg et al. | 435/69.1 |
| 4,946,778 A | 8/1990 | Ladner et al. | 435/69.6 |
| 5,122,469 A | 6/1992 | Mather et al. | 435/240.2 |
| 5,139,941 A | 8/1992 | Muzyczka et al. | 435/172.3 |
| 5,149,645 A | 9/1992 | Hoekema et al. | 435/172.3 |
| 5,168,062 A | 12/1992 | Stinski | 435/240.2 |
| 5,173,414 A | 12/1992 | Lebkowski et al. | 435/172.3 |
| 5,215,904 A | 6/1993 | Gould et al. | 435/172.3 |
| 5,225,347 A | 7/1993 | Goldberg et al. | 435/320.1 |
| 5,385,839 A | 1/1995 | Stinski | 435/240.2 |
| 5,508,184 A | 4/1996 | Negrutiu et al. | 435/172.3 |
| 5,512,421 A | 4/1996 | Burns et al. | 435/320.1 |
| 5,512,443 A | 4/1996 | Schlom et al. | 435/7.23 |
| 5,591,624 A | 1/1997 | Barber et al. | 435/240.2 |
| 5,618,682 A | 4/1997 | Scheirer | 435/8 |
| 5,627,058 A | 5/1997 | Ruley et al. | 435/172.3 |
| 5,670,113 A | 9/1997 | Akong et al. | 422/63 |
| 5,674,713 A | 10/1997 | McElroy et al. | 435/69.7 |
| 5,686,120 A | 11/1997 | Mertz et al. | 435/320.1 |
| 5,686,279 A | 11/1997 | Finer et al. | 435/172.3 |
| 5,716,832 A | 2/1998 | Barber et al. | 435/172.3 |
| 5,719,055 A | 2/1998 | Cooper | 435/320.1 |
| 5,721,121 A | 2/1998 | Etcheverry et al. | 435/69.7 |
| 5,807,689 A | 9/1998 | Daggett et al. | 435/78 |
| 5,817,491 A | 10/1998 | Yee et al. | 435/172.3 |
| 5,834,256 A | 11/1998 | Finer et al. | 435/91.33 |
| 5,843,742 A | 12/1998 | Natsoulis et al. | 435/172.3 |
| 5,850,000 A | 12/1998 | Bleck et al. | 800/2 |
| 5,858,740 A | 1/1999 | Finer et al. | 435/172.3 |
| 5,866,400 A | 2/1999 | Palsson et al. | 435/235.1 |
| 5,874,540 A | 2/1999 | Hensen et al. | 530/387.3 |
| 5,876,946 A | 3/1999 | Burbaum et al. | 435/7.1 |
| 5,914,267 A | 6/1999 | Mertz et al. | 435/320.1 |
| 5,922,601 A | 7/1999 | Baetscher et al. | 435/456 |
| 5,948,675 A | 9/1999 | Klatzmann et al. | 435/320.1 |
| 5,952,212 A | 9/1999 | Moller et al. | 435/194 |
| 5,955,592 A | 9/1999 | Ullrich et al. | 536/23.2 |
| 5,958,719 A | 9/1999 | Ullrich et al. | 435/21 |
| 5,958,775 A | 9/1999 | Wickstrom et al. | 435/455 |
| 5,965,443 A | 10/1999 | Reznikoff et al. | 435/473 |
| 5,968,785 A | 10/1999 | Devine et al. | 435/91.41 |
| 5,976,796 A | 11/1999 | Szalay et al. | 435/6 |
| 5,976,852 A | 11/1999 | Cheng et al. | 435/196 |
| 5,976,853 A | 11/1999 | Guthridge et al. | 435/196 |
| 5,981,251 A | 11/1999 | Ullrich et al. | 435/196 |
| 5,993,813 A | 11/1999 | Mezes et al. | 424/133.1 |
| 5,994,074 A | 11/1999 | Beach et al. | 435/6 |
| 5,994,136 A | 11/1999 | Naldini et al. | 435/455 |
| 6,004,791 A | 12/1999 | Aoki et al. | 435/194 |
| 6,013,455 A | 1/2000 | Bandman et al. | 435/6 |
| 6,013,464 A | 1/2000 | Abo et al. | 435/15 |

(List continued on next page.)

FOREIGN PATENT DOCUMENTS

| | | |
|---|---|---|
| WO | WO 87/00195 | 1/1987 |
| WO | WO 90/03430 | 4/1990 |
| WO | WO 92/01070 | 1/1992 |
| WO | WO 93/02108 | 2/1993 |
| WO | WO 93/03143 | 2/1993 |
| WO | WO 93/03769 | 3/1993 |
| WO | WO 94/05786 | 3/1994 |
| WO | WO 94/24870 | 11/1994 |
| WO | WO 96/11013 | 4/1996 |
| WO | WO99/14310 | 3/1999 |
| WO | WO 99/43795 | 9/1999 |

OTHER PUBLICATIONS

Hellerman et al (PNAS 81:5340–5344, 1984).*
Mathor et al (PNAS 93:10371–10376, 1996).*
Wang et al (Gene 182:145–50, 1996).*
von Ruden et al (Bio Techniques 18:484–489, 1995).*
Arai et al (Virology 260:109–115, Jul. 20, 1999).*
Akkina et al (Journal of Virology 70:2581–2585, 1996).*
Yee et al (Methods in Cell Biology 43:99–112, 1994).*

(List continued on next page.)

*Primary Examiner*—Mary E. Mosher
(74) *Attorney, Agent, or Firm*—Medlen & Carroll, LLP

(57) ABSTRACT

The present invention relates to the production of proteins in host cells, and, more particularly to host cells containing multiple integrated copies of an integrating vector. Suitable integrating vectors for use in the present invention include retrovirus vectors, lentivirus vectors, transposon vectors, and adeno-associated virus vectors. Methods are provided in which the host cells are prepared by using the integrating vectors at a high multiplicity of infection. The host cells are useful for producing pharmaceutical proteins, variants of proteins for use in screening assays, and for direct use in high throughput screening.

32 Claims, 35 Drawing Sheets

U.S. PATENT DOCUMENTS

| | | | |
|---|---|---|---|
| 6,013,516 A | 1/2000 | Verma et al. | 435/325 |
| 6,015,807 A | 1/2000 | Engel et al. | 514/183 |
| 6,020,306 A | 2/2000 | Boyd et al. | 514/2 |
| 6,025,192 A | 2/2000 | Beach et al. | 435/320.1 |
| 6,027,722 A | 2/2000 | Hodgson | 424/93.21 |
| 6,027,875 A | 2/2000 | Weinberger | 435/6 |
| 6,030,788 A | 2/2000 | Gerhold | 435/6 |
| 6,030,822 A | 2/2000 | Lechner et al. | 435/194 |
| 6,034,228 A | 3/2000 | Norris et al. | 536/23.1 |
| 6,051,427 A | 4/2000 | Finer et al. | 435/369 |
| 6,061,427 A | 5/2000 | Ryoo | 379/1 |
| 6,074,859 A | 6/2000 | Hirokawa et al. | 435/189 |
| 6,080,912 A | 6/2000 | Bremel et al. | 800/23 |
| 6,136,597 A * | 10/2000 | Hope et al. | 435/325 |
| 6,187,287 B1 | 2/2001 | Leung et al. | 424/9.1 |
| 6,255,071 B1 | 7/2001 | Beach et al. | 435/69.1 |
| 6,291,740 B1 | 9/2001 | Bremel et al. | 800/23 |
| 6,306,605 B1 * | 10/2001 | Acevedo et al. | 435/6 |
| 6,319,707 B1 | 11/2001 | Adam et al. | 435/320.1 |
| 6,331,415 B1 | 12/2001 | Cabilly et al. | 435/69.6 |
| 6,333,195 B1 | 12/2001 | Respess et al. | 435/456 |
| 6,368,862 B1 | 4/2002 | Palmer et al. | 435/455 |
| 6,410,316 B1 | 6/2002 | Sheridan et al. | 435/320.1 |

OTHER PUBLICATIONS

Mielke et al., Biochem. 35:2239–52 [1996].
Schroder and Friedl, Biotech. Bioeng. 53(6):547–59 [1997].
Weidle et al., Gene 66:193–203 [1988].
McBurney et al., Somatic Cell Molec. Genet. 20:529–40 [1994].
Allen et al., Plant Cell 5:603–13 [1993].
Mehtali et al., Gene 91:179–84 [1990].
Kricker et al., Proc. Natl. Acad. Sci. 89:1075–79 [1992].
Dorer and Henikoff, Cell 77:993–1002 [1994].
Zwizinski et al., J. Biol. Chem. 255(16): 7973–77 [1980].
Gray et al., Gene 39(2): 247–54 [1985].
Martial et al., Science 205: 602–607 [1979].
Shelling and Smith, Gene Therapy 1:165–169 [1994].
Zhou et al., J. Exp. Med. 179:1867–1875 [1994].
Han et al., Proc. Natl. Acad. Sci. USA 88:4313–4317 [1991].
Uhlmann et al., Chem. Rev. 90:543–584 [1990].
Helene et al., Biochim. Biophys. Acta. 1049:99–125 [1990].
Agarwal et al., Proc. Natl. Acad. Sci. USA 85:7079–7083 [1989].
Heikkila et al., Nature 328:445–449 [1987].
Cech et al. (1992) J. Biol. Chem. 267:17479–17482.
Kotin, Human Gene Therapy 5:793–801 [1994].
Berns, K.I. "Parvoviridae and their Replication" in Fundamental Virology, 2nd Edition, (B.N. Fields and D.M. Knipe, eds.).
Ullrich and Schlessinger, Cell 61:203–212 [1990].
Neer, 1995, Cell 80:249–257 [1995].
Stermweis and Smrcka, Trends in Biochem. Sci. 17:502–506 [1992].
Charbonneau, H. and Tonks, Annu. Rev. Cell Biol. 8:463–93 [1992].
Saito et al., Cell Growth and Diff. 2:59–65 [1991].
Krueger et al., Proc. Natl. Acad. Sci. USA 89:7417–7421 [1992].
deWet et al., Mol. Cell. Biol. 7:725 [1987].
Graham et al., J. Gen Virol., 36:59 [1977].
Mather, Biol. Reprod. 23:243–251 [1980].
Mather et al., Annals N.Y. Acad. Sci., 383:44–68 [1982].
Evans et al., *Handbook of Plant Cell Culture*, 1: 124–176, MacMillan Publishing Co., New York [1983].
Potrykus and Shillito, *Methods in Enzymology,* vol. 118, Plant Molecular Biology, A. and H. Weissbach eds., Academic Press, Orlando [1986].
Hoess et al., Nucleic Acids Res. 14:2287–2300 [1986].
O'Gorman et al., Science 251:1351–55 [1991].
van Deursen et al., Proc. Natl. Acad. Sci. USA 92:7376–80 1995.
Adams et al., Proc. Natl. Acad. Sci. USA 89:8981 [1992].
Carter, B.J., Current Opinion in Biotechnology 3:533–539 [1992].
de la Cruz et al., J. Bact. 175: 6932–38 [1993].
Craig, Curr. Topics Microbiol. Immunol. 204: 27–48 [1996].
Morisato and Kleckner, Cell 51:101–111 [1987].
Wilson et al., Cell, 37:767 [1984].
Denyer et al., Drug Discov. Today 3:323–32 [1998].
Gonzales et al., Drug Discov. Today 4:431–39 [1999].
Goff et al., J. Virol. 38:239 [1981].
Quade, Virol. 98:461 [1979].
Yee et al., Meth. Cell Biol. 43:99 [1994].
Chen and Okayama (Mol. Cell. Biol., 7:2745, 1987.
Shillito, et al., Plant Cell Reports, 2, 244–247 (1983).
Harlow and Lane, *Antibodies: A Laboratory Manual,* Cold Spring Harbor Laboratory Press, Cold Spring Harbor, NY.
Brun et al., Intervirol, 38:274 (1995).
Masters et al., Virol. 171:285 (1990).
Mebatsion et al., J. Virol. 69:1444 (1995).
Scheper et al., Biochem. 76: 801–809 [1994].
Meyer et al., J. Virol. 69: 2819–2824 [1995].
Jang et al., 1988, J. Virol. 62: 2636–2643 [1998].
Haller et al., J. Virol. 66: 5075–5086 [1995].
Lebkowski et al., Molec. Cell. Biol. 8:3988–3996 [1988].
Carter, Current Opinion in Biotechnology 3:533–539 [1992].
Muzyczka, Current Topics in Microbiol. and Immunol. 158:97–129 [1992].
Rogers et al., Strategies 13:97–99 (2000).
Felts et al., Strategies 13:15–18 (2000).
Felts et al., Strategies 12:74–77 (1999).
Poul et al., Immunotechnology, Elsevier Science Publishers BV, NL 1:189–196 (1995).
Zufferey et al., J. of Virology 73:2886–2892 (1999).
Vaillancourt et al., Strategies 13:50–53 (2000).
Han et al., PNAS 88:4313–4317 (1991).

* cited by examiner

Figure 4
SEQ ID NO:1
Hybrid Human-Bovine Alpha-Lactalbumin Promoter

```
1     GATCAGTCCTGGGTGGTCATTGAAAGGACTGATGCTGAAGTTGAAGCTCC
51    AATACTTTGGCCACCTGATGCGAAGAACTGACTCATGTGATAAGACCCTG
101   ATACTGGGAAAGATTGAAGGCAGGAGGAGAAGGGATGACAGAGGATGGAA
151   GAGTTGGATGGAATCACCAACTCGATGGACATGAGTTTGAGCAAGCTTCC
201   AGGAGTTGGTAATGGGCAGGGAAGCCTGGCGTGCTGCAGTCCATGGGGTT
251   GCAAAGAGTTGGACACTACTGAGTGACTGAACTGAACTGATAGTGTAATC
301   CATGGTACAGAATATAGGATAAAAAAGAGGAAGAGTTTGCCCTGATTCTG
351   AAGAGTTGTAGGATATAAAAGTTTAGAATACCTTTAGTTTGGAAGTCTTA
401   AATTATTTACTTAGGATGGGTACCCACTGCAATATAAGAAATCAGGCTTT
451   AGAGACTGATGTAGAGAGAATGAGCCCTGGCATACCAGAAGCTAACAGCT
501   ATTGGTTATAGCTGTTATAACCAATATATAACCAATATATTGGTTATATA
551   GCATGAAGCTTGATGCCAGCAATTTGAAGGAACCATTTAGAACTAGTATC
601   CTAAACTCTACATGTTCCAGGACACTGATCTTAAAGCTCAGGTTCAGAAT
651   CTTGTTTTATAGGCTCTAGGTGTATATTGTGGGGCTTCCCTGGTGGCTCA
701   GATGGTAAAGTGTCTGCCTGCAATGTGGGTGATCTGGGTTCGATCCCTGG
751   CTTGGGAAGATCCCCTGGAGAAGGAAATGGCAACCCACTCTAGTACTCTT
801   ACCTGGAAAATTCCATGGACAGAGGAGCCTTGTAAGCTACAGTCCATGGG
851   ATTGCAAAGAGTTGAACACAACTGAGCAACTAAGCACAGCACAGTACAGT
900   ATACACCTGTGAGGTGAAGTGAAGTGAAGGTTCAATGCAGGGTCTCCTGC
951   ATTGCAGAAAGATTCTTTACCATCTGAGCCACCAGGGAAGCCCAAGAATA
1001  CTGGAGTGGGTAGCCTATTCCTTCTCCAGGGGATCTTCCCATCCCAGGAA
1051  TTGAACTGGAGTCTCCTGCATTTCAGGTGGATTCTTCACCAGCTGAACTA
1101  CCAGGTGGATACTACTCCAATATTAAAGTGCTTAAAGTCCAGTTTTCCCA
1151  CCTTTCCCAAAAAGGTTGGGTCACTCTTTTTTAACCTTCTGTGGCCTACT
1201  CTGAGGCTGTCTACAAGCTTATATATTTATGAACACATTTATTGCAAGTT
1251  GTTAGTTTTAGATTTACAATGTGGTATCTGGCTATTTAGTGGTATTGGTG
1301  GTTGGGGATGGGGAGGCTGATAGCATCTCAGAGGGCAGCTAGATACTGTC
1351  ATACACACTTTTCAAGTTCTCCATTTTTGTGAAATAGAAAGTCTCTGGAT
1401  CTAAGTTATATGTGATTCTCAGTCTCTGTGGTCATATTCTATTCTACTCC
1451  TGACCACTCAACAAGGAACCAAGATATCAAGGGACACTTGTTTTGTTTCA
1501  TGCCTGGGTTGAGTGGGCCATGACATATGTTCTGGGCCTTGTTACATGGC
1551  TGGATTGGTTGGACAAGTGCCAGCTCTGATCCTGGACTGGTTGGCATGTGA
1601  TGACATACACCCCCTCTCCACATTCTGCATGTCTCTAGGGGGGAAGGGGG
1651  AAGCTCGGTATAGAACCTTTATTGTATTTTCTGATTGCCTCACTTCTTAT
1701  ATTGCCCCCATGCCCTTCTTTGTTCCTCAAGTAACCAGAGACAGTGCTTC
1751  CCAGAACCAACCCTACAAGAAACAAAGGGCTAAACAAAGCCAAATGGGAA
1801  GCAGGATCATGGTTTGAACTCTTTCTGGCCAGAGAACAATACCTGCTATG
1851  GACTAGATACTGGGAGAGGGAAAGGAAAAGTAGGGTGAATTATGGAAGGA
1901  AGCTGGCAGGCTCAGCGTTTCTGTCTTGGCATGACCAGTCTCTCTTCATT
1951  CTCTTCCTAGATGTAGGGCTTGGTACCAGAGCCCCTGAGGCTTTCTGCAT
2001  GAATATAAATATATGAAACTGAGTGATGCTTCCATTTCAGGTTCTTGGGG
2051  GCGCCGAATTCGAGCTCGGTACCCGGGGATCTCGAGGGGGGGCCCGGTAC
2101  C
```

1 - 1525     Bovine alpha lactalbumin 5' flanking region (-2000 to -550 from the bovine alpha-lactalbumin transcription start point)
1526 - 2056  Human alpha-lactalbumin 5' flanking region (-600 to +15 from the human alpha-lactalbumin transcription start point)
2057 - 2101  Multiple cloning site Figure 5
SEQ ID NO:2
Mutated PPE Sequence

```
  1    GATTACTTACTGGCAGGTGCTGGGGGCTTCCGAGACAATCGCGAACATCT
 51    ACACCACACAACACCGCCTCGACCAGGGTGAGATATCGGCCGGGGACGCG
101    GCGGTGGTAATTACAAGCGAGGATCCGATTACTTACTGGCAGGTGCTGGG
151    GGCTTCCGAGACAATCGCGAACATCTACACCACACAACACCGCCTCGACC
201    AGGGTGAGATATCGGCCGGGGACGCGGCGGTGGTAATTACAAGCG
```

| | |
|---|---|
| 1 - 119 | Mutated PPE |
| 120 - 126 | Linker |
| 127 - 245 | Mutated PPE |

Figure 6
SEQ ID NO:3
IRES-Signal Peptide Sequence

```
  1    GGAATTCGCCCCTCTCCCTCCCCCCCCCCTAACGTTACTGGCCGAAGCCG
 51    CTTGGAATAAGGCCGGTGTGCGTTTGTCTATATGTTATTTTCCACCATAT
101    TGCCGTCTTTTGGCAATGTGAGGGCCCGGAAACCTGGCCCTGTCTTCTTG
151    ACGAGCATTCCTAGGGGTCTTTCCCCTCTCGCCAAAGGAATGCAAGGTCT
201    GTTGAATGTCGTGAAGGAAGCAGTTCCTCTGGAAGCTTCTTGAAGACAAA
251    CAACGTCTGTAGCGACCCTTTGCAGGCAGCGGAACCCCCCACCTGGCGAC
301    AGGTGCCTCTGCGGCCAAAAGCCACGTGTATAAGATACACCTGCAAAGGC
351    GGCACAACCCCAGTGCCACGTTGTGAGTTGGATAGTTGTGGAAAGAGTCA
401    AATGGCTCTCCTCAAGCGTATTCAACAAGGGGCTGAAGGATGCCCAGAAG
451    GTACCCCATTGTATGGGATCTGATCTGGGGCCTCGGTGCACATGCTTTAC
501    ATGTGTTTAGTCGAGGTTAAAAAAACGTCTAGGCCCCCCGAACCACGGGG
551    ACGTGGTTTTCCTTTGAAAAACACGATGATAATATGGCCTCCTTTGTCTC
601    TCTGCTCCTGGTAGGCATCCTATTCCATGCCACCCAGGCCGGCGCCATGG
651    GATATCTAGATCTCGAGCTCGCGAAAGCTT
```

1 - 583      IRES
584 - 640    Modified bovine alpha-lactalbumin signal peptide coding region
641 - 680    Multiple cloning site Figure 7a
SEQ ID NO:4
CMV MN14 Vector

```
   1  CGGATCCGGCCATTAGCCATATTATTCATTGGTTATATAGCATAAATCAA
  51  TATTGGCTATTGGCCATTGCATACGTTGTATCCATATCATAATATGTACA
 101  TTTATATTGGCTCATGTCCAACATTACCGCCATGTTGACATTGATTATTG
 151  ACTAGTTATTAATAGTAATCAATTACGGGGTCATTAGTTCATAGCCCATA
 201  TATGGAGTTCCGCGTTACATAACTTACGGTAAATGGCCCGCCTGGCTGAC
 251  CGCCCAACGACCCCCGCCCATTGACGTCAATAATGACGTATGTTCCCATA
 301  GTAACGCCAATAGGGACTTTCCATTGACGTCAATGGGTGGAGTATTTACG
 351  GTAAACTGCCCACTTGGCAGTACATCAAGTGTATCATATGCCAAGTACGC
 401  CCCCTATTGACGTCAATGACGGTAAATGGCCCGCCTGGCATTATGCCCAG
 451  TACATGACCTTATGGGACTTTCCTACTTGGCAGTACATCTACGTATTAGT
 501  CATCGCTATTACCATGGTGATGCGGTTTTGGCAGTACATCAATGGGCGTG
 551  GATAGCGGTTTGACTCACGGGGATTTCCAAGTCTCCACCCCATTGACGTC
 601  AATGGGAGTTTGTTTTGGCACCAAAATCAACGGGACTTTCCAAAATGTCG
 651  TAACAACTCCGCCCCATTGACGCAAATGGGCGGTAGGCATGTACGGTGGG
 701  AGGTCTATATAAGCAGAGCTCGTTTAGTGAACCGTCAGATCGCCTGGAGA
 751  CGCCATCCACGCTGTTTTGACCTCCATAGAAGACACCGGGACCGATCCAG
 801  CCTCCGCGGCCCCAAGCTTCTCGACGGATCCCCGGGAATTCAGGACCTCA
 851  CCATGGGATGGAGCTGTATCATCCTCTTCTTGGTAGCAACAGCTACAGGT
 901  GTCCACTCCGAGGTCCAACTGGTGGAGAGCGGTGGAGGTGTTGTGCAACC
 951  TGGCCGGTCCCTGCGCCTGTCCTGCTCCGCATCTGGCTTCGATTTCACCA
1001  CATATTGGATGAGTTGGGTGAGACAGGCACCTGGAAAAGGTCTTGAGTGG
1051  ATTGGAGAAATTCATCCAGATAGCAGTACGATTAACTATGCGCCGTCTCT
1101  AAAGGATAGATTTACAATATCGCGAGACAACGCCAAGAACACATTGTTCC
1151  TGCAAATGGACAGCCTGAGACCCGAAGACACCGGGGTCTATTTTGTGCA
1201  AGCCTTTACTTCGGCTTCCCCTGGTTTGCTTATTGGGCCAAGGGACCCC
1251  GGTCACCGTCTCCTCAGCCTCCACCAAGGGCCCATCGGTCTTCCCCCTGG
1301  CACCCTCCTCCAAGAGCACCTCTGGGGGCACAGCGGCCCTGGGCTGCCTG
1351  GTCAAGGACTACTTCCCCGAACCGGTGACGGTGTCGTGGAACTCAGGCGC
1401  CCTGACCAGCGGCGTGCACACCTTCCCGGCTGTCCTACAGTCCTCAGGAC
1451  TCTACTCCCTCAGCAGCGTGGTGACCGTGCCCTCCAGCAGCTTGGGCACC
1501  CAGACCTACATCTGCAACGTGAATCACAAGCCCAGCAACACCAAGGTGGA
1551  CAAGAGAGTTGAGCCCAAATCTTGTGACAAAACTCACACATGCCCACCGT
1601  GCCCAGCACCTGAACTCCTGGGGGGACCGTCAGTCTTCCTCTTCCCCCCA
1651  AAACCCAAGGACACCCTCATGATCTCCCGGACCCCTGAGGTCACATGCGT
1701  GGTGGTGGACGTGAGCCACGAAGACCCTGAGGTCAAGTTCAACTGGTACG
1751  TGGACGGCGTGGAGGTGCATAATGCCAAGACAAAGCCGCGGGAGGAGCAG
1801  TACAACAGCACGTACCGTGTGGTCAGCGTCCTCACCGTCCTGCACCAGGA
1851  CTGGCTGAATGGCAAGGAGTACAAGTGCAAGGTCTCCAACAAAGCCCTCC
1901  CAGCCCCCATCGAGAAAACCATCTCCAAAGCCAAAGGGCAGCCCCGAGAA
1951  CCACAGGTGTACACCCTGCCCCCATCCCGGGAGGAGATGACCAAGAACCA
2001  GGTCAGCCTGACCTGCCTGGTCAAAGGCTTCTATCCCAGCGACATCGCCG
2051  TGGAGTGGGAGAGCAATGGGCAGCCGGAGAACAACTACAAGACCACGCCT
2101  CCCGTGCTGGACTCCGACGGCTCCTTCTTCCTCTATAGCAAGCTCACCGT
2151  GGACAAGAGCAGGTGGCAGCAGGGGAACGTCTTCTCATGCTCCGTGATGC
2201  ACGAGGCTCTGCACAACCACTACACGCAGAAGAGCCTCTCCCTGTCTCCC
2251  GGGAAATGAAAGCCGAATTCGCCCCTCTCCCTCCCCCCCCCCTAACGTTA
2301  CTGGCCGAAGCCGCTTGGAATAAGGCCGGTGTGCGTTTGTCTATATGTTA
2351  TTTTCCACCATATTGCCGTCTTTTGGCAATGTGAGGGCCCGGAAACCTGG
2401  CCCTGTCTTCTTGACGAGCATTCCTAGGGGTCTTTCCCCTCTCGCCAAAG
2451  GAATGCAAGGTCTGTTGAATGTCGTGAAGGAAGCAGTTCCTCTGGAAGCT
2501  TCTTGAAGACAAACAACGTCTGTAGCGACCCTTTGCAGGCAGCGGAACCC
2551  CCCACCTGGCGACAGGTGCCTCTGCGGCCAAAAGCCACGTGTATAAGATA
2601  CACCTGCAAAGGCGGCACAACCCCAGTGCCACGTTGTGAGTTGGATAGTT
2651  GTGGAAAGAGTCAAATGGCTCTCCTCAAGCGTATTCAACAAGGGGCTGAA
2701  GGATGCCCAGAAGGTACCCCATTGTATGGGATCTGATCTGGGGCCTCGGT
2751  GCACATGCTTTACATGTGTTTAGTCGAGGTTAAAAAAACGTCTAGGCCCC
2801  CCGAACCACGGGGACGTGGTTTTCCTTTGAAAAACACGATGATAATATGG
```

Figure 7b

```
2851    CCTCCTTTGTCTCTCTGCTCCTGGTAGGCATCCTATTCCATGCCACCCAG
2901    GCCGACATCCAGCTGACCCAGAGCCCAAGCAGCCTGAGCGCCAGCGTGGG
2951    TGACAGAGTGACCATCACCTGTAAGGCCAGTCAGGATGTGGGTACTTCTG
3001    TAGCCTGGTACCAGCAGAAGCCAGGTAAGGCTCCAAAGCTGCTGATCTAC
3051    TGGACATCCACCCGGCACACTGGTGTGCCAAGCAGATTCAGCGGTAGCGG
3101    TAGCGGTACCGACTTCACCTTCACCATCAGCAGCCTCCAGCCAGAGGACA
3151    TCGCCACCTACTACTGCCAGCAATATAGCCTCTATCGGTCGTTCGGCCAA
3201    GGGACCAAGGTGGAAATCAAACGAACTGTGGCTGCACCATCTGTCTTCAT
3251    CTTCCCGCCATCTGATGAGCAGTTGAAATCTGGAACTGCCTCTGTTGTGT
3301    GCCTGCTGAATAACTTCTATCCCAGAGAGGCCAAAGTACAGTGGAAGGTG
3351    GATAACGCCCTCCAATCGGGTAACTCCCAGGAGAGTGTCACAGAGCAGGA
3401    CAGCAAGGACAGCACCTACAGCCTCAGCAGCACCCTGACGCTGAGCAAAG
3451    CAGACTACGAGAAACACAAAGTCTACGCCTGCGAAGTCACCCATCAGGGC
3501    CTGAGCTCGCCCGTCACAAAGAGCTTCAACAGGGGAGAGTGTTAGAGATC
3551    TAGGCCTCCTAGGTCGACATCGATAAAATAAAAGATTTTATTTAGTCTCC
3601    AGAAAAAGGGGGGAATGAAAGACCCCACCTGTAGGTTTGGCAAGCTAGCT
3651    TAAGTAACGCCATTTTGCAAGGCATGGAAAAATACATAACTGAGAATAGA
3701    GAAGTTCAGATCAAGGTCAGGAACAGATGGAACAGCTGAATATGGGCCAA
3751    ACAGGATATCTGTGGTAAGCAGTTCCTGCCCCGGCTCAGGGCCAAGAACA
3801    GATGGAACAGCTGAATATGGGCCAAACAGGATATCTGTGGTAAGCAGTTC
3851    CTGCCCCGGCTCAGGGCCAAGAACAGATGGTCCCCAGATGCGGTCCAGCC
3901    CTCAGCAGTTTCTAGAGAACCATCAGATGTTTCCAGGGTGCCCCAAGGAC
3951    CTGAAATGACCCTGTGCCTTATTTGAACTAACCAATCAGTTCGCTTCTCG
4001    CTTCTGTTCGCGCGCTTCTGCTCCCCGAGCTCAATAAAAGAGCCCACAAC
4051    CCCTCACTCGGGGCGCCAGTCCTCCGATTGACTGAGTCGCCCGGGTACCC
4101    GTGTATCCAATAAACCCTCTTGCAGTTGCATCCGACTTGTGGTCTCGCTG
4151    TTCCTTGGGAGGGTCTCCTCTGAGTGATTGACTACCCGTCAGCGGGGGTC
4201    TTTCATT
```

| | |
|---|---|
| 1 - 812 | CMV promoter/enhancer |
| 853-855 | MN14 antibody heavy chain gene signal peptide start codon |
| 2257 - 2259 | MN14 antibody heavy chain gene start codon |
| 2271 - 2846 | EMCV IRES |
| 2847 - 2849 | Bovine alpha-lactalbumin signal peptide start codon |
| 2904 - 2906 | First codon mature MN14 antibody light chain gene |
| 3543 - 3544 | MN14 antibody light chain gene stop codon |
| 3614 - 4207 | MoMuLV 3' LTR |

Figure 8a
SEQ ID NO:5
CMV LL2 Vector

```
   1  GGATCCGGCCATTAGCCATATTATTCATTGGTTATATAGCATAAATCAAT
  51  ATTGGCTATTGGCCATTGCATACGTTGTATCCATATCATAATATGTACAT
 101  TTATATTGGCTCATGTCCAACATTACCGCCATGTTGACATTGATTATTGA
 151  CTAGTTATTAATAGTAATCAATTACGGGGTCATTAGTTCATAGCCCATAT
 201  ATGGAGTTCCGCGTTACATAACTTACGGTAAATGGCCCGCCTGGCTGACC
 251  GCCCAACGACCCCCGCCCATTGACGTCAATAATGACGTATGTTCCCATAG
 301  TAACGCCAATAGGGACTTTCCATTGACGTCAATGGGTGGAGTATTTACGG
 351  TAAACTGCCCACTTGGCAGTACATCAAGTGTATCATATGCCAAGTACGCC
 401  CCCTATTGACGTCAATGACGGTAAATGGCCCGCCTGGCATTATGCCCAGT
 451  ACATGACCTTATGGGACTTTCCTACTTGGCAGTACATCTACGTATTAGTC
 501  ATCGCTATTACCATGGTGATGCGGTTTTGGCAGTACATCAATGGGCGTGG
 551  ATAGCGGTTTGACTCACGGGGATTTCCAAGTCTCCACCCCATTGACGTCA
 601  ATGGGAGTTTGTTTTGGCACCAAAATCAACGGGACTTTCCAAAATGTCGT
 651  AACAACTCCGCCCCATTGACGCAAATGGGCGGTAGGCATGTACGGTGGGA
 701  GGTCTATATAAGCAGAGCTCGTTTAGTGAACCGTCAGATCGCCTGGAGAC
 751  GCCATCCACGCTGTTTTGACCTCCATAGAAGACACCGGGACCGATCCAGC
 801  CTCCGCGGCCCCAAGCTTCTCGACGGATCCCCGGGAATTCAGGACCTCAC
 851  CATGGGATGGAGCTGTATCATCCTCTTCTTGGTAGCAACAGCTACAGGTG
 901  TCCACTCCCAGGTCCAGCTGGTCCAATCAGGGGCTGAAGTCAAGAAACCT
 951  GGGTCATCAGTGAAGGTCTCCTGCAAGGCTTCTGGCTACACCTTTACTAG
1001  CTACTGGCTGCACTGGGTCAGGCAGGCACCTGGACAGGGTCTGGAATGGA
1051  TTGGATACATTAATCCTAGGAATGATTATACTGAGTACAATCAGAACTTC
1101  AAGGACAAGGCCACAATAACTGCAGACGAATCCACCAATACAGCCTACAT
1151  GGAGCTGAGCAGCCTGAGGTCTGAGGACACGGCATTTTATTTTTGTGCAA
1201  GAAGGGATATTACTACGTTCTACTGGGGCCAAGGCACCACGGTCACCGTC
1251  TCCTCAGCCTCCACCAAGGGCCCATCGGTCTTCCCCCTGGCACCCTCCTC
1301  CAAGAGCACCTCTGGGGGCACAGCGGCCCTGGGCTGCCTGGTCAAGGACT
1351  ACTTCCCCGAACCGGTGACGGTGTCGTGGAACTCAGGCGCCCTGACCAGC
1401  GGCGTGCACACCTTCCCGGCTGTCCTACAGTCCTCAGGACTCTACTCCCT
1451  CAGCAGCGTGGTGACCGTGCCCTCCAGCAGCTTGGGCACCCAGACCTACA
1501  TCTGCAACGTGAATCACAAGCCCAGCAACACCAAGGTGGACAAGAGAGTT
1551  GAGCCCAAATCTTGTGACAAAACTCACACATGCCCACCGTGCCCAGCACC
1601  TGAACTCCTGGGGGGACCGTCAGTCTTCCTCTTCCCCCCAAAACCCAAGG
1651  ACACCCTCATGATCTCCCGGACCCCTGAGGTCACATGCGTGGTGGTGGAC
1701  GTGAGCCACGAAGACCCTGAGGTCAAGTTCAACTGGTACGTGGACGGCGT
1751  GGAGGTGCATAATGCCAAGACAAAGCCGCGGGAGGAGCAGTACAACAGCA
1801  CGTACCGTGTGGTCAGCGTCCTCACCGTCCTGCACCAGGACTGGCTGAAT
1851  GGCAAGGAGTACAAGTGCAAGGTCTCCAACAAAGCCCTCCCAGCCCCCAT
1901  CGAGAAAACCATCTCCAAAGCCAAAGGGCAGCCCCGAGAACCACAGGTGT
1951  ACACCCTGCCCCCATCCCGGGAGGAGATGACCAAGAACCAGGTCAGCCTG
2001  ACCTGCCTGGTCAAAGGCTTCTATCCCAGCGACATCGCCGTGGAGTGGGA
2051  GAGCAATGGGCAGCCGGAGAACAACTACAAGACCACGCCTCCCGTGCTGG
2101  ACTCCGACGGCTCCTTCTTCCTCTATAGCAAGCTCACCGTGGACAAGAGC
2151  AGGTGGCAGCAGGGGAACGTCTTCTCATGCTCCGTGATGCACGAGGCTCT
2201  GCACAACCACTACACGCAGAAGAGCCTCTCCCTGTCTCCCGGGAAATGAA
2251  AGCCGAATTCGCCCCTCTCCCTCCCCCCCCCCTAACGTTACTGGCCGAAG
2301  CCGCTTGGAATAAGGCCGGTGTGCGTTTGTCTATATGTTATTTTCCACCA
2351  TATTGCCGTCTTTTGGCAATGTGAGGGCCCGGAAACCTGGCCCTGTCTTC
2401  TTGACGAGCATTCCTAGGGGTCTTTCCCCTCTCGCCAAAGGAATGCAAGG
2451  TCTGTTGAATGTCGTGAAGGAAGCAGTTCCTCTGGAAGCTTCTTGAAGAC
2501  AAACAACGTCTGTAGCGACCCTTTGCAGGCAGCGGAACCCCCCACCTGGC
2551  GACAGGTGCCTCTGCGGCCAAAAGCCACGTGTATAAGATACACCTGCAAA
2601  GGCGGCACAACCCCAGTGCCACGTTGTGAGTTGGATAGTTGTGGAAAGAG
2651  TCAAATGGCTCTCCTCAAGCGTATTCAACAAGGGGCTGAAGGATGCCCAG
2701  AAGGTACCCCATTGTATGGGATCTGATCTGGGGCCTCGGTGCACATGCTT
2751  TACATGTGTTTAGTCGAGGTTAAAAAAACGTCTAGGCCCCCCGAACCACG
2801  GGGACGTGGTTTTCCTTTGAAAAACACGATGATAATATGGCCTCCTTTGT
```

Figure 8b

```
2851  CTCTCTGCTCCTGGTAGGCATCCTATTCCATGCCACCCAGGCCGACATCC
2901  AGCTGACCCAGTCTCCATCATCTCTGAGCGCATCTGTTGGAGATAGGGTC
2951  ACTATGAGCTGTAAGTCCAGTCAAAGTGTTTTATACAGTGCAAATCACAA
3001  GAACTACTTGGCCTGGTACCAGCAGAAACCAGGGAAAGCACCTAAACTGC
3051  TGATCTACTGGGCATCCACTAGGGAATCTGGTGTCCCTTCGCGATTCTCT
3101  GGCAGCGGATCTGGGACAGATTTTACTTTCACCATCAGCTCTCTTCAACC
3151  AGAAGACATTGCAACATATTATTGTCACCAATACCTCTCCTCGTGGACGT
3201  TCGGTGGAGGGACCAAGGTGCAGATCAAACGAACTGTGGCTGCACCATCT
3251  GTCTTCATCTTCCCGCCATCTGATGAGCAGTTGAAATCTGGAACTGCCTC
3301  TGTTGTGTGCCTGCTGAATAACTTCTATCCCAGAGAGGCCAAAGTACAGT
3351  GGAAGGTGGATAACGCCCTCCAATCGGGTAACTCCCAGGAGAGTGTCACA
3401  GAGCAGGACAGCAAGGACAGCACCTACAGCCTCAGCAGCACCCTGACGCT
3451  GAGCAAAGCAGACTACGAGAAACACAAAGTCTACGCCTGCGAAGTCACCC
3501  ATCAGGGCCTGAGCTCGCCCGTCACAAAGAGCTTCAACAGGGGAGAGTGT
3551  TAGAGATCTAGGCCTCCTAGGTCGACATCGATAAAATAAAAGATTTTATT
3601  TAGTCTCCAGAAAAGGGGGGAATGAAAGACCCCACCTGTAGGTTTGGCA
3651  AGCTAGCTTAAGTAACGCCATTTTGCAAGGCATGGAAAAATACATAACTG
3701  AGAATAGAGAAGTTCAGATCAAGGTCAGGAACAGATGGAACAGCTGAATA
3751  TGGGCCAAACAGGATATCTGTGGTAAGCAGTTCCTGCCCCGGCTCAGGGC
3801  CAAGAACAGATGGAACAGCTGAATATGGGCCAAACAGGATATCTGTGGTA
3851  AGCAGTTCCTGCCCCGGCTCAGGGCCAAGAACAGATGGTCCCCAGATGCG
3901  GTCCAGCCCTCAGCAGTTTCTAGAGAACCATCAGATGTTTCCAGGGTGCC
3951  CCAAGGACCTGAAATGACCCTGTGCCTTATTTGAACTAACCAATCAGTTC
4001  GCTTCTCGCTTCTGTTCGCGCGCTTCTGCTCCCCGAGCTCAATAAAAGAG
4051  CCCACAACCCCTCACTCGGGGCGCCAGTCCTCCGATTGACTGAGTCGCCC
4101  GGGTACCCGTGTATCCAATAAACCCTCTTGCAGTTGCATCCGACTTGTGG
4151  TCTCGCTGTTCCTTGGGAGGGTCTCCTCTGAGTGATTGACTACCCGTCAG
4201  GTCTTTCATT
```

| | |
|---|---|
| 1 - 812 | CMV promoter/enhancer |
| 852 - 854 | LL2 antibody heavy chain signal peptide start codon |
| 2247 - 2249 | LL2 antibody heavy chain stop codon |
| 2261 - 2836 | EMCV IRES |
| 2837 - 2839 | Bovine alpha-lactalbumin signal peptide start codon |
| 2894 - 2896 | First codon of mature LL2 antibody light chain gene |
| 3551 - 3553 | LL2 antibody light chain gene stop codon |
| 3622 - 4210 | MoMuLV 3' LTR |

Figure 9a
SEQ ID NO:6
MMTV MN14 Vector

```
   1    CGAGCTTGGCAGAAATGGTTGAACTCCCGAGAGTGTCCTACACCTAGGGG
  51    AGAAGCAGCCAAGGGGTTGTTTCCCACCAAGGACGACCCGTCTGCGCACA
 101    AACGGATGAGCCCATCAGACAAAGACATATTCATTCTCTGCTGCAAACTT
 151    GGCATAGCTCTGCTTTGCCTGGGGCTATTGGGGGAAGTTGCGGTTCGTGC
 201    TCGCAGGGCTCTCACCCTTGACTCTTTCAATAATAACTCTTCTGTGCAAG
 251    ATTACAATCTAAACAATTCGGAGAACTCGACCTTCCTCCTGAGGCAAGGA
 301    CCACAGCCAACTTCCTCTTACAAGCCGCATCGATTTGTCCTTCAGAAAT
 351    AGAAATAAGAATGCTTGCTAAAAATTATATTTTTACCAATAAGACCAATC
 401    CAATAGGTAGATTATTAGTTACTATGTTAAGAAATGAATCATTATCTTTT
 451    AGTACTATTTTTACTCAAATTCAGAAGTTAGAAATGGGAATAGAAAATAG
 501    AAAGAGACGCTCAACCTCAATTGAAGAACAGGTGCAAGGACTATTGACCA
 551    CAGGCCTAGAAGTAAAAAAGGGAAAAAAGAGTGTTTTTGTCAAAATAGGA
 601    GACAGGTGGTGGCAACCAGGGACTTATAGGGGACCTTACATCTACAGACC
 651    AACAGATGCCCCCTTACCATATACAGGAAGATATGACTTAAATTGGGATA
 701    GGTGGGTTACAGTCAATGGCTATAAAGTGTTATATAGATCCCTCCCCTTT
 751    CGTGAAAGACTCGCCAGAGCTAGACCTCCTTGGTGTATGTTGTCTCAAGA
 801    AAAGAAAGACGACATGAAACAACAGGTACATGATTATATTTATCTAGGAA
 851    CAGGAATGCACTTTGGGGAAAGATTTTCCATACCAAGGAGGGGACAGTG
 901    GCTGGACTAATAGAACATTATTCTGCAAAAACTTATGGCATGAGTTATTA
 951    TGATTAGCCTTGATTTGCCCAACCTTGCGGTTCCCAAGGCTTAAGTAAGT
1001    TTTTGGTTACAAACTGTTCTTAAAACAAGGATGTGAGACAAGTGGTTTCC
1051    TGACTTGGTTTGGTATCAAAGGTTCTGATCTGAGCTCTGAGTGTTCTATT
1101    TTCCTATGTTCTTTTGGAATTTATCCAAATCTTATGTAAATGCTTATGTA
1151    AACCAAGATATAAAAGAGTGCTGATTTTTGAGTAAACTTGCAACAGTCC
1201    TAACATTCACCTCTTGTGTGTTTGTGTCTGTTCGCCATCCCGTCTCCGCT
1251    CGTCACTTATCCTTCACTTTCCAGAGGGTCCCCCCGCAGACCCCGGCGAC
1301    CCTCAGGTCGGCCGACTGCGGCAGCTGGCGCCCGAACAGGGACCCTCGGA
1351    TAAGTGACCCTTGTCTTTATTTCTACTATTTTGTGTTCGTCTTGTTTTGT
1401    CTCTATCTTGTCTGGCTATCATCACAAGAGCGGAACGGACTCACCTCAGG
1451    GAACCAAGCTAGCCCGGGGTCGACGGATCCGATTACTTACTGGCAGGTGC
1501    TGGGGGCTTCCGAGACAATCGCGAACATCTACACCACACAACACCGCCTC
1551    GACCAGGGTGAGATATCGGCCGGGGACGCGGCGGTGGTAATTACAAGCGA
1601    GATCCGATTACTTACTGGCAGGTGCTGGGGCTTCCGAGACAATCGCGAA
1651    CATCTACACCACACAACACCGCCTCGACCAGGGTGAGATATCGGCCGGGG
1701    ACGCGGCGGTGGTAATTACAAGCGAGATCCCCGGGAATTCAGGACCTCAC
1751    CATGGGATGGAGCTGTATCATCCTCTTCTTGGTAGCAACAGCTACAGGTG
1801    TCCACTCCGAGGTCCAACTGGTGGAGAGCGGTGGAGGTGTTGTGCAACCT
1851    GGCCGGTCCCTGCGCCTGTCCTGCTCCGCATCTGGCTTCGATTTCACCAC
1901    ATATTGGATGAGTTGGGTGAGACAGGCACCTGGAAAAGGTCTTGAGTGGA
1951    TTGGAGAAATTCATCCAGATAGCAGTACGATTAACTATGCGCCGTCTCTA
2001    AAGGATAGATTTACAATATCGCGAGACAACGCCAAGAACACATTGTTCCT
2051    GCAAATGGACAGCCTGAGACCCGAAGACACCGGGGTCTATTTTGTGCAA
2101    GCCTTTACTTCGGCTTCCCCTGGTTTGCTTATTGGGCCAAGGGACCCCG
2151    GTCACCGTCTCCTCAGCCTCCACCAAGGGCCCATCGGTCTTCCCCCTGGC
2201    ACCCTCCTCCAAGAGCACCTCTGGGGGCACAGCGGCCCTGGGCTGCCTGG
2251    TCAAGGACTACTTCCCCGAACCGGTGACGGTGTCGTGGAACTCAGGCGCC
2301    CTGACCAGCGGCGTGCACACCTTCCCGGCTGTCCTACAGTCCTCAGGACT
2351    CTACTCCCTCAGCAGCGTGGTGACCGTGCCCTCCAGCAGCTTGGGCACCC
2401    AGACCTACATCTGCAACGTGAATCACAAGCCCAGCAACACCAAGGTGGAC
2451    AAGAGAGTTGAGCCCAAATCTTGTGACAAAACTCACACATGCCCACCGTG
2501    CCCAGCACCTGAACCTCCTGGGGGGACCGTCAGTCTTCCTCTTCCCCCCAA
2551    AACCCAAGGACACCCTCATGATCTCCCGGACCCCTGAGGTCACATGCGTG
2601    GTGGTGGACGTGAGCCACGAAGACCCTGAGGTCAAGTTCAACTGGTACGT
2651    GGACGGCGTGGAGGTGCATAATGCCAAGACAAAGCCGCGGGAGGAGCAGT
2701    ACAACAGCACGTACCGTGTGGTCAGCGTCCTCACCGTCCTGCACCAGGAC
2751    TGGCTGAATGGCAAGGAGTACAAGTGCAAGGTCTCCAACAAAGCCCTCCC
2801    AGCCCCCATCGAGAAAACCATCTCCAAAGCCAAAGGGCAGCCCCGAGAAC
```

Figure 9b

```
2851  CACAGGTGTACACCCTGCCCCCATCCCGGGAGGAGATGACCAAGAACCAG
2901  GTCAGCCTGACCTGCCTGGTCAAAGGCTTCTATCCCAGCGACATCGCCGT
2951  GGAGTGGGAGAGCAATGGGCAGCCGGAGAACAACTACAAGACCACGCCTC
3001  CCGTGCTGGACTCCGACGGCTCCTTCTTCCTCTATAGCAAGCTCACCGTG
3051  GACAAGAGCAGGTGGCAGCAGGGGAACGTCTTCTCATGCTCCGTGATGCA
3101  CGAGGCTCTGCACAACCACTACACGCAGAAGAGCCTCTCCCTGTCTCCCG
3151  GGAAATGAAAGCCGAATTCGCCCCTCTCCCTCCCCCCCCCCTAACGTTAC
3201  TGGCCGAAGCCGCTTGGAATAAGGCCGGTGTGCGTTTGTCTATATGTTAT
3251  TTTCCACCATATTGCCGTCTTTTGGCAATGTGAGGGCCCGGAAACCTGGC
3301  CCTGTCTTCTTGACGAGCATTCCTAGGGGTCTTTCCCCTCTCGCCAAAGG
3351  AATGCAAGGTCTGTTGAATGTCGTGAAGGAAGCAGTTCCTCTGGAAGCTT
3401  CTTGAAGACAAACAACGTCTGTAGCGACCCTTTGCAGGCAGCGGAACCCC
3451  CCACCTGGCGACAGGTGCCTCTGCGGCCAAAAGCCACGTGTATAAGATAC
3501  ACCTGCAAAGGCGGCACAACCCCAGTGCCACGTTGTGAGTTGGATAGTTG
3551  TGGAAAGAGTCAAATGGCTCTCCTCAAGCGTATTCAACAAGGGGCTGAAG
3601  GATGCCCAGAAGGTACCCCATTGTATGGGATCTGATCTGGGGCCTCGGTG
3651  CACATGCTTTACATGTGTTTAGTCGAGGTTAAAAAAACGTCTAGGCCCCC
3701  CGAACCACGGGGACGTGGTTTTCCTTTGAAAAACACGATGATAATATGGC
3751  CTCCTTTGTCTCTCTGCTCCTGGTAGGCATCCTATTCCATGCCACCCAGG
3801  CCGACATCCAGCTGACCCAGAGCCCAAGCAGCCTGAGCGCCAGCGTGGGT
3851  GACAGAGTGACCATCACCTGTAAGGCCAGTCAGGATGTGGGTACTTCTGT
3901  AGCCTGGTACCAGCAGAAGCCAGGTAAGGCTCCAAAGCTGCTGATCTACT
3951  GGACATCCACCCGGCACACTGGTGTGCCAAGCAGATTCAGCGGTAGCGGT
4001  AGCGGTACCGACTTCACCTTCACCATCAGCAGCCTCCAGCCAGAGGACAT
4051  CGCCACCTACTACTGCCAGCAATATAGCCTCTATCGGTCGTTCGGCCAAG
4101  GGACCAAGGTGGAAATCAAACGAACTGTGGCTGCACCATCTGTCTTCATC
4151  TTCCCGCCATCTGATGAGCAGTTGAAATCTGGAACTGCCTCTGTTGTGTG
4201  CCTGCTGAATAACTTCTATCCCAGAGAGGCCAAAGTACAGTGGAAGGTGG
4251  ATAACGCCCTCCAATCGGGTAACTCCCAGGAGAGTGTCACAGAGCAGGAC
4301  AGCAAGGACAGCACCTACAGCCTCAGCAGCACCCTGACGCTGAGCAAAGC
4351  AGACTACGAGAAACACAAAGTCTACGCCTGCGAAGTCACCCATCAGGGCC
4401  TGAGCTCGCCCGTCACAAAGAGCTTCAACAGGGGAGAGTGTTAGAGATCC
4451  CCCGGGCTGCAGGAATTCGATATCAAGCTTATCGATAATCAACCTCTGGA
4501  TTACAAAATTTGTGAAAGATTGACTGGTATTCTTAACTATGTTGCTCCTT
4551  TTACGCTATGTGGATACGCTGCTTTAATGCCTTTGTATCATGCTATTGCT
4601  TCCCGTATGGCTTTCATTTTCTCCTCCTTGTATAAATCCTGGTTGCTGTC
4651  TCTTTATGAGGAGTTGTGGCCCGTTGTCAGGCAACGTGGCGTGGTGTGCA
4701  CTGTGTTTGCTGACGCAACCCCCACTGGTTGGGGCATTGCCACCACCTGT
4751  CAGCTCCTTTCCGGGACTTTCGCTTTCCCCCTCCCTATTGCCACGGCGGA
4801  ACTCATCGCCGCCTGCCTTGCCCGCTGCTGGACAGGGGCTCGGCGTGTTGG
4851  GCACTGACAATTCCGTGGTGTTGTCGGGGAAATCATCGTCCTTTCCTTGG
4901  CTGCTCGCCTGTGTTGCCACCTGGATTCTGCGCGGGACGTCCTTCTGCTA
4951  CGTCCCTTCGGCCCTCAATCCAGCGGACCTTCCTTCCCGCGGCCTGCTGC
5001  CGGCTCTGCGGCCTCTTCCGCGTCTTCGCCTTCGCCCTCAGACGAGTCGG
5051  ATCTCCCTTTGGGCCGCCTCCCCGCCTGATCGATACCGTCAACATCGATA
5101  AAATAAAAGATTTTATTTAGTCTCCAGAAAAAGGGGGGAATGAAAGACCC
5151  CACCTGTAGGTTTGGCAAGCTAGCTTAAGTAACGCCATTTTGCAAGGCAT
5201  GGAAAATACATAACTGAGAATAGAGAAGTTCAGATCAAGGTCAGGAACA
5251  GATGGAACAGCTGAATATGGGCCAAACAGGATATCTGTGGTAAGCAGTTC
5301  CTGCCCCGGCTCAGGGCCAAGAACAGATGGAACAGCTGAATATGGGCCAA
5351  ACAGGATATCTGTGGTAAGCAGTTCCTGCCCCGGCTCAGGGCCAAGAACA
5401  GATGGTCCCCAGATGCGGTCCAGCCCTCAGCAGTTTCTAGAGAACCATCA
5451  GATGTTTCCAGGGTGCCCCAAGGACCTGAAATGACCCTGTGCCTTATTTG
5501  AACTAACCAATCAGTTCGCTTCTCGCTTCTGTTCGCGCGCTTCTGCTCCC
5551  CGAGCTCAATAAAAGAGCCCACAACCCCTCACTCGGGGCGCCAGTCCTCC
5601  GATTGACTGAGTCGCCCGGGTACCCGTGTATCCAATAAACCCTCTTGCAG
5651  TTGCATCCGACTTGTGGTCTCGCTGTTCCTTGGGAGGGTCTCCTCTGAGT
5701  GATTGACTACCCGTCAGCGGGGGTCTTTCATT
```

1 - 1457    Mouse mammary tumor virus LTR
1475 - 1726  Double mutated PPE sequence

Figure 9c

| | |
|---|---|
| 1752 - 1754 | MN14 heavy chain signal peptide start codon |
| 3156 - 3158 | MN14 heavy chain stop codon |
| 3170 - 3745 | EMCV IRES |
| 3746 - 3748 | Bovine alpha-lactalbumin signal peptide start codon |
| 3803 - 3805 | First codon of mature MN14 light chain gene |
| 4442 - 4444 | MN14 antibody light chain gene stop codon |
| 4487 - 5078 | WPRE sequence |
| 5133 - 5372 | MoMuLV 3' LTR |

Figure 10a
SEQ ID NO:7
Alpha-Lactalbumin MN14 Vector

| | |
|---|---|
| 1 | AAAGACCCCACCCGTAGGTGGCAAGCTAGCTTAAGTAACGCCACTTTGCA |
| 51 | AGGCATGGAAAAATACATAACTGAGAATAGAAAAGTTCAGATCAAGGTCA |
| 101 | GGAACAAAGAAACAGCTGAATACCAAACAGGATATCTGTGGTAAGCGGTT |
| 151 | CCTGCCCCGGCTCAGGGCCAAGAACAGATGAGACAGCTGAGTGATGGGCC |
| 201 | AAACAGGATATCTGTGGTAAGCAGTTCCTGCCCCGGCTCGGGGCCAAGAA |
| 251 | CAGATGGTCCCCAGATGCGGTCCAGCCCTCAGCAGTTTCTAGTGAATCAT |
| 301 | CAGATGTTTCCAGGGTGCCCCAAGGACCTGAAAATGACCCTGTACCTTAT |
| 351 | TTGAACTAACCAATCAGTTCGCTTCTCGCTTCTGTTCGCGCGCTTCCGCT |
| 401 | CTCCGAGCTCAATAAAAGAGCCCACAACCCCTCACTCGGCGCGCCAGTCT |
| 451 | TCCGATAGACTGCGTCGCCCGGGTACCCGTATTCCCAATAAAGCCTCTTG |
| 501 | CTGTTTGCATCCGAATCGTGGTCTCGCTGTTCCTTGGGAGGGTCTCCTCT |
| 551 | GAGTGATTGACTACCCACGACGGGGGTCTTTCATTTGGGGGCTCGTCCGG |
| 601 | GATTTGGAGACCCCTGCCCAGGGACCACCGACCCACCACCGGGAGGTAAG |
| 651 | CTGGCCAGCAACTTATCTGTGTCTGTCCGATTGTCTAGTGTCTATGTTTG |
| 701 | ATGTTATGCGCCTGCGTCTGTACTAGTTAGCTAACTAGCTCTGTATCTGG |
| 751 | CGGACCCGTGGTGGAACTGACGAGTTCTGAACACCCGGCCGCAACCCTGG |
| 801 | GAGACGTCCCAGGGACTTTGGGGGCCGTTTTGTGGCCCGACCTGAGGAA |
| 851 | GGGAGTCGATGTGGAATCCGACCCCGTCAGGATATGTGGTTCTGGTAGGA |
| 901 | GACGAGAACCTAAAACAGTTCCCGCCTCCGTCTGAATTTTTGCTTTCGGT |
| 951 | TTGGAACCGAAGCCGCGCGTCTTGTCTGCTGCAGCGCTGCAGCATCGTTC |
| 1001 | TGTGTTGTCTCTGTCTGACTGTGTTTCTGTATTTGTCTGAAAATTAGGGC |
| 1051 | CAGACTGTTACCACTCCCTTAAGTTTGACCTTAGGTCACTGGAAAGATGT |
| 1101 | CGAGCGGATCGCTCACAACCAGTCGGTAGATGTCAAGAAGAGACGTTGGG |
| 1151 | TTACCTTCTGCTCTGCAGAATGGCCAACCTTTAACGTCGGATGGCCGCGA |
| 1201 | GACGGCACCTTTAACCGAGACCTCATCACCCAGGTTAAGATCAAGGTCTT |
| 1251 | TTCACCTGGCCCGCATGGACACCCAGACCAGGTCCCCTACATCGTGACCT |
| 1301 | GGGAAGCCTTGGCTTTTGACCCCCCTCCCTGGGTCAAGCCCTTTGTACAC |
| 1351 | CCTAAGCCTCCGCCTCCTCTTCCTCCATCCGCCCCGTCTCTCCCCCTTGA |
| 1401 | ACCTCCTCGTTCGACCCCGCCTCGATCCTCCCTTTATCCAGCCCTCACTC |
| 1451 | CTTCTCTAGGCGCCGGAATTCCGATCTGATCAAGAGACAGGATGAGGATC |
| 1501 | GTTTCGCATGATTGAACAAGATGGATTGCACGCAGGTTCTCCGGCCGCTT |
| 1551 | GGGTGGAGAGGCTATTCGGCTATGACTGGGCACAACAGACAATCGGCTGC |
| 1601 | TCTGATGCCGCCGTGTTCCGGCTGTCAGCGCAGGGGCGCCCGGTTCTTTT |
| 1651 | TGTCAAGACCGACCTGTCCGGTGCCCTGAATGAACTGCAGGACGAGGCAG |
| 1701 | CGCGGCTATCGTGGCTGGCCACGACGGGCGTTCCTTGCGCAGCTGTGCTC |
| 1751 | GACGTTGTCACTGAAGCGGGAAGGGACTGGCTGCTATTGGGCGAAGTGCC |
| 1801 | GGGGCAGGATCTCCTGTCATCTCACCTTGCTCCTGCCGAGAAAGTATCCA |
| 1851 | TCATGGCTGATGCAATGCGGCGGCTGCATACGCTTGATCCGGCTACCTGC |
| 1901 | CCATTCGACCACCAAGCGAAACATCGCATCGAGCGAGCACGTACTCGGAT |
| 1951 | GGAAGCCGGTCTTGTCGATCAGGATGATCTGGACGAAGAGCATCAGGGGC |
| 2001 | TCGCGCCAGCCGAACTGTTCGCCAGGCTCAAGGCGCGCATGCCCGACGGC |
| 2051 | GAGGATCTCGTCGTGACCCATGGCGATGCCTGCTTGCCGAATATCATGGT |
| 2101 | GGAAAATGGCCGCTTTTCTGGATTCATCGACTGTGGCCGGCTGGGTGTGG |
| 2151 | CGGACCGCTATCAGGACATAGCGTTGGCTACCCGTGATATTGCTGAAGAG |
| 2201 | CTTGGCGGCGAATGGGCTGACCGCTTCCTCGTGCTTTACGGTATCGCCGC |
| 2251 | TCCCGATTCGCAGCGCATCGCCTTCTATCGCCTTCTTGACGAGTTCTTCT |
| 2301 | GAGCGGGACTCTGGGGTTCGAAATGACCGACCAAGCGACGCCCAACCTGC |
| 2351 | CATCACGAGATTTCGATTCCACCGCCGCCTTCTATGAAAGGTTGGGCTTC |
| 2401 | GGAATCGTTTTCCGGGACGCCGGCTGGATGATCCTCCAGCGCGGGGATCT |
| 2451 | CATGCTGGAGTTCTTCGCCCACCCCGGGCTCGATCCCCTCGCGAGTTGGT |
| 2501 | TCAGCTGCTGCCTGAGGCTGGACGACCTCGCGGAGTTCTACCGGCAGTGC |
| 2551 | AAATCCGTCGGCATCCAGGAAACCAGCAGCGGCTATCCGCGCATCCATGC |
| 2601 | CCCCGAACTGCAGGAGTGGGGAGGCACGATGGCCGCTTTGGTCGAGGCGG |
| 2651 | ATCCTAGAACTAGCGAAAATGCAAGAGCAAAGACGAAAACATGCCACACA |
| 2701 | TGAGGAATACCGATTCTCTCATTAACATATTCAGGCCAGTTATCTGGGCT |
| 2751 | TAAAAGCAGAAGTCCAACCCAGATAACGATCATATACATGGTTCTCTCCA |
| 2801 | GAGGTTCATTACTGAACACTCGTCCGAGAATAACGAGTGGATCAGTCCTG |

Figure 10b

```
2851 GGTGGTCATTGAAAGGACTGATGCTGAAGTTGAAGCTCCAATACTTTGGC
2901 CACCTGATGCGAAGAACTGACTCATGTGATAAGACCCTGATACTGGGAAA
2951 GATTGAAGGCAGGAGGAGAAGGGATGACAGAGGATGGAAGAGTTGGATGG
3001 AATCACCAACTCGATGGACATGAGTTTGAGCAAGCTTCCAGGAGTTGGTA
3051 ATGGGCAGGGAAGCCTGGCGTGCTGCAGTCCATGGGGTTGCAAAGAGTTG
3101 GACACTACTGAGTGACTGAACTGAACTGATAGTGTAATCCATGGTACAGA
3151 ATATAGGATAAAAAAGAGGAAGAGTTTGCCCTGATTCTGAAGAGTTGTAG
3201 GATATAAAAGTTTAGAATACCTTTAGTTTGGAAGTCTTAAATTATTTACT
3251 TAGGATGGGTACCCACTGCAATATAAGAAATCAGGCTTTAGAGACTGATG
3301 TAGAGAGAATGAGCCCTGGCATACCAGAAGCTAACAGCTATTGGTTATAG
3351 CTGTTATAACCAATATATAACCAATATATTGGTTATATAGCATGAAGCTT
3401 GATGCCAGCAATTTGAAGGAACCATTTAGAACTAGTATCCTAAACTCTAC
3451 ATGTTCCAGGACACTGATCTTAAAGCTCAGGTTCAGAATCTTGTTTTATA
3501 GGCTCTAGGTGTATATTGTGGGCTTCCCTGGTGGCTCAGATGGTAAAGT
3551 GTCTGCCTGCAATGTGGGTGATCTGGGTTCGATCCCTGGCTTGGGAAGAT
3601 CCCCTGGAGAAGGAAATGGCAACCCACTCTAGTACTCTTACCTGGAAAAT
3651 TCCATGGACAGAGGAGCCTTGTAAGCTACAGTCCATGGGATTGCAAAGAG
3701 TTGAACACAACTGAGCAACTAAGCACAGCACAGTACAGTATACACCTGTG
3751 AGGTGAAGTGAAGTGAAGGTTCAATGCAGGGTCTCCTGCATTGCAGAAAG
3801 ATTCTTTACCATCTGAGCCACCAGGGAAGCCCAAGAATACTGGAGTGGGT
3851 AGCCTATTCCTTCTCCAGGGGATCTTCCCATCCCAGGAATTGAACTGGAG
3901 TCTCCTGCATTTCAGGTGGATTCTTCACCAGCTGAACTACCAGGTGGATA
3951 CTACTCCAATATTAAAGTGCTTAAAGTCCAGTTTTCCCACCTTTCCCAAA
4001 AAGGTTGGGTCACTCTTTTTTAACCTTCTGTGGCCTACTCTGAGGCTGTC
4051 TACAAGCTTATATATTTATGAACACATTTATTGCAAGTTGTTAGTTTTAG
4101 ATTTACAATGTGGTATCTGGCTATTTAGTGGTATTGGTGGTTGGGGATGG
4151 GGAGGCTGATAGCATCTCAGAGGGCAGCTAGATACTGTCATACACACTTT
4201 TCAAGTTCTCCATTTTTGTGAAATAGAAAGTCTCTGGATCTAAGTTATAT
4251 GTGATTCTCAGTCTCTGTGGTCATATTCTATTCTACTCCTGACCACTCAA
4301 CAAGGAACCAAGATATCAAGGGACACTTGTTTTGTTTCATGCCTGGGTTG
4351 AGTGGGCCATGACATATGTTCTGGGCCTTGTTACATGGCTGGATTGGTTG
4401 GACAAGTGCCAGCTCTGATCCTGGGACTGTGGCATGTGATGACATACACC
4451 CCCTCTCCACATTCTGCATGTCTCTAGGGGGAAGGGGGAAGCTCGGTAT
4501 AGAACCTTTATTGTATTTTCTGATTGCCTCACTTCTTATATTGCCCCCAT
4551 GCCCTTTGTTCCTCAAGTAACCAGAGACAGTGCTTCCCAGAACCAAC
4601 CCTACAAGAAACAAAGGGCTAAACAAAGCCAAATGGGAAGCAGGATCATG
4651 GTTTGAACTCTTTCTGGCCAGAGAACAATACCTGCTATGGACTAGATACT
4701 GGGAGAGGGAAAGGAAAAGTAGGGTGAATTATGGAAGGAAGCTGGCAGGC
4751 TCAGCGTTTCTGTCTTGGCATGACCAGTCTCTCTTCATTCTCTTCCTAGA
4801 TGTAGGGCTTGGTACCAGAGCCCCTGAGGCTTTCTGCATGAATATAAATA
4851 TATGAAACTGAGTGATGCTTCCATTTCAGGTTCTTGGGGCGCCGAATTC
4901 GAGCTCGGTACCCGGGGATCTCGACGGATCCGATTACTTACTGGCAGGTG
4951 CTGGGGCTTCCGAGACAATCGCGAACATCTACACCACACAACACCGCCT
5001 CGACCAGGGTGAGATATCGGCCGGGGACGCGGCGGTGGTAATTACAAGCG
5051 AGATCCGATTACTTACTGGCAGGTGCTGGGGGCTTCCGAGACAATCGCGA
5101 ACATCTACACCACACAACACCGCCTCGACCAGGGTGAGATATCGGCCGGG
5151 GACGCGGCGGTGGTAATTACAAGCGAGATCCCCGGGAATTCAGGACCTCA
5201 CCATGGGATGGAGCTGTATCATCCTCTTCTTGGTAGCAACAGCTACAGGT
5251 GTCCACTCCGAGGTCCAACTGGTGGAGAGCGGTGGAGGTGTTGTGCAACC
5301 TGGCCGGTCCCTGCGCCTGTCCTGCTCCGCATCTGGCTTCGATTTCACCA
5351 CATATTGGATGAGTTGGGTGAGACAGGCACCTGGAAAAGGTCTTGAGTGG
5401 ATTGGAGAAATTCATCCAGATAGCAGTACGATTAACTATGCGCCGTCTCT
5451 AAAGGATAGATTTACAATATCGCGAGACAACGCCAAGAACACATTGTTCC
5501 TGCAAATGGACAGCCTGAGACCCGAAGACACCGGGGTCTATTTTTGTGCA
5551 AGCCTTTACTTCGGCTTCCCCTGGTTTGCTTATTGGGGCCAAGGGACCCC
5601 GGTCACCGTCTCCTCAGCCTCCACCAAGGGCCCATCGGTCTTCCCCCTGG
5651 CACCCTCCTCCAAGAGCACCTCTGGGGGCACAGCGGCCCTGGGCTGCCTG
5701 GTCAAGGACTACTTCCCCGAACCGGTGACGGTGTCGTGGAACTCAGGCGC
5751 CCTGACCAGCGGCGTGCACACCTTCCCGGCTGTCCTACAGTCCTCAGGAC
5801 TCTACTCCCTCAGCAGCGTGGTGACCGTGCCCTCCAGCAGCTTGGGCACC
5851 CAGACCTACATCTGCAACGTGAATCACAAGCCCAGCAACACCAAGGTGGA
5901 CAAGAGAGTTGAGCCCAAATCTTGTGACAAAACTCACACATGCCCACCGT
```

Figure 10c

```
5951  GCCCAGCACCTGAACTCCTGGGGGGACCGTCAGTCTTCCTCTTCCCCCCA
6001  AAACCCAAGGACACCCTCATGATCTCCCGGACCCCTGAGGTCACATGCGT
6051  GGTGGTGGACGTGAGCCACGAAGACCCTGAGGTCAAGTTCAACTGGTACG
6101  TGGACGGCGTGGAGGTGCATAATGCCAAGACAAAGCCGCGGGAGGAGCAG
6151  TACAACAGCACGTACCGTGTGGTCAGCGTCCTCACCGTCCTGCACCAGGA
6201  CTGGCTGAATGGCAAGGAGTACAAGTGCAAGGTCTCCAACAAAGCCCTCC
6251  CAGCCCCCATCGAGAAAACCATCTCCAAAGCCAAAGGGCAGCCCCGAGAA
6301  CCACAGGTGTACACCCTGCCCCCATCCCGGGAGGAGATGACCAAGAACCA
6351  GGTCAGCCTGACCTGCCTGGTCAAAGGCTTCTATCCCAGCGACATCGCCG
6401  TGGAGTGGGAGAGCAATGGGCAGCCGGAGAACAACTACAAGACCACGCCT
6451  CCCGTGCTGGACTCCGACGGCTCCTTCTTCCTCTATAGCAAGCTCACCGT
6501  GGACAAGAGCAGGTGGCAGCAGGGGAACGTCTTCTCATGCTCCGTGATGC
6551  ACGAGGCTCTGCACAACCACTACACGCAGAAGAGCCTCTCCCTGTCTCCC
6601  GGGAAATGAAAGCCGAATTCGCCCCTCTCCCTCCCCCCCCCCTAACGTTA
6651  CTGGCCGAAGCCGCTTGGAATAAGGCCGGTGTGCGTTTGTCTATATGTTA
6701  TTTTCCACCATATTGCCGTCTTTTGGCAATGTGAGGGCCCGGAAACCTGG
6751  CCCTGTCTTCTTGACGAGCATTCCTAGGGGTCTTTCCCCTCTCGCCAAAG
6801  GAATGCAAGGTCTGTTGAATGTCGTGAAGGAAGCAGTTCCTCTGGAAGCT
6851  TCTTGAAGACAAACAACGTCTGTAGCGACCCTTTGCAGGCAGCGGAACCC
6901  CCCACCTGGCGACAGGTGCCTCTGCGGCCAAAAGCCACGTGTATAAGATA
6951  CACCTGCAAAGGCGGCACAACCCCAGTGCCACGTTGTGAGTTGGATAGTT
7001  GTGGAAAGAGTCAAATGGCTCTCCTCAAGCGTATTCAACAAGGGGCTGAA
7051  GGATGCCCAGAAGGTACCCCATTGTATGGGATCTGATCTGGGGCCTCGGT
7101  GCACATGCTTTACATGTGTTTAGTCGAGGTTAAAAAAACGTCTAGGCCCC
7151  CCGAACCACGGGGACGTGGTTTTCCTTTGAAAAACACGATGATAATATGG
7201  CCTCCTTTGTCTCTCTGCTCCTGGTAGGCATCCTATTCCATGCCACCCAG
7251  GCCGACATCCAGCTGACCCAGAGCCCAAGCAGCCTGAGCGCCAGCGTGGG
7301  TGACAGAGTGACCATCACCTGTAAGGCCAGTCAGGATGTGGGTACTTCTG
7351  TAGCCTGGTACCAGCAGAAGCCAGGTAAGGCTCCAAAGCTGCTGATCTAC
7401  TGGACATCCACCCGGCACACTGGTGTGCCAAGCAGATTCAGCGGTAGCGG
7451  TAGCGGTACCGACTTCACCTTCACCATCAGCAGCCTCCAGCCAGAGGACA
7501  TCGCCACCTACTACTGCCAGCAATATAGCCTCTATCGGTCGTTCGGCCAA
7551  GGGACCAAGGTGGAAATCAAACGAACTGTGGCTGCACCATCTGTCTTCAT
7601  CTTCCCGCCATCTGATGAGCAGTTGAAATCTGGAACTGCCTCTGTTGTGT
7651  GCCTGCTGAATAACTTCTATCCCAGAGAGGCCAAAGTACAGTGGAAGGTG
7701  GATAACGCCCTCCAATCGGGTAACTCCCAGGAGAGTGTCACAGAGCAGGA
7751  CAGCAAGGACAGCACCTACAGCCTCAGCAGCACCCTGACGCTGAGCAAAG
7801  CAGACTACGAGAAACACAAAGTCTACGCCTGCGAAGTCACCCATCAGGGC
7851  CTGAGCTCGCCCGTCACAAAGAGCTTCAACAGGGGAGAGTGTTAGAGATC
7901  CCCCGGGCTGCAGGAATTCGATATCAAGCTTATCGATAATCAACCTCTGG
7951  ATTACAAAATTTGTGAAAGATTGACTGGTATTCTTAACTATGTTGCTCCT
8001  TTTACGCTATGTGGATACGCTGCTTTAATGCCTTTGTATCATGCTATTGC
8051  TTCCCGTATGGCTTTCATTTTCTCCTCCTTGTATAAATCCTGGTTGCTGT
8101  CTCTTTATGAGGAGTTGTGGCCCGTTGTCAGGCAACGTGGCGTGGTGTGC
8151  ACTGTGTTTGCTGACGCAACCCCCACTGGTTGGGGCATTGCCACCACCTG
8201  TCAGCTCCTTTCCGGGACTTTCGCTTTCCCCCTCCCTATTGCCACGGCGG
8251  AACTCATCGCCGCCTGCCTTGCCCGCTGCTGGACAGGGGCTCGGCTGTTG
8301  GGCACTGACAATTCCGTGGTGTTGTCGGGGAAATCATCGTCCTTTCCTTG
8351  GCTGCTCGCCTGTGTTGCCACCTGGATTCTGCGCGGGACGTCCTTCTGCT
8401  ACGTCCCTTCGGCCCTCAATCCAGCGGACCTTCCTTCCCGCGGCCTGCTG
8451  CCGGCTCTGCGGCCTCTTCCGCGTCTTCGCCTTCGCCCTCAGACGAGTCG
8501  GATCTCCCTTTGGGCCGCCTCCCCGCCTGATCGATACCGTCAACATCGAT
8551  AAAATAAAAGATTTTATTTAGTCTCCAGAAAAAGGGGGGAATGAAAGACC
8601  CCACCTGTAGGTTTGGCAAGCTAGCTTAAGTAACGCCATTTTGCAAGGCA
8651  TGGAAAATACATAACTGAGAATAGAGAAGTTCAGATCAAGGTCAGGAAC
8701  AGATGGAACAGCTGAATATGGGCCAAACAGGATATCTGTGGTAAGCAGTT
8751  CCTGCCCCGGCTCAGGGCCAAGAACAGATGGAACAGCTGAATATGGGCCA
8801  AACAGGATATCTGTGGTAAGCAGTTCCTGCCCCGGCTCAGGGCCAAGAAC
8851  AGATGGTCCCCAGATGCGGTCCAGCCCTCAGCAGTTTCTAGAGAACCATC
8901  AGATGTTTCCAGGGTGCCCCAAGGACCTGAAATGACCCTGTGCCTTATTT
8951  GAACTAACCAATCAGTTCGCTTCTCGCTTCTGTTCGCGCGCTTCTGCTCC
9001  CCGAGCTCAATAAAAGAGCCCACAACCCCTCACTCGGGGCGCCAGTCCTC
```

Figure 10d

```
9051   CGATTGACTGAGTCGCCCGGGTACCCGTGTATCCAATAAACCCTCTTGCA
9101   GTTGCATCCGACTTGTGGTCTCGCTGTTCCTTGGGAGGGTCTCCTCTGAG
9151   TGATTGACTACCCGTCAGCGGGGGTCTTTCATT
```

| | |
|---|---|
| 1 - 658 | MoMuSV 5' LTR |
| 659 - 1468 | Extended packaging region |
| 1512 - 2306 | Neomycin resistance gene |
| 2661 - 4896 | Bovine/human alpha-lactalbumin 5' flanking region |
| 5084 - 5327 | Double mutated PPE sequence |
| 6207 - 6209 | MN14 antibody heavy chain gene signal peptide start codon |
| 6611-6613 | MN14 antibody heavy chain stop codon |
| 6625 - 7200 | EMCV IRES |
| 7201 - 7203 | Bovine alpha-lactalbumin signal peptide start codon |
| 7258 - 7260 | First codon of mature MN14 antibody light chain gene |
| 7897 - 7899 | MN14 antibody light gene stop codon |
| 7938 - 8529 | WPRE sequence |
| 8600 - 9138 | Moloney murine leukemia virus 3' LTR |

Figure 11a
SEQ ID NO:8
Alpha-Lactalbumin Bot Vector

```
   1   GATCAGTCCTGGGTGGTCATTGAAAGGACTGATGCTGAAGTTGAAGCTCC
  51   AATACTTTGGCCACCTGATGCGAAGAACTGACTCATGTGATAAGACCCTG
 101   ATACTGGGAAAGATTGAAGGCAGGAGGAGAAGGGATGACAGAGGATGGAA
 151   GAGTTGGATGGAATCACCAACTCGATGGACATGAGTTTGAGCAAGCTTCC
 201   AGGAGTTGGTAATGGGCAGGGAAGCCTGGCGTGCTGCAGTCCATGGGGTT
 251   GCAAAGAGTTGGACACTACTGAGTGACTGAACTGATAGTGTAATC
 301   CATGGTACAGAATATAGGATAAAAAAGAGGAAGAGTTTGCCCTGATTCTG
 351   AAGAGTTGTAGGATATAAAAGTTTAGAATACCTTTAGTTTGGAAGTCTTA
 401   AATTATTTACTTAGGATGGGTACCCACTGCAATATAAGAAATCAGGCTTT
 451   AGAGACTGATGTAGAGAGAATGAGCCCTGGCATACCAGAAGCTAACAGCT
 501   ATTGGTTATAGCTGTTATAACCAATATATAACCAATATATTGGTTATATA
 551   GCATGAAGCTTGATGCCAGCAATTTGAAGGAACCATTTAGAACTAGTATC
 601   CTAAACTCTACATGTTCCAGGACACTGATCTTAAAGCTCAGGTTCAGAAT
 651   CTTGTTTTATAGGCTCTAGGTGTATATTGTGGGGCTTCCCTGGTGGCTCA
 701   GATGGTAAAGTGTCTGCCTGCAATGTGGGTGATCTGGGTTCGATCCCTGG
 751   CTTGGGAAGATCCCCTGGAGAAGGAAATGGCAACCCACTCTAGTACTCTT
 801   ACCTGGAAAATTCCATGGACAGAGGAGCCTTGTAAGCTACAGTCCATGGG
 851   ATTGCAAAGAGTTGAACACAACTGAGCAACTAAGCACAGCACAGTACAGT
 901   ATACACCTGTGAGGTGAAGTGAAGTGAAGGTTCAATGCAGGGTCTCCTGC
 951   ATTGCAGAAAGATTCTTTACCATCTGAGCCACCAGGGAAGCCCAAGAATA
1001   CTGGAGTGGGTAGCCTATTCCTTCTCCAGGGGATCTTCCCATCCCAGGAA
1051   TTGAACTGGAGTCTCCTGCATTTCAGGTGGATTCTTCACCAGCTGAACTA
1101   CCAGGTGGATACTACTCCAATATTAAAGTGCTTAAAGTCCAGTTTTCCCA
1151   CCTTTCCCAAAAAGGTTGGGTCACTCTTTTTTAACCTTCTGTGGCCTACT
1201   CTGAGGCTGTCTACAAGCTTATATATTTATGAACACATTTATTGCAAGTT
1251   GTTAGTTTTAGATTTACAATGTGGTATCTGGCTATTTAGTGGTATTGGTG
1301   GTTGGGGATGGGGAGGCTGATAGCATCTCAGAGGGCAGCTAGATACTGTC
1351   ATACACTTTTCAAGTTCTCCATTTTTGTGAAATAGAAAGTCTCTGGAT
1401   CTAAGTTATATGTGATTCTCAGTCTCTGTGGTCATATTCTATTCTACTCC
1451   TGACCACTCAACAAGGAACCAAGATATCAAGGGACACTTGTTTTGTTTCA
1501   TGCCTGGGTTGAGTGGGCCATGACATATGTTCTGGGCCTTGTTACATGGC
1551   TGGATTGGTTGGACAAGTGCCAGCTCTGATCCTGGGACTGTGGCATGTGA
1601   TGACATACACCCCCTCTCCACATTCTGCATGTCTCTAGGGGGGAAGGGGG
1651   AAGCTCGGTATAGAACCTTTATTGTATTTTCTGATTGCCTCACTTCTTAT
1701   ATTGCCCCATGCCCTTCTTTGTTCCTCAAGTAACCAGAGACAGTGCTTC
1751   CCAGAACCAACCCTACAAGAAACAAAGGGCTAAACAAAGCCAAATGGGAA
1801   GCAGGATCATGGTTTGAACTCTTTCTGGCCAGAGAACAATACCTGCTATG
1851   GACTAGATACTGGGAGAGGGAAAGGAAAAGTAGGGTGAATTATGGAAGGA
1901   AGCTGGCAGGCTCAGCGTTTCTGTCTTGGCATGACCAGTCTCTCTTCATT
1951   CTCTTCCTAGATGTAGGGCTTGGTACCAGAGCCCTGAGGCTTTCTGCAT
2001   GAATATAAATATATGAAACTGAGTGATGCTTCCATTTCAGGTTCTTGGGG
2051   GCGCCGAATTCGAGCTCGGTACCCGGGGATCTCGACGGATCCGATTACTT
2101   ACTGGCAGGTGCTGGGGCTTCCGAGACAATCGCGAACATCTACACCACA
2151   CAACACCGCCTCGACCAGGGTGAGATATCGGCCGGGGACGCGGCGGTGGT
2201   AATTACAAGCGAGATCCGATTACTTACTGGCAGGTGCTGGGGGCTTCCGA
2251   GACAATCGCGAACATCTACACCACACAACACCGCCTCGACCAGGGTGAGA
2301   TATCGGCCGGGGACGCGGCGGTGGTAATTACAAGCGAGATCTCGAGAAGC
2351   TTGTTGGGAATTCAGGCCATCGATCCCGCCGCCACCATGGAATGGAGCTG
2401   GGTCTTTCTCTTCTTCCTGTCAGTAACTACAGGTGTCCACTCCGACATCC
2451   AGATGACCCAGTCTCCAGCCTCCCTATCTGCATCTGTGGGAGAAACTGTC
2501   ACTATCACATGTCGAGCAAGTGGGAATATTCACAATTATTTAGCATGGTA
2551   TCAGCAGAAACAGGGAAAATCTCCTCAGCTCCTGGTCTATAATGCAAAAA
2601   CCTTAGCAGATGGTGTGCCATCAAGGTTCAGTGGCAGTGGATCAGGAACA
2651   CAATATTCTCTCAAGATCAACAGCCTGCAGCCTGAAGATTTTGGGAGTTA
2701   TTACTGTCAACATTTTTGGAGTACTCCGTGGACGTTCGGTGGAGGCACCA
2751   AGCTGGAAATCAAACGGGCTGATGCTGCACCAACTGTATCCATCTTCCCA
2801   CCATCCAGTGAGCAGTTAACATCTGGAGGTGCCTCAGTCGTGTGCTTCTT
```

Figure 11b

```
2851  GAACAACTTCTACCCCAAAGACATCAATGTCAAGTGGAAGATTGATGGCA
2901  GTGAACGACAAAATGGCGTCCTGAACAGTTGGACTGATCAGGACAGCAAA
2951  GACAGCACCTACAGCATGAGCAGCACCCTCACATTGACCAAGGACGAGTA
3001  TGAACGACATAACAGCTATACCTGTGAGGCCACTCACAAGACATCAACTT
3051  CACCCATTGTCAAGAGCTTCAACAGGAATGAGTGTTGAAAGCATCGATTT
3101  CCCCTGAATTCGCCCCTCTCCCTCCCCCCCCCTAACGTTACTGGCCGAA
3151  GCCGCTTGGAATAAGGCCGGTGTGCGTTTGTCTATATGTTATTTTCCACC
3201  ATATTGCCGTCTTTTGGCAATGTGAGGGCCCGGAAACCTGGCCCTGTCTT
3251  CTTGACGAGCATTCCTAGGGGTCTTTCCCCTCTCGCCAAAGGAATGCAAG
3301  GTCTGTTGAATGTCGTGAAGGAAGCAGTTCCTCTGGAAGCTTCTTGAAGA
3351  CAAACAACGTCTGTAGCGACCCTTTGCAGGCAGCGGAACCCCCACCTGG
3401  CGACAGGTGCCTCTGCGGCCAAAAGCCACGTGTATAAGATACACCTGCAA
3451  AGGCGGCACAACCCCAGTGCCACGTTGTGAGTTGGATAGTTGTGGAAAGA
3501  GTCAAATGGCTCTCCTCAAGCGTATTCAACAAGGGGCTGAAGGATGCCCA
3551  GAAGGTACCCCATTGTATGGGATCTGATCTGGGCCTCGGTGCACATGCT
3601  TTACATGTGTTTAGTCGAGGTTAAAAAAACGTCTAGGCCCCCGAACCAC
3651  GGGGACGTGGTTTTCCTTTGAAAAACACGATGATAATATGGCCTCCTTTG
3701  TCTCTCTGCTCCTGGTAGGCATCCTATTCCATGCCACCCAGGCCGAGGTT
3751  CAGCTTCAGCAGTCTGGGGCAGAGCTTGTGAAGCCAGGGGCCTCAGTCAA
3801  GTTGTCCTGCACAGCTTCTGGCTTCAACATTAAAGACACCTTTATGCACT
3851  GGGTGAAGCAGAGGCCTGAACAGGGCCTGGAGTGGATTGGAAGGATTGAT
3901  CCTGCGAATGGGAATACTGAATATGACCCGAAGTTCCAGGGCAAGGCCAC
3951  TATAACAGCAGACACATCCTCCAACACAGTCAACCTGCAGCTCAGCAGCC
4001  TGACATCTGAGGACACTGCCGTCTATTACTGTGCTAGTGGAGGGGAACTG
4051  GGGTTTCCTTACTGGGGCCAAGGGACTCTGGTCACTGTCTCTGCAGCCAA
4101  AACGACACCCCATCTGTCTATCCACTGGCCCCTGGATCTGCTGCCCAAA
4151  CTAACTCCATGGTGACCCTGGGATGCCTGGTCAAGGGCTATTTCCCTGAG
4201  CCAGTGACAGTGACCTGGAACTCTGGATCCCTGTCCAGCGGTGTGCACAC
4251  CTTCCCAGCTGTCCTGCAGTTTGACCTCTACACTCTGAGCAGCTCAGTGA
4301  CTGTCCCCTCCAGCACCTGGCCCAGCGAGACCGTCACCTGCAACGTTGCC
4351  CACCCGGCCAGCAGCACCAAGGTGGACAAGAAAATTGTGCCCAGGGATTG
4401  TACTAGTGGAGGTGGAGGTAGCCACCATCACCATCACCATTAATCTAGAG
4451  TTAAGCGGCCGTCGAGATCTCGACATCGATAATCAACCTCTGGATTACAA
4501  AATTTGTGAAAGATTGACTGGTATTCTTAACTATGTTGCTCCTTTTACGC
4551  TATGTGGATACGCTGCTTTAATGCCTTTGTATCATGCTATTGCTTCCCGT
4601  ATGGCTTTCATTTTCTCCTCCTTGTATAAATCCTGGTTGCTGTCTCTTTA
4651  TGAGGAGTTGTGGCCCGTTGTCAGGCAACGTGGCGTGGTGTGCACTGTGT
4701  TTGCTGACGCAACCCCACTGGTTGGGCATTGCCACCACCTGTCAGCTC
4751  CTTTCCGGGACTTTCGCTTTCCCCCTCCCTATTGCCACGGCGGAACTCAT
4801  CGCCGCCTGCCTTGCCCGCTGCTGGACAGGGGCTCGGCTGTTGGGCACTG
4851  ACAATTCCGTGGTGTTGTCGGGGAAATCATCGTCCTTTCCTTGGCTGCTC
4901  GCCTGTGTTGCCACCTGGATTCTGCGCGGGACGTCCTTCTGCTACGTCCC
4951  TTCGGCCCTCAATCCAGCGGACCTTCCTTCCGCGGCCTGCTGCCGGCTC
5001  TGCGGCCTCTTCCGCGTCTTCGCCTTCGCCCTCAGACGAGTCGGATCTCC
5051  CTTTGGGCCGCCTCCCCGCCTGATCGATAAAATAAAAGATTTTATTTAGT
5101  CTCCAGAAAAGGGGGGAATGAAAGACCCCACCTGTAGGTTTGGCAAGCT
5151  AGCTTAAGTAACGCCATTTTGCAAGGCATGGAAAATACATAACTGAGAA
5201  TAGAGAAGTTCAGATCAAGGTCAGGAACAGATGGAACAGCTGAATATGGG
5251  CCAAACAGGATATCTGTGGTAAGCAGTTCCTGCCCCGGCTCAGGGCCAAG
5301  AACAGATGGAACAGCTGAATATGGGCCAAACAGGATATCTGTGGTAAGCA
5351  GTTCCTGCCCCGGCTCAGGGCCAAGAACAGATGGTCCCCAGATGCGGTCC
5401  AGCCCTCAGCAGTTTCTAGAGAACCATCAGATGTTTCCAGGGTGCCCCAA
5451  GGACCTGAAATGACCCTGTGCCTTATTTGAACTAACCAATCAGTTCGCTT
5501  CTCGCTTCTGTTCGCGCGCTTCTGCTCCCCGAGCTCAATAAAAGAGCCCA
5551  CAACCCCTCACTCGGGGCGCCAGTCCTCCGATTGACTGAGTCGCCCGGGT
5601  ACCCGTGTATCCAATAAACCCTCTTGCAGTTGCATCCGACTTGTGGTCTC
```

Figure 11c
```
5651   GCTGTTCCTTGGGAGGGTCTCCTCTGAGTGATTGACTACCCGTCAGCGGG
5701   GGTCTTTCATT
```

| | |
|---|---|
| 1 - 2053 | Bovine/human alpha-lactalbumin 5' flanking region |
| 2093 - 2336 | Double mtated PPE sequence |
| 2387 - 2443 | cc49 signal peptide coding region |
| 2444 - 3088 | Bot antibody light chain Fab coding region |
| 3112 - 3686 | EMCV IRES |
| 3687 - 3745 | Bovine alpha-lactalbumin signal peptide coding region |
| 3746 - 4443 | Bot antibody heavy chain Fab coding region |
| 4481 - 5072 | WPRE sequence |
| 5118 - 5711 | Moloney murine leukemia virus 3' LTR |

Figure 12a
SEQ ID NO:9
LSNRL Vector

```
   1  TTTGAAAGACCCCACCCGTAGGTGGCAAGCTAGCTTAAGTAACGCCACTT
  51  TGCAAGGCATGGAAAAATACATAACTGAGAATAGAAAAGTTCAGATCAAG
 101  GTCAGGAACAAAGAAACAGCTGAATACCAAACAGGATATCTGTGGTAAGC
 151  GGTTCCTGCCCCGGCTCAGGGCCAAGAACAGATGAGACAGCTGAGTGATG
 201  GGCCAAACAGGATATCTGTGGTAAGCAGTTCCTGCCCCGGCTCGGGGCCA
 251  AGAACAGATGGTCCCCAGATGCGGTCCAGCCCTCAGCAGTTTCTAGTGAA
 301  TCATCAGATGTTTCCAGGGTGCCCCAAGGACCTGAAAATGACCCTGTACC
 351  TTATTTGAACTAACCAATCAGTTCGCTTCTCGCTTCTGTTCGCGCGCTTC
 401  CGCTCTCCGAGCTCAATAAAAGAGCCCACAACCCCTCACTCGGCGCGCCA
 451  GTCTTCCGATAGACTGCGTCGCCCGGGTACCCGTATTCCCAATAAAGCCT
 501  CTTGCTGTTTGCATCCGAATCGTGGTCTCGCTGTTCCTTGGGAGGGTCTC
 551  CTCTGAGTGATTGACTACCCACGACGGGGGTCTTTCATTTGGGGGCTCGT
 601  CCGGGATTTGGAGACCCCTGCCCAGGGACCACCGACCCACCACCGGGAGG
 651  TAAGCTGGCCAGCAACTTATCTGTGTCTGTCCGATTGTCTAGTGTCTATG
 701  TTTGATGTTATGCGCCTGCGTCTGTACTAGTTAGCTAACTAGCTCTGTAT
 751  CTGGCGGACCCGTGGTGGAACTGACGAGTTCTGAACACCCGGCCGCAACC
 801  CTGGGAGACGTCCCAGGGACTTTGGGGGCCGTTTTGTGGCCCGACCTGA
 851  GGAAGGGAGTCGATGTGGAATCCGACCCCGTCAGGATATGTGGTTCTGGT
 901  AGGAGACGAGAACCTAAAACAGTTCCCGCCTCCGTCTGAATTTTTGCTTT
 951  CGGTTTGGAACCGAAGCCGCGCGTCTTGTCTGCTGCAGCCAAGCTTGGGC
1001  TGCAGGTCGAGGACTGGGGACCCTGCACCGAACATGGAGAACACAACATC
1051  AGGATTCCTAGGACCCCTGCTCGTGTTACAGGCGGGGTTTTCTTGTTGA
1101  CAAGAATCCTCACAATACCACAGAGTCTAGACTCGTGGTGGACTTCTCTC
1151  AATTTTCTAGGGGGAGCACCCACGTGTCCTGGCCAAAATTCGCAGTCCCC
1201  AACCTCCAATCACTCACCAACCTCTTGTCCTCCAATTTGTCCTGGCTATC
1251  GCTGGATGTGTCTGCGGCGTTTTATCATATTCCTCTTCATCCTGCTGCTA
1301  TGCCTCATCTTCTTGTTGGTTCTTCTGGACTACCAAGGTATGTTGCCCGT
1351  TTGTCCTCTACTTCCAGGAACATCAACTACCAGCACGGGACCATGCAAGA
1401  CCTGCACGATTCCTGCTCAAGGAACCTCTATGTTTCCCTCTTGTTGCTGT
1451  ACAAAACCTTCGGACGGAAACTGCACTTGTATTCCCATCCCATCATCCTG
1501  GGCTTTCGCAAGATTCCTATGGGAGTGGGCCTCAGTCCGTTTCTCCTGGC
1551  TCAGTTTACTAGTGCCATTTGTTCAGTGGTTCGTAGGGCTTTCCCCCACT
1601  GTTTGGCTTTCAGTTATATGGATGATGTGGTATTGGGGCCAAGTCTGTA
1651  CAACATCTTGAGTCCCTTTTTACCTCTATTACCAATTTTCTTTTGTCTTT
1701  GGGTATACATTTAAACCCTAATAAAACCAAACGTTGGGGCTACTCCCTTA
1751  ACTTCATGGGATATGTAATTGGATGTTGGGGTACTTTACCGCAAGAACAT
1801  ATTGTACTAAAAATCAAGCAATGTTTCGAAAACTGCCTGTAAATAGACC
1851  TATTGATTGGAAAGTATGTCAGAGACTTGTGGGTCTTTTGGGCTTTGCTG
1901  CCCCTTTTACACAATGTGGCTATCCTGCCTTAATGCCTTTATATGCATGT
1951  ATACAATCTAAGCAGGCTTTCACTTTCTCGCCAACTTACAAGGCCTTTCT
2001  GTGTAAACAATATCTGAACCTTTACCCCGTTGCCCGGCAACGGTCAGGTC
2051  TCTGCCAAGTGTTTGCTGACGCAACCCCCACTGGATGGGGCTTGGCTATC
2101  GGCCATAGCCGCATGCGCGGACCTTTGTGGCTCCTCTGCCGATCCATACT
2151  GCGGAACTCCTAGCAGCTTGTTTTGCTCGCAGGCGGTCTGGAGCGAAACT
2201  TATCGGCACCGACAACTCTGTTGTCCTCTCTCGGAAATACACCTCCTTTC
2251  CATGGCTGCTAGGGTGTGCTGCCAACTGGATCCCCTCAGGATATAGTAGT
2301  TTCGCTTTTGCATAGGGAGGGGGAAATGTAGTCTTATGCAATACACTTGT
2351  AGTCTTGCAACATGGTAACGATGAGTTAGCAACATGCCTTACAAGGAGAG
2401  AAAAAGCACCGTGCATGCCGATTGGTGGAAGTAAGGTGGTACGATCGTGC
2451  CTTATTAGGAAGGCAACAGACAGGTCTGACATGGATTGGACGAACCACTG
2501  AATTCCGCATTGCAGAGATAATTGTATTTAAGTGCCTAGCTCGATACAGC
2551  AAACGCCATTTTTGACCATTCACCACATTGGTGTGCACCTTCCAAAGCTT
2601  CACGCTGCCGCAAGCACTCAGGGCGCAAGGGCTGCTAAAGGAAGCGGAAC
2651  ACGTAGAAAGCCAGTCCGCAGAAACGGTGCTGACCCCGGATGAATGTCAG
2701  CTACTGGGCTATCTGGACAAGGGAAAACGCAAGCGCAAAGAGAAAGCAGG
2751  TAGCTTGCAGTGGGCTTACATGGCGATAGCTAGACTGGGCGGTTTTATGG
2801  ACAGCAAGCGAACCGGAATTGCCAGCTGGGGCGCCCTCTGGTAAGGTTGG
```

Figure 12b

```
2851 GAAGCCCTGCAAAGTAAACTGGATGGCTTTCTTGCCGCCAAGGATCTGAT
2901 GGCGCAGGGGATCAAGATCTGATCAAGAGACAGGATGAGGATCGTTTCGC
2951 ATGATTGAACAAGATGGATTGCACGCAGGTTCTCCGGCCGCTTGGGTGGA
3001 GAGGCTATTCGGCTATGACTGGGCACAACAGACAATCGGCTGCTCTGATG
3051 CCGCCGTGTTCCGGCTGTCAGCGCAGGGGCGCCCGGTTCTTTTTGTCAAG
3101 ACCGACCTGTCCGGTGCCCTGAATGAACTGCAGGACGAGGCAGCGCGGCT
3151 ATCGTGGCTGGCCACGACGGGCGTTCCTTGCGCAGCTGTGCTCGACGTTG
3201 TCACTGAAGCGGGAAGGGACTGGCTGCTATTGGGCGAAGTGCCGGGGCAG
3251 GATCTCCTGTCATCTCACCTTGCTCCTGCCGAGAAAGTATCCATCATGGC
3301 TGATGCAATGCGGCGGCTGCATACGCTTGATCCGGCTACCTGCCCATTCG
3351 ACCACCAAGCGAAACATCGCATCGAGCGAGCACGTACTCGGATGGAAGCC
3401 GGTCTTGTCGATCAGGATGATCTGGACGAAGAGCATCAGGGGCTCGCGCC
3451 AGCCGAACTGTTCGCCAGGCTCAAGGCGCGCATGCCCGACGGCGAGGATC
3501 TCGTCGTGACCCATGGCGATGCCTGCTTGCCGAATATCATGGTGGAAAAT
3551 GGCCGCTTTTCTGGATTCATCGACTGTGGCCGGCTGGGTGTGGCGGACCG
3601 CTATCAGGACATAGCGTTGGCTACCCGTGATATTGCTGAAGAGCTTGGCG
3651 GCGAATGGGCTGACCGCTTCCTCGTGCTTTACGGTATCGCCGCTCCCGAT
3701 TCGCAGCGCATCGCCTTCTATCGCCTTCTTGACGAGTTCTTCTGAGCGGG
3751 ACTCTGGGGTTCGAAATGACCGACCAAGCGACGCCCAACCTGCCATCACG
3801 AGATTTCGATTCCACCGCCGCCTTCTATGAAAGGTTGGGCTTCGGAATCG
3851 TTTTCCGGGACGCCGGCTGGATGATCCTCCAGCGCGGGGATCTCATGCTG
3901 GAGTTCTTCGCCCACCCCAACCCTGGCCCTATTATTGGGTGGACTAACCA
3951 TGGGGGGAATTGCCGCTGGAATAGGAACAGGGACTACTGCTCTAATGGCC
4001 ACTCAGCAATTCCAGCAGCTCCAAGCCGCAGTACAGGATGATCTCAGGGA
4051 GGTTGAAAATCAATCTCTAACCTAGAAAAGTCTCTCACTTCCCTGTCTG
4101 AAGTTGTCCTACAGAATCGAAGGGGCCTAGACTTGTTATTTCTAAAAGAA
4151 GGAGGGCTGTGTGCTGCTCTAAAAGAAGAATGTTGCTTCTATGCGGACCA
4201 CACAGGACTAGTGAGAGACAGCATGGCCAAATTGAGAGAGAGGCTTAATC
4251 AGAGACAGAAACTGTTTGAGTCAACTCAAGGATGGTTTGAGGGACTGTTT
4301 AACAGATCCCCTTGGTTTACCACCTTGATATCTACCATTATGGGACCCCT
4351 CATTGTACTCCTAATGATTTTGCTCTTCGGACCCTGCATTCTTAATCGAT
4401 TAGTCCAATTTGTTAAAGACAGGATATCAGTGGTCCAGGCTCTAGTTTTG
4451 ACTCAACAATATCACCAGCTGAAGCCTATAGAGTACGAGCCATAGATAAA
4501 ATAAAAGATTTTATTTAGTCTCCAGAAAAGGGGGGAATGAAAGACCCCA
4551 CCTGTAGGTTTGGCAAGCTAGCTTAAGTAACGCCATTTTGCAAGGCATGG
4601 AAAAATACATAACTGAGAATAGAGAAGTTCAGATCAAGGTCAGGAACAGA
4651 TGGAACAGCTGAATATGGGCCAAACAGGATATCTGTGGTAAGCAGTTCCT
4701 GCCCCGGCTCAGGGCCAAGAACAGATGGAACAGCTGAATATGGGCCAAAC
4751 AGGATATCTGTGGTAAGCAGTTCCTGCCCCGGCTCAGGGCCAAGAACAGA
4801 TGGTCCCCAGATGCGGTCCAGCCCTCAGCAGTTTCTAGAGAACCATCAGA
4851 TGTTTCCAGGGTGCCCCAAGGACCTGAAATGACCCTGTGCCTTATTTGAA
4901 CTAACCAATCAGTTCGCTTCTCGCTTCTGTTCGCGCGCTTCTGCTCCCCG
4951 AGCTCAATAAAAGAGCCCACAACCCCTCACTCGGGGCGCCAGTCCTCCGA
5001 TTGACTGAGTCGCCCGGGTACCCGTGTATCCAATAAACCCTCTTGCAGTT
5051 GCATCCGACTTGTGGTCTCGCTGTTCCTTGGGAGGGTCTCCTCTGAGTGA
5101 TTGACTACCCGTCAGCGGGGGTCTTTCATT
```

| | |
|---|---|
| 1 - 589 | MoMuSV 5' LTR |
| 659 - 897 | Retroviral packaging region |
| 1034 - 1714 | Hepatitis B surface antigen |
| 2279 - 2595 | RSV promoter |
| 2951 - 3745 | Neomycin phosphotransferase gene |
| 4537 - 5130 | MoMuLV 3' LTR |

Figure 13a
SEQ ID NO:10
Alpha-Lactalbumin cc49IL2 Vector

```
   1  GATCAGTCCTGGGTGGTCATTGAAAGGACTGATGCTGAAGTTGAAGCTCC
  51  AATACTTTGGCCACCTGATGCGAAGAACTGACTCATGTGATAAGACCCTG
 101  ATACTGGGAAAGATTGAAGGCAGGAGGAGAAGGGATGACAGAGGATGGAA
 151  GAGTTGGATGGAATCACCAACTCGATGGACATGAGTTTGAGCAAGCTTCC
 201  AGGAGTTGGTAATGGGCAGGGAAGCCTGGCGTGCTGCAGTCCATGGGGTT
 251  GCAAAGAGTTGGACACTACTGAGTGACTGAACTGACTGATAGTGTAATC
 301  CATGGTACAGAATATAGGATAAAAAAGAGGAAGAGTTTGCCCTGATTCTG
 351  AAGAGTTGTAGGATATAAAAGTTTAGAATACCTTTAGTTTGGAAGTCTTA
 401  AATTATTTACTTAGGATGGGTACCCACTGCAATATAAGAAATCAGGCTTT
 451  AGAGACTGATGTAGAGAGAATGAGCCCTGGCATACCAGAAGCTAACAGCT
 501  ATTGGTTATAGCTGTTATAACCAATATATAACCAATATATTGGTTATATA
 551  GCATGAAGCTTGATGCCAGCAATTTGAAGGAACCATTTAGAACTAGTATC
 601  CTAAACTCTACATGTTCCAGGACACTGATCTTAAAGCTCAGGTTCAGAAT
 651  CTTGTTTTATAGGCTCTAGGTGTATATTGTGGGGCTTCCCTGGTGGCTCA
 701  GATGGTAAAGTGTCTGCCTGCAATGTGGGTGATCTGGGTTCGATCCCTGG
 751  CTTGGGAAGATCCCCTGGAGAAGGAAATGGCAACCCACTCTAGTACTCTT
 801  ACCTGGAAAATTCCATGGACAGAGGAGCCTTGTAAGCTACAGTCCATGGG
 851  ATTGCAAAGAGTTGAACACAACTGAGCAACTAAGCACAGCACAGTACAGT
 901  ATACACCTGTGAGGTGAAGTGAAGTGAAGGTTCAATGCAGGGTCTCCTGC
 951  ATTGCAGAAAGATTCTTTACCATCTGAGCCACCAGGGAAGCCCAAGAATA
1001  CTGGAGTGGGTAGCCTATTCCTTCTCCAGGGGATCTTCCCATCCCAGGAA
1051  TTGAACTGGAGTCTCCTGCATTTCAGGTGGATTCTTCACCAGCTGAACTA
1101  CCAGGTGGATACTACTCCAATATTAAAGTGCTTAAAGTCCAGTTTTCCCA
1151  CCTTTCCCAAAAAGGTTGGGTCACTCTTTTTTAACCTTCTGTGGCCTACT
1201  CTGAGGCTGTCTACAAGCTTATATATTTATGAACACATTTATTGCAAGTT
1251  GTTAGTTTTAGATTTACAATGTGGTATCTGGCTATTTAGTGGTATTGGTG
1301  GTTGGGGATGGGGAGGCTGATAGCATCTCAGAGGGCAGCTAGATACTGTC
1351  ATACACTTTTCAAGTTCTCCATTTTTGTGAAATAGAAAGTCTCTGGAT
1401  CTAAGTTATATGTGATTCTCAGTCTCTGTGGTCATATTCTATTCTACTCC
1451  TGACCACTCAACAAGGAACCAAGATATCAAGGGACACTTGTTTTGTTTCA
1501  TGCCTGGGTTGAGTGGGCCATGACATATGTTCTGGGCCTTGTTACATGGC
1551  TGGATTGGTTGGACAAGTGCCAGCTCTGATCCTGGGACTGTGGCATGTGA
1601  TGACATACACCCCCTCTCCACATTCTGCATGTCTCTAGGGGGAAGGGGG
1651  AAGCTCGGTATAGAACCTTTATTGTATTTTCTGATTGCCTCACTTCTTAT
1701  ATTGCCCCCATGCCCTTCTTTGTTCCTCAAGTAACCAGAGACAGTGCTTC
1751  CCAGAACCAACCCTACAAGAAACAAAGGGCTAAACAAAGCCAAATGGGAA
1801  GCAGGATCATGGTTTGAACTCTTTCTGGCCAGAGAACAATACCTGCTATG
1851  GACTAGATACTGGGAGAGGGAAAGGAAAAGTAGGGTGAATTATGGAAGGA
1901  AGCTGGCAGGCTCAGCGTTTCTGTCTTGGCATGACCAGTCTCTCTTCATT
1951  CTCTTCCTAGATGTAGGGCTTGGTACCAGAGCCCCTGAGGCTTTCTGCAT
2001  GAATATAAATATATGAAACTGAGTGATGCTTCCATTTCAGGTTCTTGGGG
2051  GCGCCGAATTCGAGCTCGGTACCCGGGGATCTCGAGAAGCTTTAACCATG
2101  GAATGGAGCTGGGTCTTTCTCTTCTTCCTGTCAGTAACTACAGGTGTCCA
2151  CTCCCAGGTTCAGTTGCAGCAGTCTGACGCTGAGTTGGTGAAACCTGGGG
2201  CTTCAGTGAAGATTTCCTGCAAGGCTTCTGGCTACACCTTCACTGACCAT
2251  GCAATTCACTGGGTGAAACAGAACCCTGAACAGGGCCTGGAATGGATTGG
2301  ATATTTTTCTCCCGGAAATGATGATTTTAAATACAATGAGAGGTTCAAGG
2351  GCAAGGCCACACTGACTGCAGACAAATCCTCCAGCACTGCCTACGTGCAG
2401  CTCAACAGCCTGACATCTGAGGATTCTGCAGTGTATTTCTGTACAAGATC
2451  CCTGAATATGGCCTACTGGGGTCAAGGAACCTCAGTCACCGTCTCCTCAG
2501  GAGGCGGAGGCAGCGGAGGCGGTGGCTCGGGAGGCGGAGGCTCGGACATT
2551  GTGATGTCACAGTCTCCATCCTCCCTACCTGTGTCAGTTGGCGAGAAGGT
2601  TACTTTGAGCTGCAAGTCCAGTCAGAGCCTTTTATATAGTGGTAATCAAA
2651  AGAACTACTTGGCCTGGTACCAGCAGAAACCAGGGCAGTCTCCTAAACTG
2701  CTGATTTACTGGGCATCCGCTAGGGAATCTGGGGTCCCTGATCGCTTCAC
2751  AGGCAGTGGATCTGGGACAGATTTCACTCTCTCCATCAGCAGTGTGAAGA
2801  CTGAAGACCTGGCAGTTTATTACTGTCAGCAGTATTATAGCTATCCCCTC
```

Figure 13b

```
2851  ACGTTCGGTGCTGGGACCAAGCTGGTGCTGAAACGGGCCGCCGAGCCCAA
2901  ATCTCCTGACAAAACTCACACATGCCCACCGTGCCCAGCACCTGAACTCC
2951  TGGGGGGACCGTCAGTCTTCCTCTTCCCCCCAAAACCCAAGGACACCCTC
3001  ATGATCTCCCGGACCCCTGAGGTCACATGCGTGGTGGTGGACGTGAGCCA
3051  CGAAGACCCTGAGGTCAAGTTCAACTGGTACGTGGACGGCGTGGAGGTGC
3101  ATAATGCCAAGACAAAGCCGCGGGAGGAGCAGTACAACAGCACGTACCGT
3151  GTGGTCAGCGTCCTCACCGTCCTGCACCAGGACTGGCTGAATGGCAAGGA
3201  GTACAAGTGCAAGGTCTCCAACAAAGCCCTCCCAGCCCCCATCGAGAAAA
3251  CCATCTCCAAAGCCAAAGGGCAGCCCCGAGAACCACAGGTGTACACCCTG
3301  CCCCCATCCCGGGATGAGCTGACCAAGAACCAGGTCAGCCTGACCTGCCT
3351  GGTCAAAGGCTTCTATCCCAGCGACATCGCCGTGGAGTGGGAGAGCAATG
3401  GGCAGCCGGAGAACAACTACAAGACCACGCCTCCCGTGCTGGACTCCGAC
3451  GGCTCCTTCTTCCTCTACAGCAAGCTCACCGTGGACAAGAGCAGGTGGCA
3501  GCAGGGGAACGTCTTCTCATGCTCCGTGATGCATGAGGCTCTGCACAACC
3551  ACTACACGCAGAAGAGCCTCTCCCTGTCTCCGGGTAAAGGAGGCGGATCA
3601  GGAGGTGGCGCACCTACTTCAAGTTCTACAAAGAAAACACAGCTACAACT
3651  GGAGCATTTACTGCTGGATTTACAGATGATTTTGAATGGAATTAATAATT
3701  ACAAGAATCCCAAACTCACCAGGATGCTCACATTTAAGTTTTACATGCCC
3751  AAGAAGGCCACAGAACTGAAACATCTTCAGTGTCTAGAAGAAGAACTCAA
3801  ACCTCTGGAGGAAGTGCTAAATTTAGCTCAAAGCAAAAACTTTCACTTAA
3851  GACCCAGGGACTTAATCAGCAATATCAACGTAATAGTTCTGGAACTAAAG
3901  GGATCTGAAACAACATTCATGTGTGAATATGCTGATGAGACAGCAACCAT
3951  TGTAGAATTTCTGAACAGATGGATTACCTTTTGTCAAAGCATCATCTCAA
4001  CACTAACTTGAAGCTTGTTAACATCGATAAAATAAAAGATTTTATTTAGT
4051  CTCCAGAAAAGGGGGAATGAAAGACCCCACCTGTAGGTTTGGCAAGCT
4101  AGCTTAAGTAACGCCATTTTGCAAGGCATGGAAAAATACATAACTGAGAA
4151  TAGAGAAGTTCAGATCAAGGTCAGGAACAGATGGAACAGCTGAATATGGG
4201  CCAAACAGGATATCTGTGGTAAGCAGTTCCTGCCCCGGCTCAGGGCCAAG
4251  AACAGATGGAACAGCTGAATATGGGCCAAACAGGATATCTGTGGTAAGCA
4301  GTTCCTGCCCCGGCTCAGGGCCAAGAACAGATGGTCCCCAGATGCGGTCC
4351  AGCCCTCAGCAGTTTCTAGAGAACCATCAGATGTTTCCAGGGTGCCCCAA
4401  GGACCTGAAATGACCCTGTGCCTTATTTGAACTAACCAATCAGTTCGCTT
4451  CTCGCTTCTGTTCGCGCGCTTCTGCTCCCCGAGCTCAATAAAAGAGCCCA
4501  CAACCCCTCACTCGGGGCGCCAGTCCTCCGATTGACTGAGTCGCCCGGGT
4551  ACCCGTGTATCCAATAAACCCTCTTGCAGTTGCATCCGACTTGTGGTCTC
4601  GCTGTTCCTTGGGAGGGTCTCCTCTGAGTGATTGACTACCCGTCAGCGGG
4651  GGTCTTTCATT
```

1 - 2055    Bovine/human alpha-lactalbumin 5' flanking region
2098 - 4011    cc49-IL2 coding region
4068 - 4661    MoMuLV 3' LTR Figure 14a
SEQ ID NO:11
Alpha-Lactalbumin YP Vector

```
1     GATCAGTCCTGGGTGGTCATTGAAAGGACTGATGCTGAAGTTGAAGCTCC
51    AATACTTTGGCCACCTGATGCGAAGAACTGACTCATGTGATAAGACCCTG
101   ATACTGGGAAAGATTGAAGGCAGGAGGAGAAGGGATGACAGAGGATGGAA
151   GAGTTGGATGGAATCACCAACTCGATGGACATGAGTTTGAGCAAGCTTCC
201   AGGAGTTGGTAATGGGCAGGGAAGCCTGGCGTGCTGCAGTCCATGGGGTT
251   GCAAAGAGTTGGACACTACTGAGTGACTGAACTGAACTGATAGTGTAATC
301   CATGGTACAGAATATAGGATAAAAAAGAGGAAGAGTTTGCCCTGATTCTG
351   AAGAGTTGTAGGATATAAAAGTTTAGAATACCTTTAGTTTGGAAGTCTTA
401   AATTATTTACTTAGGATGGGTACCCACTGCAATATAAGAAATCAGGCTTT
451   AGAGACTGATGTAGAGAATGAGCCCTGGCATACCAGAAGCTAACAGCT
501   ATTGGTTATAGCTGTTATAACCAATATATAACCAATATATTGGTTATATA
551   GCATGAAGCTTGATGCCAGCAATTTGAAGGAACCATTTAGAACTAGTATC
601   CTAAACTCTACATGTTCCAGGACACTGATCTTAAAGCTCAGGTTCAGAAT
651   CTTGTTTTATAGGCTCTAGGTGTATATTGTGGGGCTTCCCTGGTGGCTCA
701   GATGGTAAAGTGTCTGCCTGCAATGTGGGTGATCTGGGTTCGATCCCTGG
751   CTTGGGAAGATCCCCTGGAGAAGGAAATGGCAACCCACTCTAGTACTCTT
801   ACCTGGAAAATTCCATGGACAGAGGAGCCTTGTAAGCTACAGTCCATGGG
851   ATTGCAAAGAGTTGAACACAACTGAGCAACTAAGCACAGCACAGTACAGT
901   ATACACCTGTGAGGTGAAGTGAAGTGAAGGTTCAATGCAGGGTCTCCTGC
951   ATTGCAGAAAGATTCTTTACCATCTGAGCCACCAGGGAAGCCCAAGAATA
1001  CTGGAGTGGGTAGCCTATTCCTTCTCCAGGGGATCTTCCCATCCCAGGAA
1051  TTGAACTGGAGTCTCCTGCATTTCAGGTGGATTCTTCACCAGCTGAACTA
1101  CCAGGTGGATACTACTCCAATATTAAAGTGCTTAAAGTCCAGTTTTCCCA
1151  CCTTTCCCAAAAAGGTTGGGTCACTCTTTTTTAACCTTCTGTGGCCTACT
1201  CTGAGGCTGTCTACAAGCTTATATATTTATGAACACATTTATTGCAAGTT
1251  GTTAGTTTTAGATTTACAATGTGGTATCTGGCTATTTAGTGGTATTGGTG
1301  GTTGGGGATGGGGAGGCTGATAGCATCTCAGAGGGCAGCTAGATACTGTC
1351  ATACACACTTTTCAAGTTCTCCATTTTGTGAAATAGAAAGTCTCTGGAT
1401  CTAAGTTATATGTGATTCTCAGTCTCTGTGGTCATATTCTATTCTACTCC
1451  TGACCACTCAACAAGGAACCAAGATATCAAGGGACACTTGTTTTGTTTCA
1501  TGCCTGGGTTGAGTGGGCCATGACATATGTTCTGGGCCTTGTTACATGGC
1551  TGGATTGGTTGGACAAGTGCCAGCTCTGATCCTGGGACTGTGGCATGTGA
1601  TGACATACACCCCCTCTCCACATTCTGCATGTCTCTAGGGGGAAGGGGG
1651  AAGCTCGGTATAGAACCTTTATTGTATTTTCTGATTGCCTCACTTCTTAT
1701  ATTGCCCCCATGCCCTTCTTTGTTCCTCAAGTAACCAGAGACAGTGCTTC
1751  CCAGAACCAACCCTACAAGAAACAAAGGGCTAAACAAAGCCAAATGGGAA
1801  GCAGGATCATGGTTTGAACTCTTTCTGGCCAGAGAACAATACCTGCTATG
1851  GACTAGATACTGGGAGAGGGAAAGGAAAAGTAGGGTGAATTATGGAAGGA
1901  AGCTGGCAGGCTCAGCGTTTCTGTCTTGGCATGACCAGTCTCTCTTCATT
1951  CTCTTCCTAGATGTAGGGCTTGGTACCAGAGCCCCTGAGGCTTTCTGCAT
2001  GAATATAAATATATGAAACTGAGTGATGCTTCCATTTCAGGTTCTTGGGG
2051  GCGCCGAATTCGAGCTCGGTACCCGGGGATCTCGACGGATCCGATTACTT
2101  ACTGGCAGGTGCTGGGGCTTCCGAGACAATCGCGAACATCTACACCACA
2151  CAACACCGCCTCGACCAGGGTGAGATATCGGCCGGGGACGCGGCGGTGGT
2201  AATTACAAGCGAGATCCGATTACTTACTGGCAGGTGCTGGGGGCTTCCGA
2251  GACAATCGCGAACATCTACACCACACAACACCGCCTCGACCAGGGTGAGA
2301  TATCGGCCGGGACGCGGCGGTGGTAATTACAAGCGAGATCTCGAGTTAA
2351  CAGATCTAGGCCTCCTAGGTCGACGGATCCCCGGGAATTCGGCGCCGCCA
2401  CCATGATGTCCTTTGTCTCTCTGCTCCTGGTAGGCATCCTATTCCATGCC
2451  ACCCAGGCCCAGGTCCAACTGCAGCAGTCTGGGCCTGAGCTGGTGAAGCC
2501  TGGGACTTCAGTGAGGATATCCTGCAAGGCTTCTGGCTACACCTTCACAA
2551  GCTACTATTTACACTGGGTGAAGCAGAGGCCTGGACAGGGACTTGAGTGG
2601  ATTGCATGGATTTATCCTGGAAATGTTATTACTACGTACAATGAGAAGTT
2651  CAAGGGCAAGGCCACACTGACTGCAGACAAATCCTCCAGCACAGCCTACA
2701  TGCACCTCAACAGCCTGACCTCTGAGGACTCTGCGGTCTATTTCTGTGCA
2751  AGGGGTGACCATGATCTTGACTACTGGGGCCAAGGCACCACTCTCACAGT
2801  CTCCTCAGCCAAAACGACACCCCCATCTGTCTATCCACTGGCCCCTGGAT
```

Figure 14b

```
2851  CTGCTGCCCAAACTAACTCCATGGTGACCCTGGGATGCCTGGTCAAGGGC
2901  TATTTCCTGAGCCAGTGACAGTGACCTGGAACTCTGGATCCCTGTCCAG
2951  CGGTGTGCACACCTTCCCAGCTGTCCTGCAGTCTGACCTCTACACTCTGA
3001  GCAGCTCAGTGACTGTCCCCTCCAGCACCTGGCCCAGCGAGACCGTCACC
3051  TGCAACGTTGCCCACCCGGCCAGCAGCACCAAGGTGGACAAGAAAATTGT
3101  GCCCAGGGATTGTACTAGTGGAGGTGGAGGTAGCTAAGGGAGATCTCGAC
3151  GGATCCCCGGGAATTCGCCCCTCTCCCTCCCCCCCCCCTAACGTTACTGG
3201  CCGAAGCCGCTTGGAATAAGGCCGGTGTGCGTTTGTCTATATGTTATTTT
3251  CCACCATATTGCCGTCTTTTGGCAATGTGAGGGCCCGGAAACCTGGCCCT
3301  GTCTTCTTGACGAGCATTCCTAGGGGTCTTTCCCCTCTCGCCAAAGGAAT
3351  GCAAGGTCTGTTGAATGTCGTGAAGGAAGCAGTTCCTCTGGAAGCTTCTT
3401  GAAGACAAACAACGTCTGTAGCGACCCTTTGCAGGCAGCGGAACCCCCCA
3451  CCTGGCGACAGGTGCCTCTGCGGCCAAAAGCCACGTGTATAAGATACACC
3501  TGCAAAGGCGGCACAACCCCAGTGCCACGTTGTGAGTTGGATAGTTGTGG
3551  AAAGAGTCAAATGGCTCTCCTCAAGCGTATTCAACAAGGGGCTGAAGGAT
3601  GCCCAGAAGGTACCCCATTGTATGGGATCTGATCTGGGGCCTCGGTGCAC
3651  ATGCTTTACATGTGTTTAGTCGAGGTTAAAAAAACGTCTAGGCCCCCCGA
3701  ACCACGGGGACGTGGTTTTCCTTTGAAAAACACGATGATAATATGGCCTC
3751  CTTTGTCTCTCTGCTCCTGGTAGGCATCCTATTCCATGCCACCCAGGCCG
3801  ACATTGTGCTGACACAATCTCCAGCAATCATGTCTGCATCTCCAGGGGAG
3851  AAGGTCACCATGACCTGCAGTGCCACCTCAAGTGTAAGTTACATACACTG
3901  GTACCAGCAGAAGTCAGGCACCTCCCCCAAAAGATGGATTTATGACACAT
3951  CCAAACTGGCTTCTGGAGTCCCTGCTCGCTTCAGTGGCAGTGGGTCTGGG
4001  ACCTCTCACTCTCTCACACTCAGCAGCATGGAGGCTGAAGATGCTGCCAC
4051  TTATTACTGCCAGCAGTGGGGTAGTTACCTCACGTTCGGTGCGGGGACCA
4101  AGCTGGAGCTGAAACGGGCTGATGCTGCACCAACTGTATCCATCTTCCCA
4151  CCATCCAGTGAGCAGTTAACATCTGGAGGTGCCTCAGTCGTGTGCTTCTT
4201  GAACAACTTCTACCCCAAAGACATCAATGTCAAGTGGAAGATTGATGGCA
4251  GTGAACGACAAAATGGCGTCCTGAACAGTTGGACTGATCAGGACAGCAAA
4301  GACAGCACCTACAGCATGAGCAGCACCCTCACGTTGACCAAGGACGAGTA
4351  TGAACGACATAACAGCTATACCTGTGAGGCCACTCACAAGACATCAACTT
4401  CACCCATTGTCAAGAGCTTCAACAGGAATGAGTGTTAATAGGGGAGATCT
4451  CGACATCGATAATCAACCTCTGGATTACAAAATTTGTGAAAGATTGACTG
4501  GTATTCTTAACTATGTTGCTCCTTTTACGCTATGTGGATACGCTGCTTTA
4551  ATGCCTTTGTATCATGCTATTGCTTCCCGTATGGCTTTCATTTTCTCCTC
4601  CTTGTATAAATCCTGGTTGCTGTCTCTTTATGAGGAGTTGTGGCCCGTTG
4651  TCAGGCAACGTGGCGTGGTGTGCACTGTGTTTGCTGACGCAACCCCCACT
4701  GGTTGGGGCATTGCCACCACCTGTCAGCTCCTTTCCGGGACTTTCGCTTT
4751  CCCCCTCCCTATTGCCACGGCGGAACTCATCGCCGCCTGCCTTGCCCGCT
4801  GCTGGACAGGGGCTCGGCTGTTGGGCACTGACAATTCCGTGGTGTTGTCG
4851  GGGAAATCATCGTCCTTTCCTTGGCTGCTCGCCTGTGTTGCCACCTGGAT
4901  TCTGCGCGGGACGTCCTTCTGCTACGTCCCTTCGGCCCTCAATCCAGCGG
4951  ACCTTCCTTCCCGCGGCCTGCTGCCGGCTCTGCGGCCTCTTCCGCGTCTT
5001  CGCCTTCGCCCTCAGACGAGTCGGATCTCCCTTTGGGCCGCCTCCCCGCC
5051  TGATCGATAAAATAAAAGATTTTATTTAGTCTCCAGAAAAAGGGGGGAAT
5101  GAAAGACCCCACCTGTAGGTTTGGCAAGCTAGCTTAAGTAACGCCATTTT
5151  GCAAGGCATGGAAAATACATAACTGAGAATAGAGAAGTTCAGATCAAGG
5201  TCAGGAACAGATGGAACAGCTGAATATGGGCCAAACAGGATATCTGTGGT
5251  AAGCAGTTCCTGCCCCGGCTCAGGGCCAAGAACAGATGGAACAGCTGAAT
5301  ATGGGCCAAACAGGATATCTGTGGTAAGCAGTTCCTGCCCCGGCTCAGGG
5351  CCAAGAACAGATGGTCCCCAGATGCGGTCCAGCCCTCAGCAGTTTCTAGA
5401  GAACCATCAGATGTTTCCAGGGTGCCCCAAGGACCTGAAATGACCCTGTG
5451  CCTTATTTGAACTAACCAATCAGTTCGCTTCTCGCTTCTGTTCGCGCGCT
5501  TCTGCTCCCCGAGCTCAATAAAAGAGCCCACAACCCCTCACTCGGGGCGC
5551  CAGTCCTCCGATTGACTGAGTCGCCCGGGTACCCGTGTATCCAATAAACC
5601  CTCTTGCAGTTGCATCCGACTTGTGGTCTCGCTGTTCCTTGGGAGGGTCT
```

Figure 14c
5651    CCTCTGAGTGATTGACTACCCGTCAGCGGGGGTCTTTCATT

| | |
|---|---|
| 1 - 2053 | Bovine/Human Alpha-lactalbumin 5' flanking region |
| 2093 - 2336 | Double mutated PPE sequence |
| 2403 - 2459 | Bovine alpha-lactalbumin signal peptide coding region |
| 2460 - 3137 | Yersenia pestis heavy chain Fab gene coding region |
| 3167 - 3742 | EMCV IRES |
| 3743 - 3799 | Bovine alpha-lactalbumin signal peptide coding region |
| 3800 - 4441 | Yersenia pestis light chain Fab gene coding region |
| 4461 - 5052 | WPRE sequence |
| 5098 - 5691 | Moloney murine leukemia virus 3' LTR |

Figure 15
SEQ ID NO:12
IRES-Casein Signal Peptide Sequence

```
  1  GGAATTCGCCCCTCTCCCTCCCCCCCCCCTAACGTTACTGGCCGAAGCCG
 51  CTTGGAATAAGGCCGGTGTGCGTTTGTCTATATGTTATTTTCCACCATAT
101  TGCCGTCTTTTGGCAATGTGAGGGCCCGGAAACCTGGCCCTGTCTTCTTG
151  ACGAGCATTCCTAGGGGTCTTTCCCCTCTCGCCAAAGGAATGCAAGGTCT
201  GTTGAATGTCGTGAAGGAAGCAGTTCCTCTGGAAGCTTCTTGAAGACAAA
251  CAACGTCTGTAGCGACCCTTTGCAGGCAGCGGAACCCCCCACCTGGCGAC
301  AGGTGCCTCTGCGGCCAAAAGCCACGTGTATAAGATACACCTGCAAAGGC
351  GGCACAACCCCAGTGCCACGTTGTGAGTTGGATAGTTGTGGAAAGAGTCA
401  AATGGCTCTCCTCAAGCGTATTCAACAAGGGGCTGAAGGATGCCCAGAAG
451  GTACCCCATTGTATGGGATCTGATCTGGGGCCTCGGTGCACATGCTTTAC
501  ATGTGTTTAGTCGAGGTTAAAAAAACGTCTAGGCCCCCCGAACCACGGGG
551  ACGTGGTTTTCCTTTGAAAAACACGATGATAATATGGCCTTGCTCATCCT
601  TACCTGTCTTGTGGCTGTTGCTCTTGCCGGCGCCATGGGATATCTAGATC
651  TCGAGCTCGCGAAAGCTT
```

| | |
|---|---|
| 1 - 583 | IRES |
| 584 - 628 | Modified bovine alpha-S1 casein signal peptide coding region |
| 629 - 668 | Multiple cloning site |

Figure 16a

SEQ ID NO: 13

LNBOTDC Vector

```
   1 TTTGAAAGACCCCACCCGTAGGTGGCAAGCTAGCTTAAGTAACGCCACTT
  51 TGCAAGGCATGGAAAAATACATAACTGAGAATAGAAAAGTTCAGATCAAG
 101 GTCAGGAACAAAGAAACAGCTGAATACCAAACAGGATATCTGTGGTAAGC
 151 GGTTCCTGCCCCGGCTCAGGGCCAAGAACAGATGAGACAGCTGAGTGATG
 201 GGCCAAACAGGATATCTGTGGTAAGCAGTTCCTGCCCCGGCTCGGGGCCA
 251 AGAACAGATGGTCCCCAGATGCGGTCCAGCCCTCAGCAGTTTCTAGTGAA
 301 TCATCAGATGTTTCCAGGGTGCCCCAAGGACCTGAAAATGACCCTGTACC
 351 TTATTTGAACTAACCAATCAGTTCGCTTCTCGCTTCTGTTCGCGCGCTTC
 401 CGCTCTCCGAGCTCAATAAAAGAGCCCACAACCCCTCACTCGGCGCGCCA
 451 GTCTTCCGATAGACTGCGTCGCCCGGGTACCCGTATTCCCAATAAAGCCT
 501 CTTGCTGTTTGCATCCGAATCGTGGTCTCGCTGTTCCTTGGGAGGGTCTC
 551 CTCTGAGTGATTGACTACCCACGACGGGGGTCTTTCATTTGGGGGCTCGT
 601 CCGGGATTTGGAGACCCCTGCCCAGGGACCACCGACCCACCACCGGGAGG
 651 TAAGCTGGCCAGCAACTTATCTGTGTCTGTCCGATTGTCTAGTGTCTATG
 701 TTTGATGTTATGCGCCTGCGTCTGTACTAGTTAGCTAACTAGCTCTGTAT
 751 CTGGCGGACCCGTGGTGGAACTGACGAGTTCTGAACACCCGGCCGCAACC
 801 CTGGGAGACGTCCCAGGGACTTTGGGGGCGTTTTTGTGGCCCGACCTGA
 851 GGAAGGGAGTCGATGTGGAATCCGACCCCGTCAGGATATGTGGTTCTGGT
 901 AGGAGACGAGAACCTAAAACAGTTCCCGCCTCCGTCTGAATTTTTGCTTT
 951 CGGTTTGGAACCGAAGCCGCGCGTCTTGTCTGCTGCAGCGCTGCAGCATC
1001 GTTCTGTGTTGTCTCTGTCTGACTGTGTTTCTGTATTTGTCTGAAAATTA
1051 GGGCCAGACTGTTACCACTCCCTTAAGTTTGACCTTAGGTCACTGGAAAG
1101 ATGTCGAGCGGATCGCTCACAACCAGTCGGTAGATGTCAAGAAGAGACGT
1151 TGGGTTACCTTCTGCTCTGCAGAATGGCCAACCTTTAACGTCGGATGGCC
1201 GCGAGACGGCACCTTTAACCGAGACCTCATCACCCAGGTTAAGATCAAGG
1251 TCTTTTCACCTGGCCCGCATGGACACCCAGACCAGGTCCCCTACATCGTG
1301 ACCTGGGAAGCCTTGGCTTTTGACCCCCCTCCCTGGGTCAAGCCCTTTGT
1351 ACACCCTAAGCCTCCGCCTCCTCTTCCTCCATCCGCCCGTCTCTCCCCC
1401 TTGAACCTCCTCGTTCGACCCCGCCTCGATCCTCCCTTTATCCAGCCCTC
1451 ACTCCTTCTCTAGGCGCCGGAATTCCGATCTGATCAAGAGACAGGATGAG
1501 GATCGTTTCGCATGATTGAACAAGATGGATTGCACGCAGGTTCTCCGGCC
1551 GCTTGGGTGGAGAGGCTATTCGGCTATGACTGGGCACAACAGACAATCGG
1601 CTGCTCTGATGCCGCCGTGTTCCGGCTGTCAGCGCAGGGGCGCCCGGTTC
1651 TTTTTGTCAAGACCGACCTGTCCGGTGCCCTGAATGAACTGCAGGACGAG
1701 GCAGCGCGGCTATCGTGGCTGGCCACGACGGGCGTTCCTTGCGCAGCTGT
1751 GCTCGACGTTGTCACTGAAGCGGGAAGGGACTGGCTGCTATTGGGCGAAG
1801 TGCCGGGGCAGGATCTCCTGTCATCTCACCTTGCTCCTGCCGAGAAAGTA
1851 TCCATCATGGCTGATGCAATGCGGCGGCTGCATACGCTTGATCCGGCTAC
1901 CTGCCCATTCGACCACCAAGCGAAACATCGCATCGAGCGAGCACGTACTC
1951 GGATGGAAGCCGGTCTTGTCGATCAGGATGATCTGGACGAAGAGCATCAG
2001 GGGCTCGCGCCAGCCGAACTGTTCGCCAGGCTCAAGGCGCGCATGCCCGA
2051 CGGCGAGGATCTCGTCGTGACCCATGGCGATGCCTGCTTGCCGAATATCA
2101 TGGTGGAAAATGGCCGCTTTTCTGGATTCATCGACTGTGGCCGGCTGGGT
2151 GTGGCGGACCGCTATCAGGACATAGCGTTGGCTACCCGTGATATTGCTGA
2201 AGAGCTTGGCGGCGAATGGGCTGACCGCTTCCTCGTGCTTTACGGTATCG
2251 CCGCTCCCGATTCGCAGCGCATCGCCTTCTATCGCCTTCTTGACGAGTTC
2301 TTCTGAGCGGGACTCTGGGGTTCGAAATGACCGACCAAGCGACGCCCAAC
2351 CTGCCATCACGAGATTTCGATTCCACCGCCGCCTTCTATGAAAGGTTGGG
2401 CTTCGGAATCGTTTTCCGGGACGCCGGCTGGATGATCCTCCAGCGCGGGG
2451 ATCTCATGCTGGAGTTCTTCGCCCACCCCGGGCTCGATCCCCTCGCGAGT
2501 TGGTTCAGCTGCTGCCTGAGGCTGGACGACCTCGCGGAGTTCTACCGGCA
2551 GTGCAAATCCGTCGGCATCCAGGAAACCAGCAGCGGCTATCCGCGCATCC
2601 ATGCCCCGAACTGCAGGAGTGGGGAGGCACGATGGCCGCTTTGGTCGAG
2651 GCGGATCCGGCCATTAGCCATATTATTCATTGGTTATATAGCATAAATCA
2701 ATATTGGCTATTGGCCATTGCATACGTTGTATCCATATCATAATATGTAC
2751 ATTTATATTGGCTCATGTCCAACATTACCGCCATGTTGACATTGATTATT
```

Figure 16b

```
2801 GACTAGTTATTAATAGTAATCAATTACGGGGTCATTAGTTCATAGCCCAT
2851 ATATGGAGTTCCGCGTTACATAACTTACGGTAAATGGCCCGCCTGGCTGA
2901 CCGCCCAACGACCCCCGCCCATTGACGTCAATAATGACGTATGTTCCCAT
2951 AGTAACGCCAATAGGGACTTTCCATTGACGTCAATGGGTGGAGTATTTAC
3001 GGTAAACTGCCCACTTGGCAGTACATCAAGTGTATCATATGCCAAGTACG
3051 CCCCCTATTGACGTCAATGACGGTAAATGGCCCGCCTGGCATTATGCCCA
3101 GTACATGACCTTATGGGACTTTCCTACTTGGCAGTACATCTACGTATTAG
3151 TCATCGCTATTACCATGGTGATGCGGTTTTGGCAGTACATCAATGGGCGT
3201 GGATAGCGGTTTGACTCACGGGGATTTCCAAGTCTCCACCCCATTGACGT
3251 CAATGGGAGTTTGTTTTGGCACCAAAATCAACGGGACTTTCCAAAATGTC
3301 GTAACAACTCCGCCCCATTGACGCAAATGGGCGGTAGGCATGTACGGTGG
3351 GAGGTCTATATAAGCAGAGCTCGTTTAGTGAACCGTCAGATCGCCTGGAG
3401 ACGCCATCCACGCTGTTTTGACCTCCATAGAAGACACCGGGACCGATCCA
3451 GCCTCCGCGGCCCCAAGCTTCTCGACGGATCCCCGGGAATTCAGGCCATC
3501 GATCCCGCCGCCACCATGGAATGGAGCTGGGTCTTTCTCTTCTTCCTGTC
3551 AGTAACTACAGGTGTCCACTCCGACATCCAGATGACCCAGTCTCCAGCCT
3601 CCCTATCTGCATCTGTGGGAGAAACTGTCACTATCACATGTCGAGCAAGT
3651 GGGAATATTCACAATTATTTAGCATGGTATCAGCAGAAACAGGGAAAATC
3701 TCCTCAGCTCCTGGTCTATAATGCAAAAACCTTAGCAGATGGTGTGCCAT
3751 CAAGGTTCAGTGGCAGTGGATCAGGAACACAATATTCTCTCAAGATCAAC
3801 AGCCTGCAGCCTGAAGATTTTGGGAGTTATTACTGTCAACATTTTTGGAG
3851 TACTCCGTGGACGTTCGGTGGAGGCACCAAGCTGGAAATCAAACGGGCTG
3901 ATGCTGCACCAACTGTATCCATCTTCCCACCATCCAGTGAGCAGTTAACA
3951 TCTGGAGGTGCCTCAGTCGTGTGCTTCTTGAACAACTTCTACCCCAAAGA
4001 CATCAATGTCAAGTGGAAGATTGATGGCAGTGAACGACAAAATGGCGTCC
4051 TGAACAGTTGGACTGATCAGGACAGCAAAGACAGCACCTACAGCATGAGC
4101 AGCACCCTCACATTGACCAAGGACGAGTATGAACGACATAACAGCTATAC
4151 CTGTGAGGCCACTCACAAGACATCAACTTCACCCATTGTCAAGAGCTTCA
4201 ACAGGAATGAGTGTTGAAAGCATCGATTTCCCCTGAATTCGCCCCTCTCC
4251 CTCCCCCCCCCCTAACGTTACTGGCCGAAGCCGCTTGGAATAAGGCCGGT
4301 GTGCGTTTGTCTATATGTTATTTTCCACCATATTGCCGTCTTTTGGCAAT
4351 GTGAGGGCCCGGAAACCTGGCCCTGTCTTCTTGACGAGCATTCCTAGGGG
4401 TCTTTCCCCTCTCGCCAAAGGAATGCAAGGTCTGTTGAATGTCGTGAAGG
4451 AAGCAGTTCCTCTGGAAGCTTCTTGAAGACAAACAACGTCTGTAGCGACC
4501 CTTTGCAGGCAGCGGAACCCCCCACCTGGCGACAGGTGCCTCTGCGGCCA
4551 AAAGCCACGTGTATAAGATACACCTGCAAAGGCGGCACAACCCCAGTGCC
4601 ACGTTGTGAGTTGGATAGTTGTGGAAAGAGTCAAATGGCTCTCCTCAAGC
4651 GTATTCAACAAGGGGCTGAAGGATGCCCAGAAGGTACCCCATTGTATGGG
4701 ATCTGATCTGGGGCCTCGGTGCACATGCTTTACATGTGTTTAGTCGAGGT
4751 TAAAAAAACGTCTAGGCCCCCCGAACCACGGGGACGTGGTTTTCCTTTGA
4801 AAAACACGATGATAATATGGCCTCCTTTGTCTCTCTGCTCCTGGTAGGCA
4851 TCCTATTCCATGCCACCCAGGCCGAGGTTCAGCTTCAGCAGTCTGGGGCA
4901 GAGCTTGTGAAGCCAGGGGCCTCAGTCAAGTTGTCCTGCACAGCTTCTGG
4951 CTTCAACATTAAAGACACCTTTATGCACTGGGTGAAGCAGAGGCCTGAAC
5001 AGGGCCTGGAGTGGATTGGAAGGATTGATCCTGCGAATGGGAATACTGAA
5051 TATGACCCGAAGTTCCAGGGCAAGGCCACTATAACAGCAGACACATCCTC
5101 CAACACAGTCAACCTGCAGCTCAGCAGCCTGACATCTGAGGACACTGCCG
5151 TCTATTACTGTGCTAGTGGAGGGAACTGGGGTTTCCTTACTGGGGCCAA
5201 GGGACTCTGGTCACTGTCTCTGCAGCCAAAACGACACCCCCATCTGTCTA
5251 TCCACTGGCCCCTGGATCTGCTGCCCAAACTAACTCCATGGTGACCCTGG
5301 GATGCCTGGTCAAGGGCTATTTCCCTGAGCCAGTGACAGTGACCTGGAAC
5351 TCTGGATCCCTGTCCAGCGGTGTGCACACCTTCCCAGCTGTCCTGCAGTC
5401 TGACCTCTACACTCTGAGCAGCTCAGTGACTGTCCCCTCCAGCACCTGGC
5451 CCAGCGAGACCGTCACCTGCAACGTTGCCCACCCGGCCAGCAGCACCAAG
5501 GTGGACAAGAAAATTGTGCCCAGGGATTGTACTAGTGGAGGTGGAGGTAG
5551 CCACCATCACCATCACCATTAATCTAGAGTTAAGCGGCCGTCGAGATCTA
5601 GGCCTCCTAGGTCGACATCGATAAAATAAAAGATTTTATTTAGTCTCCAG
5651 AAAAAGGGGGGAATGAAAGACCCCACCTGTAGGTTTGGCAAGCTAGCTTA
5701 AGTAACGCCATTTTGCAAGGCATGGAAAAATACATAACTGAGAATAGAGA
5751 AGTTCAGATCAAGGTCAGGAACAGATGGAACAGCTGAATATGGGCCAAAC
5801 AGGATATCTGTGGTAAGCAGTTCCTGCCCCGGCTCAGGGCCAAGAACAGA
5851 TGGAACAGCTGAATATGGGCCAAACAGGATATCTGTGGTAAGCAGTTCCT
```

Figure 16c
```
5901 GCCCCGGCTCAGGGCCAAGAACAGATGGTCCCCAGATGCGGTCCAGCCCT
5951 CAGCAGTTTCTAGAGAACCATCAGATGTTTCCAGGGTGCCCCAAGGACCT
6001 GAAATGACCCTGTGCCTTATTTGAACTAACCAATCAGTTCGCTTCTCGCT
6051 TCTGTTCGCGCGCTTCTGCTCCCCGAGCTCAATAAAAGAGCCCACAACCC
6101 CTCACTCGGGGCGCCAGTCCTCCGATTGACTGAGTCGCCCGGGTACCCGT
6151 GTATCCAATAAACCCTCTTGCAGTTGCATCCGACTTGTGGTCTCGCTGTT
6201 CCTTGGGAGGGTCTCCTCTGAGTGATTGACTACCCGTCAGCGGGGGTCTT
     TCATT
```

| | |
|---|---|
| Moloney Murine Sarcoma Virus 5' LTR | 1 - 589 |
| Moloney Murine Leukemia Virus Extended Packaging Region | 659 - 1468 |
| Neomycin Resistance Gene | 1512 - 2306 |
| CMV Promoter | 2656 - 3473 |
| cc49 Signal Peptide Coding Region | 3516 - 3572 |
| Bot Fab 5 Light Chain | 3573 - 4217 |
| EMCV IRES (Clonetech) | 4235 - 4816 |
| Modified Bovine α-LA Signal Peptide Coding Region | 4817 - 4873 |
| Bot Fab 5 Heavy Chain | 4874 - 5572 |
| Moloney Murine Leukemia Virus 3' LTR | 5662 - 6255 |

Figure 17. CMV construct containing cell lines.
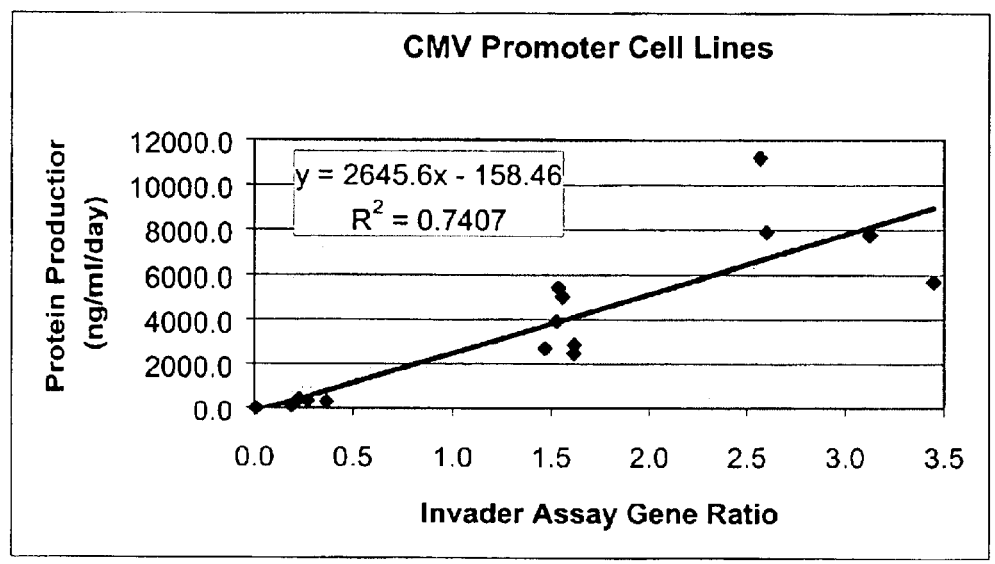

Figure 18: α-Lactalbumin construct containing cell lines
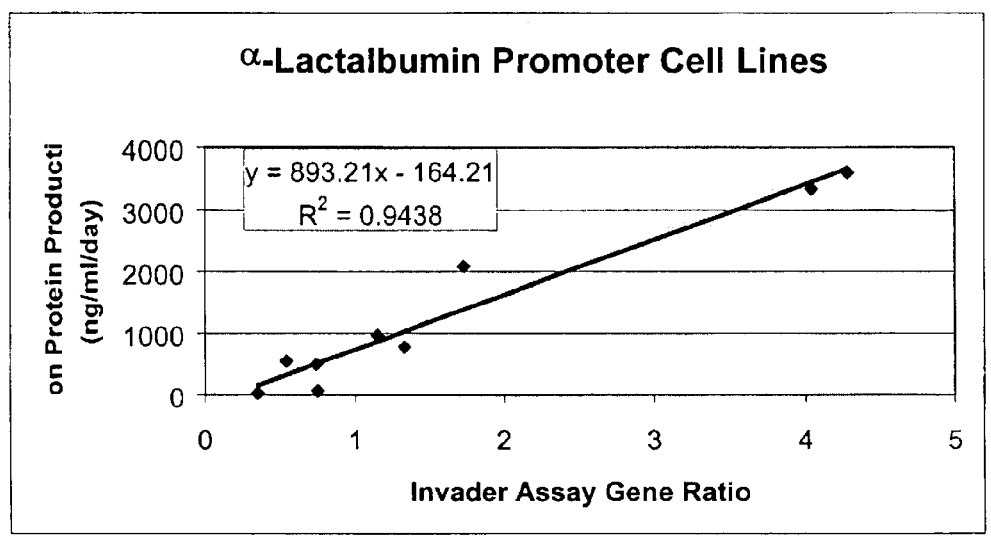

Figure 19a
SEQ ID NO: 34
LNBOTDC Vector

```
   1 GAATTAATTCATACCAGATCACCGAAAACTGTCCTCCAAATGTGTCCCCC
  51 TCACACTCCCAAATTCGCGGGCTTCTGCCTCTTAGACCACTCTACCCTAT
 101 TCCCCACACTCACCGGAGCCAAAGCCGCGGCCCTTCCGTTTCTTTGCTTT
 151 TGAAAGACCCCACCCGTAGGTGGCAAGCTAGCTTAAGTAACGCCACTTTG
 201 CAAGGCATGGAAAAATACATAACTGAGAATAGAAAAGTTCAGATCAAGGT
 251 CAGGAACAAAGAAACAGCTGAATACCAAACAGGATATCTGTGGTAAGCGG
 301 TTCCTGCCCCGGCTCAGGGCCAAGAACAGATGAGACAGCTGAGTGATGGG
 351 CCAAACAGGATATCTGTGGTAAGCAGTTCCTGCCCCGGCTCGGGGCCAAG
 401 AACAGATGGTCCCCAGATGCGGTCCAGCCCTCAGCAGTTTCTAGTGAATC
 451 ATCAGATGTTTCCAGGGTGCCCCAAGGACCTGAAAATGACCCTGTACCTT
 501 ATTTGAACTAACCAATCAGTTCGCTTCTCGCTTCTGTTCGCGCGCTTCCG
 551 CTCTCCGAGCTCAATAAAAGAGCCCACAACCCCTCACTCGGCGCGCCAGT
 601 CTTCCGATAGACTGCGTCGCCCGGGTACCCGTATTCCCAATAAAGCCTCT
 651 TGCTGTTTGCATCCGAATCGTGGTCTCGCTGTTCCTTGGGAGGGTCTCCT
 701 CTGAGTGATTGACTACCCACGACGGGGGTCTTTCATTTGGGGGCTCGTCC
 751 GGGATTTGGAGACCCCTGCCCAGGGACCACCGACCCACCACCGGGAGGTA
 801 AGCTGGCCAGCAACTTATCTGTGTCTGTCCGATTGTCTAGTGTCTATGTT
 851 TGATGTTATGCGCCTGCGTCTGTACTAGTTAGCTAACTAGCTCTGTATCT
 901 GGCGGACCCGTGGTGGAACTGACGAGTTCTGAACACCCGGCCGCAACCCT
 951 GGGAGACGTCCCAGGGACTTTGGGGGCCGTTTTTGTGGCCCGACCTGAGG
1001 AAGGGAGTCGATGTGGAATCCGACCCCGTCAGGATATGTGGTTCTGGTAG
1051 GAGACGAGAACCTAAAACAGTTCCCGCCTCCGTCTGAATTTTTGCTTTCG
1101 GTTTGGAACCGAAGCCGCGCGTCTTGTCTGCTGCAGCGCTGCAGCATCGT
1151 TCTGTGTTGTCTCTGTCTGACTGTGTTTCTGTATTTGTCTGAAAATTAGG
1201 GCCAGACTGTTACCACTCCCTTAAGTTTGACCTTAGGTCACTGGAAAGAT
1251 GTCGAGCGGATCGCTCACAACCAGTCGGTAGATGTCAAGAAGAGACGTTG
1301 GGTTACCTTCTGCTCTGCAGAATGGCCAACCTTTAACGTCGGATGGCCGC
1351 GAGACGGCACCTTTAACCGAGACCTCATCACCCAGGTTAAGATCAAGGTC
1401 TTTTCACCTGGCCCGCATGGACACCCAGACCAGGTCCCCTACATCGTGAC
1451 CTGGGAAGCCTTGGCTTTTGACCCCCCTCCCTGGGTCAAGCCCTTTGTAC
1501 ACCCTAAGCCTCCGCCTCCTCTTCCTCCATCCGCCCCGTCTCTCCCCCTT
1551 GAACCTCCTCGTTCGACCCCGCCTCGATCCTCCCTTTATCCAGCCCTCAC
1601 TCCTTCTCTAGGCGCCGGAATTCCGATCTGATCAAGAGACAGGATGAGGG
1651 AGCTTGTATATCCATTTTCGGATCTGATCAGCACGTGTTGACAATTAATC
1701 ATCGGCATAGTATATCGGCATAGTATAATACGACAAGGTGAGGAACTAAA
1751 CCATGGCCAAGCCTTTGTCTCAAGAAGAATCCACCCTCATTGAAAGAGCA
1801 ACGGCTACAATCAACAGCATCCCCATCTCTGAAGACTACAGCGTCGCCAG
1851 CGCAGCTCTCTCTAGCGACGGCCGCATCTTCACTGGTGTCAATGTATATC
1901 ATTTTACTGGGGGACCTTGTGCAGAACTCGTGGTGCTGGGCACTGCTGCT
1951 GCTGCGGCAGCTGGCAACCTGACTTGTATCGTCGCGATCGGAAATGAGAA
2001 CAGGGGCATCTTGAGCCCCTGCGGACGGTGTCGACAGGTGCTTCTCGATC
2051 TGCATCCTGGGATCAAAGCGATAGTGAAGGACAGTGATGGACAGCCGACG
2101 GCAGTTGGGATTCGTGAATTGCTGCCCTCTGGTTATGTGTGGGAGGGCTA
2151 AGCACTTCGTGGCCGAGGAGCAGGACTGACACGTGCTACGAGATTTCGAT
2201 TCCACCGCCGCCTTCTATGAAAGGTTGGGCTTCGGAATCGTTTTCCGGGA
2251 CGCCGGCTGGATGATCCTCCAGCGCGGGATCTCATGCTGGAGTTCTTCG
2301 CCCACCCCAACTTGTTTATTGCAGCTTATAATGGTTACAAATAAAGCAAT
2351 AGCATCACAAATTTCACAAATAAAGCATTTTTTCACTGCATTCTAGTTG
2401 TGGTTTGTCCAAACTCATCAATGTATCTTATCATGTCTGTACGAGTTGGT
2451 TCAGCTGCTGCCTGAGGCTGGACGACCTCGCGGAGTTCTACCGGCAGTGC
2501 AAATCCGTCGGCATCCAGGAAACCAGCAGCGGCTATCCGCGCATCCATGC
2551 CCCCGAACTGCAGGAGTGGGGAGGCACGATGGCCGCTTTGGTCGAGGCGG
2601 ATCCGGCCATTAGCCATATTATTCATTGGTTATATAGCATAAATCAATAT
2651 TGGCTATTGGCCATTGCATACGTTGTATCCATATCATAATATGTACATTT
2701 ATATTGGCTCATGTCCAACATTACCGCCATGTTGACATTGATTATTGACT
2751 AGTTATTAATAGTAATCAATTACGGGGTCATTAGTTCATAGCCCATATAT
2801 GGAGTTCCGCGTTACATAACTTACGGTAAATGGCCCGCCTGGCTGACCGC
2851 CCAACGACCCCCGCCCATTGACGTCAATAATGACGTATGTTCCCATAGTA
```

Figure 19b

```
2901 ACGCCAATAGGGACTTTCCATTGACGTCAATGGGTGGAGTATTTACGGTA
2951 AACTGCCCACTTGGCAGTACATCAAGTGTATCATATGCCAAGTACGCCCC
3001 CTATTGACGTCAATGACGGTAAATGGCCCGCCTGGCATTATGCCCAGTAC
3051 ATGACCTTATGGGACTTTCCTACTTGGCAGTACATCTACGTATTAGTCAT
3101 CGCTATTACCATGGTGATGCGGTTTTGGCAGTACATCAATGGGCGTGGAT
3151 AGCGGTTTGACTCACGGGGATTTCCAAGTCTCCACCCCATTGACGTCAAT
3201 GGGAGTTTGTTTTGGCACCAAAATCAACGGGACTTTCCAAAATGTCGTAA
3251 CAACTCCGCCCCATTGACGCAAATGGGCGGTAGGCATGTACGGTGGGAGG
3301 TCTATATAAGCAGAGCTCGTTTAGTGAACCGTCAGATCGCCTGGAGACGC
3351 CATCCACGCTGTTTTGACCTCCATAGAAGACACCGGGACCGATCCAGCCT
3401 CCGCGGCCCCAAGCTTCTCGAGTTAACAGATCTAGGCTGGCACGACAGGT
3451 TTCCCGACTGGAAAGCGGGCAGTGAGCGCAACGCAATTAATGTGAGTTAG
3501 CTCACTCATTAGGCACCCCAGGCTTTACACTTTATGCTTCCGGCTCGTAT
3551 GTTGTGTGGAATTGTGAGCGGATAACAATTTCACACAGGAAACAGCTATG
3601 ACCATGATTACGCCAAGCTTGGCTGCAGGTCGACGGATCCACTAGTAACG
3651 GCCGCCAGTGTGCTGGAATTCACCATGGGGCAACCCGGGAACGGCAGCGC
3701 CTTCTTGCTGGCACCCAATGGAAGCCATGCGCCGGACCACGACGTCACGC
3751 AGCAAAGGGACGAGGTGTGGGTGGTGGGCATGGGCATCGTCATGTCTCTC
3801 ATCGTCCTGGCCATCGTGTTTGGCAATGTGCTGGTCATCACAGCCATTGC
3851 CAAGTTCGAGCGTCTGCAGACGGTCACCAACTACTTCATCACAAGCTTGG
3901 CCTGTGCTGATCTGGTCATGGGCTAGCAGTGGTGCCCTTTGGGGCCGCC
3951 CATATTCTCATGAAAATGTGGACTTTTGGCAACTTCTGGTGCGAGTTCTG
4001 GACTTCCATTGATGTGCTGTGCGTCACGGCATCGATTGAGACCCTGTGCG
4051 TGATCGCAGTCGACCGCTACTTTGCCATTACTAGTCCTTTCAAGTACCAG
4101 AGCCTGCTGACCAAGAATAAGGCCCGGGTGATCATTCTGATGGTGTGGAT
4151 TGTGTCAGGCCTTACCTCCTTCTTGCCCATTCAGATGCACTGGTACAGGG
4201 CCACCCACCAGGAAGCCATCAACTGCTATGCCAATGAGACCTGCTGTGAC
4251 TTCTTCACGAACCAAGCCTATGCCATTGCCTCTTCCATCGTGTCCTTCTA
4301 CGTTCCCCTGGTGATCATGGTCTTCGTCTACTCCAGGGTCTTTCAGGAGG
4351 CCAAAAGGCAGCTCCAGAAGATTGACAAATCTGAGGGCCGCTTCCATGTC
4401 CAGAACCTTAGCCAGGTGGAGCAGGATGGGCGGACGGGGCATGGACTCCG
4451 CAGATCTTCCAAGTTCTGCTTGAAGGAGCACAAAGCCCTCAAGACGTTAG
4501 GCATCATCATGGGCACTTTCACCCTCTGCTGGCTGCCCTTCTTCATCGTT
4551 AACATTGTGCATGTGATCCAGGATAACCTCATCCGTAAGGAAGTTTACAT
4601 CCTCCTAAATTGGATAGGCTATGTCAATTCTGGTTTCAATCCCCTTATCT
4651 ACTGCCGGAGCCCAGATTTCAGGATTGCCTTCCAGGAGCTTCTGTGCCTG
4701 CGCAGGTCTTCTTTGAAGGCCTATGGCAATGGCTACTCCAGCAACGGCAA
4751 CACAGGGGAGCAGAGTGGATATCACGTGGAACAGGAGAAAGAAAATAAAC
4801 TGCTGTGTGAAGACCTCCCAGGCACGGAAGACTTTGTGGGCCATCAAGGT
4851 ACTGTGCCTAGCGATAACATTGATTCACAAGGGAGGAATTGTAGTACAAA
4901 TGACTCACTGCTCTCGAGAATCGAGGGGCGGCACCACCATCATCACCACG
4951 TCGACCCCGGGGACTACAAGGATGACGATGACAAGTAAGCTTTATCCATC
5001 ACACTGGCGGCCGCTCGAGCATGCATCTAGCGGCCGCTCGAGGCCGGCAA
5051 GGCCGGATCCCCGGGAATTCGCCCCTCTCCCTCCCCCCCCCCTAACGTTA
5101 CTGGCCGAAGCCGCTTGGAATAAGGCCGGTGTGCGTTTGTCTATATGTTA
5151 TTTTCCACCATATTGCCGTCTTTTGGCAATGTGAGGGCCCGGAAACCTGG
5201 CCCTGTCTTCTTGACGAGCATTCCTAGGGGTCTTTCCCCTCTCGCCAAAG
5251 GAATGCAAGGTCTGTTGAATGTCGTGAAGGAAGCAGTTCCTCTGGAAGCT
5301 TCTTGAAGACAAACAACGTCTGTAGCGACCCTTTGCAGGCAGCGGAACCC
5351 CCCACCTGGCGACAGGTGCCTCTGCGGCCAAAAGCCACGTGTATAAGATA
5401 CACCTGCAAAGGCGGCACAACCCCAGTGCCACGTTGTGAGTTGGATAGTT
5451 GTGGAAAGAGTCAAATGGCTCTCCTCAAGCGTATTCAACAAGGGGCTGAA
5501 GGATGCCCAGAAGGTACCCCATTGTATGGGATCTGATCTGGGGCCTCGGT
5551 GCACATGCTTTACATGTGTTTAGTCGAGGTTAAAAAAACGTCTAGGCCCC
5601 CCGAACCACGGGGACGTGGTTTTCCTTTGAAAACACGATGATAATATGG
5651 CCTCCTTTGTCTCTCTGCTCCTGGTAGGCATCCTATTCCATGCCACCCAG
5701 GCCGAGCTCACCCAGTCTCCAGACTCCCTGGCTGTGTCTCTGGGCGAGAG
5751 GGCCACCATCAACTGCAAGTCCAGCCAGAGTGTTTTGTACAGCTCCAACA
5801 ATAAGAACTATTTAGCTTGGTATCAGCAGAAACCAGGACAGCCTCCTAAG
5851 CTGCTCATTTACTGGGCATCTACCCGGGAATCCGGGGTCCCTGACCGATT
5901 CAGTGGCAGCGGGTCTGGGACAGATTTCACTCTCACCATCAGCAGCCTGC
5951 AGGCTGAAGATGTGGCAGTTTATTACTGTCAGCAATATTATAGTACTCAG
```

Figure 19c

```
6001 ACGTTCGGCCAAGGGACCAAGGTGGAAATCAAACGAACTGTGGCTGCACC
6051 ATCTGTCTTCATCTTCCCGCCATCTGATGAGCAGTTGAAATCTGGAACTG
6101 CCTCTGTTGTGTGCCTGCTGAATAACTTCTATCCCAGAGAGGCCAAAGTA
6151 CAGTGGAAGGTGGATAACGCCCTCCAATCGGGTAACTCCCAGGAGAGTGT
6201 CACAGAGCAGGACAGCAAGGACAGCACCTACAGCCTCAGCAGCACCCTGA
6251 CGCTGAGCAAAGCAGACTACGAGAAACACAAACTCTACGCCTGCGAAGTC
6301 ACCCATCAGGGCCTGAGATCGCCCGTCACAAAGAGCTTCAACAAGGGGAG
6351 AGTGTTAGTTCTAGATAATTAATTAGGAGGAGATCTCGAGCTCGCGAAAG
6401 CTTGGCACTGGCCGTCGTTTTACAACGTCGTGACTGGGAAAACCCTGGCG
6451 TTACCCAACTTAATCGCCTTGCAGCACATCCCCCTTTCGCCAGCCTCCTA
6501 GGTCGACATCGATAAAATAAAAGATTTTATTTAGTCTCCAGAAAAAGGGG
6551 GGAATGAAAGACCCCACCTGTAGGTTTGGCAAGCTAGCTTAAGTAACGCC
6601 ATTTTGCAAGGCATGGAAAAATACATAACTGAGAATAGAGAAGTTCAGAT
6651 CAAGGTCAGGAACAGATGGAACAGCTGAATATGGGCCAAACAGGATATCT
6701 GTGGTAAGCAGTTCCTGCCCCGGCTCAGGGCCAAGAACAGATGGAACAGC
6751 TGAATATGGGCCAAACAGGATATCTGTGGTAAGCAGTTCCTGCCCCGGCT
6801 CAGGGCCAAGAACAGATGGTCCCCAGATGCGGTCCAGCCCTCAGCAGTTT
6851 CTAGAGAACCATCAGATGTTTCCAGGGTGCCCCAAGGACCTGAAATGACC
6901 CTGTGCCTTATTTGAACTAACCAATCAGTTCGCTTCTCGCTTCTGTTCGC
6951 GCGCTTCTGCTCCCCGAGCTCAATAAAAGAGCCCACAACCCCTCACTCGG
7001 GGCGCCAGTCCTCCGATTGACTGAGTCGCCCGGGTACCCGTGTATCCAAT
7051 AAACCCTCTTGCAGTTGCATCCGACTTGTGGTCTCGCTGTTCCTTGGGAG
7101 GGTCTCCTCTGAGTGATTGACTACCCGTCAGCGGGGGTCTTTCATTTGGG
7151 GGCTCGTCCGGGATCGGGAGACCCCTGCCCAGGGACCACCGACCCACCAC
7201 CGGGAGGTAAGCTGGCTGCCTCGCGCGTTTCGGTGATGACGGTGAAAACC
7251 TCTGACACATGCAGCTCCCGGAGACGGTCACAGCTTGTCTGTAAGCGGAT
7301 GCCGGGAGCAGACAAGCCCGTCAGGGCGCGTCAGCGGGTGTTGGCGGGTG
7351 TCGGGGCGCAGCCATGACCCAGTCACGTAGCGATAGCGGAGTGTATACTG
7401 GCTTAACTATGCGGCATCAGAGCAGATTGTACTGAGAGTGCACCATATGC
7451 GGTGTGAAATACCGCACAGATGCGTAAGGAGAAAATACCGCATCAGGCGC
7501 TCTTCCGCTTCCTCGCTCACTGACTCGCTGCGCTCGGTCGTTCGGCTGCG
7551 GCGAGCGGTATCAGCTCACTCAAAGGCGGTAATACGGTTATCCACAGAAT
7601 CAGGGGATAACGCAGGAAAGAACATGTGAGCAAAAGGCCAGCAAAAGGCC
7651 AGGAACCGTAAAAAGGCCGCGTTGCTGGCGTTTTTCCATAGGCTCCGCCC
7701 CCCTGACGAGCATCACAAAAATCGACGCTCAAGTCAGAGGTGGCGAAACC
7751 CGACAGGACTATAAAGATACCAGGCGTTTCCCCCTGGAAGCTCCCTCGTG
7801 CGCTCTCCTGTTCCGACCCTGCCGCTTACCGGATACCTGTCCGCCTTTCT
7851 CCCTTCGGGAAGCGTGGCGCTTTCTCATAGCTCACGCTGTAGGTATCTCA
7901 GTTCGGTGTAGGTCGTTCGCTCCAAGCTGGGCTGTGTGCACGAACCCCCC
7951 GTTCAGCCCGACCGCTGCGCCTTATCCGGTAACTATCGTCTTGAGTCCAA
8001 CCCGGTAAGACACGACTTATCGCCACTGGCAGCAGCCACTGGTAACAGGA
8051 TTAGCAGAGCGAGGTATGTAGGCGGTGCTACAGAGTTCTTGAAGTGGTGG
8101 CCTAACTACGGCTACACTAGAAGGACAGTATTTGGTATCTGCGCTCTGCT
8151 GAAGCCAGTTACCTTCGGAAAAAGAGTTGGTAGCTCTTGATCCGGCAAAC
8201 AAACCACCGCTGGTAGCGGTGGTTTTTTTGTTTGCAAGCAGCAGATTACG
8251 CGCAGAAAAAAAGGATCTCAAGAAGATCCTTTGATCTTTTCTACGGGGTC
8301 TGACGCTCAGTGGAACGAAAACTCACGTTAAGGGATTTTGGTCATGAGAT
8351 TATCAAAAAGGATCTTCACCTAGATCCTTTTAAATTAAAAATGAAGTTTT
8401 AAATCAATCTAAAGTATATATGAGTAAACTTGGTCTGACAGTTACCAATG
8451 CTTAATCAGTGAGGCACCTATCTCAGCGATCTGTCTATTTCGTTCATCCA
8501 TAGTTGCCTGACTCCCCGTCGTGTAGATAACTACGATACGGGAGGGCTTA
8551 CCATCTGGCCCCAGTGCTGCAATGATACCGCGAGACCCACGCTCACCGGC
8601 TCCAGATTTATCAGCAATAAACCAGCCAGCCGGAAGGGCCGAGCGCAGAA
8651 GTGGTCCTGCAACTTTATCCGCCTCCATCCAGTCTATTAATTGTTGCCGG
8701 GAAGCTAGAGTAAGTAGTTCGCCAGTTAATAGTTTGCGCAACGTTGTTGC
8751 CATTGCTGCAGGCATCGTGGTGTCACGCTCGTCGTTTGGTATGGCTTCAT
8801 TCAGCTCCGGTTCCCAACGATCAAGGCGAGTTACATGATCCCCCATGTTG
8851 TGCAAAAAAGCGGTTAGCTCCTTCGGTCCTCCGATCGTTGTCAGAAGTAA
8901 GTTGGCCGCAGTGTTATCACTCATGGTTATGGCAGCACTGCATAATTCTC
8951 TTACTGTCATGCCATCCGTAAGATGCTTTTCTGTGACTGGTGAGTACTCA
9001 ACCAAGTCATTCTGAGAATAGTGTATGCGGCGACCGAGTTGCTCTTGCCC
9051 GGCGTCAACACGGGATAATACCGCGCCACATAGCAGAACTTTAAAAGTGC
```

Figure 19d
```
9101  TCATCATTGGAAAACGTTCTTCGGGGCGAAAACTCTCAAGGATCTTACCG
9151  CTGTTGAGATCCAGTTCGATGTAACCCACTCGTGCACCCAACTGATCTTC
9201  AGCATCTTTTACTTTCACCAGCGTTTCTGGGTGAGCAAAAACAGGAAGGC
9251  AAAATGCCGCAAAAAAGGGAATAAGGGCGACACGGAAATGTTGAATACTC
9301  ATACTCTTCCTTTTTCAATATTATTGAAGCATTTATCAGGGTTATTGTCT
9351  CATGAGCGGATACATATTTGAATGTATTTAGAAAAATAAACAAATAGGGG
9401  TTCCGCGCACATTTCCCCGAAAAGTGCCACCTGACGTCTAAGAAACCATT
9451  ATTATCATGACATTAACCTATAAAAATAGGCGTATCACGAGGCCCTTTCG
   1. TCTTCAAGAAT Features:
149-737     Moloney murine sarcoma virus 5' LTR
807-1616    Extended Packaging Region
1680-1735   EM7 promoter (bacteriophage T7 promoter)
1754-2151   Blasticidin resistance gene coding sequence
2310-2440   SV40 poly A signal and site
2603-3420   CMV IE promoter
3675-4988   G-protein-coupled receptor (GPCR)
5071-5646   IRES
5647-5703   Bovine a-lactalbumin signal peptide
5704-6372   'humanized' antibody light chain
6553-7146   MoMuLV 3' LTR
7683Origin  of replication
9302-8442   b-Lactmase coding sequence
```

HOST CELLS CONTAINING MULTIPLE INTEGRATING VECTORS

This application claims priority to provisional appl. 60/215,925, filed Jul. 3, 2000.

FIELD OF THE INVENTION

The present invention relates to the production of proteins in host cells, and more particularly to host cells containing multiple integrated copies of an integrating vector.

BACKGROUND OF THE INVENTION

The pharmaceutical biotechnology industry is based on the production of recombinant proteins in mammalian cells. These proteins are essential to the therapeutic treatment of many diseases and conditions. In many cases, the market for these proteins exceeds a billion dollars a year. Examples of proteins produced recombinantly in mammalian cells include erythropoietin, factor VIII, factor IX, and insulin. For many of these proteins, expression in mammalian cells is preferred over expression in prokaryotic cells because of the need for correct post-translational modification (e.g., glycosylation or silation; see, e.g., U.S. Pat. No. 5,721,121, incorporated herein by reference).

Several methods are known for creating host cells that express recombinant proteins. In the most basic methods, a nucleic acid construct containing a gene encoding a heterologous protein and appropriate regulatory regions is introduced into the host cell and allowed to integrate. Methods of introduction include calcium phosphate precipitation, microinjection, lipofection, and electroporation. In other methods, a selection scheme is used to amplify the introduced nucleic acid construct. In these methods, the cells are co-transfected with a gene encoding an amplifiable selection marker and a gene encoding a heterologous protein (See, e.g., Schroder and Friedl, Biotech. Bioeng. 53(6):547–59 [1997]). After selection of the initial tranformants, the transfected genes are amplified by the stepwise increase of the selective agent (e.g., dihydrofolate reductase) in the culture medium. In some cases, the exogenous gene may be amplified several hundred-fold by these procedures. Other methods of recombinant protein expression in mammalian cells utilize transfection with episomal vectors (e.g., plasmids).

Current methods for creating mammalian cell lines for expression of recombinant proteins suffer from several drawbacks. (See, e.g., Mielke et al., Biochem. 35:2239–52 [1996]). Episomal systems allow for high expression levels of the recombinant protein, but are frequently only stable for a short time period (See, e.g., Klehr and Bode, Mol. Genet. (Life Sci. Adv.) 7:47–52 [1988]). Mammalian cell lines containing integrated exogenous genes are somewhat more stable, but there is increasing evidence that stability depends on the presence of only a few copies or even a single copy of the exogenous gene.

Standard transfection techniques favor the introduction of multiple copies of the transgene into the genome of the host cell. Multiple integration of the transgene has, in many cases, proven to be intrinsically unstable. This intrinsic instability may be due to the characteristic head-to-tail mode of integration which promotes the loss of coding sequences by homologous recombination (See, e.g., Weidle et al., Gene 66:193–203 [1988]) especially when the transgenes are transcribed (See, e.g., McBurney et al., Somatic Cell Molec. Genet. 20:529–40 [1994]). Host cells also have epigenetic defense mechanisms directed against multiple copy integration events. In plants, this mechanism has been termed "cosuppression." (See, e.g., Allen et al., Plant Cell 5:603–13 [1993]). Indeed, it is not uncommon that the level of expression is inversely related to copy number. These observations are consistent with findings that multiple copies of exogenous genes become inactivated by methylation (See, e.g., Mehtali et al., Gene 91:179–84 [1990]) and subsequent mutagenesis (See, e.g., Kricker et al., Proc. Natl. Acad. Sci. 89:1075–79 [1992]) or silenced by heterochromatin formation (See, e.g., Dorer and Henikoff, Cell 77:993–1002 [1994]).

Accordingly, what is needed in the art are improved methods for making host cells that express recombinant proteins. Preferably, the host cells will be stable over extended periods of time and express the protein encoded by a transgene at high levels.

SUMMARY OF THE INVENTION

The present invention relates to the production of proteins in host cells, and more particularly to host cells containing multiple integrated copies of an integrating vector. The present invention is not limited to host cells transfected with a particular number of integrating vectors. Indeed, host cells containing a wide range of integrating vectors are contemplated. In some embodiments, the present invention provides a host cell comprising a genome containing preferably at least about two integrated integrating vectors. In still further embodiments, the genome preferably comprises at least 3 integrated integrating vectors and most preferably at least 4 integrated integrating vectors, 5 integrated integrating vectors, 6 integrated integrating vectors, 7 integrated integrating vectors, 10 integrated integrating vectors, 15 integrated integrating vectors, 20 integrated integrating vectors, or 50 integrated integrating vectors.

The present invention is not limited to host cells containing vectors encoding a single protein of interest (i.e., exogenous protein). Indeed, it is contemplated that the host cells are transfected with vectors encoding multiple proteins of interest. In some embodiments, the integrating vector comprises at least two exogenous genes. In some preferred embodiments, the at least two exogenous genes are arranged in a polycistronic sequence. In some particularly preferred embodiments, the at least two exogenous genes are separated by an internal ribosome entry site. In other preferred embodiments, the at least two exogenous genes are arranged in a polycistronic sequence. In still further embodiments, the two exogenous genes comprise a heavy chain of an immunoglobulin molecule and a light chain of an immunoglobulin molecule. In other embodiments, one of the at least two exogenous genes is a selectable marker. In still other embodiments, the host cells comprise at least 2 integrated copies of a first integrating vector comprising a first exogenous gene, and at least 1 integrated copy of a second integrating vector or other vector comprising a second exogenous gene. In still further embodiments, the host cells comprise at least 10 integrated copies of a first integrating vector comprising a first exogenous gene, and at least 1 integrated copy of a second integrating vector or other vector comprising a second exogenous gene.

In some preferred embodiments, the integrating vectors comprise at least one exogenous gene operably linked to a promoter. The present invention is not limited to vectors containing a particular promoter. Indeed, a variety of promoters are contemplated. In some embodiments of the present invention, the promoter is selected from the group consisting of the alpha-lactalbumin promoter, cytomegalovirus promoter and the long terminal repeat of Moloney murine leukemia virus. In other preferred embodiments, the integrating vectors further comprise a secretion signal operably linked to the exogenous gene. In still other embodiments, the integrating vectors further comprise an RNA export element operably linked to the exogenous gene. The present invention is not limited to a particular integrating vector. Indeed, a variety of integrating vectors are contemplated. In some embodiments of the present invention, the integrating vector is selected from the group consisting of a retroviral vector, a lentiviral vector, and a transposon vector. In some preferred embodiments, the retroviral vector is a pseudotyped retroviral vector. In other preferred embodiments, the pseudotyped retroviral vector comprises a G glycoprotein. The retroviral vectors of the present invention are not limited to a particular G glycoprotein. Indeed, a variety of G glycoproteins are contemplated. In some particularly preferred embodiments, the G glycoprotein is selected from the group consisting of vesicular stomatitis virus, Piry virus, Chandipura virus, Spring viremia of carp virus and Mokola virus G glycoproteins. In still further embodiments, the retroviral vector comprises long terminal repeats. The retroviral vectors of the present invention are not limited to a particular LTR. Indeed, a variety of LTRs are contemplated, including, but not limited to MoMLV, MoMuSV, MMTV long terminal repeats.

In other embodiments, the retroviral vector is a lentiviral vector. In some preferred embodiments, the lentiviral vector is pseudotyped. In some particularly preferred embodiments, the lentiviral vector comprises a G glycoprotein. In still further embodiments, the G glycoprotein is selected from the group consisting of vesicular stomatitis virus, Piry virus, Chandipura virus, Spring viremia of carp virus and Mokola virus G glycoproteins. In still other embodiments, the lentiviral vector comprises long terminal repeats selected from the group consisting of HIV and equine infectious anemia long terminal repeats.

In still further embodiments of the present invention, the integrating vector is a transposon vector. In some preferred embodiments, the transposon vector is selected from Tn5, Tn7, and Tn10 transposon vectors.

The present invention is not limited to a particular host cell. Indeed, a variety of host cells are contemplated. In some embodiments of the present invention, the host cell is cultured in vitro. In still further embodiments of the present invention, the host cell is selected from chinese hamster ovary cells, baby hamster kidney cells, and bovine mammary epithelial cells. In some preferred embodiments, the host cells are clonally derived. In other embodiments, the host cells are non-clonally derived. In some embodiments, the genome of the host cell is stable for greater than 10 passages. In other embodiments, the genome is stable for greater than 50 passages, while in still other embodiments, the genome is stable for greater than 100 passages. In still other embodiments, the host cells can be an embryonic stem cell, oocyte, or embryo. In some embodiments, the integrated vector is stable in the absence of selection.

The present invention is not limited to vectors encoding a particular protein of interest. Indeed, vectors encoding a variety of proteins of interest encoded by exogenous genes are contemplated. In some embodiments, the protein of interest is selected from hepatitis B surface antigen, MN14 antibody, LL2 antibody, botulinum toxin antibody and cc491L2. In some embodiments, the genes encoding the protein of interest are intronless, while in other embodiments, the genes encoding the protein of interest include at least one intron.

The present invention also provides a method for transfecting or transducing host cells comprising: 1) providing: a) a host cell comprising a genome, and b) a plurality of integrating vectors; and 2) contacting the host cell with the plurality of integrating vectors under conditions such that at least two integrating vectors integrate into the genome of the host cell. In some embodiments, the conditions comprise contacting the host cells at a multiplicity of infection of greater than 10. In other embodiments, the conditions comprise contacting the host cells at a multiplicity of infection of from about 10 to 1,000,000. In still further embodiments, the conditions comprise contacting the host cells at a multiplicity of infection of from about 100 to 10,000. In still further embodiments, the conditions comprise contacting the host cells at a multiplicity of infection of from about 100 to 1,000. In still other embodiments of the present invention, the method further comprises transfecting said host cells with at least two integrating vectors, each of said two integrating comprising a different exogenous gene. In still other embodiments, the conditions comprise serial transfection or transduction or host cells wherein the host cells are transfected or transduced in at least a first transfection or transduction with a vector encoding a protein of interest and then re-transfected or re-transduced in a separate transfection or transduction step.

The present invention further provides a method of producing a protein of interest comprising: 1) providing a host cell comprising a genome, the genome comprising at least two integrated copies of at least one integrating vector comprising an exogenous gene operably linked to a promotor, wherein the exogenous gene encodes a protein of interest, and 2) culturing the host cells under conditions such that the protein of interest is produced. In some preferred embodiments, the integrating vector further comprises a secretion signal sequence operably linked to said exogenous gene. In other embodiments, the methods further comprise step 3) isolating the protein of interest. The present invention is not limited to any particular culture system. Indeed, a variety of culture systems are contemplated, including, but not limited to roller bottle cultures, perfusion cultures, batch fed cultures, and petri dish cultures. In some embodiments, the cell line is clonally selected, while in other embodiments, the cells are non-clonally selected.

The methods of the present invention are not limited to host cells containing any particular number of integrated integrating vectors. Indeed, in some embodiments, the genome of the host cell comprises greater than 3 integrated copies of the integrating vector; in other embodiments, genome of the host cell comprises greater than 4 integrated copies of the integrating vector; in still other embodiments, the genome of the host cell comprises greater than 5 integrated copies of the integrating vector; in further embodiments, the genome of the host cell comprises greater than 7 integrated copies of the integrating vector; while in still further embodiments, the genome of the host cell comprises greater than 10 integrated copies of the integrating vector. In other embodiments, the genome of the host cell comprises between about 2 and 20 integrated copies of the integrating vector. In some embodiments, the genome of the host cell comprises between about 3 and 10 integrated copies of the integrating vector.

The methods of the present invention are not limited to any particular integrating vector. Indeed, the use of a variety of integrating vectors is contemplated. In some embodiments, the integrating vector is a retroviral vector. In some preferred embodiments, the retroviral vector is a pseudotyped retroviral vector. In other embodiments, the retroviral vector is a lentiviral vector.

The methods of the present invention are not limited to the use of any particular host cell. Indeed, the use of a variety of host cells is contemplated, including, but not limited to, Chinese hamster ovary cells, baby hamster kidney cells, bovine mammary epithelial cells, oocytes, embryos, stem cells, and embryonic stem cells.

The methods of the present invention are not limited to the production of any particular amount of exogenous protein (i.e., protein of interest) from the host cells. Indeed, it is contemplated that a variety of expression levels are acceptable from the methods of the present invention. In some embodiments, the host cells synthesize greater than about 1 picogram per cell per day of the protein of interest. In other embodiments, the host cells synthesize greater than about 10 picograms per cell per day of the protein of interest. In still further embodiments, the host cells synthesize greater than about 50 picograms per cell per day of the protein of interest.

In other embodiments, the present invention provides a method for screening compounds comprising: 1) providing a) a host cell comprising a genome, the genome comprising at least two integrated copies of at least one integrating vector comprising an exogenous gene operably linked to a promotor, wherein the exogenous gene encodes a protein of interest; and b) one or more test compounds; 2) culturing the host cells under conditions such that the protein of interest is expressed; 3) treating the host cells with one or more test compounds; and 4) assaying for the presence or absence of a response in the host cells to the test compound. In some embodiments of the present invention, the exogenous gene encodes a protein selected from the group consisting of reporter proteins, membrane receptor proteins, nucleic acid binding proteins, cytoplasmic receptor proteins, ion channel proteins, signal transduction proteins, protein kinases, protein phosphatases, and proteins encoded by oncogenes.

In still further embodiments, the host cell further comprises a reporter gene. In some particularly preferred embodiments, the reporter gene is selected from the group consisting of green fluorescent protein, luciferase, beta-galactosidase, and beta-lactamase. In some embodiments, the assaying step further comprises detecting a signal from the reporter gene. In other embodiments, the genome of the host cell comprises at least two integrating vectors, each comprising a different exogenous gene.

In still other embodiments, the present invention provides methods for comparing protein activity comprising: 1) providing a) a first host cell comprising a first integrating vector comprising a promoter operably to a first exogenous gene, wherein the first exogenous gene encodes a first protein of interest, and b) at least a second host cell comprising a second integrating vector comprising a promoter operably linked to a second exogenous gene, wherein the second exogenous gene encodes a second exogenous gene that is a variant of the first protein of interest; 2) culturing the host cells under conditions such that the first and second proteins of interest are produced; and 3) comparing the activities of the first and second proteins of interest.

In some embodiments, the exogenous gene encodes a protein selected from the group consisting of membrane receptor proteins, nucleic acid binding proteins, cytoplasmic receptor proteins, ion channel proteins, signal transduction proteins, protein kinases, protein phosphatases, cell cycle proteins, and proteins encoded by oncogenes. In other embodiments, the first and second proteins of interest differ by a single amino acid. In still further embodiments, the first and second proteins of interest are greater than 95% identical, preferably greater than 90% identical, and most preferably greater than 80% identical.

In other embodiments, the present invention provides methods comprising: 1) providing: a) a host cell comprising a genome comprising at least one integrated exogenous gene; and b) a plurality of integrating vectors; and 2) contacting the host cell with the plurality of integrating vectors under conditions such that at least two of the integrating vectors integrate into the genome of the host cell. In some embodiments, the integrated exogenous gene comprises an integrating vector. In other embodiments, the host cell is clonally selected. In alternative embodiments, the host cell is non-clonally selected.

In still further embodiments, the present invention provides methods of indirectly detecting the expression of a protein of interest comprising providing a host cell transfected with a vector encoding a polycistronic sequence, wherein the polycistronic sequence comprises a signal protein and a protein of interest operably linked by an IRES, and culturing the host cells under conditions such that the signal protein and protein of interest are produced, wherein the presence of the signal protein indicates the presence of the protein of interest. The methods of the present invention are not limited to the expression of any particular protein of interest. Indeed, the expression of a variety of proteins of interest is contemplated, including, but not limited to, G-protein coupled receptors. The present invention is not limited to the use of any particular signal protein. Indeed, the use of variety of signal proteins is contemplated, including, but not limited to, immunoglobulin heavy and light chains, beta-galactosidase, beta-lactamase, green fluorescent protein, and luciferase. In particularly preferred embodiments, expression of the signal protein and protein of interest is driven by the same promoter and the signal protein and protein of interest are transcribed as a single transcriptional unit.

DESCRIPTION OF THE FIGURES

FIG. 4 provides the sequence for the hybrid human-bovine alpha-lactalbumin promoter (SEQ ID NO:1).

FIG. 5 provides the sequence for the mutated PPE sequence (SEQ ID NO:2).

FIG. 6 provides the sequence for the mES-Signal peptide sequence (SEQ ID NO:3).

FIGS. 7a and 7b provide the sequence for CMV MN14 vector (SEQ ID NO:4).

FIGS. 8a and 8b provide the sequence for the CMV LL2 vector (SEQ ID NO:5).

FIGS. 9a–c provide the sequence for the MMTV MN14 vector (SEQ ID NO:6).

FIGS. 10a–d provide the sequence for the alpha-lactalbumin MN14 Vector (SEQ ID NO:7).

FIGS. 11a–c provide the sequence for the alpha-lactalbumin Bot vector (SEQ ID NO:8).

FIGS. 12a–b provide the sequence for the LSRNL vector (SEQ ID NO:9).

FIGS. 13a–b provide the sequence for the alpha-lactalbumin cc491L2 vector (SEQ ID NO:10).

FIGS. 14a–c provides the sequence for the alpha-lactalbumin YP vector (SEQ ID NO:11).

FIG. 15 provides the sequence for the IRES-Casein signal peptide sequence (SEQ ID NO:12).

FIGS. 16a–c provide the sequence for the LNBOTDC vector (SEQ ID NO:13).

FIG. 17 provides a graph depicting the INVADER Assay gene ratio in CMV promoter cell lines.

FIG. 18 provides a graph depicting the INVADER Assay gene ratio in α-lactalbumin promotor cell lines.

FIGS. 19a–d provide the sequence of a retroviral vector that expresses a G-Protein coupled receptor and antibody light chain.

DEFINITIONS

Figure 1:
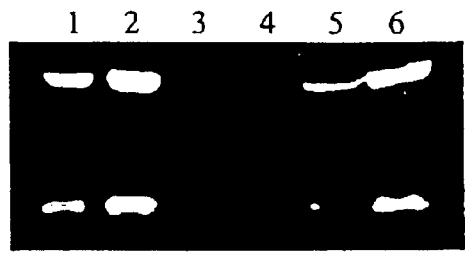
FIG. 1 is a western blot of a 15% SDS-PAGE gel run under denaturing conditions and probed with anti-human IgG (Fc) and anti-human IgG (Kappa).

To facilitate understanding of the invention, a number of terms are defined below.

As used herein, the term "host cell" refers to any eukaryotic cell (e.g., mammalian cells, avian cells, amphibian cells, plant cells, fish cells, and insect cells), whether located in vitro or in vivo.

As used herein, the term "cell culture" refers to any in vitro culture of cells. Included within this term are continuous cell lines (e.g., with an immortal phenotype), primary cell cultures, finite cell lines (e.g., non-transformed cells), and any other cell population maintained in vitro, including oocytes and embryos.

As used herein, the term "vector" refers to any genetic element, such as a plasmid, phage, transposon, cosmid, chromosome, virus, virion, etc., which is capable of replication when associated with the proper control elements and which can transfer gene sequences between cells. Thus, the term includes cloning and expression vehicles, as well as viral vectors.

As used herein, the term "integrating vector" refers to a vector whose integration or insertion into a nucleic acid (e.g., a chromosome) is accomplished via an integrase. Examples of "integrating vectors" include, but are not limited to, retroviral vectors, transposons, and adeno associated virus vectors.

As used herein, the term "integrated" refers to a vector that is stably inserted into the genome (i.e., into a chromosome) of a host cell.

As used herein, the term "multiplicity of infection" or "MOI" refers to the ratio of integrating vectors:host cells used during transfection or transduction of host cells. For example, if 1,000,000 vectors are used to transduce 100,000 host cells, the multiplicity of infection is 10. The use of this term is not limited to events involving transduction, but instead encompasses introduction of a vector into a host by methods such as lipofection, microinjection, calcium phosphate precipitation, and electroporation.

As used herein, the term "genome" refers to the genetic material (e.g., chomosomes) of an organism.

The term "nucleotide sequence of interest" refers to any nucleotide sequence (e.g., RNA or DNA), the manipulation of which may be deemed desirable for any reason (e.g., treat disease, confer improved qualities, expression of a protein of interest in a host cell, expression of a ribozyme, etc.), by one of ordinary skill in the art. Such nucleotide sequences include, but are not limited to, coding sequences of structural genes (e.g., reporter genes, selection marker genes, oncogenes, drug resistance genes, growth factors, etc.), and non-coding regulatory sequences which do not encode an mRNA or protein product (e.g., promoter sequence, polyadenylation sequence, termination sequence, enhancer sequence, etc.).

As used herein, the term "protein of interest" refers to a protein encoded by a nucleic acid of interest.

As used herein, the term "signal protein" refers to a protein that is co-expressed with a protein of interest and which, when detected by a suitable assay, provides indirect evidence of expression of the protein of interest. Examples of signal protein useful in the present invention include, but are not limited to, immunoglobulin heavy and light chains, beta-galactosidase, beta-lactamase, green fluorescent protein, and luciferase.

As used herein, the term "exogenous gene" refers to a gene that is not naturally present in a host organism or cell, or is artificially introduced into a host organism or cell.

The term "gene" refers to a nucleic acid (e.g., DNA or RNA) sequence that comprises coding sequences necessary for the production of a polypeptide or precursor (e.g., proinsulin). The polypeptide can be encoded by a full length coding sequence or by any portion of the coding sequence so long as the desired activity or functional properties (e.g., enzymatic activity, ligand binding, signal transduction, etc.) of the full-length or fragment are retained. The term also encompasses the coding region of a structural gene and includes sequences located adjacent to the coding region on both the 5' and 3' ends for a distance of about 1 kb or more on either end such that the gene corresponds to the length of the full-length mRNA. The sequences that are located 5' of the coding region and which are present on the mRNA are referred to as 5' untranslated sequences. The sequences that are located 3' or downstream of the coding region and which are present on the mRNA are referred to as 3' untranslated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene which are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

As used herein, the term "gene expression" refers to the process of converting genetic information encoded in a gene into RNA (e.g., mRNA, rRNA, tRNA, or snRNA) through "transcription" of the gene (i.e., via the enzymatic action of an RNA polymerase), and for protein encoding genes, into protein through "translation" of mRNA. Gene expression can be regulated at many stages in the process. "Upregulation" or "activation" refers to regulation that increases the production of gene expression products (i.e., RNA or protein), while "down-regulation" or "repression" refers to regulation that decrease production. Molecules (e.g., transcription factors) that are involved in up-regulation or down-regulation are often called "activators" and "repressors," respectively.

Where "amino acid sequence" is recited herein to refer to an amino acid sequence of a naturally occurring protein molecule, "amino acid sequence" and like terms, such as "polypeptide" or "protein" are not meant to limit the amino acid sequence to the complete, native amino acid sequence associated with the recited protein molecule.

As used herein, the terms "nucleic acid molecule encoding," "DNA sequence encoding," "DNA encoding," "RNA sequence encoding," and "RNA encoding" refer to the order or sequence of deoxyribonucleotides or ribonucleotides along a strand of deoxyribonucleic acid or ribonucleic acid. The order of these deoxyribonucleotides or ribonucleotides determines the order of amino acids along the polypeptide (protein) chain. The DNA or RNA sequence thus codes for the amino acid sequence.

As used herein, the term "variant," when used in reference to a protein, refers to proteins encoded by partially homologous nucleic acids so that the amino acid sequence of the proteins varies. As used herein, the term "variant" encompasses proteins encoded by homologous genes having both conservative and nonconservative amino acid substitutions that do not result in a change in protein function, as well as proteins encoded by homologous genes having amino acid substitutions that cause decreased (e.g., null mutations) protein function or increased protein function.

As used herein, the terms "complementary" or "complementarity" are used in reference to polynucleotides (i.e., a sequence of nucleotides) related by the base-pairing rules. For example, for the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

The terms "homology" and "percent identity" when used in relation to nucleic acids refers to a degree of complementarity. There may be partial homology (i.e., partial identity) or complete homology (i.e., complete identity). A partially complementary sequence is one that at least partially inhibits a completely complementary sequence from hybridizing to a target nucleic acid sequence and is referred to using the functional term "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe (i.e., an oligonucleotide which is capable of hybridizing to another oligonucleotide of interest) will compete for and inhibit the binding (i.e., the hybridization) of a completely homologous sequence to a target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target which lacks even a partial degree of complementarity (e.g., less than about 30% identity); in the absence of non-specific binding the probe will not hybridize to the second non-complementary target. The art knows well that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered is and the hybridization solution may be varied to generate conditions of low stringency hybridization different from, but equivalent to, the above listed conditions. In addition, the art knows conditions that promote hybridization under conditions of high stringency (e.g., increasing the temperature of the hybridization and/or wash steps, the use of formamide in the hybridization solution, etc.).

When used in reference to a double-stranded nucleic acid sequence such as a cDNA or genomic clone, the term "substantially homologous" refers to any probe that can hybridize to either or both strands of the double-stranded nucleic acid sequence under conditions of low stringency as described above.

When used in reference to a single-stranded nucleic acid sequence, the term "substantially homologous" refers to any probe that can hybridize (i.e., it is the complement of) the single-stranded nucleic acid sequence under conditions of low stringency as described above.

As used herein, the term "hybridization" is used in reference to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids. A single molecule that contains pairing of complementary nucleic acids within its structure is said to be "self-hybridized."

As used herein, the term "$T_m$" is used in reference to the "melting temperature" of a nucleic acid. The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m=81.5+0.41(\% \text{ G+C})$, when a nucleic acid is in aqueous solution at 1 M NaCl (See e.g., Anderson and Young, Quantitative Filter Hybridization, in Nucleic Acid Hybridization [1985]). Other references include more sophisticated computations that take structural as well as sequence characteristics into account for the calculation of $T_m$.

As used herein the term "stringency" is used in reference to the conditions of temperature, ionic strength, and the presence of other compounds such as organic solvents, under which nucleic acid hybridizations are conducted. With "high stringency" conditions, nucleic acid base pairing will occur only between nucleic acid fragments that have a high frequency of complementary base sequences. Thus, conditions of "weak" or "low" stringency are often required with nucleic acids that are derived from organisms that are genetically diverse, as the frequency of complementary sequences is usually less.

"High stringency conditions" when used in reference to nucleic acid hybridization comprise conditions equivalent to binding or hybridization at 42° C. in a solution consisting of 5×SSPE (43.8 g/l NaCl, 6.9 g/l $NaH_2PO_4.H_2O$ and 1.85 g/l EDTA, pH adjusted to 7.4 with NaOH), 0.5% SDS, 5× Denhardt's reagent and 100 µg/ml denatured salmon sperm DNA followed by washing in a solution comprising 0.1× SSPE, 1.0% SDS at 42° C. when a probe of about 500 nucleotides in length is employed.

"Medium stringency conditions" when used in reference to nucleic acid hybridization comprise conditions equivalent to binding or hybridization at 42° C. in a solution consisting of 5×SSPE (43.8 g/l NaCl, 6.9 g/l $NaH_2PO_4.H_2O$ and 1.85 g/l EDTA, pH adjusted to 7.4 with NaOH), 0.5% SDS, 5× Denhardt's reagent and 100 µg/ml denatured salmon sperm DNA followed by washing in a solution comprising 1.0× SSPE, 1.0% SDS at 42° C. when a probe of about 500 nucleotides in length is employed.

"Low stringency conditions" comprise conditions equivalent to binding or hybridization at 42° C. in a solution consisting of 5×SSPE (43.8 g/l NaCl, 6.9 g/l $NaH_2PO_4.H_2O$ and 1.85 g/l EDTA, pH adjusted to 7.4 with NaOH), 0.1% SDS, 5× Denhardt's reagent [50× Denhardt's contains per 500 ml: 5 g Ficoll (Type 400, Pharamcia), 5 g BSA (Fraction V;

Sigma)] and 100 μg/ml denatured salmon sperm DNA followed by washing in a solution comprising 5×SSPE, 0.1% SDS at 42° C. when a probe of about 500 nucleotides in length is employed.

A gene may produce multiple RNA species that are generated by differential splicing of the primary RNA transcript. cDNAs that are splice variants of the same gene will contain regions of sequence identity or complete homology (representing the presence of the same exon or portion of the same exon on both cDNAs) and regions of complete non-identity (for example, representing the presence of exon "A" on cDNA 1 wherein cDNA 2 contains exon "B" instead). Because the two cDNAs contain regions of sequence identity they will both hybridize to a probe derived from the entire gene or portions of the gene containing sequences found on both cDNAs; the two splice variants are therefore substantially homologous to such a probe and to each other.

The terms "in operable combination," "in operable order," and "operably linked" as used herein refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

As used herein, the term "selectable marker" refers to a gene that encodes an enzymatic activity that confers the ability to grow in medium lacking what would otherwise be an essential nutrient (e.g. the HIS3 gene in yeast cells); in addition, a selectable marker may confer resistance to an antibiotic or drug upon the cell in which the selectable marker is expressed. Selectable markers may be "dominant"; a dominant selectable marker encodes an enzymatic activity that can be detected in any eukaryotic cell line. Examples of dominant selectable markers include the bacterial aminoglycoside 3' phosphotransferase gene (also referred to as the neo gene) that confers resistance to the drug G418 in mammalian cells, the bacterial hygromycin G phosphotransferase (hyg) gene that confers resistance to the antibiotic hygromycin and the bacterial xanthine-guanine phosphoribosyl transferase gene (also referred to as the gpt gene) that confers the ability to grow in the presence of mycophenolic acid. Other selectable markers are not dominant in that their use must be in conjunction with a cell line that lacks the relevant enzyme activity. Examples of non-dominant selectable markers include the thymidine kinase (tk) gene that is used in conjunction with tk⁻ cell lines, the CAD gene which is used in conjunction with CAD-deficient cells and the mammalian hypoxanthine-guanine phosphoribosyl transferase (hpri) gene which is used in conjunction with hprt cell lines. A review of the use of selectable markers in mammalian cell lines is provided in Sambrook, J. et al., *Molecular Cloning: A Laboratory Manual,* 2nd ed., Cold Spring Harbor Laboratory Press, New York (1989) pp.16.9–16.15.

As used herein, the term "regulatory element" refers to a genetic element which controls some aspect of the expression of nucleic acid sequences. For example, a promoter is a regulatory element that facilitates the initiation of transcription of an operably linked coding region. Other regulatory elements are splicing signals, polyadenylation signals, termination signals, RNA export elements, internal ribosome entry sites, etc. (defined infra).

Transcriptional control signals in eukaryotes comprise "promoter" and "enhancer" elements. Promoters and enhancers consist of short arrays of DNA sequences that interact specifically with cellular proteins involved in transcription (Maniatis et al., Science 236:1237 [1987]). Promoter and enhancer elements have been isolated from a variety of eukaryotic sources including genes in yeast, insect and mammalian cells, and viruses (analogous control elements, i.e., promoters, are also found in prokaryotes). The selection of a particular promoter and enhancer depends on what cell type is to be used to express the protein of interest. Some eukaryotic promoters and enhancers have a broad host range while others are functional in a limited subset of cell types (for review see, Voss et al., Trends Biochem. Sci., 11:287 [1986]; and Maniatis et al., supra). For example, the SV40 early gene enhancer is very active in a wide variety of cell types from many mammalian species and has been widely used for the expression of proteins in mammalian cells (Dijkema et al, EMBO J. 4:761 [1985]). Two other examples of promoter/enhancer elements active in a broad range of mammalian cell types are those from the human elongation factor 1α gene (Uetsuki et al., J. Biol. Chem., 264:5791 [1989]; Kim et al., Gene 91:217 [1990]; and Mizushima and Nagata, Nuc. Acids. Res., 18:5322 [1990]) and the long terminal repeats of the Rous sarcoma virus (Gorman et al., Proc. Natl. Acad. Sci. USA 79:6777 [1982]) and the human cytomegalovirus (Boshart et al., Cell 41:521 [1985]).

As used herein, the term "promoter/enhancer" denotes a segment of DNA which contains sequences capable of providing both promoter and enhancer functions (i.e., the functions provided by a promoter element and an enhancer element, see above for a discussion of these functions). For example, the long terminal repeats of retroviruses contain both promoter and enhancer functions. The enhancer/promoter may be "endogenous" or "exogenous" or "heterologous." An "endogenous" enhancer/promoter is one which is naturally linked with a given gene in the genome. An "exogenous" or "heterologous" enhancer/promoter is one which is placed in juxtaposition to a gene by means of genetic manipulation (i.e., molecular biological techniques such as cloning and recombination) such that transcription of that gene is directed by the linked enhancer/promoter.

Regulatory elements may be tissue specific or cell specific. The term "tissue specific" as it applies to a regulatory element refers to a regulatory element that is capable of directing selective expression of a nucleotide sequence of interest to a specific type of tissue (e.g., liver) in the relative absence of expression of the same nucleotide sequence of interest in a different type of tissue (e.g., lung).

Tissue specificity of a regulatory element may be evaluated by, for example, operably linking a reporter gene to a promoter sequence (which is not tissue-specific) and to the regulatory element to generate a reporter construct, introducing the reporter construct into the genome of an animal such that the reporter construct is integrated into every tissue of the resulting transgenic animal, and detecting the expression of the reporter gene (e.g., detecting mRNA, protein, or the activity of a protein encoded by the reporter gene) in different tissues of the transgenic animal. The detection of a greater level of expression of the reporter gene in one or more tissues relative to the level of expression of the reporter gene in other tissues shows that the regulatory element is "specific" for the tissues in which greater levels of expression are detected. Thus, the term "tissue-specific" (e.g., liver-specific) as used herein is a relative term that does not require absolute specificity of expression. In other words, the term "tissue-specific" does not require that one tissue have extremely high levels of expression and another tissue have no expression. It is sufficient that expression is greater in one tissue than another. By contrast, "strict" or "absolute" tissue-specific expression is meant to indicate expression in a single tissue type (e.g., liver) with no detectable expression in other tissues.

The term "cell type specific" as applied to a regulatory element refers to a regulatory element which is capable of directing selective expression of a nucleotide sequence of interest in a specific type of cell in the relative absence of expression of the same nucleotide sequence of interest in a different type of cell within the same tissue. The term "cell type specific" when applied to a regulatory element also means a regulatory element capable of promoting selective expression of a nucleotide sequence of interest in a region within a single tissue.

Cell type specificity of a regulatory element may be assessed using methods well known in the art (e.g., immunohistochemical staining and/or Northern blot analysis). Briefly, for immunohistochemical staining, tissue sections are embedded in paraffin, and paraffin sections are reacted with a primary antibody specific for the polypeptide product encoded by the nucleotide sequence of interest whose expression is regulated by the regulatory element. A labeled (e.g., peroxidase conjugated) secondary antibody specific for the primary antibody is allowed to bind to the sectioned tissue and specific binding detected (e.g., with avidin/biotin) by microscopy. Briefly, for Northern blot analysis, RNA is isolated from cells and electrophoresed on agarose gels to fractionate the RNA according to size followed by transfer of the RNA from the gel to a solid support (e.g., nitrocellulose or a nylon membrane). The immobilized RNA is then probed with a labeled oligo-deoxyribonucleotide probe or DNA probe to detect RNA species complementary to the probe used. Northern blots are a standard tool of molecular biologists.

The term "promoter," "promoter element," or "promoter sequence" as used herein, refers to a DNA sequence which when ligated to a nucleotide sequence of interest is capable of controlling the transcription of the nucleotide sequence of interest into mRNA. A promoter is typically, though not necessarily, located 5' (i.e., upstream) of a nucleotide sequence of interest whose transcription into mRNA it controls, and provides a site for specific binding by RNA polymerase and other transcription factors for initiation of transcription.

Promoters may be constitutive or regulatable. The term "constitutive" when made in reference to a promoter means that the promoter is capable of directing transcription of an operably linked nucleic acid sequence in the absence of a stimulus (e.g., heat shock, chemicals, etc.). In contrast, a "regulatable" promoter is one which is capable of directing a level of transcription of an operably linked nucleic acid sequence in the presence of a stimulus (e.g., heat shock, chemicals, etc.) which is different from the level of transcription of the operably linked nucleic acid sequence in the absence of the stimulus.

The presence of "splicing signals" on an expression vector often results in higher levels of expression of the recombinant transcript. Splicing signals mediate the removal of introns from the primary RNA transcript and consist of a splice donor and acceptor site (Sambrook et al., *Molecular Cloning: A Laboratory Manual,* 2nd ed., Cold Spring Harbor Laboratory Press, New York [1989], pp.16.7–16.8). A commonly used splice donor and acceptor site is the splice junction from the 16S RNA of SV40.

Efficient expression of recombinant DNA sequences in eukaryotic cells requires expression of signals directing the efficient termination and polyadenylation of the resulting transcript. Transcription termination signals are generally found downstream of the polyadenylation signal and are a few hundred nucleotides in length. The term "poly A site" or "poly A sequence" as used herein denotes a DNA sequence that directs both the termination and polyadenylation of the nascent RNA transcript. Efficient polyadenylation of the recombinant transcript is desirable as transcripts lacking a poly A tail are unstable and are rapidly degraded. The poly A signal utilized in an expression vector may be "heterologous" or "endogenous." An endogenous poly A signal is one that is found naturally at the 3' end of the coding region of a given gene in the genome. A heterologous poly A signal is one that is isolated from one gene and placed 3' of another gene. A commonly used heterologous poly A signal is the SV40 poly A signal. The SV40 poly A signal is contained on a 237 bp BamHI/BclI restriction fragment and directs both termination and polyadenylation (Sambrook, supra, at 16.6–16.7).

Eukaryotic expression vectors may also contain "viral replicons" or "viral origins of replication." Viral replicons are viral DNA sequences that allow for the extrachromosomal replication of a vector in a host cell expressing the appropriate replication factors. Vectors that contain either the SV40 or polyoma virus origin of replication replicate to high "copy number" (up to $10^4$ copies/cell) in cells that express the appropriate viral T antigen. Vectors that contain the replicons from bovine papillomavirus or Epstein-Barr virus replicate extrachromosomally at "low copy number" (~100 copies/cell). However, it is not intended that expression vectors be limited to any particular viral origin of replication.

As used herein, the term "long terminal repeat" of "LTR" refers to transcriptional control elements located in or isolated from the U3 region 5' and 3' of a retroviral genome. As is known in the art, long terminal repeats may be used as control elements in retroviral vectors, or isolated from the retroviral genome and used to control expression from other types of vectors.

As used herein, the term "secretion signal" refers to any DNA sequence which when operably linked to a recombinant DNA sequence encodes a signal peptide which is capable of causing the secretion of the recombinant polypeptide. In general, the signal peptides comprise a series of about 15 to 30 hydrophobic amino acid residues (See, e.g., Zwizinski et al., J. Biol. Chem. 255(16): 7973–77 [1980], Gray et al., Gene 39(2): 247–54 [1985], and Martial et al., Science 205: 602–607 [1979]). Such secretion signal sequences are preferably derived from genes encoding polypeptides secreted from the cell type targeted for tissue-specific expression (e.g., secreted milk proteins for expression in and secretion from mammary secretory cells). Secretory DNA sequences, however, are not limited to such sequences. Secretory DNA sequences from proteins secreted from many cell types and organisms may also be used (e.g., the secretion signals for t-PA, serum albumin, lactoferrin, and growth hormone, and secretion signals from microbial genes encoding secreted polypeptides such as from yeast, filamentous fungi, and bacteria).

As used herein, the terms "RNA export element" or "Pre-mRNA Processing Enhancer (PPE)" refer to 3' and 5' cis-acting post-transcriptional regulatory elements that enhance export of RNA from the nucleus. "PPE" elements include, but are not limited to Mertz sequences (described in U.S. Pat. Nos. 5,914,267 and 5,686,120, all of which are incorporated herein by reference) and woodchuck mRNA processing enhancer (WPRE; WO99/14310 and U.S. Pat. No. 6,136,597, each of which is incorporated herein by reference).

As used herein, the term "polycistronic" refers to an mRNA encoding more than polypeptide chain (See, e.g., WO 93/03143, WO 88/05486, and European Pat. No. 117058, all of which are incorporated herein by reference). Likewise, the term "arranged in polycistronic sequence" refers to the arrangement of genes encoding two different polypeptide chains in a single mRNA.

As used herein, the term "internal ribosome entry site" or "IRES" refers to a sequence located between polycistronic genes that permits the production of the expression product originating from the second gene by internal initiation of the translation of the dicistronic mRNA. Examples of internal ribosome entry sites include, but are not limited to, those derived from foot and mouth disease virus (FDV), encephalomyocarditis virus, poliovirus and RDV (Scheper et al., Biochem. 76: 801–809 [1994]; Meyer et al., J. Virol. 69: 2819–2824 [1995]; Jang et al., 1988, J. Virol. 62: 2636–2643 [1998]; Haller et al., J. Virol. 66: 5075–5086 [1995]). Vectors incorporating IRES's may be assembled as is known in the art. For example, a retroviral vector containing a polycistronic sequence may contain the following elements in operable association: nucleotide polylinker, gene of interest, an internal ribosome entry site and a mammalian selectable marker or another gene of interest. The polycistronic cassette is situated within the retroviral vector between the 5' LTR and the 3' LTR at a position such that transcription from the 5' LTR promoter transcribes the polycistronic message cassette. The transcription of the polycistronic message cassette may also be driven by an internal promoter (e.g., cytomegalovirus promoter) or an inducible promoter, which may be preferable depending on the use. The polycistronic message cassette can further comprise a cDNA or genomic DNA (GDNA) sequence operatively associated within the polylinker. Any mammalian selectable marker can be utilized as the polycistronic message cassette mammalian selectable marker. Such mammalian selectable markers are well known to those of skill in the art and can include, but are not limited to, kanamycin/G418, hygromycin B or mycophenolic acid resistance markers.

As used herein, the term "retrovirus" refers to a retroviral particle which is capable of entering a cell (i.e., the particle contains a membrane-associated protein such as an envelope protein or a viral G glycoprotein which can bind to the host cell surface and facilitate entry of the viral particle into the cytoplasm of the host cell) and integrating the retroviral genome (as a double-stranded provirus) into the genome of the host cell. The term "retrovirus" encompasses Oncovirinae (e.g., Moloney murine leukemia virus (MoMOLV), Moloney murine sarcoma virus (MoMSV), and Mouse mammary tumor virus (MMTV), Spumavirinae, amd Lentivirinae (e.g., Human immunodeficiency virus, Simian immunodeficiency virus, Equine infection anemia virus, and Caprine arthritis-encephalitis virus; See, e.g., U.S. Pat. Nos. 5,994,136 and 6,013,516, both of which are incorporated herein by reference).

As used herein, the term "retroviral vector" refers to a retrovirus that has been modified to express a gene of interest. Retroviral vectors can be used to transfer genes efficiently into host cells by exploiting the viral infectious process. Foreign or heterologous genes cloned (i.e., inserted using molecular biological techniques) into the retroviral genome can be delivered efficiently to host cells which are susceptible to infection by the retrovirus.

Through well known genetic manipulations, the replicative capacity of the retroviral genome can be destroyed. The resulting replication-defective vectors can be used to introduce new genetic material to a cell but they are unable to replicate. A helper virus or packaging cell line can be used to permit vector particle assembly and egress from the cell. Such retroviral vectors comprise a replication-deficient retroviral genome containing a nucleic acid sequence encoding at least one gene of interest (i.e., a polycistronic nucleic acid sequence can encode more than one gene of interest), a 5' retroviral long terminal repeat (5' LTR); and a 3' retroviral long terminal repeat (3' LTR).

The term "pseudotyped retroviral vector" refers to a retroviral vector containing a heterologous membrane protein. The term "membrane-associated protein" refers to a protein (e.g., a viral envelope glycoprotein or the G proteins of viruses in the *Rhabdoviridae* family such as VSV, Piry, Chandipura and Mokola) which are associated with the membrane surrounding a viral particle; these membrane-associated proteins mediate the entry of the viral particle into the host cell. The membrane associated protein may bind to specific cell surface protein receptors, as is the case for retroviral envelope proteins or the membrane-associated protein may interact with a phospholipid component of the plasma membrane of the host cell, as is the case for the G proteins derived from members of the *Rhabdoviridae* family.

The term "heterologous membrane-associated protein" refers to a membrane-associated protein which is derived from a virus which is not a member of the same viral class or family as that from which the nucleocapsid protein of the vector particle is derived. "Viral class or family" refers to the taxonomic rank of class or family, as assigned by the International Committee on Taxonomy of Viruses.

The term "Rhabdoviridae" refers to a family of enveloped RNA viruses that infect animals, including humans, and plants. The Rhabdoviridae family encompasses the genus Vesiculovirus which includes vesicular stomatitis virus (VSV), Cocal virus, Piry virus, Chandipura virus, and Spring viremia of carp virus (sequences encoding the Spring viremia of carp virus are available under GenBank accession number U18101). The G proteins of viruses in the Vesiculovirus genera are virally-encoded integral membrane proteins that form externally projecting homotrimeric spike glycoproteins complexes that are required for receptor binding and membrane fusion. The G proteins of viruses in the Vesiculovirus genera have a covalently bound palmititic acid ($C_{16}$) moiety. The amino acid sequences of the G proteins from the Vesiculoviruses are fairly well conserved. For example, the Piry virus G protein share about 38% identity and about 55% similarity with the VSV G proteins (several strains of VSV are known, e.g., Indiana, New Jersey, Orsay, San Juan, etc., and their G proteins are highly homologous). The Chandipura virus G protein and the VSV G proteins share about 37% identity and 52% similarity. Given the high degree of conservation (amino acid sequence) and the related functional characteristics (e.g., binding of the virus to the host cell and fusion of membranes, including syncytia formation) of the G proteins of the Vesiculoviruses, the G proteins from non-VSV Vesiculoviruses may be used in place of the VSV G protein for the pseudotyping of viral particles. The G proteins of the Lyssa viruses (another genera within the *Rhabdoviridae* family) also share a fair degree of conservation with the VSV G proteins and function in a similar manner (e.g., mediate fusion of membranes) and therefore may be used in place of the VSV G protein for the pseudotyping of viral particles. The Lyssa viruses include the Mokola virus and the Rabies viruses (several strains of Rabies virus are known and their G proteins have been cloned and sequenced). The Mokola virus G protein shares stretches of homology (particularly over the extracellular and transmembrane domains) with the VSV G proteins which show about 31% identity and 48% similarity with the VSV G proteins. Preferred G proteins share at least 25% identity, preferably at least 30% identity and most preferably at least 35% identity with the VSV G proteins. The VSV G protein from which New Jersey strain (the sequence of this G protein is provided in GenBank accession numbers M27165 and M21557) is employed as the reference VSV G protein.

As used herein, the term "lentivirus vector" refers to retroviral vectors derived from the *Lentiviridae* family (e.g., human immunodeficiency virus, simian immunodeficiency virus, equine infectious anemia virus, and caprine arthritis-encephalitis virus) that are capable of integrating into non-dividing cells (See, e.g., U.S. Pat. Nos. 5,994,136 and 6,013,516, both of which are incorporated herein by reference).

The term "pseudotyped lentivirus vector" refers to lentivirus vector containing a heterologous membrane protein (e.g., a viral envelope glycoprotein or the G proteins of viruses in the *Rhabdoviridae* family such as VSV, Piry, Chandipura and Mokola).

As used herein, the term "transposon" refers to transposable elements (e.g., Tn5, Tn7, and Tn10) that can move or transpose from one position to another in a genome. In general, the transposition is controlled by a transposase. The term "transposon vector," as used herein, refers to a vector encoding a nucleic acid of interest flanked by the terminal ends of transposon. Examples of transposon vectors include, but are not limited to, those described in U.S. Pat. Nos. 6,027,722; 5,958,775; 5,968,785; 5,965,443; and 5,719,055, all of which are incorporated herein by reference.

As used herein, the term "adeno-associated virus (AAV) vector" refers to a vector derived from an adeno-associated virus serotype, including without limitation, AAV-1, AAV-2, AAV-3, AAV-4, AAV-5, AAVX7, etc. AAV vectors can have one or more of the AAV wild-type genes deleted in whole or in part, preferably the rep and/or cap genes, but retain functional flanking ITR sequences.

AAV vectors can be constructed using recombinant techniques that are known in the art to include one or more heterologous nucleotide sequences flanked on both ends (5' and 3') with functional AAV ITRs. In the practice of the invention, an AAV vector can include at least one AAV ITR and a suitable promoter sequence positioned upstream of the heterologous nucleotide sequence and at least one AAV ITR positioned downstream of the heterologous sequence. A "recombinant AAV vector plasmid" refers to one type of recombinant AAV vector wherein the vector comprises a plasmid. As with AAV vectors in general, 5' and 3' ITRs flank the selected heterologous nucleotide sequence.

AAV vectors can also include transcription sequences such as polyadenylation sites, as well as selectable markers or reporter genes, enhancer sequences, and other control elements which allow for the induction of transcription. Such control elements are described above.

As used herein, the term "AAV virion" refers to a complete virus particle. An AAV virion may be a wild type AAV virus particle (comprising a linear, single-stranded AAV nucleic acid genome associated with an AAV capsid, i.e., a protein coat), or a recombinant AAV virus particle (described below). In this regard, single-stranded AAV nucleic acid molecules (either the sense/coding strand or the antisense/anticoding strand as those terms are generally defined) can be packaged into an AAV virion; both the sense and the antisense strands are equally infectious.

As used herein, the term "recombinant AAV virion" or "rAAV" is defined as an infectious, replication-defective virus composed of an AAV protein shell encapsidating (i.e., surrounding with a protein coat) a heterologous nucleotide sequence, which in turn is flanked 5' and 3' by AAV ITRs. A number of techniques for constructing recombinant AAV virions are known in the art (See, e.g., U.S. Pat. No. 5,173,414; WO 92/01070; WO 93/03769; Lebkowski et al., Molec. Cell. Biol. 8:3988–3996 [1988]; Vincent et al., Vaccines 90 [1990] (Cold Spring Harbor Laboratory Press); Carter, Current Opinion in Biotechnology 3:533–539 [1992]; Muzyczka, Current Topics in Microbiol. and Immunol. 158:97–129 [1992]; Kotin, Human Gene Therapy 5:793–801 [1994]; Shelling and Smith, Gene Therapy 1:165–169 [1994]; and Zhou et al., J. Exp. Med. 179:1867–1875 [1994], all of which are incorportaed herein by reference).

Suitable nucleotide sequences for use in AAV vectors (and, indeed, any of the vectors described herein) include any functionally relevant nucleotide sequence. Thus, the AAV vectors of the present invention can comprise any desired gene that encodes a protein that is defective or missing from a target cell genome or that encodes a non-native protein having a desired biological or therapeutic effect (e.g., an antiviral function), or the sequence can correspond to a molecule having an antisense or ribozyme function. Suitable genes include those used for the treatment of inflammatory diseases, autoimmune, chronic and infectious diseases, including such disorders as AIDS, cancer, neurological diseases, cardiovascular disease, hypercholestemia; various blood disorders including various anemias, thalasemias and hemophilia; genetic defects such as cystic fibrosis, Gaucher's Disease, adenosine deaminase (ADA) deficiency, emphysema, etc. A number of antisense oligonucleotides (e.g., short oligonucleotides complementary to sequences around the translational initiation site (AUG codon) of an mRNA) that are useful in antisense therapy for cancer and for viral diseases have been described in the art. (See, e.g., Han et al., Proc. Natl. Acad. Sci. USA 88:4313–4317 [1991]; Uhlmann et al., Chem. Rev. 90:543–584 [1990]; Helene et al., Biochim. Biophys. Acta. 1049:99–125 [1990]; Agarwal et al., Proc. Natl. Acad. Sci. USA 85:7079–7083 [1989]; and Heikkila et al., Nature 328:445–449 [1987]). For a discussion of suitable ribozymes, see, e.g., Cech et al. (1992) J. Biol. Chem. 267:17479–17482 and U.S. Pat. No. 5,225,347, incorporated herein by reference.

By "adeno-associated virus inverted terminal repeats" or "AAV ITRs" is meant the art-recognized palindromic regions found at each end of the AAV genome which function together in cis as origins of DNA replication and as packaging signals for the virus. For use with the present invention, flanking AAV ITRs are positioned 5' and 3' of one or more selected heterologous nucleotide sequences and, together with the rep coding region or the Rep expression product, provide for the integration of the selected sequences into the genome of a target cell.

The nucleotide sequences of AAV ITR regions are known (See, e.g., Kotin, Human Gene Therapy 5:793–801 [1994]; Berns, K. I. "Parvoviridae and their Replication" in Fundamental Virology, 2nd Edition, (B. N. Fields and D. M. Knipe, eds.) for the AAV-2 sequence. As used herein, an "AAV ITR" need not have the wild-type nucleotide sequence depicted, but may be altered, e.g., by the insertion, deletion or substitution of nucleotides. Additionally, the AAV ITR may be derived from any of several AAV serotypes, including without limitation, AAV-1, AAV-2, AAV-3, AAV-4, AAV-5, AAVX7, etc. The 5' and 3' ITRs which flank a selected heterologous nucleotide sequence need not necessarily be identical or derived from the same AAV serotype or isolate, so long as they function as intended, i.e., to allow for the integration of the associated heterologous sequence into the target cell genome when the rep gene is present (either on the same or on a different vector), or when the Rep expression product is present in the target cell.

As used herein the term, the term "in vitro" refers to an artificial environment and to processes or reactions that occur within an artificial environment. In vitro environments can consist of, but are not limited to, test tubes and cell cultures. The term "in vivo" refers to the natural environment (e.g., an animal or a cell) and to processes or reaction that occur within a natural environment.

As used herein, the term "clonally derived" refers to a cell line that it derived from a single cell.

As used herein, the term "non-clonally derived" refers to a cell line that is derived from more than one cell.

As used herein, the term "passage" refers to the process of diluting a culture of cells that has grown to a particular density or confluency (e.g., 70% or 80% confluent), and then allowing the diluted cells to regrow to the particular density or confluency desired (e.g., by replating the cells or establishing a new roller bottle culture with the cells.

As used herein, the term "stable," when used in reference to genome, refers to the stable maintenance of the information content of the genome from one generation to the next, or, in the particular case of a cell line, from one passage to the next. Accordingly, a genome is considered to be stable if no gross changes occur in the genome (e.g., a gene is deleted or a chromosomal translocation occurs). The term "stable" does not exclude subtle changes that may occur to the genome such as point mutations.

As used herein, the term "response," when used in reference to an assay, refers to the generation of a detectable signal (e.g., accumulation of reporter protein, increase in ion concentration, accumulation of a detectable chemical product).

As used herein, the term "membrane receptor protein" refers to membrane spanning proteins that bind a ligand (e.g., a hormone or neurotransmitter). As is known in the art, protein phosphorylation is a common regulatory mechanism used by cells to selectively modify proteins carrying regulatory signals from outside the cell to the nucleus. The proteins that execute these biochemical modifications are a group of enzymes known as protein kinases. They may further be defined by the substrate residue that they target for phosphorylation. One group of protein kinases are the tyrosine kinases (TKs) which selectively phosphorylate a target protein on its tyrosine residues. Some tyrosine kinases are membrane-bound receptors (RTKs), and, upon activation by a ligand, can autophosphorylate as well as modify substrates. The initiation of sequential phosphorylation by ligand stimulation is a paradigm that underlies the action of such effectors as, for example, epidermal growth factor (EGF), insulin, platelet-derived growth factor (PDGF), and fibroblast growth factor (FGF). The receptors for these ligands are tyrosine kinases and provide the interface between the binding of a ligand (hormone, growth factor) to a target cell and the transmission of a signal into the cell by the activation of one or more biochemical pathways. Ligand binding to a receptor tyrosine kinase activates its intrinsic enzymatic activity (See, e.g., Ullrich and Schlessinger, Cell 61:203–212 [1990]). Tyrosine kinases can also be cytoplasmic, non-receptor-type enzymes and act as a downstream component of a signal transduction pathway.

As used herein, the term "signal transduction protein" refers to a proteins that are activated or otherwise effected by ligand binding to a membrane receptor protein or some other stimulus. Examples of signal transduction protein include adenyl cyclase, phospholipase C, and G-proteins. Many membrane receptor proteins are coupled to G-proteins (i.e., G-protein coupled receptors (GPCRs); for a review, see Neer, 1995, Cell 80:249–257 [1995]).

Typically, GPCRs contain seven transmembrane domains. Putative GPCRs can be identified on the basis of sequence homology to known GPCRs.

GPCRs mediate signal transduction across a cell membrane upon the binding of a ligand to an extracellular portion of a GPCR. The intracellular portion of a GPCR interacts with a G-protein to modulate signal transduction from outside to inside a cell. A GPCR is therefore said to be "coupled" to a G-protein. G-proteins are composed of three polypeptide subunits: an a subunit, which binds and hydrolyses GTP, and a dimeric $\beta\gamma$ subunit. In the basal, inactive state, the G-protein exists as a heterotrimer of the $\alpha$ and $\beta\gamma$ subunits. When the G-protein is inactive, guanosine diphosphate (GDP) is associated with the $\alpha$ subunit of the G-protein. When a GPCR is bound and activated by a ligand, the GPCR binds to the G-protein heterotrimer and decreases the affinity of the G$\alpha$ subunit for GDP. In its active state, the G subunit exchanges GDP for guanine triphosphate (GTP) and active G$\alpha$ subunit disassociates from both the receptor and the dimeric $\beta\gamma$ subunit. The disassociated, active Ga subunit transduces signals to effectors that are "downstream" in the G-protein signalling pathway within the cell. Eventually, the G-protein's endogenous GTPase activity returns active G subunit to its inactive state, in which it is associated with GDP and the dimeric $\beta\gamma$ subunit.

Numerous members of the heterotrimeric G-protein family have been cloned, including more than 20 genes encoding various Ga subunits. The various G subunits have been categorized into four families, on the basis of amino acid sequences and functional homology.

These four families are termed $G\alpha_s$, $G\alpha_i$, $G\alpha_q$, and $G\alpha_{12}$. Functionally, these four families differ with respect to the intracellular signaling pathways that they activate and the GPCR to which they couple.

For example, certain GPCRs normally couple with $G\alpha_s$ and, through $G\alpha_s$, these GPCRs stimulate adenylyl cyclase activity. Other GPCRs normally couple with $GG\alpha_q$, and through $GG\alpha_q$, these GPCRs can activate phospholipase C (PLC), such as the $\beta$ isoform of phospholipase C (i.e., PLC), Stermweis and Smrcka, Trends in Biochem. Sci. 17:502–506 [1992]).

As used herein, the term "nucleic acid binding protein" refers to proteins that bind to nucleic acid, and in particular to proteins that cause increased (i.e., activators or transcription factors) or decreased (i.e., inhibitors) transcription from a gene.

As used herein, the term "ion channel protein" refers to proteins that control the ingress or egress of ions across cell membranes. Examples of ion channel proteins include, but are not limited to, the $Na^+$—$K^+$ ATPase pump, the $Ca^{2+}$ pump, and the $K^+$ leak channel.

As used herein, the term "protein kinase" refers to proteins that catalyze the addition of a phosphate group from a nucleoside triphosphate to an amino acid side chain in a protein. Kinases comprise the largest known enzyme superfamily and vary widely in their target proteins. Kinases may be categorized as protein tyrosine kinases (PTKs), which phosphorylate tyrosine residues, and protein serine/threonine kinases (STKs), which phosphorylate serine and/or threonine residues. Some kinases have dual specificity for both serine/threonine and tyrosine residues. Almost all kinases contain a conserved 250–300 amino acid catalytic domain. This domain can be further divided into 11 subdomains. N-terminal subdomains I–IV fold into a two-lobed structure which binds and orients the ATP donor molecule, and subdomain V spans the two lobes. C-terminal subdomains VI–XI bind the protein substrate and transfer the gamma phosphate from ATP to the hydroxyl group of a serine, threonine, or tyrosine residue. Each of the 11 subdomains contains specific catalytic residues or amino acid motifs characteristic of that subdomain. For example, subdomain I contains an 8-amino acid glycine-rich ATP binding consensus motif, subdomain II contains a critical lysine residue required for maximal catalytic activity, and subdomains VI through IX comprise the highly conserved catalytic core. STKs and PTKs also contain distinct sequence motifs in subdomains VI and VIII which may confer hydroxyamino acid specificity. Some STKs and PTKs possess structural characteristics of both families. In addition, kinases may also be classified by additional amino acid sequences, generally between 5 and 100 residues, which either flank or occur within the kinase domain.

Non-transmembrane PTKs form signaling complexes with the cytosolic domains of plasma membrane receptors. Receptors that signal through non-transmembrane PTKs include cytokine, hormone, and antigen-specific lymphocytic receptors. Many PTKs were first identified as oncogene products in cancer cells in which PTK activation was no longer subject to normal cellular controls. In fact, about one third of the known oncogenes encode PTKs. Furthermore, cellular transformation (oncogenesis) is often accompanied by increased tyrosine phosphorylation activity (See, e.g., Carbonneau, H. and Tonks, Annu. Rev. Cell Biol. 8:463–93 [1992]). Regulation of PTK activity may therefore be an important strategy in controlling some types of cancer.

Examples of protein kinases include, but are not limited to, cAMP-dependent protein kinase, protein kinase C, and cyclin-dependent protein kinases (See, e.g., U.S. Pat. Nos. 6,034,228; 6,030,822; 6,030,788; 6,020,306; 6,013,455; 6,013,464; and 6,015,807, all of which are incorporated herein by reference).

As used herein, the term "protein phosphatase" refers to proteins that remove a phosphate group from a protein. Protein phosphatases are generally divided into two groups, receptor and non-receptor type proteins. Most receptor-type protein tyrosine phosphatases contain two conserved catalytic domains, each of which encompasses a segment of 240 amino acid residues. (See, e.g., Saito et al., Cell Growth and Diff. 2:59–65 [1991]).

Receptor protein tyrosine phosphatases can be subclassified further based upon the amino acid sequence diversity of their extracellular domains. (See, e.g., Krueger et al., Proc. Natl. Acad. Sci. USA 89:7417–7421 [1992]). Examples of protein phosphatases include, but are not limited to, cdc25 a, b, and c, PTP20, PTPID, and PTPλ. (See, e.g., U.S. Pat. Nos. 5,976,853; 5,994,074; 6,004,791; 5,981,251; 5,976,852; 5,958,719; 5,955,592; and 5,952,212, all of which are incorporated herein by reference).

As used herein, the term "protein encoded by an oncogene" refers to proteins that cause, either directly or indirectly, the neoplastic transformation of a host cell. Examples of oncogenes include, but are not limited to, the following genes: src, fps, fes, fgr, ros, H-ras, abl, ski, erbA, erbB, fms, fos, mos, sis, myc, myb, rel, kit, raf K-ras, and ets.

As used herein, the term "immunoglobulin" refers to proteins which bind a specific antigen. Immunoglobulins include, but are not limited to, polyclonal, monoclonal, chimeric, and humanized antibodies, Fab fragments, F(ab')$_2$ fragments, and includes immunoglobulins of the following classes: IgG, IgA, IgM, IgD, IbE, and secreted immunoglobulins (sig). Immunoglobulins generally comprise two identical heavy chains ($\gamma$, $\alpha$, $\mu$, $\delta$, or $\epsilon$) and two light chains ($\kappa$ or $\lambda$).

As used herein, the term "antigen binding protein" refers to proteins which bind to a specific antigen. "Antigen binding proteins" include, but are not limited to, immunoglobulins, including polyclonal, monoclonal, chimeric, and humanized antibodies; Fab fragments, F(ab')$_2$ fragments, and Fab expression libraries; and single chain antibodies. Various procedures known in the art are used for the production of polyclonal antibodies. For the production of an antibody, various host animals can be immunized by injection with the peptide corresponding to the desired epitope including but not limited to rabbits, mice, rats, sheep, goats, etc. In a preferred embodiment, the peptide is conjugated to an immunogenic carrier (e.g., diphtheria toxoid, bovine serum albumin (BSA), or keyhole limpet hemocyanin (KLH)). Various adjuvants are used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (Bacille Calmette-Guerin) and *Corynebacterium parvum*.

For preparation of monoclonal antibodies, any technique that provides for the production of antibody molecules by continuous cell lines in culture may be used (See, e.g., Harlow and Lane, Antibodies: A Laboratory Manual, Cold Spring Harbor Laboratory Press, Cold Spring Harbor, N.Y.). These include, but are not limited to, the hybridoma technique originally developed by Köhler and Milstein (Köhler and Milstein, Nature 256:495–497 [1975]), as well as the trioma technique, the human B-cell hybridoma technique (See e.g., Kozbor et al. Immunol. Today 4:72 [1983]), and the EBV-hybridoma technique to produce human monoclonal antibodies (Cole et al., in *Monoclonal Antibodies and Cancer Therapy*, Alan R. Liss, Inc., pp. 77–96 [1985]).

According to the invention, techniques described for the production of single chain antibodies (U.S. Pat. No. 4,946,778; herein incorporated by reference) can be adapted to produce specific single chain antibodies as desired. An additional embodiment of the invention utilizes the techniques known in the art for the construction of Fab expression libraries (Huse et al., Science 246:1275–1281 [1989]) to allow rapid and easy identification of monoclonal Fab fragments with the desired specificity.

Antibody fragments that contain the idiotype (antigen binding region) of the antibody molecule can be generated by known techniques. For example, such fragments include but are not limited to: the F(ab')$_2$ fragment that can be produced by pepsin digestion of an antibody molecule; the Fab' fragments that can be generated by reducing the disulfide bridges of an F(ab')$_2$ fragment, and the Fab fragments that can be generated by treating an antibody molecule with papain and a reducing agent.

Genes encoding antigen binding proteins can be isolated by methods known in the art. In the production of antibodies, screening for the desired antibody can be accomplished by techniques known in the art (e.g., radioimmunoassay, ELISA (enzyme-linked immunosorbant assay), "sandwich" immunoassays, immunoradiometric assays, gel diffusion precipitin reactions, immunodiffusion assays, in situ immunoassays (using colloidal gold, enzyme or radioisotope labels, for example), Western Blots, precipitation reactions, agglutination assays (e.g., gel agglutination assays, hemagglutination assays, etc.), complement fixation assays, immunofluorescence assays, protein A assays, and immunoelectrophoresis assays, etc.) etc.

As used herein, the term "reporter gene" refers to a gene encoding a protein that may be assayed. Examples of reporter genes include, but are not limited to, luciferase (See, e.g., deWet et al., Mol. Cell. Biol. 7:725 [1987] and U.S. Pat Nos. 6,074,859; 5,976,796; 5,674,713; and 5,618,682; all of which are incorporated herein by reference), green fluorescent protein (e.g., GenBank Accession Number U43284; a number of GFP variants are commercially available from CLONTECH Laboratories, Palo Alto, Calif.), chloramphenicol acetyltransferase, β-galactosidase, alkaline phosphatase, and horse radish peroxidase.

As used herein, the term "purified" refers to molecules, either nucleic or amino acid sequences, that are removed from their natural environment, isolated or separated. An "isolated nucleic acid sequence" is therefore a purified nucleic acid sequence. "Substantially purified" molecules are at least 60% free, preferably at least 75% free, and more preferably at least 90% free from other components with which they are naturally associated.

The term "test compound" refers to any chemical entity, pharmaceutical, drug, and the like contemplated to be useful in the treatment and/or prevention of a disease, illness, sickness, or disorder of bodily function, or otherwise alter the physiological or cellular status of a sample. Test compounds comprise both known and potential therapeutic compounds. A test compound can be determined to be therapeutic by screening using the screening methods of the present invention. A "known therapeutic compound" refers to a therapeutic compound that has been shown (e.g., through animal trials or prior experience with administration to humans) to be effective in such treatment or prevention.

DETAILED DESCRIPTION OF THE INVENTION

The present invention relates to the production of proteins in host cells, and more particularly to host cells containing multiple integrated copies of an integrating vector. The present invention utilizes integrating vectors (i.e., vectors that integrate via an integrase or transposase) to create cell lines containing a high copy number of a nucleic acid encoding a gene of interest. The transfected genomes of the high copy number cells are stable through repeated passages (e.g., at least 10 passages, preferably at least 50 passages, and most preferably at least 100 passages). Furthermore, the host cells of the present invention are capable of producing high levels of protein (e.g., more than 1 µg/cell/day, preferably more than 10 µg/cell/day, more preferably more than 50 µg/cell/day, and most preferably more than 100 µg/cell/day.)

The genomic stability and high expression levels of the host cells of the present invention provide distinct advantages over previously described methods of cell culture. For example, mammalian cell lines containing multiple copies of genes are known in the art to be intrinsically unstable. Indeed, this instability is a recognized problem facing researchers desiring to use mammalian cell lines for various purposes, including high throughput screening assays (See, e.g., Sittampalam et al., Curr. Opin. Chem. Biol. 1(3):384–91 [1997]).

It is not intended that the present invention be limited to particular mechanism of action. Indeed, an understanding of the mechanism is not necessary to make and use the present invention. However, the high genomic stability and protein expression levels of the host cells of the present invention are thought to be due to unique properties of the integrating vectors (e.g., retroviral vectors). For example, it is known that retroviruses are inherited elements in the germ line of many organisms. Indeed, as much as 5–10% of the mammalian genome may consist of elements contributed by reverse transcription, indicating a high degree of stability. Likewise, many of these types of vectors target active (e.g., DNase I hypersensitive sites) transcriptional sites in the genome.

Many investigations have focused on the deleterious effects of retroviral and transposon integration. The property of targeting active regions of the genome has led to the use of retroviral vectors and transposon vectors in promoter trap schemes and for saturation mutagenesis (See, e.g., U.S. Pat. Nos. 5,627,058 and 5,922,601, all of which are herein incorporated by reference). In promoter trap schemes, the cells are infected with a promoterless reporter vector. If the promoterless vector integrates downstream of a promoter (i.e., into a gene), the reporter gene encoded by the vector is activated. The promoter can then be cloned and further characterized.

As can be seen, these schemes rely on the disruption of an endogenous gene. Therefore, it is surprising that the methods of the present invention, which utilize integrating vectors at high multiplicities of infection that would normally be thought to lead to gene disruption, led to the development of stable cell lines that express high quantities of a protein of interest. The development of these cell lines is described more fully below. The description is divided into the following sections: I) Host Cells; II) Vectors and Methods of Transfection; and III) Uses of Transfected Host Cells.

I. Host Cells

The present invention contemplates the transfection of a variety of host cells with integrating vectors. A number of mammalian host cell lines are known in the art. In general, these host cells are capable of growth and survival when placed in either monolayer culture or in suspension culture in a medium containing the appropriate nutrients and growth factors, as is described in more detail below. Typically, the cells are capable of expressing and secreting large quantities of a particular protein of interest into the culture medium. Examples of suitable mammalian host cells include, but are not limited to Chinese hamster ovary cells (CHO-K1, ATCC CCl-61); bovine mammary epithelial cells (ATCC CRL 10274; bovine mammary epithelial cells); monkey kidney CV1 line transformed by SV40 (COS-7, ATCC CRL 1651); human embryonic kidney line (293 or 293 cells subcloned for growth in suspension culture; see, e.g., Graham et al., J. Gen Virol., 36:59 [1977]); baby hamster kidney cells (BHK, ATCC CCL 10); mouse sertoli cells (TM4, Mather, Biol. Reprod. 23:243–251 [1980]); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TR1 cells (Mather et al., Annals N.Y. Acad. Sci., 383:44–68 [1982]); MRC 5 cells; FS4 cells; rat fibroblasts (208F cells); MDBK cells (bovine kidney cells); and a human hepatoma line (Hep G2).

In addition to mammalian cell lines, the present invention also contemplates the transfection of plant protoplasts with integrating vectors at a low or high multiplicity of infection. For example, the present invention contemplates a plant cell or whole plant comprising at least one integrated integrating vector, preferably a retroviral vector, and most preferably a pseudotyped retroviral vector. All plants that can be produced by regeneration from protoplasts can also be transfected using the process according to the invention (e.g., cultivated plants of the genera *Solanum, Nicotiana, Brassica, Beta, Pisum, Phaseolus, Glycine, Helianthus, Allium, Avena, Hordeum, Oryzae, Setaria, Secale, Sorghum, Triticum, Zea, Musa, Cocos, Cydonia, Pyrus, Malus, Phoenix, Elaeis, Rubus, Fragaria, Prunus, Arachis, Panicum, Saccharum, Coffea, Camellia, Ananas, Vitis* or *Citrus*). In general, protoplasts are produced in accordance with conventional methods (See, e.g., U.S. Pat. Nos. 4,743,548; 4,677,066, 5,149,645; and 5,508,184; all of which are incorporated herein by reference). Plant tissue may be dispersed in an appropriate medium having an appropriate osmotic potential (e.g., 3 to 8 wt. % of a sugar polyol) and one or more polysaccharide hydrolases (e.g., pectinase, cellulase, etc.), and the cell wall degradation allowed to proceed for a sufficient time to provide protoplasts. After filtration the protoplasts may be isolated by centrifugation and may then be resuspended for subsequent treatment or use. Regeneration of protoplasts kept in culture to whole plants is performed by methods known in the art (See, e.g., Evans et al., *Handbook of Plant Cell Culture,* 1: 124–176, MacMillan Publishing Co., New York [1983]; Binding, *Plant Protoplasts, p.* 21–37, CRC Press, Boca Raton [1985]) and Potrykus and Shillito, *Methods in Enzymology, Vol.* 118, Plant Molecular Biology, A. and H. Weissbach eds., Academic Press, Orlando [1986]).

The present invention also contemplates the use of amphibian and insect host cell lines. Examples of suitable insect host cell lines include, but are not limited to, mosquito cell lines (e.g., ATCC CRL-1660). Examples of suitable amphibian host cell lines include, but are not limited to, toad cell lines (e.g., ATCC CCL-102).

II. Vectors and Methods for Transfection

According to the present invention, host cells such as those described above are transduced or transfected with integrating vectors. Examples of integrating vectors include, but are not limited to, retroviral vectors, lentiviral vectors, adeno-associated viral vectors, and transposon vectors. The design, production, and use of these vectors in the present invention is described below.

A. Retroviral Vectors

Retroviruses (family *Retroviridae*) are divided into three groups: the spumaviruses (e.g., human foamy virus); the lentiviruses (e.g., human immunodeficiency virus and sheep visna virus) and the oncoviruses (e.g., MLV, Rous sarcoma virus).

Retroviruses are enveloped (i.e., surrounded by a host cell-derived lipid bilayer membrane) single-stranded RNA viruses which infect animal cells. When a retrovirus infects a cell, its RNA genome is converted into a double-stranded linear DNA form (i.e., it is reverse transcribed). The DNA form of the virus is then integrated into the host cell genome as a provirus. The provirus serves as a template for the production of additional viral genomes and viral mRNAs. Mature viral particles containing two copies of genomic RNA bud from the surface of the infected cell. The viral particle comprises the genomic RNA, reverse transcriptase and other pol gene products inside the viral capsid (which contains the viral gag gene products) which is surrounded by a lipid bilayer membrane derived from the host cell containing the viral envelope glycoproteins (also referred to as membrane-associated proteins).

The organization of the genomes of numerous retroviruses is well known to the art and this has allowed the adaptation of the retroviral genome to produce retroviral vectors. The production of a recombinant retroviral vector carrying a gene of interest is typically achieved in two stages.

First, the gene of interest is inserted into a retroviral vector which contains the sequences necessary for the efficient expression of the gene of interest (including promoter and/or enhancer elements which may be provided by the viral long terminal repeats (LTRs) or by an internal promoter/enhancer and relevant splicing signals), sequences required for the efficient packaging of the viral RNA into infectious virions (e.g., the packaging signal (Psi), the tRNA primer binding site (—PBS), the 3' regulatory sequences required for reverse transcription (+PBS)) and the viral LTRs. The LTRs contain sequences required for the association of viral genomic RNA, reverse transcriptase and integrase functions, and sequences involved in directing the expression of the genomic RNA to be packaged in viral particles. For safety reasons, many recombinant retroviral vectors lack functional copies of the genes which are essential for viral replication (these essential genes are either deleted or disabled); therefore, the resulting virus is said to be replication defective.

Second, following the construction of the recombinant vector, the vector DNA is introduced into a packaging cell line. Packaging cell lines provide proteins required in trans for the packaging of the viral genomic RNA into viral particles having the desired host range (i.e., the viral-encoded gag, pol and env proteins). The host range is controlled, in part, by the type of envelope gene product expressed on the surface of the viral particle. Packaging cell lines may express ecotrophic, amphotropic or xenotropic envelope gene products. Alternatively, the packaging cell line may lack sequences encoding a viral envelope (env) protein. In this case the packaging cell line will package the viral genome into particles which lack a membrane-associated protein (e.g., an env protein). In order to produce viral particles containing a membrane associated protein which will permit entry of the virus into a cell, the packaging cell line containing the retroviral sequences is transfected with sequences encoding a membrane-associated protein (e.g., the G protein of vesicular stomatitis virus (VSV)). The transfected packaging cell will then produce viral particles which contain the membrane-associated protein expressed by the transfected packaging cell line; these viral particles which contain viral genomic RNA derived from one virus encapsidated by the envelope proteins of another virus are said to be pseudotyped virus particles.

The retroviral vectors of the present invention can be further modified to include additional regulatory sequences. As described above, the retroviral vectors of the present invention include the following elements in operable association: a) a 5' LTR; b) a packaging signal; c) a 3' LTR and d) a nucleic acid encoding a protein of interest located between the 5' and 3' LTRs. In some embodiments of the present invention, the nucleic acid of interest may be arranged in opposite orientation to the 5' LTR when transcription from an internal promoter is desired. Suitable internal promoters include, but are not limited to, the alpha-lactalbumin promoter, the CMV promoter (human or ape), and the thymidine kinase promoter.

In other embodiments of the present invention, where secretion of the protein of interest is desired, the vectors are modified by including a signal peptide sequence in operable association with the protein of interest. The sequences of several suitable signal peptides are known to those in the art, including, but not limited to, those derived from tissue plasminogen activator, human growth hormone, lactoferrin, alpha-casein, and alpha-lactalbumin.

In other embodiments of the present invention, the vectors are modified by incorporating an RNA export element (See e.g., U.S. Pat. Nos. 5,914,267; 6,136,597; and 5,686,120; and WO99/14310, all of which are incorporated herein by reference) either 3' or 5' to the nucleic acid sequence encoding the protein of interest. It is contemplated that the use of RNA export elements allows high levels of expression of the protein of interest without incorporating splice signals or introns in the nucleic acid sequence encoding the protein of interest.

In still other embodiments, the vector further comprises at least one internal ribosome entry site (IRES) sequence. The sequences of several suitable IRES's are available, including, but not limited to, those derived from foot and mouth disease virus (FDV), encephalomyocarditis virus, and poliovirus. The IRES sequence can be interposed between two transcriptional units (e.g., nucleic acids encoding different proteins of interest or subunits of a multisubunit protein such as an antibody) to form a polycistronic sequence so that the two transcriptional units are transcribed from the sane promoter.

The retroviral vectors of the present invention may also further comprise a selectable marker allowing selection of transformed cells. A number of selectable markers find use in the present invention, including, but not limited to the bacterial aminoglycoside 3' phosphotransferase gene (also referred to as the neo gene) that confers resistance to the drug G418 in mammalian cells, the bacterial hygromycin G phosphotransferase (hyg) gene that confers resistance to the antibiotic hygromycin and the bacterial xanthine-guanine phosphoribosyl transferase gene (also referred to as the gpt gene) that confers the ability to grow in the presence of mycophenolic acid. In some embodiments, the selectable marker gene is provided as part of polycistronic sequence that also encodes the protein of interest.

In still other embodiments of the present invention, the retroviral vectors may comprise recombination elements recognized by a recombination system (e.g., the cre/loxP or flp recombinase systems, see, e.g., Hoess et al., Nucleic Acids Res. 14:2287–2300 [1986], O'Gorman et al., Science 251:1351–55 [1991], van Deursen et al., Proc. Natl. Acad. Sci. USA 92:7376–80 [1995], and U.S. Pat. No. 6,025,192, herein incorporated by reference). After integration of the vectors into the genome of the host cell, the host cell can be transiently transfected (e.g., by electroporation, lipofection, or microinjection) with either a recombinase enzyme (e.g., Cre recombinase) or a nucleic acid sequence encoding the recombinase enzyme and one or more nucleic acid sequences encoding a protein of interest flanked by sequences recognized by the recombination enzyme so that the nucleic acid sequence is inserted into the integrated vector.

Viral vectors, including recombinant retroviral vectors, provide a more efficient means of transferring genes into cells as compared to other techniques such as calcium phosphate-DNA co-precipitation or DEAE-dextran-mediated transfection, electroporation or microinjection of nucleic acids. It is believed that the efficiency of viral transfer is due in part to the fact that the transfer of nucleic acid is a receptor-mediated process (i.e., the virus binds to a specific receptor protein on the surface of the cell to be infected). In addition, the virally transferred nucleic acid once inside a cell integrates in controlled manner in contrast to the integration of nucleic acids which are not virally transferred; nucleic acids transferred by other means such as calcium phosphate-DNA co-precipitation are subject to rearrangement and degradation.

The most commonly used recombinant retroviral vectors are derived from the amphotropic Moloney murine leukemia virus (MoMLV) (See e.g., Miller and Baltimore Mol. Cell. Biol. 6:2895 [1986]). The MoMLV system has several advantages: 1) this specific retrovirus can infect many different cell types, 2) established packaging cell lines are available for the production of recombinant MoMLV viral particles and 3) the transferred genes are permanently integrated into the target cell chromosome. The established MoMLV vector systems comprise a DNA vector containing a small portion of the retroviral sequence (e.g., the viral long terminal repeat or "LTR" and the packaging or "psi" signal) and a packaging cell line. The gene to be transferred is inserted into the DNA vector. The viral sequences present on the DNA vector provide the signals necessary for the insertion or packaging of the vector RNA into the viral particle and for the expression of the inserted gene. The packaging cell line provides the proteins required for particle assembly (Markowitz et al., J. Virol. 62:1120 [1988]).

Despite these advantages, existing retroviral vectors based upon MoMLV are limited by several intrinsic problems: 1) they do not infect non-dividing cells (Miller et al., Mol. Cell. Biol. 10:4239 [1990)), except, perhaps, oocytes; 2) they produce low titers of the recombinant virus (Miller and Rosman, BioTechniques 7: 980 [1980] and Miller, Nature 357: 455 [1990]); and 3) they infect certain cell types (e.g., human lymphocytes) with low efficiency (Adams et al., Proc. Natl. Acad. Sci. USA 89:8981 [1992]). The low titers associated with MoMLV-based vectors have been attributed, at least in part, to the instability of the virus-encoded envelope protein. Concentration of retrovirus stocks by physical means (e.g., ultracentrifugation and ultrafiltration) leads to a severe loss of infectious virus.

The low titer and inefficient infection of certain cell types by MoMLV-based vectors has been overcome by the use of pseudotyped retroviral vectors which contain the G protein of VSV as the membrane associated protein. Unlike retroviral envelope proteins which bind to a specific cell surface protein receptor to gain entry into a cell, the VSV G protein interacts with a phospholipid component of the plasma membrane (Mastromarino et al., J. Gen. Virol. 68:2359 [1977]). Because entry of VSV into a cell is not dependent upon the presence of specific protein receptors, VSV has an extremely broad host range. Pseudotyped retroviral vectors bearing the VSV G protein have an altered host range characteristic of VSV (i.e., they can infect almost all species of vertebrate, invertebrate and insect cells). Importantly, VSV G-pseudotyped retroviral vectors can be concentrated 2000-fold or more by ultracentrifugation without significant loss of infectivity (Burns et al. Proc. Natl. Acad. Sci. USA 90:8033 [1993]).

The present invention is not limited to the use of the VSV G protein when a viral G protein is employed as the heterologous membrane-associated protein within a viral particle (See, e.g., U.S. Pat. No. 5,512,421, which is incorporated herein by reference). The G proteins of viruses in the Vesiculovirus genera other than VSV, such as the Piry and Chandipura viruses, that are highly homologous to the VSV G protein and, like the VSV G protein, contain covalently linked palmitic acid (Brun et al. Intervirol. 38:274 [1995] and Masters et al., Virol. 171:285 (1990]). Thus, the G protein of the Piry and Chandipura viruses can be used in place of the VSV G protein for the pseudotyping of viral particles. In addition, the VSV G proteins of viruses within the Lyssa virus genera such as Rabies and Mokola viruses show a high degree of conservation (amino acid sequence as well as functional conservation) with the VSV G proteins. For example, the Mokola virus G protein has been shown to function in a manner similar to the VSV G protein (i.e., to mediate membrane fusion) and therefore may be used in place of the VSV G protein for the pseudotyping of viral particles (Mebatsion et al., J. Virol. 69:1444 [1995]). Viral particles may be pseudotyped using either the Piry, Chandipura or Mokola G protein as described in Example 2, with the exception that a plasmid containing sequences encoding either the Piry, Chandipura or Mokola G protein under the transcriptional control of a suitable promoter element (e.g., the CMV intermediate-early promoter; numerous expression vectors containing the CMV IE promoter are available, such as the pcDNA3.1 vectors (Invitrogen)) is used in place of pHCMV-G. Sequences encoding other G proteins derived from other members of the Rhabdoviridae family may be used; sequences encoding numerous rhabdoviral G proteins are available from the GenBank database.

The majority of retroviruses can transfer or integrate a double-stranded linear form of the virus (the provirus) into the genome of the recipient cell only if the recipient cell is cycling (i.e., dividing) at the time of infection. Retroviruses which have been shown to infect dividing cells exclusively, or more efficiently, include MLV, spleen necrosis virus, Rous sarcoma virus and human immunodeficiency virus (HIV; while HIV infects dividing cells more efficiently, HIV can infect non-dividing cells).

It has been shown that the integration of MLV virus DNA depends upon the host cell's progression through mitosis and it has been postulated that the dependence upon mitosis reflects a requirement for the breakdown of the nuclear envelope in order for the viral integration complex to gain entry into the nucleus (Roe et al., EMBO J. 12:2099 [1993]). However, as integration does not occur in cells arrested in metaphase, the breakdown of the nuclear envelope alone may not be sufficient to permit viral integration; there may be additional requirements such as the state of condensation of the genomic DNA (Roe et al., supra).

B. Lentiviral Vectors

The present invention also contemplates the use of lentiviral vectors to generate high copy number cell lines. The lentiviruses (e.g., equine infectious anemia virus, caprine arthritis-encephalitis virus, human immunodeficiency virus) are a subfamily of retroviruses that are able to integrate into non-dividing cells. The lentiviral genome and the proviral DNA have the three genes found in all retroviruses: gag, pol, and env, which are flanked by two LTR sequences. The gag gene encodes the internal structural proteins (e.g., matrix, capsid, and nucleocapsid proteins); the pol gene encodes the reverse transcriptase, protease, and integrase proteins; and the pol gene encodes the viral envelope glycoproteins. The 5' and 3' LTRs control transcription and polyadenylation of the viral RNAs. Additional genes in the lentiviral genome include the vif, vpr, tat, rev, vpu, nef and vpx genes.

A variety of lentiviral vectors and packaging cell lines are known in the art and find use in the present invention (See, e.g., U.S. Pat. Nos. 5,994,136 and 6,013,516, both of which are herein incorporated by reference). Furthermore, the VSV G protein has also been used to pseudotype retroviral vectors based upon the human immunodeficiency virus (HIV) (Naldini et al., Science 272:263 [19961). Thus, the VSV G protein may be used to generate a variety of pseudotyped retroviral vectors and is not limited to vectors based on MoMLV. The lentiviral vectors may also be modified as described above to contain various regulatory sequences (e.g., signal peptide sequences, RNA export elements, and IRES's). After the lentiviral vectors are produced, they may be used to transfect host cells as described above for retroviral vectors.

C. Adeno-Associated Viral Vectors

The present invention also contemplates the use of adeno associated virus (AAV) vectors to generate high copy number cell lines. AAV is a human DNA parvovirus which belongs to the genus *Dependovirus*. The AAV genome is composed of a linear, single-stranded DNA molecule which contains approximately 4680 bases. The genome includes inverted terminal repeats (ITRs) at each end which function in cis as origins of DNA replication and as packaging signals for the virus. The internal nonrepeated portion of the genome includes two large open reading frames, known as the AAV rep and cap regions, respectively. These regions code for the viral proteins involved in replication and packaging of the virion. A family of at least four viral proteins are synthesized from the AAV rep region, Rep 78, Rep 68, Rep 52 and Rep 40, named according to their apparent molecular weight. The AAV cap region encodes at least three proteins, VP1, VP2 and VP3 (for a detailed description of the AAV genome, see e.g., Muzyczka, Current Topics Microbiol. Immunol. 158:97–129 [1992); Kotin, Human Gene Therapy 5:793–801 [1994]).

AAV requires coinfection with an unrelated helper virus, such as adenovirus, a herpesvirus or vaccinia, in order for a productive infection to occur. In the absence of such coinfection, AAV establishes a latent state by insertion of its genome into a host cell chromosome. Subsequent infection by a helper virus rescues the integrated copy which can then replicate to produce infectious viral progeny. Unlike the non-pseudotyped retroviruses, AAV has a wide host range and is able to replicate in cells from any species so long as there is coinfection with a helper virus that will also multiply in that species. Thus, for example, human AAV will replicate in canine cells coinfected with a canine adenovirus. Furthermore, unlike the retroviruses, AAV is not associated with any human or animal disease, does not appear to alter the biological properties of the host cell upon integration and is able to integrate into nondividing cells. It has also recently been found that AAV is capable of site-specific integration into a host cell genome.

In light of the above-described properties, a number of recombinant AAV vectors have been developed for gene delivery (See, e.g., U.S. Pat. Nos. 5,173,414; 5,139,941; WO 92/01070 and WO 93/03769, both of which are incorporated herein by reference; Lebkowski et al., Molec. Cell. Biol. 8:3988–3996 [1988]; Carter, B. J., Current Opinion in Biotechnology 3:533–539 [1992]; Muzyczka, Current Topics in Microbiol. and Immunol. 158:97–129 (1992]; Kotin, R. M. (1994) Human Gene Therapy 5:793–801; Shelling and Smith, Gene Therapy 1:165–169 [1994]; and Zhou et al., J. Exp. Med. 179:1867–1875 [1994]).

Recombinant AAV virions can be produced in a suitable host cell which has been transfected with both an AAV helper plasmid and an AAV vector. An AAV helper plasmid generally includes AAV rep and cap coding regions, but lacks AAV ITRs. Accordingly, the helper plasmid can neither replicate nor package itself. An AAV vector generally includes a selected gene of interest bounded by AAV ITRs which provide for viral replication and packaging functions. Both the helper plasmid and the AAV vector bearing the selected gene are introduced into a suitable host cell by transient transfection. The transfected cell is then infected with a helper virus, such as an adenovirus, which transactivates the AAV promoters present on the helper plasmid that direct the transcription and translation of AAV rep and cap regions. Recombinant AAV virions harboring the selected gene are formed and can be purified from the preparation. Once the AAV vectors are produced, they may be used to transfect (See, e.g., U.S. Pat. No. 5,843,742, herein incorporated by reference) host cells at the desired multiplicity of infection to produce high copy number host cells. As will be understood by those skilled in the art, the AAV vectors may also be modified as described above to contain various regulatory sequences (e.g., signal peptide sequences, RNA export elements, and IRES's).

D. Transposon Vectors

The present invention also contemplates the use of transposon vectors to generate high copy number cell lines. Transposons are mobile genetic elements that can move or transpose from one location another in the genome. Transposition within the genome is controlled by a transposase enzyme that is encoded by the transposon. Many examples of transposons are known in the art, including, but not limited to, Tn5 (See e.g., de la Cruz et al., J. Bact. 175; 6932–38 [1993], Tn7 (See e.g., Craig, Curr. Topics Microbiol. Immunol. 204: 27–48 [1996]), and Tn10 (See e.g., Morisato and Kleckner, Cell 51:101–111 (1987]). The ability of transposons to integrate into genomes has been utilized to create transposon vectors (See, e.g., U.S. Pat. Nos. 5,719,055; 5,968,785; 5,958,775; and 6,027,722; all of which are incorporated herein by reference.) Because transposons are not infectious, transposon vectors are introduced into host cells via methods known in the art (e.g., electroporation, lipofection, or microinjection). Therefore, the ratio of transposon vectors to host cells may be adjusted to provide the desired multiplicity of infection to produce the high copy number host cells of the present invention.

Transposon vectors suitable for use in the present invention generally comprise a nucleic acid encoding a protein of interest interposed between two transposon insertion sequences. Some vectors also comprise a nucleic acid sequence encoding a transposase enzyme. In these vectors, the one of the insertion sequences is positioned between the transposase enzyme and the nucleic acid encoding the protein of interest so that it is not incorporated into the genome of the host cell during recombination. Alternatively, the transposase enzyme may be provided by a suitable method (e.g., lipofection or microinjection). As will be understood by those skilled in the art, the transposon vectors may also be modified as described above to contain various regulatory sequences (e.g., signal peptide sequences, RNA export elements, and IRES's).

E. Transfection at High Multiplicities of Infection

Once integrating vectors (e.g., retroviral vectors) encoding a protein of interest have been produced, they may be used to transfect or transduce host cells (examples of which are described above in Section 1). Preferably, host cells are transfected or transduced with integrating vectors at a multiplicity of infection sufficient to result in the integration of at least 1, and preferably at least 2 or more retroviral vectors. In some embodiments, multiplicities of infection of from 10 to 1,000,000 may be utilized, so that the genomes of the infected host cells contain from 2 to 100 copies of the integrated vectors, and preferably from 5 to 50 copies of the integrated vectors. In other embodiments, a multiplicity of infection of from 10 to 10,000 is utilized. When non-pseudotyped retroviral vectors are utilized for infection, the host cells are incubated with the culture medium from the retroviral producers cells containing the desired titer (i.e., colony forming units, CFUs) of infectious vectors. When pseudotyped retroviral vectors are utilized, the vectors are concentrated to the appropriate titer by ultracentrifugation and then added to the host cell culture. Alternatively, the concentrated vectors can be diluted in a culture medium appropriate for the cell type. Additionally, when expression of more than one protein of interest by the host cell is desired, the host cells can be transfected with multiple vectors each containing a nucleic acid encoding a different protein of interest.

In each case, the host cells are exposed to medium containing the infectious retroviral vectors for a sufficient period of time to allow infection and subsequent integration of the vectors. In general, the amount of medium used to overlay the cells should be kept to as small a volume as possible so as to encourage the maximum amount of integration events per cell. As a general guideline, the number of colony forming units (cfu) per milliliter should be about $10^5$ to $10^7$ cfu/ml, depending upon the number of integration events desired.

The present invention is not limited to any particular mechanism of action. Indeed, an understanding of the mechanism of action is not necessary for practicing the present invention. However, the diffusion rate of the vectors is known to be very limited (See, e.g., U.S. Pat. No. 5,866,400, herein incorporated by reference, for a discussion of diffusion rates). Therefore, it is expected that the actual integration rate will be lower (and in some cases much lower) than the multiplicity of infection. Applying the equations from U.S. Pat. No. 5,866,400, a titer of 106 cfu/ml has an average vector—vector spacing of 1 micron. The diffusion time of a MMLV vector across 100 microns is approximately 20 minutes. Accordingly, the vector can travel approximately 300 microns in one hour. If 1000 cells are plated in a T25 flask, the cells are spaced 2.5 mm apart on average. Using these values, the only 56 viral particles would be expected to contact a given cell within an hour. The Table below provides the expected contact rate for a given number of cells in a T25 flask with a particular vector titer. However, as shown below in the examples, the actual number of integrations obtained is much lower than may be predicted by these equations.

| Vector Contact Frequency As A Function of Time and Cell Spacing | | | |
| --- | --- | --- | --- |
| Vector Titer | Cells/T25 Flask | MOI | Contacts/Hour |
| $10^6$ | 1000 | 1,000 | 56 |
| $10^6$ | 100 | 10,000 | <56 |
| $10^5$ | 1000 | 100 | 5.6 |
| $10^4$ | 1000 | 10 | 0.6 |

Accordingly, it is contemplated that the actual integration rate is dependent not only on the multiplicity of infection, but also on the contact time (i.e., the length of time the host cells are exposed to infectious vector), the confluency or geometry of the host cells being transfected, and the volume of media that the vectors are contained in. It is contemplated that these conditions can be varied as taught herein to produce host cell lines containing multiple integrated copies of integrating vectors. As demonstrated in Examples 8 and 9, MOI can be varied by either holding the number of cells constant and varying CFU's (Example 9), or by holding CFU's constant and varying cell number (Example 8). In some embodiments, after transfection or transduction, the cells are allowed to multiply, and are then trypsinized and replated. Individual colonies are then selected to provide clonally selected cell lines. In still further embodiments, the clonally selected cell lines are screened by Southern blotting or INVADER assay to verify that the desired number of integration events has occurred. It is also contemplated that clonal selection allows the identification of superior protein producing cell lines. In other embodiments, the cells are not clonally selected following transfection.

In some embodiments, the host cells are transfected with vectors encoding different proteins of interest. The vectors encoding different proteins of interest can be used to transfect the cells at the same time (e.g., the host cells are exposed to a solution containing vectors encoding different proteins of interest) or the transfection can be serial (e.g., the host cells are first transfected with a vector encoding a first protein of interest, a period of time is allowed to pass, and the host cells are then transfected with a vector encoding a second protein of interest). In some preferred embodiments, the host cells are transfected with an integrating vector encoding a first protein of interest, high expressing cell lines containing multiple integrated copies of the integrating vector are selected (e.g., clonally selected), and the selected cell line is transfected with an integrating vector encoding a second protein of interest. This process may be repeated to introduce multiple proteins of interest. In some embodiments, the multiplicities of infection may be manipulated (e.g., increased or decreased) to increase or decrease the expression of the protein of interest. Likewise, the different promoters may be utilized to vary the expression of the proteins of interest. It is contemplated that these transfection methods can be used to construct host cell lines containing an entire exogenous metabolic pathway or to provide host cells with an increased capability to process proteins (e.g., the host cells can be provided with enzymes necessary for post-translational modification).

In still further embodiments, cell lines are serially transfected with vectors encoding the same gene. In some preferred embodiments, the host cells are transfected (e.g., at an MOI of about 10 to 100,000, preferably 100 to 10,000) with an integrating vector encoding a protein of interest, cell lines containing single or multiple integrated copies of the integrating vector or expressing high levels of the desired protein are selected (e.g., clonally selected), and the selected cell line is retransfected with the vector (e.g., at an MOI of about 10 to 100,000, preferably 100 to 10,000). In some embodiments, cell lines comprising at least two integrated copies of the vector are identified and selected. This process may be repeated multiple times until the desired level of protein expression is obtained and may also be repeated to introduce vectors encoding multiple proteins of interest. Unexpectedly, serial transfection with the same gene results in increases in protein production from the resulting cells that are not merely additive.

III. Uses of Transfected Host Cells

The host cells transfected at a high multiplicity of infection can be used for a variety of purposes. First, the host cells find use in the production of proteins for pharmaceutical, industrial, diagnostic, and other purposes. Second, host cells expressing a particular protein or proteins find use in screening assays (e.g., high throughput screening). Third, the host cells find use in the production of multiple variants of proteins, followed by analysis of the activity of the protein variants. Each of these uses is explained in more detail below.

A. Production of Proteins

It is contemplated that the host cells of the present invention find use in the production of proteins for pharmaceutical, industrial, diagnostic, and other uses. The present invention is not limited to the production of any particular protein. Indeed, the production of a wide variety of proteins is contemplated, including, but not limited to, erythropoietin, alpha-interferon, alpha-I proteinase inhibitor, angiogenin, antithrombin III, beta-acid decarboxylase, human growth hormone, bovine growth hormone, porcine growth hormone, human serum albumin, beta-interferon, calf intestine alkaline phosphatase, cystic fibrosis transmembrane regulator, Factor VIII, Factor IX, Factor X, insulin, lactoferrin, tissue plasminogen activator, myelin basic protein, insulin, proinsulin, prolactin, hepatitis B antigen, immunoglobulins, monoclonal antibody CTLA4 Ig, Tag 72 monoclonal antibody, Tag 72 single chain antigen binding protein, protein C, cytokines and their receptors, including, for instance tumor necrosis factors alpha and beta, their receptors and their derivatives; renin; growth hormone releasing factor; parathyroid hormone; thyroid stimulating hormone; lipoproteins; alpha-1-antitrypsin; follicle stimulating hormone; calcitonin; luteinizing hormone; glucagon; von Willebrands factor; atrial natriuretic factor; lung surfactant; urokinase; bombesin; thrombin; hemopoietic growth factor; enkephalinase; human macrophage inflammatory protein (MIP-1-alpha); a serum albumin such as mullerian-inhibiting substance; relaxin A-chain; relaxin B-chain; prorelaxin; mouse gonadotropin-associated peptide; beta-lactamase; DNase; inhibin; activin; vascular endothelial growth factor (VEGF); receptors for hormones or growth factors; integrin; protein A or D; rheumatoid factors; a neurotrophic factor such as bone-derived neurotrophic factor (BDNF), neurotrophin-3, -4, -5, or -6 (NT-3, NT-4, NT-5, or NT-6), or a nerve growth factor such as NGF-beta; platelet-derived growth factor (PDGF); fibroblast growth factor such as aFGF and bFGF; epidermal growth factor (EGF); transforming growth factor (TGF) such as TGF-alpha and TGF-beta, including TGF-$\beta$1, TGF-$\beta$2, TGF-$\beta$3, TGF-$\beta$4, or TGF-$\beta$5; insulin-like growth factor-I and —II (IGF-I and IGF-II); des(1-3)—IGF-I (brain IGF-I), insulin-slike growth factor binding proteins; CD proteins such as CD-3, CD-4, CD-8, and CD-19; osteoinductive factors; immunotoxins; a bone morphogenetic protein (BMP); an interferon such as interferon-alpha, -beta, and -gamma; colony stimulating factors (CSFs), e.g., M-CSF, GM-CSF, and G-CSF; interleukins (ILs), e.g., IL-1 to IL-10; superoxide dismutase; T-cell receptors; surface membrane proteins; decay accelerating factor; viral antigen such as, for example, a portion of the AIDS envelope; transport proteins; homing receptors; addressins; regulatory proteins; antibodies; chimeric proteins, such as immunoadhesins, and fragments of any of the above-listed polypeptides. Nucleic acid and protein sequences for these proteins are available in public databases such as GenBank.

In some embodiments, the host cells express more than one exogenous protein. For example, the host cells may be transfected vectors encoding different proteins of interest (e.g., cotransfection or infection at a multiplicity of infection of 1000 with one vector encoding a first protein of interest and a second vector encoding a second protein of interest or serial transfection or infection) so that the host cell contains at least one integrated copy of a first vector encoding a first protein of interest and at least one integrated copy of second integrating vector encoding a second protein of interest. In other embodiments, more than one protein is expressed by arranging the nucleic acids encoding the different proteins of interest in a polycistronic sequence (e.g., bicistronic or tricistronic sequences). This arrangement is especially useful when expression of the different proteins of interest in about a 1:1 molar ratio is desired (e.g., expressing the light and heavy chains of an antibody molecule).

In still further embodiments, ribozymes are expressed in the host cells. It is contemplated that the ribozyme can be utilized for down-regulating expression of a particular gene or used in conjunction with gene switches such as TET, ecdysone, glucocorticoid enhancer, etc. to provide host cells with various phenotypes.

The transfected host cells are cultured according to methods known in the art. Suitable culture conditions for mammalian cells are well known in the art (See e.g., J. Immunol. Methods (1983)56:221–234 [1983], Animal Cell Culture: A Practical Approach 2nd Ed., Rickwood, D. and Hames, B. D., eds. Oxford University Press, New York [1992]).

The host cell cultures of the present invention are prepared in a media suitable for the particular cell being cultured. Commercially available media such as Ham's FIO (Sigma, St. Louis, Mo.), Minimal Essential Medium (MEM, Sigma), RPMI-1640 (Sigma), and Dulbecco's Modified Eagle's Medium (DMEM, Sigma) are exemplary nutrient solutions. Suitable media are also described in U.S. Pat. Nos. 4,767,704; 4,657,866; 4,927,762; 5,122,469; 4,560,655; and WO 90/03430 and WO 87/00195; the disclosures of which are herein incorporated by reference. Any of these media may be supplemented as necessary with serum, hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics (such as gentamycin (gentamicin), trace elements (defined as inorganic compounds usually present at final concentrations in the micromolar range) lipids (such as linoleic or other fatty acids) and their suitable carriers, and glucose or an equivalent energy source. Any other necessary supplements may also be included at appropriate concentrations that would be known to those skilled in the art. For mammalian cell culture, the osmolality of the culture medium is generally about 290–330 mOsm.

The present invention also contemplates the use of a variety of culture systems (e.g., petri dishes, 96 well plates, roller bottles, and bioreactors) for the transfected host cells. For example, the transfected host cells can be cultured in a perfusion system. Perfusion culture refers to providing a continuous flow of culture medium through a culture maintained at high cell density. The cells are suspended and do not require a solid support to grow on.

Generally, fresh nutrients must be supplied continuously with concomitant removal of toxic metabolites and, ideally, selective removal of dead cells. Filtering, entrapment and micro-capsulation methods are all suitable for refreshing the culture environment at sufficient rates.

As another example, in some embodiments a fed batch culture procedure can be employed. In the preferred fed batch culture the mammalian host, cells and culture medium are supplied to a culturing vessel initially and additional culture nutrients are fed, continuously or in discrete increments, to the culture during culturing, with or without periodic cell and/or product harvest before termination of culture. The fed batch culture can include, for example, a semi-continuous fed batch culture, wherein periodically whole culture (including cells and medium) is removed and replaced by fresh medium. Fed batch culture is distinguished from simple batch culture in which all components for cell culturing (including the cells and all culture nutrients) are supplied to the culturing vessel at the start of the culturing process. Fed batch culture can be further distinguished from perfusion culturing insofar as the supernate is not removed from the culturing vessel during the process (in perfusion culturing, the cells are restrained in the culture by, e.g., filtration, encapsulation, anchoring to microcarriers etc. and the culture medium is continuously or intermittently introduced and removed from the culturing vessel). In some particularly preferred embodiments, the batch cultures are performed in roller bottles.

Further, the cells of the culture may be propagated according to any scheme or routine that may be suitable for the particular host cell and the particular production plan contemplated. Therefore, the present invention contemplates a single step or multiple step culture procedure. In a single step culture the host cells are inoculated into a culture environment and the processes of the instant invention are employed during a single production phase of the cell culture. Alternatively, a multi-stage culture is envisioned. In the multi-stage culture cells may be cultivated in a number of steps or phases. For instance, cells may be grown in a first step or growth phase culture wherein cells, possibly removed from storage, are inoculated into a medium suitable for promoting growth and high viability. The cells may be maintained in the growth phase for a suitable period of time by the addition of fresh medium to the host cell culture.

Fed batch or continuous cell culture conditions are devised to enhance growth of the mammalian cells in the growth phase of the cell culture. In the growth phase cells are grown under conditions and for a period of time that is maximized for growth. Culture conditions, such as temperature, pH, dissolved oxygen ($dO_2$) and the like, are those used with the particular host and will be apparent to the ordinarily skilled artisan. Generally, the pH is adjusted to a level between about 6.5 and 7.5 using either an acid (e.g., $CO_2$) or a base (e.g., $Na_2CO_3$ or NaOH). A suitable temperature range for culturing mammalian cells such as CHO cells is between about 30° to 38° C. and a suitable $dO_2$ is between 5–90% of air saturation.

Following the polypeptide production phase, the polypeptide of interest is recovered from the culture medium using techniques which are well established in the art. The protein of interest preferably is recovered from the culture medium as a secreted polypeptide (e.g., the secretion of the protein of interest is directed by a signal peptide sequence), although it also may be recovered from host cell lysates. As a first step, the culture medium or lysate is centrifuged to remove particulate cell debris. The polypeptide thereafter is purified from contaminant soluble proteins and polypeptides, with the following procedures being exemplary of suitable purification procedures: by fractionation on immunoaffinity or ion-exchange columns; ethanol precipitation; reverse phase HPLC; chromatography on silica or on a cation-exchange resin such as DEAE; chromatofocusing; SDS-PAGE; ammonium sulfate precipitation; gel filtration using, for example, Sephadex G-75; and protein A Sepharose columns to remove contaminants such as IgG. A protease inhibitor such as phenyl methyl sulfonyl fluoride (PMSF) also may be useful to inhibit proteolytic degradation during purification. Additionally, the protein of interest can be fused in frame to a marker sequence which allows for purification of the protein of interest. Non-limiting examples of marker sequences include a hexahistidine tag which may be supplied by a vector, preferably a pQE-9 vector, and a hemagglutinin (HA) tag. The HA tag corresponds to an epitope derived from the influenza hemagglutinin protein (See e.g., Wilson et al., Cell, 37:767 [1984]). One skilled in the art will appreciate that purification methods suitable for the polypeptide of interest may require modification to account for changes in the character of the polypeptide upon expression in recombinant cell culture.

The host cells of the present invention are also useful for expressing G-protein coupled receptors (GPCRs) and other transmembrane proteins. It is contemplated that when these proteins are expressed, they are correctly inserted into the membrane in their native conformation. Thus, GPCRs and other transmembrane proteins may be purified as part of a membrane fraction or purified from the membranes by methods known in the art.

Furthermore, the vectors of the present invention are useful for co-expressing a protein of interest for which there is no assay or for which assays are difficult. In this system, a protein of interest and a signal protein are arranged in a polycistronic sequence. Preferably, an IRES sequence separates the signal protein and protein of interest (e.g., a GPCR) and the genes encoding the signal protein and protein of interest are expressed as a single transcriptional unit. The present invention is not limited to any particular signal protein. Indeed, the use of a variety of signal proteins for which easy assays exist is contemplated. These signal proteins include, but are not limited to, green fluorescent protein, luciferase, beta-galactosidase, and antibody heavy or light chains. It is contemplated that when the signal protein and protein of interest are co-expressed from a polycistronic sequence, the presence of the signal protein is indicative of the presence of the protein of interest. Accordingly, in some embodiments, the present invention provides methods for indirectly detecting the expression of a protein of interest comprising providing a host cell transfected with a vector encoding a polycistronic sequence, wherein the polycistronic sequence comprises a signal protein and a protein of interest operably linked by an IRES, and culturing the host cells under conditions such that the signal protein and protein of interest are produced, wherein the presence of the signal protein indicates the presence of the protein of interest.

B. Screening Compounds for Activity

The present invention contemplates the use of the high copy number cell lines for screening compounds for activity, and in particular to high throughput screening of compounds from combinatorial libraries (e.g., libraries containing greater than $10^4$ compounds). The high copy number cell lines of the present invention can be used in a variety of screening methods. In some embodiments, the cells can be used in second messenger assays that monitor signal transduction following activation of cell-surface receptors. In other embodiments, the cells can be used in reporter gene assays that monitor cellular responses at the transcription/translation level. In still further embodiments, the cells can be used in cell proliferation assays to monitor the overall growth/no growth response of cells to external stimuli.

In second messenger assays, the host cells are preferably transfected as described above with vectors encoding cell surface receptors, ion channels, cytoplasmic receptors, or other proteins involved in signal transduction (e.g., G proteins, protein kinases, or protein phosphatases) (See, e.g., U.S. Pat. Nos. 5,670,113; 5,807,689; 5,876,946; and 6,027,875; all of which are incorporated herein by reference). The host cells are then treated with a compound or plurality of compounds (e.g., from a combinatorial library) and assayed for the presence or absence of a response. It is contemplated that at least some of the compounds in the combinatorial library can serve as agonists, antagonists, activators, or inhibitors of the protein or proteins encoded by the vectors. It is also contemplated that at least some of the compounds in the combinatorial library can serve as agonists, antagonists, activators, or inhibitors of protein acting upstream or downstream of the protein encoded by the vector in a signal transduction pathway.

By way of non-limiting example, it is known that agonist engaged transmembrane receptors are functionally linked to the modulation of several well characterized promoter/enhancer elements (e.g., API, cAMP response element (CRE), serum response element (SRE), and nuclear factor of activated T-cells (NF-AT)). Upon activation of a $G_{as}$ coupling receptor, adenylyl cyclase is stimulated, producing increased concentrations of tracellular cAMP, stimulation of protein kinase A, phosphorylation of the CRE binding protein (CREB) and induction of promoters with CRE elements. $G_{ai}$ coupling receptors dampen CRE activity by inhibition of the same signal transduction components. $G_{aq}$ and some βγ pairs stimulate phospholipase C (PLC), and the generation of inositol triphosphate (IP3) and diacylglycerol (DAG). A transient flux in intracellular calcium promotes induction of calcineurin and NA-FT, as well as calmodulin (CaM)-dependent kinase and CREB. Increased DAG concentrations stimulate protein kinase C (PKC) and endosomal/lysosomal acidic sphingomyelinase (aSMase); while the aSMase pathway is dominant, both induce degradation of the NFκB inhibitor IKB as well as NFκB activation. In an alternative pathway, a receptor such as growth factor receptor is activated and recruits Sos to the plasma membrane, resulting in the stimulation of Ras, which in turn recruits the serine/threonine kinase Raf to the plasma membrane. Once activated, Raf phosphorylates MEK kinase, which phosphorylates and activates MAPK and the transcription factor ELK. ELK drives transcription from promoters with SRE elements, leading the synthesis of the transcription factors Fos and Jun, thus forming a transcription factor complex capable of activating API sites. It is contemplated that the proteins forming the described pathways, as well as other receptors, kinases, phosphatases, and nucleic binding proteins, are targets for compounds in the combinatorial library, as well as candidates for expression in the host cells of the present invention.

In some embodiments, the second messenger assays measure fluorescent signals from reporter molecules that respond to intracellular changes (e.g., $Ca^{2+}$ concentration, membrane potential, pH, $IP_3$, cAMP, arachidonic acid release) due to stimulation of membrane receptors and ion channels (e.g., ligand gated ion channels; see Denyer et al., Drug Discov. Today 3:323–32 [1998]; and Gonzales et al., Drug. Discov. Today 4:431–39 [1999]). Examples of reporter molecules include, but are not limited to, FRET (florescence resonance energy transfer) systems (e.g., Cuo-lipids and oxonols, EDAN/DABCYL), calcium sensitive indicators (e.g., Fluo-3, FURA 2, INDO 1, and FLUO3/AM, BAPTA AM), chloride-sensitive indicators (e.g., SPQ, SPA), potassium-sensitive indicators (e.g., PBFI), sodium-sensitive indicators (e.g., SBFI), and pH sensitive indicators (e.g., BCECF).

In general, the host cells are loaded with the indicator prior to exposure to the compound. Responses of the host cells to treatment with the compounds can be detected by methods known in the art, including, but not limited to, fluorescence microscopy, confocal microscopy (e.g., FCS systems), flow cytometry, microfluidic devices, FLIPR systems (See, e.g., Schroeder and Neagle, J. Biomol. Screening 1:75–80 [1996]), and plate-reading systems. In some preferred embodiments, the response (e.g., increase in fluorescent intensity) caused by compound of unknown activity is compared to the response generated by a known agonist and expressed as a percentage of the maximal response of the known agonist. The maximum response caused by a known agonist is defined as a 100% response. Likewise, the maximal response recorded after addition of an agonist to a sample containing a known or test antagonist is detectably lower than the 100% response.

The cells are also useful in reporter gene assays. Reporter gene assays involve the use of host cells transfected with vectors encoding a nucleic acid comprising transcriptional control elements of a target gene (i.e., a gene that controls the biological expression and function of a disease target) spliced to a coding sequence for a reporter gene. Therefore, activation of the target gene results in activation of the reporter gene product. Examples of reporter genes finding use in the present invention include, but are not limited to, chloramphenicol transferase, alkaline phosphatase, firefly and bacterial luciferases, β-galactosidase, β-lactamase, and green fluorescent protein. The production of these proteins, with the exception of green fluorescent protein, is detected through the use of chemiluninescent, colorimetric, or bioluminecent products of specific substrates (e.g., X-gal and luciferin). Comparsions between compounds of known and unknown activities may be conducted as described above.

C. Comparison of Variant Protein Activity

The present invention also contemplates the use of the high copy number host cells to produce variants of proteins so that the activity of the variants can be compared. In some embodiments, the variants differ by a single nucleotide polymorphism (SNP) causing a single amino acid difference. In other embodiments, the variants contain multiple amino acid substitutions. In some embodiments, the activity of the variant proteins are assayed in vivo or in cell extracts. In other embodiments, the proteins are purified and assayed in vitro. It is also contemplated that in some embodiments the variant proteins are fused to a sequence that allows easy purification (e.g., a his-tag sequence) or to a reporter gene (e.g., green fluorescent protein). Activity of the proteins may be assayed by appropriate methods known in the art (e.g., conversion of a substrate to a product). In some preferred embodiments, the activity of a wild-type protein is determined, and the activity of variant versions of the wild-type proteins are expressed as a percentage of the activity of the wild-type protein. Furthermore, the intracellular activity of variant proteins may be compared by constructing a plurality of host cells lines, each of which expresses a different variant of the wild-type protein. The activity of the variant proteins (e.g., variants of proteins involved in signal transduction pathways) may then be compared using the reporter systems for second messenger assays described above. Therefore, in some embodiments, the direct or indirect response (e.g., through downstream or upstream activation of signal transduction pathway) of variant proteins to stimulation or binding by agonists or antagonists is compared. In some preferred embodiments, the response of a wild-type protein is determined, and the responses of variant versions of the wild-type proteins are expressed as a percentage of the response of the wild-type protein.

EXPERIMENTAL

The following examples serve to illustrate certain preferred embodiments and aspects of the present invention and are not to be construed as limiting the scope thereof.

In the experimental disclosure which follows, the following abbreviations apply: M (molar); mM (millimolar); μM (micromolar); nM (nanomolar); mol (moles); mmol (millimoles); μmol (micromoles); nmol (nanomoles); gm (grams); mg (milligrams); pg (micrograms); μg (picograms); L (liters); ml (milliliters); μl (microliters); cm (centimeters); mm (millimeters); μm (micrometers); nm (nanometers); ° C. (degrees Centigrade); AMP (adenosine 5'-monophosphate); BSA (bovine serum albumin); cDNA (copy or complimentary DNA); CS (calf serum); DNA (deoxyribonucleic acid); ssDNA (single stranded DNA); dsDNA (double stranded DNA); dNTP (deoxyribonucleotide triphosphate); LH (luteinizing hormone); NIH (National Institues of Health, Besthesda, MD); RNA (ribonucleic acid); PBS (phosphate buffered saline); g (gravity); OD (optical density); HEPES (N-[2-Hydroxyethyl]piperazine-N-[2-ethanesulfonic acid]); HBS (HEPES buffered saline); PBS (phosphate buffered saline); SDS (sodium dodecylsulfate); Tris-HCl (tris [Hydroxymethyl]aminomethane-hydrochloride); Klenow (DNA polymerase I large (Klenow) fragment); rpm (revolutions per minute); EGTA (ethylene glycol-bis(β-aminoethyl ether) N,N, N',N'-tetraacetic acid); EDTA (ethylenediaminetetracetic acid); bla (β-lactamase or ampicillin-resistance gene); OR1 (plasmid origin of replication); lacI (lac repressor); X-gal (5-bromo-4-chloro-3-indolyl-β-D-galactoside); ATCC (American Type Culture Collection, Rockville, Md.); GIBCOIBRL (GIBCOIBRL, Grand Island, N.Y.); Perkin-Elmer (Perkin-Elmer, Norwalk, Conn.); and Sigma (Sigma Chemical Company, St. Louis, Mo.).

Example 1

Vector Construction

The following Example describes the construction of vectors used in the experiments below.

A. CMV MN14

The CMV MN14 vector (SEQ ID NO:4; MN14 antibody is described in U.S. Pat. No. 5,874,540, incorporated herein by reference) comprises the following elements, arranged in 5' to 3' order: CMV promoter; MN14 heavy chain signal peptide, MN14 antibody heavy chain; IRES from encephalomyocarditis virus; bovine α-lactalbumin signal peptide; MN 14 antibody light chain; and 3' MoMuLV LTR. In addition to sequences described in SEQ ID NO: 4, the CMV MN14 vector further comprises a 5' MoMuLV LTR, a MoMuLV extended viral packaging signal, and a neomycin phosphotransferase gene (these additional elements are provided in SEQ ID NO:7; the 5' LTR is derived from Moloney Murine Sarcoma Virus in each of the constructs described herein, but is converted to the MoMuLV 5' LTR when integrated).

This construct uses the 5' MoMuLV LTR to control production of the neomycin phosphotransferase gene. The expression of MN14 antibody is controlled by the CMV promoter. The MN14 heavy chain gene and light chain gene are attached together by an IRES sequence. The CMV promoter drives production of a mRNA containing the heavy chain gene and the light chain gene attached by the IRES. Ribosomes attach to the mRNA at the CAP site and at the IRES sequence. This allows both heavy and light chain protein to be produced from a single mRNA. The mRNA expression from the LTR as well as from the CMV promoter is terminated and poly adenylated in the 3' LTR. The construct was cloned by similar methods as described in section B below.

The IRES sequence (SEQ ID NO:3) comprises a fusion of the IRES from the plasmid pLXIN (Clontech) and the bovine α-lactalbumin signal peptide. The initial ATG of the signal peptide was attached to the IRES to allow the most efficient translation initiation from the IRES. The 3' end of the signal peptide provides a multiple cloning site allowing easy attachment of any protein of interest to create a fusion protein with the signal peptide. The IRES sequence can serve as a translational enhancer as well as creating a second translation initiation site that allows two proteins to be produced from a single mRNA.

The IRES-bovine α-lactalbumin signal peptide was constructed as follows. The portion of the plasmid pLXIN (Clontech, Palo Alto, Calif.) containing the ECMV IRES was PCR amplified using the following primers.

Primer 1 (SEQ ID NO: 35): 5' GATCCACTAGTAACG-GCCGCCAGAATTCGC 3'

Primer 2 (SEQ ID NO: 36): 5'CAGAGAGACAAAG-GAGGCCATATTATCATCGTGTTTTTCAAAG 3'

Primer 2 attaches a tail corresponding to the start of the bovine α-lactalbumin signal peptide coding region to the IRES sequence. In addition, the second triplet codon of the α-lactalbumin signal peptide was mutated from ATG to GCC to allow efficient translation from the IRES sequence. This mutation results in a methionine to alanine change in the protein sequence. This mutation was performed because the IRES prefers an alanine as the second amino acid in the protein chain. The resulting IRES PCR product contains an EcOR1 site on the 5' end of the fragment (just downstream of Primer 1 above).

Next, the α-lactalbumin signal peptide containing sequence was PCR amplified from the α-LA Signal Peptide vector construct using the following primers.

Primer 3 (SEQ ID NO: 14): 5'CTTTGAAAAACACGAT-GATAATATGGCCTCCTTTGTCTCTCTG 3'

Primer 4 (SEQ ID NO: 15): 5' TTCGCGAGCTC-GAGATCTAGATATCCCATG 3'

Primer 3 attaches a tail corresponding to the 3' end of the IRES sequence to the α-lactalbumin signal peptide coding region. As stated above, the second triplet codon of the bovine α-lactalbumin signal peptide was mutated to allow efficient translation from the IRES sequence. The resulting signal peptide PCR fragment contains NaeI, NcoI, EcORV, XbaI, BglII and XhoI sites on the 3' end.

After the IRES and signal peptide were amplified individually using the primers shown above, the two reaction products were mixed and PCR was performed using primer 1 and primer 4. The resultant product of this reaction is a spliced fragment that contains the IRES attached to the full length α-lactalbumin signal peptide. The ATG encoding the start of the signal peptide is placed at the same location as the ATG encoding the start of the neomycin phosphotransferase gene found in the vector pLXIN. The fragment also contains the EcOR1 site on the 5' end and NaeI, NcoI, EcORV, XbaI, BglII and XhoI sites on the 3' end.

The spliced IRES/α-lactalbumin signal peptide PCR fragment was digested with EcOR1 and XhoI. The α-LA Signal Peptide vector construct was also digested with EcOR1 and XhoI. These two fragments were ligated together to give the pIRES construct.

The IRES/α-lactalbumin signal peptide portion of the pIRES vector was sequenced and found to contain mutations in the 5' end of the IRES. These mutations occur in a long stretch of C's and were found in all clones that were isolated.

To repair this problem, pLXIN DNA was digested with EcOR1 and BsmFI. The 500 bp band corresponding to a portion of the !RES sequence was isolated. The mutated IRES/(α-lactalbumin signal peptide construct was also digested with EcOR1 and BsmFI and the mutated IRES fragment was removed. The IRES fragment from pLXIN was then substituted for the IRES fragment of the mutated IRES/α-lactalbumin signal peptide construct. The IRES/α-LA signal peptide portion of resulting plasmid was then verified by DNA sequencing.

The resulting construct was found to have a number of sequence differences when compared to the expected pLXIN sequence obtained from Clontech. We also sequenced the IRES portion of pLXIN purchased from Clontech to verify its sequence. The differences from the expected sequence also appear to be present in the pLXIN plasmid that we obtained from Clontech. Four sequence differences were identified:

bp 347 T—was G in pLXIN sequence bp 786–788 ACG—was GC in LXIN sequence.

B. CMV LL2

The CMV LL2 (SEQ ID NO:5; LL2 antibody is described in U.S. Pat. No. 6,187,287, incorporated herein by reference) construct comprises the following elements, arranged in 5' to 3' order: 5'CMV promoter (Clonetech), LL2 heavy chain signal peptide, LL2 antibody heavy chain; IRES from encephalomyocarditis virus; bovine α-LA signal peptide; LL2 antibody light chain; and 3' MoMuLV LTR. In addition to sequences described in SEQ ID NO:5, the CMV LL2 vector further comprises a 5' MoMuLV LTR, a MoMuLV extended viral packaging signal, and a neomycin phosphotransferase gene (these additional elements are provided in SEQ ID NO:7).

This construct uses the 5' MoMuLV LTR to control production of the neomycin phosphotransferase gene. The expression of LL2 antibody is controlled by the CMV promoter (Clontech). The LL2 heavy chain gene and light chain gene are attached together by an IRES sequence. The CMV promoter drives production of a mRNA containing the heavy chain gene and the light chain gene attached by the IRES. Ribosomes attach to the mRNA at the CAP site and at the IRES sequence. This allows both heavy and light chain protein to be produced from a single mRNA. The mRNA expression from the LTR as well as from the CMV promoter is terminated and poly adenylated in the 3' LTR.

The IRES sequence (SEQ ID NO:3) comprises a fusion of the IRES from the plasmid pLXIN (Clontech) and the bovine alpha-lactalbumin signal peptide. The initial ATG of the signal peptide was attached to the IRES to allow the most efficient translation initiation from the IRES. The 3' end of the signal peptide provides a multiple cloning site allowing easy attachment of any protein of interest to create a fusion protein with the signal peptide. The IRES sequence can serve as a translational enhancer as well as creating a second translation initiation site that allows two proteins to be produced from a single mRNA.

The LL2 light chain gene was attached to the IRES α-lactalbumin signal peptide as follows. The LL2 light chain was PCR amplified from the vector pCRLL2 using the following primers.

Primer 1 (SEQ ID NO: 16): 5'CTACAGGTGTCCACGTC-GACATCCAGCTGACCCAG 3'

Primer 2 (SEQ ID NO: 17): 5'CTGCAGAATA-GATCTCTAACACTCTCCCCTGTTG 3'

These primers add a HincII site right at the start of the coding region for mature LL2 light chain. Digestion of the PCR product with HincII gives a blunt end fragment starting with the initial GAC encoding mature LL2 on the 5' end. Primer 2 adds a BglII site to the 3' end of the gene right after the stop codon. The resulting PCR product was digested with HincII and BglII and cloned directly into the IRES-Signal Peptide plasmid that was digested with NacI and BgII.

The Kozak sequence of the LL2 heavy chain gene was then modified. The vector pCRMN14HC was digested with XhoI and AvrII to remove about a 400 bp fragment. PCR was then used to amplify the same portion of the LL2 heavy chain construct that was removed by the XhoI-AvrII digestion. This amplification also mutated the 5' end of the gene to add a better Kozak sequence to the clone. The Kozak sequence was modified to resemble the typical IgG Kozak sequence. The PCR primers are shown below.

Primer 1 (SEQ ID NO: 18): 5'CAGTGTGATCTCGAGAAT-TCAGGACCTCACCATGGGATGGAGCTGTATCAT 3'

Primer 2 (SEQ ID NO: 19): 5'AGGCTGTATTGGTGGAT-TCGTCT 3'

The PCR product was digested with XhoI and AvrII and inserted back into the previously digested plasmid backbone.

The "good" Kozak sequence was then added to the light chain gene. The "good" Kozak LL2 heavy chain gene construct was digested with EcOR1 and the heavy chain gene containing fragment was isolated. The IRES α-Lactalbumin Signal Peptide LL2 light chain gene construct was also digested with EcOR1. The heavy chain gene was then cloned into the EcOR1 site of IRES light chain construct. This resulted in the heavy chain gene being placed at the 5' end of the IRES sequence.

Next, a multiple cloning site was added into the LNCX retroviral backbone plasmid. The LNCX plasmid was digested with HindIII and ClaI. Two oligonucleotide primers were produced and annealed together to create an double stranded DNA multiple cloning site. The following primers were annealed together.

Primer 1 (SEQ ID NO: 20): 5'AGCTTCTCGAGTTAACA-GATCTAGGCCTCCTAGGTCGACAT 3'

Primer 2 (SEQ ID NO: 21): 5' CGATGTCGACCTAGGAG-GCCTAGATCTGTTAACTCGAGA 3'

After annealing, the multiple cloning site was ligated into LNCX to create LNC-MCS.

Next, the double chain gene fragment was ligated into the retroviral backbone gene construct. The double chain gene construct created above was digested with SalI and BglII and the double chain containing fragment was isolated. The retroviral expression plasmid LNC-MCS was digested with XhoI and BglII. The double chain fragment was then cloned into the LNC-MCS retroviral expression backbone.

Next, an RNA splicing problem in the construct was corrected. The construct was digested with NsiI. The resulting fragment was then partially digested with EcOR1. The fragments resulting from the partial digest that were approximately 9300 base pairs in size were gel purified. A linker was created to mutate the splice donor site at the 3' end of the LL2 heavy chain gene. The linker was again created by annealing two oligonucleotide primers together to form the double stranded DNA linker. The two primers used to create the linker are shown below.

Primer 1 (SEQ ID NO: 22): 5'CGAGGCTCTGCACAAC-CACTACACGCAGAAGAGCCTCTCCCT-GTCTCCCGGGAAAT GAAAGCCG 3'

Primer 2 (SEQ ID NO: 23): 5'AATTCGGCTTTCATTTC-CCGGGAGACAGGGAGAGGCTCTTCT-GCGTGTAGTGGTTG TGCAGAGCCTCGTGCA 3'

After annealing the linker was substituted for the original NsiI/EcOR1 fragment that was removed during the partial digestion.

C. MMTV MN14

The MMTV MN14 (SEQ ID NO:6) construct comprises the following elements, arranged in 5' to 3' order: 5' MMTV promoter; double mutated PPE sequence; MN 14 antibody heavy chain; IRES from encephalomyocarditis virus; bovine αLA signal peptide MN 14 antibody light chain; WPRE sequence; and 3' MoMuLV LTR. In addition to the sequences described in SEQ ID NO:6, the MMTV MN14 vector further comprises a MoMuLV LTR, MoMuLV extended viral packaging signal; neomycin phosphotransferase gene located 5' of the MMTV promoter (these additional elements are provided in SEQ ID NO: 7).

This construct uses the 5' MoMuLV LTR to control production of the neomycin phosphotransferase gene. The expression of MN14 antibody is controlled by the MMTV promoter (Pharmacia). The MN14 heavy chain gene and light chain gene are attached together by an IRES/bovine α-LA signal peptide sequence (SEQ ID NO: 3). The MMTV promoter drives production of a mRNA containing the heavy chain gene and the light chain gene attached by the IRES/bovine α-LA signal peptide sequence. Ribosomes attach to the mRNA at the CAP site and at the IRES/bovine α-LA signal peptide sequence. This allows both heavy and light chain protein to be produced from a single mRNA. In addition, there are two genetic elements contained within the mRNA to aid in export of the mRNA from the nucleus to the cytoplasm and aid in poly-adenylation of the mRNA. The PPE sequence is contained between the RNA CAP site and the start of the MN14 protein coding region, the WPRE is contained between the end of MN14 protein coding and the poly-adenylation site. The mRNA expression from the LTR as well as from the MMTV promoter is terminated and poly-adenylated in the 3' LTR.

ATG sequences within the PPE element (SEQ ID NO:2) were mutated to prevent potential unwanted translation initiation. Two copies of this mutated sequence were used in a head to tail array. This sequence is placed just downstream of the promoter and upstream of the Kozak sequence and signal peptide-coding region. The WPRE is isolated from woodchuck hepatitis virus and also aids in the export of mRNA from the nucleus and creating stability in the mRNA. If this sequence is included in the 3' untranslated region of the RNA, level of protein expression from this RNA increases up to 10-fold.

D. α-LA MN14

The α-LA MN14 (SEQ ID NO:7) construct comprises the following elements, arranged in 5' to 3' order: 5' MoMuLV LTR, MoMuLV extended viral packaging signal, neomycin phosphotransferase gene, bovine/human alpha-lactalbumin hybrid promoter, double mutated PPE element, MN14 heavy chain signal peptide, MN14 antibody heavy chain, IRES from encephalomyocarditis virus/bovine αLA signal peptide, MN14 antibody light chain, WPRE sequence; and 3' MoMuLV LTR.

This construct uses the 5' MoMuLV LTR to control production of the neomycin phosphotransferase gene. The expression of MN14 antibody is controlled by the hybrid α-LA promoter (SEQ ID NO:1). The MN14 heavy chain gene and light chain gene are attached together by an IRES sequence/bovine α-LA signal peptide (SEQ ID NO:3). The (x-LA promoter drives production of a mRNA containing the heavy chain gene and the light chain gene attached by the IRES. Ribosomes attach to the mRNA at the CAP site and at the IRES sequence. This allows both heavy and light chain protein to be produced from a single mRNA.

In addition, there are two genetic elements contained within the mRNA to aid in export of the mRNA from the nucleus to the cytoplasm and aid in poly-adenylation of the mRNA. The mutated PPE sequence (SEQ ID NO:2) is contained between the RNA CAP site and the start of the MN14 protein coding region. ATG sequences within the PPE element (SEQ ID NO:2) were mutated to prevent potential unwanted translation initiation. Two copies of this mutated sequence were used in a head to tail array. This sequence is placed just downstream of the promoter and upstream of the Kozak sequence and signal peptide-coding region. The WPRE was isolated from woodchuck hepatitis virus and also aids in the export of mRNA from the nucleus and creating stability in the mRNA. If this sequence is included in the 3' untranslated region of the RNA, level of protein expression from this RNA increases up to 10-fold. The WPRE is contained between the end of MN14 protein coding and the poly-adenylation site. The mRNA expression from the LTR as well as from the bovine/human alpha-lactalbumin hybrid promoter is terminated and poly adenylated in the 3' LTR.

The bovine/human alpha-lactalbumin hybrid promoter (SEQ ID NO:1) is a modular promoter/enhancer element derived from human and bovine alpha-lactalbumin promoter sequences. The human portion of the promoter is from +15 relative to transcription start point (tsp) to −600 relative to the tsp. The bovine portion is then attached to the end of the human portion and corresponds to −550 to −2000 relative to the tsp. The hybrid was developed to remove poly-adenylation signals that were present in the bovine promoter and hinder retroviral RNA production. It was also developed to contain genetic control elements that are present in the human gene, but not the bovine.

For construction of the bovine/human α-lactalbumin promoter, human genomic DNA was isolated and purified. A portion of the human α-lactalbumin promoter was PCR amplified using the following two primers:
Primer 1 (SEQ ID NO: 24): 5'AAAGCATATGT-TCTGGGCCTTGTTACATGGCTGGATTGGTT 3'
Primer 2 (SEQ ID NO: 25): 5'TGAATTCGGCGC-CCCCAAGAACCTGAAATGGAAGCAT-CACTCAGTTT CATATAT 3'

This two primers created a NdeI site on the 5' end of the PCR fragment and a EcOR1 site on the 3' end of the PCR fragment.

The human PCR fragment created using the above primers was double digested with the restriction enzymes NdeI and EcOR1. The plasmid pKBaP-1 was also double digested with NdeI and EcOR1. The plasmid pKBaP-1 contains the bovine α-lactalbumin 5' flanking region attached to a multiple cloning site. This plasmid allows attachment of various genes to the bovine α-lactalbumin promoter.

Subsequently, the human fragment was ligated/substituted for the bovine fragment of the promoter that was removed from the pKBaP-1 plasmid during the double digestion. The resulting plasmid was confirmed by DNA sequencing to be a hybrid of the Bovine and Human α-lactalbumin promoter/regulatory regions.

Attachment of the MN14 light chain gene to the IRES α-lactalbumin signal peptide was accomplished as follows. The MN14 light chain was PCR amplified from the vector pCRMN14LC using the following primers.
Primer 1 (SEQ ID NO: 26): 5'CTACAGGTGTCCACGTC-GACATCCAGCTGACCCAG 3'
Primer 2 (SEQ ID NO: 27): 5'CTGCAGAATA-GATCTCTAACACTCTCCCCTGTTG 3'

These primers add a HincII site right at the start of the coding region for mature MN14 light chain. Digestion of the PCR product with HincII gives a blunt end fragment starting with the initial GAC encoding mature MN14 on the 5' end. Primer 2 adds a BglII site to the 3' end of the gene right after the stop codon. The resulting PCR product was digested with HincII and BglII and cloned directly into the IRES-Signal Peptide plasmid that was digested with NaeI and BglII.

Next, the vector pCRMN14HC was digested with XhoI and NruI to remove about a 500 bp fragment. PCR was then used to amplify the same portion of the MN14 heavy chain construct that was removed by the XhoI-NruI digestion. This amplification also mutated the 5' end of the gene to add a better Kozak sequence to the clone. The Kozak sequence was modified to resemble the typical IgG Kozak sequence. The PCR primers are shown below.
Primer 1 (SEQ ID NO: 28): 5'CAGTGTGATCTCGAGAAT-TCAGGACCTCACCATGGGATGGAGCTGTATCAT 3'
Primer 2 (SEQ ID NO: 29): 5'GTGTCTTCGGGTCTCAG-GCTGT 3'

The PCR product was digested with XhoI and NruI and inserted back into the previously digested plasmid backbone.

Next, the "good" Kozak MN14 heavy chain gene construct was digested with EcOR1 and the heavy chain gene containing fragment was isolated. The IRES α-Lactalbumin Signal Peptide MN14 light chain gene construct was also digested with EcOR1. The heavy chain gene was then cloned into the EcOR1 site of IRES light chain construct. This resulted in the heavy chain gene being placed at the 5' end of the IRES sequence.

A multiple cloning site was then added to the LNCX retroviral backbone plasmid.

The LNCX plasmid was digested with HindIII and ClaI. Two oligonucleotide primers were produced and annealed together to create an double stranded DNA multiple cloning site. The following primers were annealed together.
Primer 1 (SEQ ID NO: 30): 5' AGCTTCTCGAGTTAACA-GATCTAGGCCTCCTAGGTCGACAT 3'
Primer 2 (SEQ ID NO: 31): 5'CGATGTCGACCTAGGAG-GCCTAGATCTGTTAACTCGAGA 3'

After annealing the multiple cloning site was ligated into LNCX to create LNC-MCS.

The double chain gene fragment was then inserted into a retroviral backbone gene construct. The double chain gene construct created in step 3 was digested with SalI and BglII and the double chain containing fragment was isolated. The retroviral expression plasmid LNC-MCS was digested with XhoI and BglII. The double chain fragment was then cloned into the LNC-MCS retroviral expression backbone.

Next, a RNA splicing problem in the construct was repaired. The construct was digested with NsiI. The resulting fragment was then partially digested with EcOR1. The fragments resulting from the partial digest that were approximately 9300 base pairs in size, were gel purified. A linker was created to mutate the splice donor site at the 3' end of the MN14 heavy chain gene. The linker was again created by annealing two oligonucleotide primers together to form the double stranded DNA linker. The two primers used to create the linker are shown below.
Primer 1 (SEQ ID NO: 32): 5'CGAGGCTCTGCACAAC-CACTACACGCAGAAGAGCCTCTCCCT-GTCTCCCGGGAAAT GAAAGCCG 3'
Primer 2 (SEQ ID NO: 33): 5'AATTCGGCTTTCATTTC-CCGGGAGACAGGGAGAGGCTCTTCT-GCGTGTAGTGGTTG TGCAGAGCCTCGTGCA 3'

After annealing the linker was substituted for the original NsiI/EcOR1 fragment that was removed during the partial digestion.

Next, the mutated double chain fragment was inserted into the α-Lactalbumin expression retroviral backbone LN α-LA-Mertz-MCS. The gene construct produced above was digested with BamHI and BglII and the mutated double chain gene containing fragment was isolated. The LN α-LA-Mertz-MCS retroviral backbone plasmid was digested with BglI. The BamHI/BglII fragment was then inserted into the retroviral backbone plasmid.

A WPRE element was then inserted into the gene construct. The plasmid Bluescriptil SK+ WPRE-B11 was digested with BamHI and HincII to remove the WPRE element and the element was isolated. The vector created above was digested with BglII and HpaI. The WPRE fragment was ligated into the BglII and HpaI sites to create the final gene construct.

E. α-LA Bot

The α-LA Bot (SEQ ID NO:8, botulinum toxin antibody) construct comprises the following elements, arranged in 5' to 3' order: bovine/human alpha-lactalbumin hybrid promoter, mutated PPE element, cc49 signal peptide, botulinum toxin antibody light chain, IRES from encephalomyocarditis virus/bovine α-LA signal peptide, botulinum toxin antibody heavy chain, WPRE sequence, and 3' MoMuLV LTR. In addition, the α-LA botulinum toxin antibody vector further comprises a 5' MoMuLV LTR, a MoMuLV extended viral packaging signal, and a neomycin phosphotransferase gene (these additional elements are provided in SEQ ID NO: 7).

This construct uses the 5' MoMuLV LTR to control production of the neomycin phosphotransferase gene. The expression of botulinum toxin antibody is controlled by the hybrid α-LA promoter. The botulinum toxin antibody light chain gene and heavy chain gene are attached together by an IRES/bovine α-LA signal peptide sequence. The bovine/human alpha-lactalbumin hybrid promoter drives production of a mRNA containing the light chain gene and the heavy chain gene attached by the IRES. Ribosomes attach to the mRNA at the CAP site and at the IRES sequence. This allows both light and heavy chain protein to be produced from a single mRNA.

In addition, there are two genetic elements contained within the mRNA to aid in export of the mRNA from the nucleus to the cytoplasm and aid in poly-adenylation of the mRNA. The mutated PPE sequence (SEQ ID NO:2) is contained between the RNA CAP site and the start of the MN14 protein coding region. ATG sequences within the PPE element (SEQ ID NO:2) were mutated to prevent potential unwanted translation initiation. Two copies of this mutated sequence were used in a head to tail array. This sequence was placed just downstream of the promoter and upstream of the Kozak sequence and signal peptide-coding region. The WPRE was isolated from woodchuck hepatitis virus and also aids in the export of mRNA from the nucleus and creating stability in the mRNA. If this sequence is included in the 3' untranslated region of the RNA, level of protein expression from this RNA increases up to 10-fold. The WPRE is contained between the end of MN14 protein coding and the poly-adenylation site. The mRNA expression from the LTR as well as from the bovine/human alpha-lactalbumin hybrid promoter is terminated and poly adenylated in the 3' LTR.

The bovine/human α-lactalbumin hybrid promoter (SEQ ID NO:1) is a modular promoter/enhancer element derived from human and bovine α-lactalbumin promoter sequences. The human portion of the promoter is from +15 relative to transcription start point to −600 relative to the tsp. The bovine portion is then attached to the end of the human portion and corresponds to −550 to −2000 relative to the tsp. The hybrid was developed to remove poly-adenylation signals that were present in the bovine promoter and hinder retroviral RNA production. It was also developed to contain genetic control elements that are present in the human gene, but not the bovine. Likewise, the construct contains control elements present in the bovine but not in the human.

F. LSRNL

The LSRNL (SEQ ID NO:9) construct comprises the following elements, arranged in 5' to 3' order: 5' MoMuLV LTR, MoMuLV viral packaging signal; hepatitis B surface antigen; RSV promoter; neomycin phosphotransferase gene; and 3' MoMuLV LTR.

This construct uses the 5' MoMuLV LTR to control production of the Hepatitis B surface antigen gene. The expression of the neomycin phosphotransferase gene is controlled by the RSV promoter. The mRNA expression from the LTR as well as from the RSV promoter is terminated and poly adenylated in the 3' LTR.

G. α-LA cc491L2

The α-LA cc491L2 (SEQ ID NO:10; the cc49 antibody is described in U.S. Pat. Nos. 5,512,443; 5,993,813; and 5,892,019; each of which is herein incorporated by reference) construct comprises the following elements, arranged in 5' to 3' order: 5' bovine/human α-lactalbumin hybrid promoter; cc49-IL2 coding region; and 3' MoMuLV LTR. This gene construct expresses a fusion protein of the single chain antibody cc49 attached to Interleukin-2. Expression of the fusion protein is controlled by the bovine/human α-lactalbumin hybrid promoter.

The bovine/human α-lactalbumin hybrid promoter (SEQ ID NO:1) is a modular promoter/enhancer element derived from human and bovine alpha-lactalbumin promoter sequences. The human portion of the promoter is from +15 relative to transcription start point to −600 relative to the tsp. The bovine portion is then attached to the end of the human portion and corresponds to −550 to −2000 relative to the tsp. The hybrid was developed to remove poly-adenylation signals that were present in the bovine promoter and hinder retroviral RNA production. It was also developed to contain genetic control elements that are present in the human gene, but not the bovine. Likewise, the construct contains control elements present in the bovine but not in the human. The 3' viral LTR provide the poly-adenylation sequence for the mRNA.

H. α-LA YP

The α-LA YP (SEQ ID NO: 11) construct comprises the following elements, arranged in 5' to 3' order: 5' bovine/human alpha-lactalbumin hybrid promoter; double mutated PPE sequence; bovine αLA signal peptide; *Yersenia pestis* antibody heavy chain Fab coding region; EMCV IRES/bovineα-LA signal peptide; *Yersenia pestis* antibody light chain Fab coding region; WPRE sequence; 3' MoMuLV LTR.

This gene construct will cause the expression of *Yersenia pestis* mouse Fab antibody. The expression of the gene construct is controlled by the bovine/human α-lactalbumin hybrid promoter. The PPE sequence and the WPRE sequence aid in moving the mRNA from the nucleus to the cytoplasm. The IRES sequence allows both the heavy and the light chain genes to be translated from the same mRNA. The 3' viral LTR provides the poly-adenylation sequence for the mRNA.

In addition, there are two genetic elements contained within the mRNA to aid in export of the mRNA from the nucleus to the cytoplasm and aid in poly-adenylation of the mRNA. The mutated PPE sequence (SEQ ID NO:2) is contained between the RNA CAP site and the start of the MN14 protein coding region. ATG sequences within the PPE element (SEQ ID NO:2) were mutated (bases 4,112, 131, and 238 of SEQ ID NO: 2 were changed from a G to a T) to prevent potential unwanted translation initiation. Two copies of this mutated sequence were used in a head to tail array. This sequence was placed just downstream of the promoter and upstream of the Kozak sequence and signal peptide-coding region. The WPRE was isolated from woodchuck hepatitis virus and also aids in the export of mRNA from the nucleus and creating stability in the mRNA. If this sequence is included in the 3' untranslated region of the RNA, level of protein expression from this RNA increases up to 10-fold. The WPRE is contained between the end of MN14 protein coding and the poly-adenylation site. The mRNA expression from the LTR as well as from the bovine/human alpha-lactalbumin hybrid promoter is terminated and poly adenylated in the 3' LTR.

The bovine/human alpha-lactalbumin hybrid promoter (SEQ ID NO:1) is a modular promoter/enhancer element derived from human and bovine alpha-lactalbumin promoter sequences. The human portion of the promoter is from +15 relative to transcription start point to −600 relative to the tsp. The bovine portion is then attached to the end of the human portion and corresponds to −550 to −2000 relative to the tsp. The hybrid was developed to remove poly-adenylation signals that were present in the bovine promoter and hinder retroviral RNA production. It was also developed to contain genetic control elements that are present in the human gene, but not the bovine. Likewise, the construct contains control elements present in the bovine but not in the human.

Example 2

Generation of Cell Lines Stably Expressing the MoMLV gag and pol Proteins

Examples 2–5 describe the production of pseudotyped retroviral vectors. These methods are generally applicable to the production of the vectors described above. The expression of the fusogenic VSV G protein on the surface of cells results in syncytium formation and cell death. Therefore, in order to produce retroviral particles containing the VSV G protein as the membrane-associated protein a two-step approach was taken. First, stable cell lines expressing the gag and pot proteins from MoMLV at high levels were generated (e.g., 293 GP$^{SD}$ cells). The stable cell line which expresses the gag and pol proteins produces noninfectious viral particles lacking a membrane-associated protein (e.g., an envelope protein). The stable cell line was then co-transfected, using the calcium phosphate precipitation, with VSV-G and gene of interest plasmid DNAs. The pseudotyped vector generated was used to infect 293GP$^{SD}$ cells to produce stably transformed cell lines. Stable cell lines can be transiently transfected with a plasmid capable of directing the high level expression of the VSV G protein (see below). The transiently transfected cells produce VSV G-pseudotyped retroviral vectors which can be collected from the cells over a period of 3 to 4 days before the producing cells die as a result of syncytium formation.

The first step in the production of VSV G-pseudotyped retroviral vectors, the generation of stable cell lines expressing the MoMLV gag and pol proteins is described below. The human adenovirus Ad-5-transformed embryonal kidney cell line 293 (ATCC CRL 1573) was cotransfected with the pCMVgag-pol and the gene encoding for phleomycin. pCMV gag-pol contains the MoMLV gag and pol genes under the control of the CMV promoter (pCMV gag-pol is available from the ATCC).

The plasmid DNA was introduced into the 293 cells using calcium phosphate co-precipitation (Graham and Van der Eb, Virol. 52:456 [1973]). Approximately 5×10$^5$ 293 cells were plated into a 100 mm tissue culture plate the day before the DNA co-precipitate was added. Stable transformants were selected by growth in DMEM-high glucose medium containing 10% FCS and 10 μg/ml phleomycin (selective medium). Colonies which grew in the selective medium were screened for extracellular reverse transcriptase activity (Goff et al., J. Virol. 38:239 [1981]) and intracellular p30gag expression. The presence of p30gag expression was determined by Western blotting using a goat-anti p30 antibody (NCI antiserum 77S000087). A clone which exhibited stable expression of the retroviral genes was selected. This clone was named 293GP$^{SD}$ (293 gag-pol-San Diego). The 293GP$^{SD}$ cell line, a derivative of the human Ad-5-transformed embryonal kidney cell line 293, was grown in DMEM-high glucose medium containing 10% FCS.

Example 3

Preparation of Pseudotyped Retroviral Vectors Bearing the G Glycoprotein of VSV

In order to produce VSV G protein pseudotyped retrovirus the following steps were taken. The 293GP$^{SD}$ cell line was co-transfected with VSV-G plasmid and DNA plasmid of interest. This co-transfection generates the infectious particles used to infect 293GP$^{SD}$ cells to generate the packaging cell lines. This Example describes the production of pseudotyped LNBOTDC virus. This general method may be used to produce any of the vectors described in Example 1.

a) Cell Lines and Plasmids

The packaging cell line, 293GP$^{SD}$ was grown in alpha-MEM-high glucose medium containing 10% FCS The titer of the pseudo-typed virus may be determined using either 208F cells (Quade, Virol. 98:461 [1979]) or NIH/3T3 cells (ATCC CRL 1658); 208F and NIH/3T3 cells are grown in DMEM-high glucose medium containing 10% CS.

The plasmid LNBOTDC contains the gene encoding BOTD under the transcriptional control of cytomegalovirus intermediate-early promoter followed by the gene encoding neomycin phosphotransferase (Neo) under the transcriptional control of the LTR promoter. The plasmid pHCMV-G contains the VSV G gene under the transcriptional control of the human cytomegalovirus intermediate-early promoter (Yee et al., Meth. Cell Biol. 43:99 [1994]).

b) Production of Stable Packaging Cell Lines, Pseudotyped Vector and Titering of Pseudotyped LNBOTDC Vector LNBOTDC DNA (SEQ ID NO: 13) was co-transfected with pHCMV-G DNA into the packaging line 293GP$^{SD}$ to produce LNBOTDC virus. The resulting LNBOTDC virus was then used to infect 293GP$^{SD}$ cells to transform the cells. The procedure for producing pseudotyped LNBOTDC virus was carried out as described (Yee et al., Meth. Cell Biol. 43:99 [1994].

This is a retroviral gene construct that upon creation of infectious replication defective retroviral vector will cause the insertion of the sequence described above into the cells of interest. Upon insertion the CMV regulatory sequences control the expression of the botulinum toxin antibody heavy and light chain genes. The IRES sequence allows both the heavy and the light chain genes to be translated from the same mRNA. The 3' viral LTR provides the poly-adenylation sequence for the mRNA.

Both heavy and light chain protein for botulinum toxin antibody are produced from this signal mRNA. The two proteins associated to form active botulinum toxin antibody. The heavy and light chain proteins also appear to be formed in an equal molar ratio to each other.

Briefly, on day 1, approximately 5×10$^4$ 293GP$^{SD}$ cells were placed in a 75 cm$^2$ tissue culture flask. On the following day (day 2), the 293GP$^{SD}$ cells were transfected with 25 µg of pLNBOTDC plasmid DNA and 25 µg of VSV-G plasmid DNA using the standard calcium phosphate co-precipitation procedure (Graham and Van der Eb, Virol. 52:456 [1973]). A range of 10 to 40 µg of plasmid DNA may be used. Because 293GP$^{SD}$ cells may take more than 24 hours to attach firmly to tissue culture plates, the 293GP$^{SD}$ cells may be placed in 75 cm³ flasks 48 hours prior to transfection. The transfected 293GP$^{SD}$ cells provide pseudotyped LNBOTDC virus.

On day 3, approximately 1×10⁵ 293GP$^{SD}$ cells were placed in a 75 cm² tissue culture flask 24 hours prior to the harvest of the pseudotyped virus from the transfected 293GP$^{SD}$ cells. On day 4, culture medium was harvested from the transfected $_{2093}$ GpSD cells 48 hours after the application of the pLNBOTDC and VSV-G DNA. The culture medium was filtered through a 0.45 µm filter and polybrene was added to a final concentration of 8 µg/ml. The culture medium containing LNBOTDC virus was used to infect the 293GP$^{SD}$ cells as follows. The culture medium was removed from the 293GP$^{SD}$ cells and was replaced with the LNBOTDC virus containing culture medium. Polybrene was added to the medium following addition to cells. The virus containing medium was allowed to remain on the 293 GP$^{SD}$ cells for 24 hours. Following the 16 hour infection period (on day 5), the medium was removed from the 293GP$^{SD}$ cells and was replaced with fresh medium containing 400 µg/ml G418 (GIBCO/BRL). The medium was changed approximately every 3 days until G418-resistant colonies appeared approximately two weeks later.

The G418-resistant 293 colonies were plated as single cells in 96 wells. Sixty to one hundred G418-resistant colonies were screened for the expression of the BOTDC antibody in order to identify high producing clones. The top 10 clones in 96-well plates were transferred 6-well plates and allowed to grow to confluency.

The top 10 clones were then expanded to screen for high titer production. Based on protein expression and titer production, 5 clonal cell lines were selected. One line was designated the master cell bank and the other 4 as backup cell lines. Pseudotyped vector was generated as follows. Approximately 1×10⁶ 293GP$^{SD}$/LNBOTDC cells were placed into a 75 cm² tissue culture flask. Twenty-four hours later, the cells were transfected with 25 µg of pHCMV-G plasmid DNA using calcium phosphate co-precipitation. Six to eight hours after the calcium-DNA precipitate was applied to the cells, the DNA solution was replaced with fresh culture medium (lacking G418). Longer transfection times (overnight) were found to result in the detachment of the majority of the 293GP$^{SD}$/LNBOTDC cells from the plate and are therefore avoided. The transfected 293GP$^{SD}$/LNBOTDC cells produce pseudotyped LNBOTDC virus.

The pseudotyped LNBOTDC virus generated from the transfected 293GP$^{SD}$/LNBOTDC cells can be collected at least once a day between 24 and 96 hr after transfection. The highest virus titer was generated approximately 48 to 72 hr after initial pHCMV-G transfection.

While syncytium formation became visible about 48 hr after transfection in the majority of the transfected cells, the cells continued to generate pseudotyped virus for at least an additional 48 hr as long as the cells remained attached to the tissue culture plate. The collected culture medium containing the VSV G-pseudotyped LNBOTDC virus was pooled, filtered through a 0.45 μm filter and stored at −80° C. or concentrated immediately and then stored at −80° C.

The titer of the VSV G-pseudotyped LNBOTDC virus was then determined as follows. Approximately $5\times10^4$ rat 208F fibroblasts cells were plated into 6 well plates. Twenty-fours hours after plating, the cells were infected with serial dilutions of the LNBOTDC virus-containing culture medium in the presence of 8 μg/ml polybrene. Twenty four hours after infection with virus, the medium was replaced with fresh medium containing 400 μg/ml G418 and selection was continued for 14 days until G418-resistant colonies became visible.

Viral titers were typically about 0.5 to $5.0\times10^6$ colony forming units (cfu)/ml. The titer of the virus stock could be concentrated to a titer of greater than $10^9$ cfu/ml as described below.

Example 4

Concentration of Pseudotyped Retroviral Vectors

The VSV G-pseudotyped LNBOTDC viruses were concentrated to a high titer by one cycle of ultracentrifugation. However, two cycles can be performed for further concentration. The frozen culture medium collected as described in Example 2 which contained pseudotyped LNBOTDC virus was thawed in a 37° C. water bath and was then transferred to Oakridge centrifuge tubes (50 ml Oakridge tubes with sealing caps, Nalge Nunc International) previously sterilized by autoclaving. The virus was sedimented in a JA20 rotor (Beckman) at 48,000×g (20,000 rpm) at 4° C. for 120 min. The culture medium was then removed from the tubes in a biosafety hood and the media remaining in the tubes was aspirated to remove the supernatant. The virus pellet was resuspended to 0.5 to 1% of the original volume of culture medium DMEM. The resuspended virus pellet was incubated overnight at 4° C. without swirling. The virus pellet could be dispersed with gentle pipetting after the overnight incubation without significant loss of infectious virus. The titer of the virus stock was routinely increased 100- to 300-fold after one round of ultracentrifugation. The efficiency of recovery of infectious virus varied between 30 and 100%.

The virus stock was then subjected to low speed centrifugation in a microfuge for 5 min at 4° C. to remove any visible cell debris or aggregated virions that were not resuspended under the above conditions. It was noted that if the virus stock is not to be used for injection into oocytes or embryos, this centrifugation step may be omitted.

The virus stock can be subjected to another round of ultracentrifugation to further concentrate the virus stock. The resuspended virus from the first round of centrifugation is pooled and pelleted by a second round of ultracentrifugation which is performed as described above. Viral titers are increased approximately 2000-fold after the second round of ultracentrifugation (titers of the pseudotyped LNBOTDC virus are typically greater than or equal to $1\times10^9$ cfu/ml after the second round of ultracentrifugation).

The titers of the pre- and post-centrifugation fluids were determined by infection of 208F cells (NIH 3T3 or bovine mammary epithelial cells can also be employed) followed by selection of G418-resistant colonies as described above in Example 2.

Example 5

Preparation of Pseudotyped Retrovirus For Infection of Host Cells

The concentrated pseudotyped retroviruses were resuspended in 0.1×HBS (2.5 mM HEPES, pH 7.12, 14 mM NaCl, 75 μM $Na_2HPO_4$—$H_2O$) and 18 μl aliquots were placed in 0.5 ml vials (Eppendorf) and stored at −80° C. until used. The titer of the concentrated vector was determined by diluting 1 µl of the concentrated virus $10^{-7}$- or $10^{-8}$-fold with 0.1×HBS. The diluted virus solution was then used to infect 208F and bovine mammary epithelial cells and viral titers were determined as described in Example 2.

Example 6

Expression of MN14 by Host Cells

This Example describes the production of antibody MN14 from cells transfected with a high number of integrating vectors. Pseudotyped vector were made from the packaging cell lines for the following vectors: CMV MN14, α-LA MN14, and MMTV MN14. Rat fibroblasts (208F cells), MDBK cells (bovine kidney cells), and bovine mammary epithelial cells were transfected at a multiplicity of infection of 1000. One thousand cells were plated in a T25 flask and 106 colony forming units (CFU's) of vector in 3 ml media was incubated with the cells. The duration of the infection was 24 hr, followed by a media change. Following transfection, the cells were allowed to grow and become confluent.

The cell lines were grown to confluency in T25 flasks and 5 ml of media was changed daily. The media was assayed daily for the presence of MN14. All of the MN14 produced is active (an ELISA to detect human IgG gave the exact same values as the CEA binding ELISA) and Western blotting has shown that the heavy and light chains are produced at a ratio that appears to be a 1:1 ratio. In addition, a non-denaturing Western blot indicated that what appeared to be 100% of the antibody complexes were correctly formed (See FIG. 1: Lane 1, 85 ng control Mn14; Lane 2, bovine mammary cell line, α-LA promoter; Lane 3, bovine mammary cell line, CMV promoter; Lane 4, bovine kidney cell line, α-LA promoter; Lane 5, bovine kidney cell line, CMV promoter; Lane 6, 208 cell line, α-LA promoter; Lane 7, 208 cell line, CMV promoter)).

Figure 2:
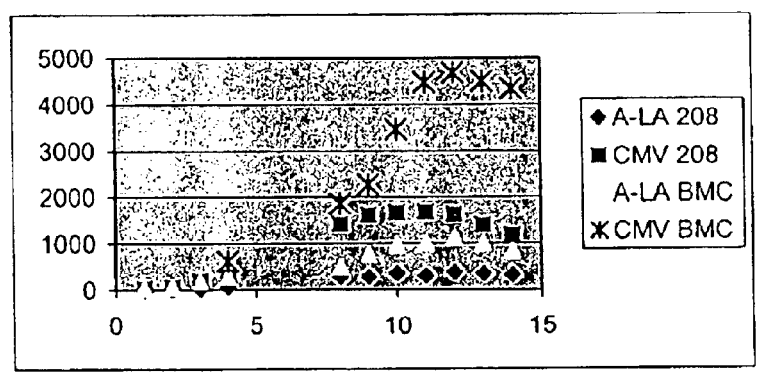
FIG. 2 is a graph of MN14 expression over time.

FIG. 2 is a graph showing the production of MN14 over time for four cell lines. The Y axis shows MN14 production in ng/ml of media. The X-axis shows the day of media collection for the experiment. Four sets of data are shown on the graph. The comparisons are between the CMV and α-LA promoter and between the 208 cells and the bovine mammary cells. The bovine mammary cell line exhibited the highest expression, followed by the 208F cells and MDBK cells. With respect to the constructs, the CMV driven construct demonstrated the highest level of expression, followed by the α-LA driven gene construct and the MMTV construct. At 2 weeks, the level of daily production of the CMV construct was 4.5 µg/ml of media (22.5 mg/day in a T25 flask). The level of expression subsequently increased slowly to 40 µg/day as the cells became very densely confluent over the subsequent week. 2.7 L of media from an α-lac-MN14 packaging cell line was processed by affinity chromatography to produce a purified stock of MN14.

Figure 3:
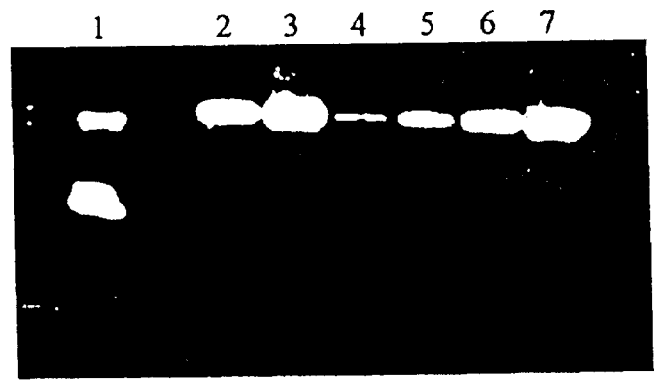
FIG. 3 is a Western blot of a 15% PAGE run under non-denaturing conditions and probed with anti-human IgG (Fc) and anti-human IgG (Kappa).

FIG. 3 is a western blot of a 15% SDS-PAGE gel run under denaturing conditions in order to separate the heavy and light chains of the MN14 antibody. Lane 1 shows 14 from bovine mammary cell line, hybrid α-LA promoter; lane 2 shows MN14 from bovine mammary cell line, CMV promoter; lane 3 shows MN14 from bovine kidney cell line, hybrid αLA promoter; lane 4 shows MN14 from bovine kidney cell line, CMV promoter; lane 5 shows MN14 from rat fibroblast cell line, hybrid α-LA promoter; lane 6 shows MN14 from rat fibroblast, CMV promoter. In agreement with FIG. 1 above, the results show that the heavy and light chains are produced in a ratio of approximately 1:1.

Example 7

Quantitation of Protein Produced Per Cell

This Example describes the quantitation of the amount of protein produced per cell in cell cultures produced according to the invention. Various cells (208F cells, MDBK cells, and bovine mammary cells) were plated in 25 $cm^2$ culture dishes at 1000 cells/dish. Three different vectors were used to infect the three cells types (CMV-MN14, MMTV-MN14, and α-LA-MN14) at an MOI of 1000 (titers: $2.8 \times 10^6$, $4.9 \times 10^6$, and $4.3 \times 10^6$, respectively). Media was collected approximately every 24 hours from all cells. Following one month of media collection, the 208F and MDBK cells were discarded due to poor health and low MN14 expression. The cells were passaged to T25 flasks and collection of media from the bovine mammary cells was continued for approximately 2 months with continued expression of MN14. After two months in T25 flasks, the cells with CMV promoters were producing 22.5 pg/cell/day and the cells with α-LA promoters were producing 2.5 µg MN14/cell/day.

After 2 months in T25 flasks, roller bottles (850 $cm^2$) were seeded to scale-up production and to determine if MN14 expression was stable following multiple passages. Two roller bottles were seeded with bovine mammary cells expressing MN14 from a CMV promoter and two roller bottles were seeded with bovine mammary cells expressing MN14 from the α-LA promoter. The cultures reached confluency after approximately two weeks and continue to express MN14. Roller bottle expression is shown in Table 1 below.

TABLE 1

Production of MN14 in Roller Bottles

| Cell Line | Promoter | MN14 Production/ Week (µg/ml) | MN14 Production/ Week - Total (µg/ml) |
|---|---|---|---|
| Bovine mammary | CMV | 2.6 | 1 - 520 |
| Bovine mammary | CMV | 10.6 | 2 - 2120 |
| Bovine mammary | CMV | 8.7 | 3 - 1740 |
| Bovine mammary | CMV | 7.8 | 4 - 1560 |
| Bovine mammary | α-LA | 0.272 | 1 - 54.4 |
| Bovine mammary | α-LA | 2.8 | 2 - 560 |
| Bovine mammary | α-LA | 2.2 | 3 - 440 |
| Bovine mammary | α-LA | 2.3 | 4 - 460 |

Example 8

Transfection at Varied Multiplicities of Infection

This Example describes the effect of transfection at varied multiplicities of infection on protein expression. 208F rat fibroblast and bovine mammary epithelial cells (BMEC) were plated in a 25 $cm^2$ plates at varied cell numbers/25 $cm^2$. Cells were infected with either the CMV MN14 vector or the αLA MN14 vector at a MOI of 1,10, 1000, and 10,000 by keeping the number of CFUs kept constant and varying the number of cells infected.

Following infection, medium was changed daily and collected approximately every 24 hours from all cells for approximately 2 months. The results of both of the vectors in bovine mammary epithelial cells are shown in Table 2 below. Cells without data indicate cultures that became infected prior to the completion of the experiment. The "# cells" column represents the number of cells at the conclusion of the experiment. The results indicate that a higher MOI results in increased MN14 production, both in terms of the amount of protein produced per day, and the total accumulation.

TABLE 2

MOI vs. Protein Production

| Cell Line | Promoter | MOI | % cell Confluency | MN14 (ng/ml) | # Cells | MN14 Production /day (pg/cell) |
|---|---|---|---|---|---|---|
| BMEC | CMV | 10000 | 100% | 4228 | 4.5E5 | 47 |
| BMEC | CMV | 1000 | 100% | 2832 | 2.0E6 | 7.1 |
| BMEC | CMV | 100 | | | | |
| BMEC | CMV | 10 | 100% | 1873 | 2.5E6 | 3.75 |
| BMEC | CMV | 1 | | | | |
| BMEC | αLA | 10000 | 100% | 1024 | 1.5E6 | 3.4 |
| BMEC | αLA | 1000 | | | | |
| BMEC | αLA | 100 | 100% | 722 | 1.8E6 | 1.9 |
| BMEC | αLA | 10 | 100% | 421234 | 2.3E6 | .925 |
| BMEC | αLA | 1 | 100% | | 1.9E6 | .325 |

Example 9

Transfection at Varied Multiplicities of Infection

This experiment describes protein production from the CMV MN14 vector at a variety of MOI values. Bovine mammary cells, CHO cells, and human embryo kidney cells (293 cells) were plated in 24 well plates (2 cm$^2$) at 100 cells/2 cm$^2$ well. Cells were infected at various dilutions with CMV MN14 to obtain MOI values of 1, 10, 100, 1000, and 10000. The CHO cells reached confluency at all MOI within 11 days of infection. However, the cells infected at a MOI of 10,000 grew more slowly. The bovine mammary and 293 cells grew slower, especially at the highest MOI of 10,000. The cells were then passaged into T25 flasks to disperse cells. Following dispersion, cells reached confluence within 1 week. the medium was collected after one week and analyzed for MN14 production. The CHO and human 293 cells did not exhibit good growth in extended culture. Thus, data were not collected from these cells. Data for bovine mammary epithelial cells are shown in Table 3 below. The results indicate that production of MN14 increased with higher MOI.

TABLE 3

MOI vs. Protein Production

| Cell Line | Promoter | MOI | % confluency | MN14 Production (ng/ml) |
|---|---|---|---|---|
| BMEC | CMV | 10000 | 100% | 1312 |
| BMEC | CMV | 1000 | 100% | 100 |
| BMEC | CMV | 100 | 100% | 7.23 |
| BMEC | CMV | 10 | 100% | 0 |
| BMEC | CMV | 1 | 100% | 0 |

Example 10

Expression of LL2 Antibody by Bovine Mammary Cells

This Example describes the expression of antibody LL2 by bovine mammary cells.

Bovine mammary cells were infected with vector CMV LL2 (7.85×10$^7$ CFU/ml) at MOI's of 1000 and 10,000 and plated in 25 cm$^2$ culture dishes. None of the cells survived transfection at the MOI of 10,000. At 20% confluency, 250 ng/ml of LL2 was present in the media.

Example 11

Expression of Botulinum Toxin Antibody by Bovine Mammary Cells

This Example describes the expression of Botulinum toxin antibody in bovine mammary cells. Bovine mammary cells were infected with vector α-LA Bot ($2.2\times10^2$ CFU/ml) and plated in 25 $cm^2$ culture dishes. At 100% confluency, 6 ng/ml of Botulinum toxin antibody was present in the media.

Example 12

Expression of Hepatitis B Surface Antigen by Bovine Mammary Cells

This Example describes the expression of hepatitis B surface antigen (HBSAg) in bovine mammary cells. Bovine mammary cells were infected with vector LSRNL (350 CFU/ml) and plated in 25 $cm^2$ culture dishes. At 100% confluency, 20 ng/ml of HBSAg was present in the media.

Example 13

Expression of cc49IL2 Antigen Binding Protein by Bovine Mammary Cells

This Example describes the expression of cc49IL2 in bovine mammary cells. Bovine mammary cells were infected with vector cc49IL2 ($3.1\times10^5$ CFU/ml) at a MOI of 1000 and plated in 25 $cm^2$ culture dishes. At 100% confluency, 10 $\mu$g/ml of cc49IL2 was present in the media.

Example 14

Expression of Multiple Proteins by Bovine Mammary Cells

This Example describes the expression of multiple proteins in bovine mammary cells. Mammary cells producing MN14 (infected with CMV-MN14 vector) were infected with cc49IL2 vector ($3.1\times10^5$ CFU/ml) at an MOI of 1000, and 1000 cells were plated in 25 $cm^2$ culture plates. At 100% confluency, the cells expressed MN14 at 2.5 g/ml and cc49IL2 at 5 $\mu$g/ml.

Example 15

Expression of Multiple Proteins by Bovine Mammary Cells

This Example describes the expression of multiple proteins in bovine mammary cells. Mammary cells producing MN14 (infected with CMV-MN14 vector) were infected with LSNRL vector (100 CFU/ml) at an MOI of 1000, and 1000 cells were plated in 25 $cm^2$ culture plates. At 100% confluency, the cells expressed MNI14 at 2.5 $\mu$g/ml and hepatitis surface antigen at 150 ng/ml.

Example 16

Expression of Multiple Proteins by Bovine Mammary Cells

This Example describes the expression of multiple proteins in bovine mammary cells. Mammary cells producing hepatitis B surface antigen (infected with LSRNL vector) were infected with cc491L2 vector at an MOI of 1000, and 1000 cells were plated in 25 cm² culture plates. At 100% confluency, the cells expressed MN14 at 2.4 μg/ml and hepatitis B surface antigen at 13 ng/ml. It will be understood that multiple proteins may be expressed in the other cell lines described above.

Example 17

Expression of Hepatitis B Surface Antigen and Botulinum Toxin Antibody in Bovine Mammary Cells This Example describes the culture of transfected cells in roller bottle cultures. 208F cells and bovine mammary cells were plated in 25 cm² culture dishes at 1000 cells/25 cm². LSRNL or α-LA Bot vectors were used to infect each cell line at a MOT of 1000. Following one month of culture and media collection, the 208F cells were discarded due to poor growth and plating. Likewise, the bovine mammary cells infected with α-LA Bot were discarded due to low protein expression. The bovine mammary cells infected with LSRNL were passaged to seed roller bottles (850 $cm^2$). Approximately 20 ng/ml hepatitis type B surface antigen was produced in the roller bottle cultures.

Example 18

Expression in Clonally Selected Cell Lines

This experiment describes expression of MN14 from clonally selected cell lines. Cell lines were grown to confluency in T25 flasks and 5 ml of media were collected daily. The media was assayed daily for the presence of MN14. All the MN14 produced was active and Western blotting indicated that the heavy and light chains were produce at a ratio that appears to be almost exactly 1:1. In addition, a non-denaturing western blot indicated that approximately 100% of the antibody complexes were correctly formed. After being in culture for about two months, the cells were expanded into roller bottles or plated as single cell clones in 96 well plates.

The production of MN14 in the roller bottles was analyzed for a 24 hour period to determine if additional medium changing would increase production over what was obtained with weekly medium changes. Three 24 hour periods were examined. The CMV promoter cells in 850 $cm^2$ roller bottles produced 909 ng/ml the first day, 1160 ng/ml the second day and 1112 ng/ml the third day. The α-LA promoter cells produced 401 ng/ml the first day, 477 ng/ml the second day and 463 ng/ml the third day. These values correspond well to the 8–10 mg/ml week that were obtained for the CMV cells and the 2–3 mg/ml that were obtained for the α-LA cells. It does not appear that more frequent media changing would increase MN14 production in roller bottles.

Single cell lines were established in 96 well plates and then passaged into the same wells to allow the cells to grow to confluency. Once the cells reached confluency, they were assayed for MN14 production over a 24 hour period. The clonal production of MN14 from CMV cell lines ranged from 19 ng/ml/day to 5500 ng/ml/day. The average production of all cell clones was 1984 ng/ml/day. The α-LA cell clones yielded similar results. The clonal production of MN14 from α-LA cell lines ranged from 1 ng/ml/day to 2800 ng/ml/day. The average production of these cell clones was 622 ng/ml/day. The results are provided in Table 4 below.

TABLE 4

Expression in Clonal Cell Lines

| CMV Clonal Cell Line Number | MN14 Production (ng/ml) | Alpha-lactalbumin Clonal Cell Line Number | MN14 Production (ng/ml) |
|---|---|---|---|
| 22 | 19 | 27 | 0 |
| 6 | 88 | 29 | 0 |
| 29 | 134 | 12 | 0.7 |
| 34 | 151 | 50 | 8 |
| 32 | 221 | 28 | 55 |
| 23 | 343 | 43 | 57 |
| 27 | 423 | 8 | 81 |
| 4 | 536 | 13 | 154 |
| 41 | 682 | 48 | 159 |
| 45 | 685 | 7 | 186 |
| 40 | 696 | 36 | 228 |
| 11 | 1042 | 39 | 239 |
| 8 | 1044 | 51 | 275 |
| 5 | 1066 | 31 | 283 |
| 19 | 1104 | 54 | 311 |
| 48 | 1142 | 38 | 317 |
| 12 | 1224 | 21 | 318 |
| 26 | 1315 | 16 | 322 |
| 39 | 1418 | 47 | 322 |
| 37 | 1610 | 17 | 325 |
| 20 | 1830 | 37 | 367 |
| 21 | 1898 | 45 | 395 |
| 47 | 1918 | 25 | 431 |
| 35 | 1938 | 5 | 441 |
| 15 | 1968 | 20 | 449 |
| 3 | 1976 | 19 | 454 |
| 28 | 1976 | 22 | 503 |
| 1 | 2166 | 55 | 510 |
| 16 | 2172 | 14 | 519 |
| 17 | 2188 | 41 | 565 |
| 33 | 2238 | 46 | 566 |
| 30 | 2312 | 23 | 570 |
| 38 | 2429 | 1 | 602 |
| 2 | 2503 | 9 | 609 |
| 14 | 2564 | 53 | 610 |
| 24 | 2571 | 56 | 631 |
| 9 | 2708 | 2 | 641 |
| 42 | 2729 | 40 | 643 |
| 44 | 2971 | 32 | 653 |
| 7 | 3125 | 24 | 664 |
| 43 | 3125 | 26 | 671 |
| 25 | 3650 | 52 | 684 |
| 46 | 3706 | 6 | 693 |
| 50 | 3947 | 33 | 758 |
| 49 | 4538 | 42 | 844 |
| 18 | 4695 | 10 | 1014 |
| 31 | 4919 | 3 | 1076 |
| 10 | 5518 | 44 | 1077 |
| | | 35 | 1469 |
| | | 34 | 1596 |
| | | 18 | 1820 |
| | | 30 | 2021 |
| | | 11 | 2585 |
| | | 4 | 2800 |

Example 19

Estimation of Insert Copy Number

This example describes the relationship of multiplicity of infection, gene copy number, and protein expression. Three DNA assays were developed using the INVADER Assay system (Third Wave Technologies, Madison, Wis.). One of the assays detects a portion of the bovine α-lactalbumin 5' flanking region. This assay is specific for bovine and does not detect the porcine or human α-lactalbumin gene. This assay will detect two copies of the α-lactalbumin gene in all control bovine DNA samples and also in bovine mammary epithelial cells. The second assay detects a portion of the extended packaging region from the MLV virus. This assay is specific for this region and does not detect a signal in the 293 human cell line, bovine mammary epithelial cell line or bovine DNA samples. Theoretically, all cell lines or other samples not infected with MLV should not produce a signal. However, since the 293GP cell line was produced with the extended packaging region of DNA, this cell line gives a signal when the assay is run. From the initial analysis, it appears that the 293GP cell line contains two copies of the extended packing region sequence that are detected by the assay. The final assay is the control assay. This assay detects a portion of the insulin-like growth factor I gene that is identical in bovine, porcine, humans and a number of other species. It is used as a control on every sample that is run in order to determine the amount of signal that is generated from this sample for a two copy gene. All samples that are tested should contain two copies of the control gene.

DNA samples can be isolated using a number of methods. Two assays are then performed on each sample. The control assay is performed along with either the bovine α-lactalbumin assay or the extended packaging region assay. The sample and the type of information needed will determine which assay is run. Both the control and the transgene detection assay are run on the same DNA sample, using the exact same quantity of DNA.

The data resulting from the assay are as follows (Counts indicate arbitrary fluorescence units):

Extended Packaging Region or α-Lactalbumin Background counts

Extended Packaging Region or α-Lactalbumin counts

Internal Control background counts

Internal Control counts

To determine net counts for the assay the background counts are subtracted from the actual counts. This occurs for both the control and transgene detection assay. Once the net counts are obtained, a ratio of the net counts for the transgene detection assay to the net counts of the control assay can be produced. This value is an indication of the number of copies of transgene compared to the number of copies of the internal control gene (in this case IGF-I). Because the transgene detection assay and the control assay are two totally different assays, they do not behave exactly the same. This means that one does not get an exact 1:1 ratio if there are two copies of the transgene and two copies of the control gene in a specific sample. However the values are generally close to the 1:1 ratio. Also, different insertion sites for the transgene may cause the transgene assay to behave differently depending on where the insertions are located.

Therefore, although the ratio is not an exact measure of copy number, it is a good indication of relative copy number between samples. The greater the value of the ratio the greater the copy number of the transgene. Thus, a ranking of samples from lowest to highest will give a very accurate comparison of the samples to one another with regard to copy number. Table 5 provides actual data for the EPR assay:

TABLE 5

| Sample # | Control Counts | Control Background Counts | Net Control Counts | Transgene Counts | Transgene Background Counts | Net Transgene Counts | Net Ratio |
|---|---|---|---|---|---|---|---|
| 293 | 116 | 44 | 72 | 46.3 | 46 | 0.3 | 0 |
| 293GP | 112 | 44 | 68 | 104 | 46 | 58 | .84 |
| 1 | 74 | 40 | 34 | 88 | 41 | 47 | 1.38 |
| 2 | 64 | 40 | 24 | 83 | 41 | 43 | 1.75 |
| 3 | 62 | 44 | 18 | 144 | 46 | 98 | 5.57 |

From this data, it can be determined that the 293 cell line has no copies of the extended packaging region/transgene. However the 293 GP cells appear to have two copies of the extended packaging region. The other three cell lines appear to have three or more copies of the extended packaging region (one or more additional copies compared to 293GP cells).

Invader Assay Gene Ratio and Cell Line Protein Production

Bovine mammary epithelial cells were infected with either the CMV driven MN14 construct or the α-lactalbumin driven MN14 construct. The cells were infected at a 1000 to 1 vector to cell ratio. The infected cells were expanded. Clonal cell lines were established for both the α-LA and CMV containing cells from this initial pooled population of cells. Approximately 50 cell lines were produced for each gene construct. Individual cells were placed in 96 well plates and then passaged into the same well to allow the cells to grow to confluency. Once the cells lines reached confluency, they were assayed for MN14 production over a 24 hour period. The clonal production of MN14 from CMV cell lines ranged from 0 ng/ml/day to 5500 ng/ml/day. The average production of all cell clones was 1984 ng/ml day. The α-LA cell clones showed similar trends. The clonal production of MN14 from α-LA cell lines ranged from 0 ng/ml/day to 2800 ng/ml/day. The average production of these cell clones was 622 ng/m1/day.

For further analysis of these clonal lines, fifteen CMV clones and fifteen α-LA clones were selected. Five highest expressing, five low expressing and five mid-level expressing lines were chosen. These thirty cell lines were expanded and banked. DNA was isolated from most all of the thirty cell lines. The cell lines were passed into 6 well plates and grown to confluency. Once at confluency, the media was changed every 24 hours and two separate collections from each cell line were assayed for MN14 production. The results of these two assays were averaged and these numbers were used to create Tables 6 and 7 below. DNA from the cell lines was run using the Invader extended packaging region assay and the results are shown below. The Tables show the cell line number, corresponding gene ratio and antibody production.

TABLE 6

| CMV Clonal Cell Line Number | Invader Gene Ratio | MN14 Production (ng/ml) |
|---|---|---|
| 6 | 0.19 | 104 |
| 7 | 1.62 | 2874 |
| 10 | 2.57 | 11202 |
| 18 | 3.12 | 7757 |
| 19 | 1.62 | 2483 |

TABLE 6-continued

| CMV Clonal Cell Line Number | Invader Gene Ratio | MN14 Production (ng/ml) |
|---|---|---|
| 21 | 1.53 | 3922 |
| 22 | 0 | 0 |
| 29 | 0.23 | 443 |
| 31 | 3.45 | 5697 |
| 32 | 0.27 | 346 |
| 34 | 0.37 | 305 |
| 38 | 1.47 | 2708 |
| 41 | 1.54 | 5434 |
| 49 | 2.6 | 7892 |
| 50 | 1.56 | 5022 |
| Average of All Clones | 1.48 | 3746 |

TABLE 7

| α-LA Clonal Cell Line Number | Invader Gene Ratio | MN14 Production (ng/ml) |
|---|---|---|
| 4 | 4.28 | 3600 |
| 6 | 1.15 | 959 |
| 12 | 0.35 | 21 |
| 17 | 0.54 | 538 |
| 28 | 0.75 | 60 |
| 30 | 1.73 | 2076 |
| 31 | 0.74 | 484 |
| 34 | 4.04 | 3332 |
| 41 | 1.33 | 771 |
| Average of All Clones | 1.66 | 1316 |

The graphs (FIGS. 17 and 18) show the comparison between protein expression and invader assay gene ratio. The results indicate that there is a direct correlation between invader assay gene ratio and protein production. It also appears that the protein production has not reached a maximum and if cells containing a higher invader assay gene ratio were produced, higher protein production would occur.

Invader Assay Gene Ratio and Multiple Cell Line Infections

Two packaging cell lines (293GP) produced using previously described methods were used to produce replication defective retroviral vector. One of the cell lines contains a retroviral gene construct that expresses the botulinum toxin antibody gene from the CMV promoter (LTR-Extended Viral Packaging Region-Neo Gene-CMV Promoter-Bot Light Chain Gene-IRES-Bot Heavy Chain Gene-LTR), the other cell line contains a retroviral gene construct that expresses the YP antibody gene from the CMV promoter (LTR-Extended Viral Packaging Region-Neo Gene-CMV Promoter-YP Heavy Chain Gene-IRES-YP Light Chain Gene-WPRE-LTR). In addition to being able to produce replication defective retroviral vector, each of these cell lines also produce either botulinum toxin antibody or YP antibody.

The vector produced from these cell lines was then used to re-infect the parent cell line. This procedure was performed in order to increase the number of gene insertions and to improve antibody production from these cell lines. The botulinum toxin parent cell line was infected with a new aliquot of vector on three successive days. The titer of the vector used to perform the infection was $1 \times 10^8$ cfu/ml. Upon completion of the final 24 hour infection, clonal selection was performed on the cells and the highest protein producing line was established for botulinum toxin antibody production. A similar procedure was performed on the YP parent cell line. This cell line was also infected with a new aliquot of vector on three successive days. The titer of the YP vector aliquots was $1 \times 10^4$. Upon completion of the final 24 hour infection, clonal selection was performed on the cells and the highest protein producing line was established for YP production.

Each of the parent cell lines and the daughter production cell lines were examined for Invader gene ratio using the extended packaging region assay and for protein production. The Bot production cell line which was generated using the highest titer vector had the highest gene ratio. It also had the highest protein production, again suggesting that gene copy number is proportional to protein production. The YP production cell line also had a higher gene ratio and produced more protein than its parent cell line, also suggesting that increasing gene copy is directly related to increases in protein production. The data is presented in Table 8.

TABLE 8

| Cell Line | Invader Gene Ratio | Antibody Production (Bot/YP) |
|---|---|---|
| Bot Parent Cell Line | 1.12 | 4.8 mg/ml |
| Bot Production Cell Line | 3.03 | 55 mg/ml |
| YP Parent Cell Line | 1.32 | 4 mg/ml |
| YP Production Cell Line | 2.04 | 25 mg/ml |

Example 20

Transfection with Lentivirus Vectors

This example describes methods for the production of lentivirus vectors and their use to infect host cells at a high multiplicity of infection. Replication-defective viral particles are produced by the transient cotransfection of the plasmids described in U.S. Pat. No. 6,013,516 in 293T human kidney cells. All plasmids are transformed and grown in E. coli HB101 bacteria following standard molecular biology procedures. For transfection of eukaryotic cells, plasmid DNA is purified twice by equilibrium centrifugation in CsCl-ethidium bromide gradients. A total of 40 μg DNA is used for the transfection of a culture in a 10 cm dish, in the following proportions: 10 μg pCMVΔR8, 20 μg pHR', and 10 μg env plasmids, either MLV/Ampho, MLV/Eco or VSV-G. 293T cells are grown in DMEM supplemented with 10% fetal calf serum and antibiotics in a 10% $CO_2$ incubator. Cells are plated at a density of $1.3 \times 10^6/10$ cm dish the day before transfection. Culture medium is changed 4 to 6 hrs before transfection. Calcium phosphate-DNA complexes are prepared according to the method of Chen and Okayama (Mol. Cell. Biol., 7:2745, 1987), and incubated overnight with the cells in an atmosphere of 5% $CO_2$. The following morning, the medium is replaced, and the cultures returned to 10% $CO_2$. Conditioned medium is harvested 48 to 60 hrs after transfection, cleared of cellular debris by low speed centrifugation (300×g 10 min), and filtered through 0.45 μm low protein binding filters.

To concentrate vector particles, pooled conditioned medium harvested as described above is layered on top of a cushion of 20% sucrose solution in PBS and centrifuged in a Beckman SW28 rotor at 50,000×g for 90 min. The pellet is resuspended by incubation and gentle pipetting in 1–4 ml PBS for 30–60 min, then centrifuged again at 50,000×g for 90 min in a Beckmann SW55 rotor. The pellet is resuspended in a minimal volume (20–50 μl) of PBS and either used directly for infection or stored in frozen aliquots at −80° C. The concentrated lentivirus vectors are titered and used to transfect an appropriate cell line (e.g., 293 cells, Hela cells, rat 208F fibroblasts)) at a multiplicity of infection of 1,000. Analysis of clonally selected cell lines expressing the exogenous protein will reveal that a portion of the selected cell lines contain more than two integrated copies of the vector. These cell lines will produce more of the exogenous protein than cell lines containing only one copy of the integrated vector.

Example 21

Expression and Assay of G-protein Coupled Receptors

This example describes the expression of a G-Protein Coupled Receptor protein (GPCR) from a retroviral vector. This example also describes the expression of a signal protein from an IRES as a marker for expression of a difficult to assay protein or a protein that has no assay such as a GPCR. The gene construct (SEQ ID NO: 34;

FIG. 19) comprises a G-protein-coupled receptor followed by the IRES-signal peptide-antibody light chain cloned into the MCS of pLBCX retroviral backbone. Briefly, a PvuII/PvuII fragment (3057 bp) containing the GPCR-IRES-antibody light chain was cloned into the StuI site of pLBCX. pLBCX contains the EM7 (T7) promoter, Blasticidin gene and SV40 polyA in place of the Neomycin resistance gene from pLNCX.

The gene construct was used to produce a replication defective retroviral packaging cell line and this cell line was used to produce replication defective retroviral vector. The vector produced from this cell line was then used to infect 293GP cells (human embryonic kidney cells). After infection, the cells were placed under Blasticidin selection and single cell Blasticidin resistant clones were isolated.

The clones were screened for expression of antibody light chain. The top 12 light chain expressing clones were selected. These 12 light chain expressing clones were then screened for expression of the GPCR using a ligand binding assay. All twelve of the samples also expressed the receptor protein. The clonal cell lines and there expression are shown in Table 9.

TABLE 9

| Cell Clone Number | Antibody Light Chain Expression | GPCR Expression |
|---|---|---|
| 4 | + | + |
| 8 | + | + |
| 13 | + | + |
| 19 | + | + |
| 20 | + | + |
| 22 | + | + |
| 24 | + | + |
| 27 | + | + |
| 30 | + | + |
| 45 | + | + |
| 46 | + | + |
| 50 | + | + |

Example 22

Multiple Infection of 293 Cells with Replication Defective Retroviral Vector

This example describes the multiple serial transfection of cells with retroviral vector. The following gene construct was used to produce a replication defective retroviral packaging cell line.

| | |
|---|---|
| 5' LTR = | Moloney murine sarcoma virus 5' long terminal repeat. |
| EPR = | Moloney murine leukemia virus extended packaging region. |
| Blast = | Blasticidin resistance gene. |
| CMV = | Human cytomegalovirus immediate early promoter. |
| Gene = | Gene encoding test protein |
| WPRE = | RNA transport element |
| 3' LTR = | Moloney murine leukemia virus 3' LTR. |

This packaging cell line was then used to produce a replication defective retroviral vector arranged as follows. The vector was produced from cells grown in T150 flasks and frozen. The frozen vector was thawed at each infection. For infection # 3 a concentrated solution of vector was used to perform the infection. All other infections were performed using non-concentrated vector. The infections were performed over a period of approximately five months by placing 5 ml of vector/media solution on a T25 flask containing 30% confluent 293 cells. Eight mg/ml of polybrene was also placed in the vector solution during infection. The vector solution was left on the cells for 24 hours and then removed. Media (DMEM with 10% fetal calf serum) was then added to the cells. Cells were grown to full confluency and passaged into a new T25 flask. The cells were then grown to 30% confluency and the infection procedure was repeated. This process was repeated 12 times and is outlined Table 10 below. After infections 1, 3, 6, 9 and 12, cells left over after passaging were used to obtain a DNA sample. The DNA was analyzed using the INVADER assay to determine an estimate of the number of vector inserts in the cells after various times in the infection procedure. The results indicate that the number of vector insertions goes up over time with the highest level being after the 12' infection. Since a value of 0.5 is approximately an average of one vector insert copy per cell, after twelve infections the average vector insert copy has yet to reach two. These data indicates that the average vector copy per cell is a little less that 1.5 copies per cell. Also, there was no real change in gene copy number from infection #6 to infection #9. Furthermore, these data indicate that transfection conducted at a standard low multiplicity of infection fail to introduce more than one copy of the retroviral vector into the cells.

TABLE 10

| Cell Line or Infection Number | Vector Titer (CFU/ml) | "Invader" Gene Ratio |
|---|---|---|
| 293 | | 0.053 |
| Infection #1 | $1.05 \times 10^3$ | 0.39 |
| Infection #2 | $1.05 \times 10^3$ | |
| Infection #3 | $7.6 \times 10^4$ | 0.45 |
| Infection #4 | $1.05 \times 10^3$ | |
| Infection #5 | $1.05 \times 10^3$ | |
| Infection #6 | $1.05 \times 10^3$ | 0.54 |
| Infection #7 | $1.05 \times 10^3$ | |
| Infection #8 | $1.05 \times 10^3$ | |
| Infection #9 | $1.05 \times 10^3$ | 0.52 |
| Infection #10 | $1.05 \times 10^3$ | |
| Infection #11 | $1.05 \times 10^3$ | |
| Infection #12 | $1.05 \times 10^3$ | 0.69 |

Example 23

Production of YP antibody

This Example demonstrates the production of *Yersinia pestis* antibody by bovine mammary epithelial cells and human kidney fibroblast cells (293 cells). Cells lines were infected with the α-LA YP vector. Both of the cell lines produced YP antibody. All of the antibody is active and the heavy and light chains are produced in 2@ a ratio approximating 1:1.

Example 24

Transduction of Plant Protoplasts

This Example describes a method for transducing plant protoplasts. Tobacco protoplasts of *Nicotiana tabacum* c.v. Petit Havanna are produced according to conventional processes from a tobacco suspension culture (Potrykus and Shillito, Methods in Enzymology, vol. 118, Plant Molecular Biology, eds. A. and H. Weissbach, Academic Press, Orlando, 1986). Completely unfolded leaves are removed under sterile conditions from 6-week-old shoot cultures and thoroughly wetted with an enzyme solution of the following composition: Enzyme solution: $H_2O$, 70 ml; sucrose, 13 g; macerozyme R10, 1 g; cellulase, 2 g; "Onozuka" R 10 (Yakult Co. Ltd., Japan) Drisellase (Chemische Fabrik Schweizerhalle, Switzerland), 0.13 g; and 2(n-morpholine)-ethanesulphonic acid (MES), 0.5 ml pH 6.0 Leaves are then cut into squares from 1 to 2 cm in size and the squares are floated on the above-mentioned enzyme solution. They are incubated overnight at a temperature of 26° C. in the dark. This mixture is then gently shaken and incubated for a further 30 minutes until digestion is complete.

The suspension is then filtered through a steel sieve having a mesh width of 100 μm, rinsed thoroughly with 0.6M sucrose (MES, pH 5.6) and subsequently centrifuged for 10 minutes at from 4000 to 5000 rpm. The protoplasts collect on the surface of the medium which is then removed from under the protoplasts, for example using a sterilized injection syringe.

The protoplasts are resuspended in a $K_3$ medium [sucrose (102.96 μl; xylose (0.25 g/l); 2,4-dichlorophenoxyacetic acid (0.10 mg/l); 1-naphthylacetic acid (1.00 mg/l); 6-benzylaminopurine (0.20 mg/l); pH 5.8](Potrylcus and Shillito, supra) that contains 0.4M sucrose.

To carry out the transformation experiments, the protoplasts are first of all washed, counted and then resuspended, at a cell density of from 1 to $2.5 \times 10^6$ cells per ml, in a $W_5$ medium [154 mM NaCl, 125 mM $CaCl_2 \times 2H_2O$, 5 mM KCl, 5 mM glucose, pH 5.6), which ensures a high survival rate of the isolated protoplasts. After incubation for 30 minutes at from 6 to 8° C., the protoplasts are then used for the transduction experiments.

The protoplasts are exposed to a pseudotyped retroviral vector (e.g., a lentiviral vector) encoding a protein of interest driven by a plant specific promoter. The vector is prepared as described above and is used at an MOI of 1,000. The protoplasts are then resuspended in fresh $K_3$ medium (0.3 ml protoplast solution in 10 ml of fresh K3 medium). Further incubation is carried out in 10 ml portions in 10 cm diameter petri dishes at 24° C. in the dark, the population density being from 4 to $8 \times 10^4$ protoplasts per ml. After 3 days, the culture medium is diluted with 0.3 parts by volume of $K_3$ medium per dish and incubation is continued for a further 4 days at 24° C. and 3000 lux of artifical light. After a total of 7 days, the clones that have developed from the protoplasts are embedded in nutrient medium that contains 50 mg/l of kanamycin and has been solidified with 1% agarose, and are cultured at 24° C. in the dark in accordance with the "bead-type" culturing method (Shillito, et al., Plant Cell Reports, 2, 244–247 (1983)). The nutrient medium is replaced every 5 days by a fresh amount of the same nutrient solution. Analysis of the clones indicates that express the gene of interest.

Example 25

Stability of Vector Insertions in Cell Lines Over Time

Two cell lines that contain gene inserts of the LN-CMV-Bot vector were analyzed for there ability to maintain the vector inserts over a number of passages with and without neomycin selection. The first cell line is a bovine mammary epithelial cell line that contains a low number of insert copies. The second cell line is a 293GP line that contains multiple copies of the vector insert. At the start of the experiment, cell cultures were split. This was at passage 10 for the bovine mammary epithelial cells and passage 8 for the 293GP cells. One sample was continually passaged in media containing the neomycin analog G418, the other culture was continually passaged in media without any antibiotic. Every 3–6 passages, cells were collected and DNA was isolated for determination of gene ratio using the INVADER assay. Cell were continually grown and passaged in T25 flasks. The results of the assays are shown below:

TABLE 11

Low Gene Copy Cell Line

| Cell Line and Treatment | Passage Number | INVADER Gene Ratio |
|---|---|---|
| BMEC/Bot #66 + G418 | 10 | 0.67 |
| BMEC/Bot #66 − G418 | 10 | 0.89 |
| BMEC/Bot #66 + G418 | 16 | 0.67 |
| BMEC/Bot #66 − G418 | 16 | 0.64 |
| BMEC/Bot #66 + G418 | 21 | 0.62 |
| BMEC/Bot #66 − G418 | 21 | 0.58 |
| BMEC/Bot #66 + G418 | 27 | 0.98 |
| BMEC/Bot #66 − G418 | 27 | 0.56 |
| BMEC/Bot #66 + G418 | 33 | 0.80 |
| BMEC/Bot #66 − G418 | 33 | 0.53 |

TABLE 12

High Gene Copy Cell Line

| Cell Line and Treatment | Passage Number | INVADER Gene Ratio |
|---|---|---|
| 293GP/Bot #23 + G418 | 8 | 3.46 |
| 293GP/Bot #23 − G418 | 8 | 3.73 |
| 293GP/Bot #23 + G418 | 14 | 3.28 |
| 293GP/Bot #23 − G418 | 14 | 3.13 |
| 293GP/Bot #23 + G418 | 17 | 3.12 |
| 293GP/Bot #23 − G418 | 17 | 2.91 |
| 293GP/Bot #23 + G418 | 22 | 3.6 |
| 293GP/Bot #23 − G418 | 22 | 2.58 |
| 293GP/Bot #23 + G418 | 28 | 2.78 |
| 293GP/Bot #23 − G418 | 28 | 3.44 |
| 293GP/Bot #23 + G418 | 36 | 2.6 |
| 293GP/Bot #23 − G418 | 36 | 2.98 |

These data show that there are no consistent differences in gene ratio between cells treated with G418 and those not treated with antibiotic. This suggests that G418 selection is not necessary to maintain the stability of the vector gene insertions. Also, these vector inserts appear to be very stable over time.

All publications and patents mentioned in the above specification are herein incorporated by reference. Various modifications and variations of the described method and

What is claimed is:

1. A clonally selected host cell comprising a genome, said genome comprising from about 20 to about 50 integrated integrating vectors, wherein said integrating vectors comprise at least one exogenous gene operably linked to a promoter, said gene encoding a secreted protein, wherein said host cell does not produce infectious retroviral particles.

2. The host cell of claim 1, wherein said integrating vectors further comprise an RNA export element operably linked to said exogenous gene.

3. The host cell of claim 1, wherein said integrating vectors comprise at least two exogenous genes.

4. The host cell of claim 3, wherein one of said at least two exogenous genes is a selectable marker.

5. The host cell of claim 1, wherein said integrating vector is a retroviral vector.

6. The host cell of claim 1, wherein said host cell is selected from Chinese hamster ovary cells, baby hamster kidney cells, and bovine mammary epithelial cells.

7. The host cell of claim 1, wherein said promoter is selected from the group consisting of alpha-lactalbumin promoter, cytomegalovirus promoter and the long terminal repeat of Moloney murine leukemia virus.

8. The host cells of claim 1, further comprising at least 1 integrated copy of a second integrating vector comprising a second exogenous gene.

9. A method for transducing host cells comprising:
1) providing:
   a) a host cell comprising a genome, and
   b) a plurality of retroviral vectors; and
2) contacting said host cell with said plurality of retroviral vectors at a multiplicity of infection of grater than 100 under conditions such that at least two retroviral vectors integrate into said genome of said host cell, wherein said retroviral vectors comprise at least one exogenous gene operably linked to a promoter, said gene encoding a secreted protein, wherein said host cell does not produce infectious retroviral particles;
3) clonally selecting a transduced host cell.

10. The method of claim 9, wherein said host cells are contacted with said plurality of retroviral vectors under conditions such that at least 3 to about 50 retroviral vectors integrate into said genome of said host cell.

11. The method of claim 9, wherein said host cells are contacted with said plurality of retroviral vectors under conditions such that at least 4 to about 50 retroviral vectors integrate into said genome of said host cell.

12. The method of claim 9, wherein said retroviral vectors comprise at least one exogenous gene operably linked to a promoter.

13. The method of claim 9, wherein said retroviral integrating vectors further comprise an RNA export element operably linked to said gene exogenous gene.

14. The method of claim 9, wherein said retroviral vectors comprises at least two exogenous genes.

15. The method of claim 9, wherein said retroviral vector is a pseudotyped retroviral vector.

16. The method of claim 9, wherein said host cell is selected from Chinese hamster ovary cells, baby hamster kidney cells, and bovine mammary epithelial cells.

17. The method of claim 9, further comprising transducing said host cells with at least two retroviral vectors, each of said two retroviral vectors comprising a different exogenous gene.

18. A method of producing a protein of interest comprising:
1) providing a clonally selected host cells comprising a genome, said genome comprising from about 20 to about 50 integrated copies of at least one integrating vector comprising an exogenous gene operably linked to a promoter, wherein said exogenous gene encodes a secretable protein of interest, and
2) culturing said host cells under conditions such that said protein of interest is produced at rate of from 10 picograms per cell per day to about 50 picograms per cell per day.

19. The method of claim 18, further comprising step
3) isolating said protein of interest.

20. The method of claim 18, wherein said conditions are selected from the group consisting of roller bottle cultures, perfusion cultures, batch fed cultures, and petri dish cultures.

21. The method of claim 18, wherein said integrating vector is a retroviral vector.

22. The method of claim 18, wherein said host cell is selected from Chinese hamster ovary cells, baby hamster kidney cells, and bovine mammary epithelial cells.

23. A method comprising:
1) providing:
   a) a host cell comprising a genome comprising at least one integrated exogenous gene; and
   b) a plurality of retroviral vectors comprising said exogenous gene, said gene encoding a secreted protein, wherein said host cell does not produce infectious retroviral particles; and
2) contacting said host cell with said plurality of retroviral vectors at a multiplicity of infection of greater than 100 such that at least two of said retroviral vectors integrate into said genome of said host cell.

24. The method of claim 23, wherein said integrated exogenous gene comprises an integrating vector.

25. The method of claim 23, wherein said host cell is clonally selected.

26. The method of claim 23, wherein said host cell is non-clonally selected.

27. The method of claim 23, wherein said host cells are contacted with said plurality of retroviral vectors under conditions such that at least 3 to about 50 retroviral vectors integrate into said genome of said host cell.

28. The method of claim 23, wherein said retroviral vector is a pseudotyped retroviral vector.

29. The method of claim 9, wherein said multiplicity of infection is greatrer than 100 to about 1000.

30. The method of claim 9, wherein said multiplicity of infection is from about 150 to about 1000.

31. The method of claim 23, wherein said multiplicity of infection is greatrer than 100 to about 1000.

32. The method of claim 23, wherein said multiplicity of infection is from about 150 to about 1000.

* * * * *

SEQUENCE LISTING

<160> NUMBER OF SEQ ID NOS: 36

<210> SEQ ID NO 1
<211> LENGTH: 2101
<212> TYPE: DNA
<213> ORGANISM: Artificial Sequence
<220> FEATURE:
<223> OTHER INFORMATION: Synthetic

<400> SEQUENCE: 1

```
gatcagtcct gggtggtcat tgaaaggact gatgctgaag ttgaagctcc aatactttgg     60
ccacctgatg cgaagaactg actcatgtga taagaccctg atactgggaa agattgaagg    120
caggaggaga agggatgaca gaggatggaa gagttggatg gaatcaccaa ctcgatggac    180
atgagtttga gcaagcttcc aggagttggt aatgggcagg gaagcctggc gtgctgcagt    240
ccatggggtt gcaaagagtt ggacactact gagtgactga actgaactga tagtgtaatc    300
catggtacag aatataggat aaaaagagg aagagtttgc cctgattctg aagagttgta    360
ggatataaaa gtttagaata cctttagttt ggaagtctta aattatttac ttaggatggg    420
tacccactgc aatataagaa atcaggcttt agagactgat gtagagagaa tgagccctgg    480
cataccagaa gctaacagct attggttata gctgttataa ccaatatata accaatatat    540
tggttatata gcatgaagct tgatgccagc aatttgaagg aaccatttag aactagtatc    600
ctaaactcta catgttccag gacactgatc ttaaagctca ggttcagaat cttgttttat    660
aggctctagg tgtatattgt ggggcttccc tggtggctca gatggtaaag tgtctgcctg    720
caatgtgggt gatctgggtt cgatccctgg cttgggaaga tccctggag aaggaaatgg    780
caacccactc tagtactctt acctggaaaa ttccatggac agaggagcct tgtaagctac    840
agtccatggg attgcaaaga gttgaacaca actgagcaac taagcacagc acagtacagt    900
atacacctgt gaggtgaagt gaagtgaagg ttcaatgcag ggtctcctgc attgcagaaa    960
gattctttac catctgagcc accaggaag cccaagaata ctggagtggg tagcctattc   1020
cttctccagg ggatcttccc atcccaggaa ttgaactgga gtctcctgca tttcaggtgg   1080
attcttcacc agctgaacta ccaggtggat actactccaa tattaaagtg cttaaagtcc   1140
agttttccca ccttccccaa aaaggttggg tcactctttt ttaaccttct gtggcctact   1200
ctgaggctgt ctacaagctt atatatttat gaacacattt attgcaagtt gttagtttta   1260
gatttacaat gtggtatctg gctatttagt ggtattggtg gttggggatg gggaggctga   1320
tagcatctca gagggcagct agatactgtc atacacactt ttcaagttct ccattttgt    1380
gaaatagaaa gtctctggat ctaagttata tgtgattctc agtctctgtg gtcatattct   1440
attctactcc tgaccactca acaaggaacc aagatatcaa gggacacttg ttttgtttca   1500
tgcctgggtt gagtgggcca tgacatatgt tctgggcctt gttacatggc tggattggtt   1560
ggacaagtgc cagctctgat cctgggactg tggcatgtga tgacatacac ccctctcca   1620
cattctgcat gtctctaggg gggaaggggg aagctcggta tagaaccttt attgtatttt   1680
ctgattgcct cacttcttat attgccccca tgcccttctt tgttcctcaa gtaaccagag   1740
```

```
acagtgcttc ccagaaccaa ccctacaaga aacaaagggc taaacaaagc caaatgggaa    1800
gcaggatcat ggtttgaact ctttctggcc agagaacaat acctgctatg gactagatac    1860
tgggagaggg aaaggaaaag tagggtgaat tatggaagga agctggcagg ctcagcgttt    1920
ctgtcttggc atgaccagtc tctcttcatt ctcttcctag atgtagggct tggtaccaga    1980
gcccctgagg ctttctgcat gaatataaat atatgaaact gagtgatgct tccatttcag    2040
gttcttgggg gcgccgaatt cgagctcggt acccggggat ctcgaggggg ggcccggtac    2100
c                                                                    2101

<210> SEQ ID NO 2
<211> LENGTH: 245
<212> TYPE: DNA
<213> ORGANISM: Artificial Sequence
<220> FEATURE:
<223> OTHER INFORMATION: Synthetic

<400> SEQUENCE: 2
gattacttac tggcaggtgc tgggggcttc cgagacaatc gcgaacatct acaccacaca      60
acaccgcctc gaccagggtg agatatcggc cggggacgcg gcggtggtaa ttacaagcga    120
ggatccgatt acttactggc aggtgctggg ggcttccgag acaatcgcga acatctacac    180
cacacaacac cgcctcgacc agggtgagat atcggccggg gacgcggcgg tggtaattac    240
aagcg                                                                245

<210> SEQ ID NO 3
<211> LENGTH: 680
<212> TYPE: DNA
<213> ORGANISM: Artificial Sequence
<220> FEATURE:
<223> OTHER INFORMATION: Synthetic

<400> SEQUENCE: 3
ggaattcgcc cctctccctc cccccccct aacgttactg gccgaagccg cttggaataa      60
ggccggtgtg cgtttgtcta tatgttattt tccaccatat tgccgtcttt tggcaatgtg    120
agggcccgga aacctggccc tgtcttcttg acgagcattc ctaggggtct ttcccctctc    180
gccaaaggaa tgcaaggtct gttgaatgtc gtgaaggaag cagttcctct ggaagcttct    240
tgaagacaaa caacgtctgt agcgacccct tgcaggcagc ggaaccccccc acctggcgac    300 aggtgcctct gcggccaaaa gccacgtgta agatacac ctgcaaaggc ggcacaaccc    360
cagtgccacg ttgtgagttg gatagttgtg gaaagagtca aatggctctc ctcaagcgta    420
ttcaacaagg ggctgaagga tgcccagaag gtacccctt gtatgggatc tgatctgggg    480
cctcggtgca catgctttac atgtgtttag tcgaggttaa aaaacgtct aggcccccg    540 aaccacgggg acgtggtttt cctttgaaaa acacgatgat aatatggcct cctttgtctc    600
tctgctcctg gtaggcatcc tattccatgc cacccaggcc ggcgccatgg gatatctaga    660
tctcgagctc gcgaaagctt                                                680

<210> SEQ ID NO 4
<211> LENGTH: 4207
<212> TYPE: DNA
<213> ORGANISM: Artificial Sequence
<220> FEATURE:
<223> OTHER INFORMATION: Synthetic

<400> SEQUENCE: 4
cggatccggc cattagccat attattcatt ggttatatag cataaatcaa tattggctat      60
```

-continued

```
tggccattgc atacgttgta tccatatcat aatatgtaca tttatattgg ctcatgtcca      120
acattaccgc catgttgaca ttgattattg actagttatt aatagtaatc aattacgggg      180
tcattagttc atagcccata tatggagttc cgcgttacat aacttacggt aaatggcccg      240
cctggctgac cgcccaacga cccccgccca ttgacgtcaa taatgacgta tgttcccata      300
gtaacgccaa tagggacttt ccattgacgt caatgggtgg agtatttacg gtaaactgcc      360
cacttggcag tacatcaagt gtatcatatg ccaagtacgc ccctattga cgtcaatgac       420
ggtaaatggc ccgcctggca ttatgcccag tacatgacct tatgggactt tcctacttgg      480
cagtacatct acgtattagt catcgctatt accatggtga tgcggttttg gcagtacatc      540
aatgggcgtg gatagcggtt tgactcacgg ggatttccaa gtctccaccc cattgacgtc      600
aatgggagtt tgttttggca ccaaaatcaa cgggactttc caaaatgtcg taacaactcc      660
gccccattga cgcaaatggg cggtaggcat gtacggtggg aggtctatat aagcagagct      720
cgtttagtga accgtcagat cgcctggaga cgccatccac gctgttttga cctccataga      780
agacaccggg accgatccag cctccgcggc cccaagcttc tcgacggatc cccgggaatt      840
caggacctca ccatgggatg gagctgtatc atcctcttct tggtagcaac agctacaggt      900
gtccactccg aggtccaact ggtggagagc ggtggaggtg ttgtgcaacc tggccggtcc      960
ctgcgcctgt cctgctccgc atctggcttc gatttcacca catattggat gagttgggtg     1020
agacaggcac ctggaaaagg tcttgagtgg attggagaaa ttcatccaga tagcagtacg     1080
attaactatg cgccgtctct aaaggataga tttacaatat cgcgagacaa cgccaagaac     1140
acattgttcc tgcaaatgga cagcctgaga cccgaagaca ccggggtcta ttttgtgca      1200
agcctttact tcggcttccc ctggtttgct tattggggcc aagggacccc ggtcaccgtc     1260
tcctcagcct ccaccaaggg cccatcggtc ttccccctgg caccctcctc caagagcacc     1320
tctgggggca cagcggccct gggctgcctg gtcaaggact acttccccga accggtgacg     1380
gtgtcgtgga actcaggcgc cctgaccagc ggcgtgcaca ccttcccggc tgtcctacag     1440
tcctcaggac tctactccct cagcagcgtg gtgaccgtgc cctccagcag cttgggcacc     1500
cagacctaca tctgcaacgt gaatcacaag cccagcaaca ccaaggtgga caagagagtt     1560
gagcccaaat cttgtgacaa aactcacaca tgcccaccgt gcccagcacc tgaactcctg     1620
gggggaccgt cagtcttcct cttccccccca aaacccaagg acaccctcat gatctcccgg     1680
acccctgagg tcacatgcgt ggtggtggac gtgagccacg aagaccctga ggtcaagttc     1740
aactggtacg tggacggcgt ggaggtgcat aatgccaaga caaagccgcg ggaggagcag     1800
tacaacagca cgtaccgtgt ggtcagcgtc ctcaccgtcc tgcaccagga ctggctgaat     1860
ggcaaggagt acaagtgcaa ggtctccaac aaagccctcc cagcccccat cgagaaaacc     1920
atctccaaag ccaaagggca gccccgagaa ccacaggtgt acaccctgcc cccatcccgg     1980
gaggagatga ccaagaacca ggtcagcctg acctgcctgg tcaaaggctt ctatcccagc     2040
gacatcgccg tggagtggga gagcaatggg cagccggaga caactacaa gaccacgcct      2100
cccgtgctgg actccgacgg ctccttcttc ctctatagca agctcaccgt ggacaagagc     2160
aggtggcagc aggggaacgt cttctcatgc tccgtgatgc acgaggctct gcacaaccac     2220
tacacgcaga agagcctctc cctgtctccc gggaaatgaa agccgaattc gcccctctcc     2280
ctccccccccc cctaacgtta ctggccgaag ccgcttggaa taaggccggt gtgcgtttgt     2340
ctatatgtta ttttccacca tattgccgtc ttttggcaat gtgagggccc ggaaacctgg     2400
```

-continued

```
ccctgtcttc ttgacgagca ttcctagggg tctttcccct ctcgccaaag gaatgcaagg      2460
tctgttgaat gtcgtgaagg aagcagttcc tctggaagct tcttgaagac aaacaacgtc      2520
tgtagcgacc ctttgcaggc agcggaaccc cccacctggc gacaggtgcc tctgcggcca      2580
aaagccacgt gtataagata cacctgcaaa ggcggcacaa ccccagtgcc acgttgtgag      2640
ttggatagtt gtggaaagag tcaaatggct ctcctcaagc gtattcaaca agggctgaa       2700 ggatgcccag aagtacccc attgtatggg atctgatctg gggcctcggt gcacatgctt       2760
tacatgtgtt tagtcgaggt taaaaaaacg tctaggcccc ccgaaccacg gggacgtggt      2820
tttcctttga aaacacgat gataatatgg cctcctttgt ctctctgctc ctggtaggca       2880
tcctattcca tgccacccag gccgacatcc agctgaccca gagcccaagc agcctgagcg      2940
ccagcgtggg tgacagagtg accatcacct gtaaggccag tcaggatgtg ggtacttctg      3000
tagcctggta ccagcagaag ccaggtaagg ctccaaagct gctgatctac tggacatcca      3060
cccggcacac tggtgtgcca agcagattca gcggtagcgg tagcggtacc gacttcaccct     3120 tcaccatcag cagcctccag ccagaggaca tcgccaccta ctactgccag caatatagcc      3180
tctatcggtc gttcggccaa gggaccaagg tggaaatcaa acgaactgtg gctgcaccat      3240
ctgtcttcat cttcccgcca tctgatgagc agttgaaatc tggaactgcc tctgttgtgt      3300
gcctgctgaa taacttctat cccagagagg ccaaagtaca gtggaaggtg gataacgccc      3360
tccaatcggg taactcccag gagagtgtca cagagcagga cagcaaggac agcacctaca      3420
gcctcagcag caccctgacg ctgagcaaag cagactacga gaaacacaaa gtctacgcct      3480
gcgaagtcac ccatcagggc ctgagctcgc ccgtcacaaa gagcttcaac aggggagagt      3540
gttagagatc taggcctcct aggtcgacat cgataaaata aaagatttta tttagtctcc      3600
agaaaaaggg gggaatgaaa gaccccacct gtaggtttgg caagctagct taagtaacgc      3660
cattttgcaa ggcatggaaa atacataac tgagaataga gaagttcaga tcaaggtcag      3720
gaacagatgg aacagctgaa tatgggccaa acaggatatc tgtggtaagc agttcctgcc      3780
ccggctcagg gccaagaaca gatggaacag ctgaatatgg gccaaacagg atatctgtgg      3840
taagcagttc ctgccccggc tcaggccaa gaacagatgg tccccagatg cggtccagcc       3900
ctcagcagtt tctagagaac catcagatgt ttccagggtg ccccaaggac ctgaaatgac      3960
cctgtgcctt atttgaacta accaatcagt tcgcttctcg cttctgttcg cgcgcttctg      4020
ctccccgagc tcaataaaag agcccacaac ccctcactcg gggcgccagt cctccgattg      4080
actgagtcgc ccgggtaccc gtgtatccaa taaaccctct tgcagttgca tccgacttgt      4140
ggtctcgctg ttccttggga gggtctcctc tgagtgattg actacccgtc agcggggtc       4200 tttcatt                                                                4207
```

<210> SEQ ID NO 5
<211> LENGTH: 4210
<212> TYPE: DNA
<213> ORGANISM: Artificial Sequence
<220> FEATURE:
<223> OTHER INFORMATION: Synthetic

<400> SEQUENCE: 5

```
ggatccggcc attagccata ttattcattg gttatatagc ataaatcaat attggctatt       60
ggccattgca tacgttgtat ccatatcata atatgtacat ttatattggc tcatgtccaa      120
cattaccgcc atgttgacat tgattattga ctagttatta atagtaatca attacggggt      180
cattagttca tagcccatat atggagttcc gcgttacata acttacggta aatggcccgc      240
```

-continued

```
ctggctgacc gcccaacgac ccccgcccat tgacgtcaat aatgacgtat gttcccatag      300
taacgccaat agggactttc cattgacgtc aatgggtgga gtatttacgg taaactgccc      360
acttggcagt acatcaagtg tatcatatgc caagtacgcc ccctattgac gtcaatgacg      420
gtaaatggcc cgcctggcat tatgcccagt acatgacctt atgggacttt cctacttggc      480
agtacatcta cgtattagtc atcgctatta ccatggtgat gcggttttgg cagtacatca      540
atgggcgtgg atagcggttt gactcacggg gatttccaag tctccacccc attgacgtca      600
atgggagttt gttttggcac caaaatcaac gggactttcc aaaatgtcgt aacaactccg      660
ccccattgac gcaaatgggc ggtaggcatg tacggtggga ggtctatata agcagagctc      720
gtttagtgaa ccgtcagatc gcctggagac gccatccacg ctgttttgac ctccatagaa      780
gacaccggga ccgatccagc ctccgcggcc ccaagcttct cgacggatcc ccgggaattc      840
aggacctcac catgggatgg agctgtatca tcctcttctt ggtagcaaca gctacaggtg      900
tccactccca ggtccagctg gtccaatcag ggctgaagt caagaaacct gggtcatcag      960
tgaaggtctc ctgcaaggct tctggctaca cctttactag ctactggctg cactgggtca     1020
ggcaggcacc tggacagggt ctggaatgga ttggatacat taatcctagg aatgattata     1080
ctgagtacaa tcagaacttc aaggacaagg ccacaataac tgcagacgaa tccaccaata     1140
cagcctacat ggagctgagc agcctgaggt ctgaggacac ggcattttat ttttgtgcaa     1200
gaagggatat tactacgttc tactggggcc aaggcaccac ggtcaccgtc tcctcagcct     1260
ccaccaaggg cccatcggtc ttcccctgg caccctcctc caagagcacc tctggggca     1320 cagcggccct gggctgcctg gtcaaggact acttccccga accggtgacg gtgtcgtgga     1380
actcaggcgc cctgaccagc ggcgtgcaca cttcccggc tgtcctacag tcctcaggac     1440
tctactccct cagcagcgtg gtgaccgtgc cctccagcag cttgggcacc cagacctaca     1500
tctgcaacgt gaatcacaag cccagcaaca ccaaggtgga cagagagtt gagcccaaat     1560 cttgtgacaa aactcacaca tgcccaccgt gcccagcacc tgaactcctg gggggaccgt     1620
cagtcttcct cttccccccca aaacccaagg acaccctcat gatctcccgg acccctgagg     1680
tcacatgcgt ggtggtggac gtgagccacg aagaccctga ggtcaagttc aactggtacg     1740
tggacggcgt ggaggtgcat aatgccaaga caaagccgcg ggaggagcag tacaacagca     1800
cgtaccgtgt ggtcagcgtc ctcaccgtcc tgcaccagga ctggctgaat ggcaaggagt     1860
acaagtgcaa ggtctccaac aaagccctcc cagcccccat cgagaaaacc atctccaaag     1920
ccaaagggca gccccgagaa ccacaggtgt acaccctgcc cccatcccgg gaggagatga     1980
ccaagaacca ggtcagcctg acctgcctgg tcaaaggctt ctatcccagc gacatcgccg     2040
tggagtggga gagcaatggg cagccggaga acaactacaa gaccacgcct cccgtgctgg     2100
actccgacgg ctccttcttc ctctatagca agctcaccgt ggacaagagc aggtggcagc     2160
aggggaacgt cttctcatgc tccgtgatgc acgaggctct gcacaaccac tacacgcaga     2220
agagcctctc cctgtctccc gggaaatgaa agccgaattc gccctctcc ctccccccc      2280 cctaacgtta ctggccgaag ccgcttggaa taaggccggt gtgcgtttgt ctatatgtta     2340
ttttccacca tattgccgtc ttttggcaat gtgagggccc ggaaacctgg ccctgtcttc     2400
ttgacgagca ttcctagggg tctttcccct ctcgccaaag gaatgcaagg tctgttgaat     2460
gtcgtgaagg aagcagttcc tctggaagct tcttgaagac aaacaacgtc tgtagcgacc     2520 cttttgcaggc agcggaaccc cccacctggc gacaggtgcc tctgcggcca aaagccacgt     2580
```

-continued

```
gtataagata cacctgcaaa ggcggcacaa ccccagtgcc acgttgtgag ttggatagtt   2640
gtggaaagag tcaaatggct ctcctcaagc gtattcaaca aggggctgaa ggatgcccag   2700
aaggtacccc attgtatggg atctgatctg gggcctcggt gcacatgctt acatgtgtt    2760 tagtcgaggt taaaaaaacg tctaggcccc ccgaaccacg gggacgtggt tttcctttga   2820
aaaacacgat gataatatgg cctcctttgt ctctctgctc ctggtaggca tcctattcca   2880
tgccacccag gccgacatcc agctgaccca gtctccatca tctctgagcg catctgttgg   2940
agatagggtc actatgagct gtaagtccag tcaaagtgtt ttatacagtg caaatcacaa   3000
gaactacttg gcctggtacc agcagaaacc agggaaagca cctaaactgc tgatctactg   3060
ggcatccact agggaatctg gtgtcccttc gcgattctct ggcagcggat ctgggacaga   3120
ttttactttc accatcagct ctcttcaacc agaagacatt gcaacatatt attgtcacca   3180
atacctctcc tcgtggacgt tcggtggagg gaccaaggtg cagatcaaac gaactgtggc   3240
tgcaccatct gtcttcatct cccgccatc tgatgagcag ttgaaatctg gaactgcctc    3300
tgttgtgtgc ctgctgaata acttctatcc cagagaggcc aaagtacagt ggaaggtgga   3360
taacgccctc caatcgggta actcccagga gagtgtcaca gagcaggaca gcaaggacag   3420
cacctacagc ctcagcagca ccctgacgct gagcaaagca gactacgaga acacaaagt    3480 ctacgcctgc gaagtcaccc atcagggcct gagctcgccc gtcacaaaga gcttcaacag   3540
gggagagtgt tagagatcta ggcctcctag gtcgacatcg ataaaataaa agattttatt   3600
tagtctccag aaaaggggg gaatgaaaga ccccacctgt aggtttggca agctagctta    3660
agtaacgcca ttttgcaagg catggaaaaa tacataactg agaatagaga agttcagatc   3720
aaggtcagga acagatggaa cagctgaata tgggccaaac aggatatctg tggtaagcag   3780
ttcctgcccc ggctcagggc caagaacaga tggaacagct gaatatgggc caaacaggat   3840
atctgtggta agcagttcct gccccggctc agggccaaga acagatggtc ccagatgcg    3900 gtccagccct cagcagtttc tagagaacca tcagatgttt ccagggtgcc caaggacct    3960 gaaatgaccc tgtgccttat ttgaactaac caatcagttc gcttctcgct tctgttcgcg   4020
cgcttctgct ccccgagctc aataaaagag cccacaaccc ctcactcggg gcgccagtcc   4080
tccgattgac tgagtcgccc gggtacccgt gtatccaata aaccctcttg cagttgcatc   4140
cgacttgtgg tctcgctgtt ccttgggagg gtctcctctg agtgattgac tacccgtcag   4200
gtctttcatt                                                           4210
```

<210> SEQ ID NO 6
<211> LENGTH: 5732
<212> TYPE: DNA
<213> ORGANISM: Artificial Sequence
<220> FEATURE:
<223> OTHER INFORMATION: Synthetic

<400> SEQUENCE: 6

```
cgagcttggc agaaatggtt gaactcccga gagtgtccta cacctagggg agaagcagcc    60
aaggggttgt ttcccaccaa ggacgacccg tctgcgcaca acggatgag cccatcagac    120 aaagacatat tcattctctg ctgcaaactt ggcatagctc tgctttgcct ggggctattg   180
ggggaagttg cggttcgtgc tcgcagggct ctcacccttg actctttcaa taataactct   240
tctgtgcaag attacaatct aaacaattcg gagaactcga ccttcctcct gaggcaagga   300
ccacagccaa cttcctctta caagccgcat cgattttgtc cttcagaaat agaaataaga   360
atgcttgcta aaaattatat ttttaccaat aagaccaatc caataggtag attattagtt   420
```

-continued

```
actatgttaa gaaatgaatc attatctttt agtactattt ttactcaaat tcagaagtta    480
gaaatgggaa tagaaaatag aaagagacgc tcaacctcaa ttgaagaaca ggtgcaagga    540
ctattgacca caggcctaga agtaaaaaag ggaaaaaaga gtgttttttgt caaaatagga   600
gacaggtggt ggcaaccagg gacttatagg ggaccttaca tctacagacc aacagatgcc    660
cccttaccat atacaggaag atatgactta aattgggata ggtgggttac agtcaatggc    720
tataaagtgt tatatagatc cctccccttt cgtgaaagac tcgccagagc tagacctcct    780
tggtgtatgt tgtctcaaga aaagaaagac gacatgaaac aacaggtaca tgattatatt    840
tatctaggaa caggaatgca cttttgggga aagattttcc ataccaagga ggggacagtg    900
gctggactaa tagaacatta ttctgcaaaa acttatggca tgagttatta tgattagcct    960
tgatttgccc aaccttgcgg ttcccaaggc ttaagtaagt ttttggttac aaactgttct   1020
taaaacaagg atgtgagaca agtggttttcc tgacttggtt tggtatcaaa ggttctgatc  1080
tgagctctga gtgttctatt ttcctatgtt cttttggaat ttatccaaat cttatgtaaa   1140
tgcttatgta aaccaagata taaaagagtg ctgattttttt gagtaaactt gcaacagtcc  1200
taacattcac ctcttgtgtg tttgtgtctg ttcgccatcc cgtctccgct cgtcacttat   1260
ccttcacttt ccagagggtc cccccgcaga ccccggcgac cctcaggtcg ccgactgcg    1320
gcagctggcg cccgaacagg gaccctcgga taagtgaccc ttgtctttat ttctactatt   1380
ttgtgttcgt cttgttttgt ctctatcttg tctggctatc atcacaagag cggaacggac   1440
tcacctcagg gaaccaagct agcccggggt cgacggatcc gattacttac tggcaggtgc   1500
tgggggcttc cgagacaatc gcgaacatct acaccacaca acaccgcctc gaccagggtg   1560
agatatcggc cggggacgcg gcggtggtaa ttacaagcga gatccgatta cttactggca   1620
ggtgctgggg gcttccgaga caatcgcgaa catctacacc acacaacacc gcctcgacca   1680
gggtgagata tcgccggggg acgcggcggt ggtaattaca agcgagatcc ccgggaattc   1740
aggacctcac catgggatgg agctgtatca tcctcttctt ggtagcaaca gctacaggtg   1800
tccactccga ggtccaactg gtggagagcg gtggaggtgt tgtgcaacct ggccggtccc   1860
tgcgcctgtc ctgctccgca tctggcttcg atttcaccac atattggatg agttgggtga   1920
gacaggcacc tggaaaaggt cttgagtgga ttggagaaat tcatccagat agcagtacga   1980
ttaactatgc gccgtctcta aaggatagat ttacaatatc gcgagacaac gccaagaaca   2040
cattgttcct gcaaatggac agcctgagac ccgaagacac cggggtctat ttttgtgcaa   2100
gcctttactt cggcttcccc tggtttgctt attggggcca agggacccccg gtcaccgtct   2160
cctcagcctc caccaagggc ccatcggtct tccccctggc accctcctcc aagagcacct   2220
ctgggggcac agcggccctg ggctgcctgg tcaaggacta cttccccgaa ccggtgacgg   2280
tgtcgtggaa ctcaggcgcc ctgaccagcg gcgtgcacac cttcccggct gtcctacagt   2340
cctcaggact ctactccctc agcagcgtgg tgaccgtgcc ctccagcagc ttgggcaccc   2400
agacctacat ctgcaacgtg aatcacaagc ccagcaacac caaggtggac aagagagttg   2460
agcccaaatc ttgtgacaaa actcacacat gcccaccgtg cccagcacct gaactcctgg   2520
ggggaccgtc agtcttcctc ttccccccaa acccaaggga cacctcatg atctcccgga    2580
cccctgaggt cacatgcgtg gtggtggacg tgagccacga agaccctgag gtcaagttca   2640
actggtacgt ggacggcgtg gaggtgcata atgccaagac aaagccgcgg gaggagcagt   2700
acaacagcac gtaccgtgtg gtcagcgtcc tcaccgtcct gcaccaggac tggctgaatg   2760
```

-continued

```
gcaaggagta caagtgcaag gtctccaaca aagccctccc agcccccatc gagaaaacca   2820
tctccaaagc caaagggcag ccccgagaac cacaggtgta caccctgccc ccatcccggg   2880
aggagatgac caagaaccag gtcagcctga cctgcctggt caaaggcttc tatcccagcg   2940
acatcgccgt ggagtgggag agcaatgggc agccggagaa caactacaag accacgcctc   3000
ccgtgctgga ctccgacggc tccttcttcc tctatagcaa gctcaccgtg gacaagagca   3060
ggtggcagca ggggaacgtc ttctcatgct ccgtgatgca cgaggctctg cacaaccact   3120
acacgcagaa gagcctctcc ctgtctcccg ggaaatgaaa gccgaattcg ccctctccc   3180 tcccccccc ctaacgttac tggccgaagc cgcttggaat aaggccggtg tgcgtttgtc   3240
tatatgttat tttccaccat attgccgtct tttggcaatg tgagggcccg gaaacctggc   3300
cctgtcttct tgacgagcat tcctaggggt ctttcccctc tcgccaaagg aatgcaaggt   3360
ctgttgaatg tcgtgaagga agcagttcct ctggaagctt cttgaagaca acaacgtct   3420 gtagcgaccc tttgcaggca gcggaacccc ccacctggcg acaggtgcct ctgcggccaa   3480
aagccacgtg tataagatac acctgcaaag gcggcacaac cccagtgcca cgttgtgagt   3540
tggatagttg tggaaagagt caaatggctc tcctcaagcg tattcaacaa ggggctgaag   3600
gatgcccaga aggtacccca ttgtatggga tctgatctgg ggcctcggtg cacatgcttt   3660
acatgtgttt agtcgaggtt aaaaaaacgt ctaggccccc cgaaccacgg ggacgtggtt   3720
ttcctttgaa aaacacgatg ataatatggc ctcctttgtc tctctgctcc tggtaggcat   3780
cctattccat gccacccagg ccgacatcca gctgacccag agcccaagca gcctgagcgc   3840
cagcgtgggt gacagagtga ccatcacctg taaggccagt caggatgtgg gtacttctgt   3900
agcctggtac cagcagaagc caggtaaggc tccaaagctg ctgatctact ggacatccac   3960
ccggcacact ggtgtgccaa gcagattcag cggtagcggt agcggtaccg acttcacctt   4020
caccatcagc agcctccagc cagaggacat cgccacctac tactgccagc aatatagcct   4080
ctatcggtcg ttcggccaag ggaccaaggt ggaaatcaaa cgaactgtgg ctgcaccatc   4140
tgtcttcatc ttcccgccat ctgatgagca gttgaaatct ggaactgcct ctgttgtgtg   4200
cctgctgaat aacttctatc ccagagaggc caaagtacag tggaaggtgg ataacgccct   4260
ccaatcgggt aactcccagg agagtgtcac agagcaggac agcaaggaca gcacctacag   4320
cctcagcagc accctgacgc tgagcaaagc agactacgag aaacacaaag tctacgcctg   4380
cgaagtcacc catcagggcc tgagctcgcc cgtcacaaag agcttcaaca ggggagagtg   4440
ttagagatcc cccgggctgc aggaattcga tatcaagctt atcgataatc aacctctgga   4500
ttacaaaatt tgtgaaagat tgactggtat tcttaactat gttgctcctt ttacgctatg   4560
tggatacgct gctttaatgc cttgtatca tgctattgct tcccgtatgg ctttcatttt   4620
ctcctccttg tataaatcct ggttgctgtc tctttatgag gagttgtggc ccgttgtcag   4680
gcaacgtggc gtggtgtgca ctgtgtttgc tgacgcaacc cccactggtt ggggcattgc   4740
caccacctgt cagctccttt ccgggacttt cgctttcccc ctccctattg ccacggcgga   4800
actcatcgcc gcctgccttg cccgctgctg acagggggct cggctgttgg gcactgacaa   4860
ttccgtggtg ttgtcgggga atcatcgtc cttccttgg ctgctcgcct gtgttgccac   4920
ctggattctg cgcgggacgt ccttctgcta cgtcccttcg ccctcaatc cagcggacct   4980 tccttcccgc ggcctgctgc cggctctgcg gcctcttccg cgtcttcgcc ttcgccctca   5040
gacgagtcga atctcccttt gggccgcctc ccgcctgat cgataccgtc aacatcgata   5100
aaataaaaga ttttatttag tctccagaaa aaggggggaa tgaaagaccc cacctgtagg   5160
```

| | |
|---|---|
| tttggcaagc tagcttaagt aacgccattt tgcaaggcat ggaaaaatac ataactgaga | 5220 |
| atagagaagt tcagatcaag gtcaggaaca gatggaacag ctgaatatgg gccaaacagg | 5280 |
| atatctgtgg taagcagttc ctgccccggc tcagggccaa gaacagatgg aacagctgaa | 5340 |
| tatgggccaa acaggatatc tgtggtaagc agttcctgcc ccggctcagg gccaagaaca | 5400 |
| gatggtcccc agatgcggtc cagccctcag cagtttctag agaaccatca gatgtttcca | 5460 |
| gggtgcccca aggacctgaa atgaccctgt gccttatttg aactaaccaa tcagttcgct | 5520 |
| tctcgcttct gttcgcgcgc ttctgctccc cgagctcaat aaaagagccc acaacccctc | 5580 |
| actcggggcg ccagtcctcc gattgactga gtcgcccggg tacccgtgta tccaataaac | 5640 |
| cctcttgcag ttgcatccga cttgtggtct cgctgttcct tgggagggtc tcctctgagt | 5700 |
| gattgactac ccgtcagcgg gggtctttca tt | 5732 |

<210> SEQ ID NO 7
<211> LENGTH: 9183
<212> TYPE: DNA
<213> ORGANISM: Artificial Sequence
<220> FEATURE:
<223> OTHER INFORMATION: Synthetic

<400> SEQUENCE: 7

| | |
|---|---|
| aaagacccca cccgtaggtg gcaagctagc ttaagtaacg ccactttgca aggcatggaa | 60 |
| aaatacataa ctgagaatag aaaagttcag atcaaggtca ggaacaaaga aacagctgaa | 120 |
| taccaaacag gatatctgtg gtaagcggtt cctgccccgg ctcagggcca agaacagatg | 180 |
| agacagctga gtgatgggcc aaacaggata tctgtggtaa gcagttcctg ccccggctcg | 240 |
| gggccaagaa cagatggtcc ccagatgcgg tccagccctc agcagtttct agtgaatcat | 300 |
| cagatgtttc cagggtgccc caaggacctg aaaatgaccc tgtacccttat ttgaactaac | 360 |
| caatcagttc gcttctcgct tctgttcgcg cgcttccgct ctccgagctc aataaaagag | 420 |
| cccacaaccc ctcactcggc gcgccagtct tccgatagac tgcgtcgccc gggtacccgt | 480 |
| attcccaata aagcctcttg ctgttttgcat ccgaatcgtg gtctcgctgt tccttgggag | 540 |
| ggtctcctct gagtgattga ctacccacga cgggggtctt tcatttgggg gctcgtccgg | 600 |
| gatttggaga cccctgccca gggaccaccg acccaccacc gggaggtaag ctggccagca | 660 |
| acttatctgt gtctgtccga ttgtctagtg tctatgtttg atgttatgcg cctgcgtctg | 720 |
| tactagttag ctaactagct ctgtatctgg cggacccgtg gtggaactga cgagttctga | 780 |
| acacccggcc gcaaccctgg gagacgtccc agggactttg ggggccgttt ttgtggcccg | 840 |
| acctgaggaa gggagtcgat gtggaatccg accccgtcag gatatgtggt tctggtagga | 900 |
| gacgagaacc taaaacagtt cccgcctccg tctgaatttt tgctttcggt ttggaaccga | 960 |
| agccgcgcgt cttgtctgct gcagcgctgc agcatcgttc tgtgttgtct ctgtctgact | 1020 |
| gtgtttctgt atttgtctga aaattagggc cagactgtta ccactcccct aagtttgacc | 1080 |
| ttaggtcact ggaaagatgt cgagcggatc gctcacaacc agtcggtaga tgtcaagaag | 1140 |
| agacgttggg ttaccttctg ctctgcagaa tggccaacct ttaacgtcgg atggccgcga | 1200 |
| gacggcacct ttaaccgaga cctcatcacc caggttaaga tcaaggtctt tcacctggc | 1260 |
| ccgcatggac acccagacca ggtcccctac atcgtgacct gggaagcctt ggcttttgac | 1320 |
| cccctccct gggtcaagcc ctttgtacac cctaagcctc cgcctcctct tcctccatcc | 1380 |
| gccccgtctc tcccccttga acctcctcgt tcgacccgc ctcgatcctc cctttatcca | 1440 |

```
gccctcactc cttctctagg cgccggaatt ccgatctgat caagagacag gatgaggatc   1500
gtttcgcatg attgaacaag atggattgca cgcaggttct ccggccgctt gggtggagag   1560
gctattcggc tatgactggg cacaacagac aatcggctgc tctgatgccg ccgtgttccg   1620
gctgtcagcg caggggcgcc cggttctttt tgtcaagacc gacctgtccg gtgccctgaa   1680
tgaactgcag gacgaggcag cgcggctatc gtggctggcc acgacgggcg ttccttgcgc   1740
agctgtgctc gacgttgtca ctgaagcggg aagggactgg ctgctattgg gcgaagtgcc   1800
ggggcaggat ctcctgtcat ctcaccttgc tcctgccgag aaagtatcca tcatggctga   1860
tgcaatgcgg cggctgcata cgcttgatcc ggctacctgc ccattcgacc accaagcgaa   1920
acatcgcatc gagcgagcac gtactcggat ggaagccggt cttgtcgatc aggatgatct   1980
ggacgaagag catcagggc tcgcgccagc cgaactgttc gccaggctca aggcgcgcat   2040
gcccgacggc gaggatctcg tcgtgaccca tggcgatgcc tgcttgccga atatcatggt   2100
ggaaaatggc cgcttttctg gattcatcga ctgtggccgg ctgggtgtgg cggaccgcta   2160
tcaggacata gcgttggcta cccgtgatat tgctgaagag cttggcggcg aatgggctga   2220
ccgcttcctc gtgctttacg gtatcgccgc tcccgattcg cagcgcatcg ccttctatcg   2280
ccttcttgac gagttcttct gagcgggact ctggggttcg aaatgaccga ccaagcgacg   2340
cccaacctgc catcacgaga tttcgattcc accgccgcct tctatgaaag gttgggcttc   2400
ggaatcgttt tccgggacgc cggctggatg atcctccagc gcgggatct catgctggag   2460
ttcttcgccc accccgggct cgatcccctc gcgagttggt tcagctgctg cctgaggctg   2520
gacgacctcg cggagttcta ccggcagtgc aaatccgtcg gcatccagga aaccagcagc   2580
ggctatccgc gcatccatgc ccccgaactg caggagtggg gaggcacgat ggccgctttg   2640
gtcgaggcgg atcctagaac tagcgaaaat gcaagagcaa agacgaaaac atgccacaca   2700
tgaggaatac cgattctctc attaacatat tcaggccagt tatctgggct taaaagcaga   2760
agtccaaccc agataacgat catatacatg gttctctcca gaggttcatt actgaacact   2820
cgtccgagaa taacgagtgg atcagtcctg ggtggtcatt gaaaggactg atgctgaagt   2880
tgaagctcca atactttggc cacctgatgc gaagaactga ctcatgtgat aagaccctga   2940
tactgggaaa gattgaaggc aggaggagaa gggatgacag aggatggaag agttggatgg   3000
aatcaccaac tcgatggaca tgagtttgag caagcttcca ggagttggta atgggcaggg   3060
aagcctggcg tgctgcagtc catggggttg caaagagttg acactactg agtgactgaa   3120
ctgaactgat agtgtaatcc atggtacaga atataggata aaaagagga agagtttgcc   3180
ctgattctga agagttgtag gatataaaag tttagaatac ctttagtttg gaagtcttaa   3240
attatttact taggatgggt acccactgca atataagaaa tcaggcttta gagactgatg   3300
tagagagaat gagccctggc ataccagaag ctaacagcta ttggttatag ctgttataac   3360
caatatataa ccaatatatt ggttatatag catgaagctt gatgccagca atttgaagga   3420
accatttaga actagtatcc taaactctac atgttccagg acactgatct aaagctcag    3480
gttcagaatc ttgttttata ggctctaggt gtatattgtg gggcttccct ggtggctcag   3540
atggtaaagt gtctgcctgc aatgtgggtg atctgggttc gatccctggc ttgggaagat   3600
cccctggaga aggaaatggc aacccactct agtactctta cctggaaaat tccatggaca   3660
gaggagcctt gtaagctaca gtccatggga ttgcaaagag ttgaacacaa ctgagcaact   3720
aagcacagca cagtacagta tacacctgtg aggtgaagtg aagtgaaggt tcaatgcagg   3780
gtctcctgca ttgcagaaag attctttacc atctgagcca ccaggaagc ccaagaatac     3840
```

-continued

```
tggagtgggt agcctattcc ttctccaggg gatcttccca tcccaggaat tgaactggag   3900
tctcctgcat ttcaggtgga ttcttcacca gctgaactac caggtggata ctactccaat   3960
attaaagtgc ttaaagtcca gttttcccac ctttcccaaa aaggttgggt cactcttttt   4020
taaccttctg tggcctactc tgaggctgtc tacaagctta tatatttatg aacacattta   4080
ttgcaagttt ttagttttag atttacaatg tggtatctgg ctatttagtg gtattggtgg   4140
ttggggatgg ggaggctgat agcatctcag agggcagcta gatactgtca tacacacttt   4200
tcaagttctc catttttgtg aaatagaaag tctctggatc taagttatat gtgattctca   4260
gtctctgtgg tcatattcta ttctactcct gaccactcaa caaggaacca agatatcaag   4320
ggacacttgt tttgtttcat gcctgggttg agtgggccat gacatatgtt ctgggccttg   4380
ttacatggct ggattggttg gacaagtgcc agctctgatc ctgggactgt ggcatgtgat   4440
gacatacacc ccctctccac attctgcatg tctctagggg ggaagggggga agctcggtat   4500 agaaccttta ttgtattttc tgattgcctc acttcttata ttgcccccat gcccttcttt   4560
gttcctcaag taaccagaga cagtgcttcc cagaaccaac cctacaagaa acaaagggct   4620
aaacaaagcc aaatgggaag caggatcatg gtttgaactc tttctggcca gagaacaata   4680
cctgctatgg actagatact gggagaggga aggaaaagt aggtgaatt atggaaggaa   4740 gctggcaggc tcagcgtttc tgtcttggca tgaccagtct ctcttcattc tcttcctaga   4800
tgtagggctt ggtaccagag cccctgaggc tttctgcatg aatataaata tatgaaactg   4860
agtgatgctt ccatttcagg ttcttggggg cgccgaattc gagctcggta cccggggatc   4920
tcgacggatc cgattactta ctggcaggtg ctgggggctt ccgagacaat cgcgaacatc   4980
tacaccacac aacaccgcct cgaccagggt gagatatcgg ccggggacgc ggcggtggta   5040
attacaagcg agatccgatt acttactggc aggtgctggg ggcttccgag acaatcgcga   5100
acatctacac cacacaacac cgcctcgacc agggtgagat atcggccggg gacgcggcgg   5160
tggtaattac aagcgagatc cccgggaatt caggacctca ccatgggatg gagctgtatc   5220
atcctcttct tggtagcaac agctacaggt gtccactccg aggtccaact ggtggagagc   5280
ggtggaggtg ttgtgcaacc tggccggtcc ctgcgcctgt cctgctccgc atctggcttc   5340
gatttcacca catattggat gagttgggtg agacaggcac ctggaaaagg tcttgagtgg   5400
attggagaaa ttcatccaga tagcagtacg attaactatg cgccgtctct aaaggataga   5460
tttacaatat cgcgagacaa cgccaagaac acattgttcc tgcaaatgga cagcctgaga   5520
cccgaagaca ccggggtcta ttttgtgca agcctttact tcggcttccc ctggtttgct   5580
tattggggcc aagggacccc ggtcaccgtc tcctcagcct ccaccaaggg cccatcggtc   5640
ttccccctgg caccctcctc caagagcacc tctgggggca gcggccct gggctgcctg   5700 gtcaaggact acttccccga accggtgacg gtgtcgtgga actcaggcgc cctgaccagc   5760
ggcgtgcaca ccttcccggc tgtcctacag tcctcaggac tctactccct cagcagcgtg   5820
gtgaccgtgc cctccagcag cttgggcacc cagacctaca tctgcaacgt gaatcacaag   5880
cccagcaaca ccaaggtgga caagagagtt gagcccaaat cttgtgacaa aactcacaca   5940
tgcccaccgt gcccagcacc tgaactcctg ggggaccgt cagtcttcct cttccccccca   6000 aaacccaagg acaccctcat gatctcccgg acccctgagg tcacatgcgt ggtggtggac   6060
gtgagccacg aagaccctga ggtcaagttc aactggtacg tggacggcgt ggaggtgcat   6120
aatgccaaga caaagccgcg ggaggagcag tacaacagca cgtaccgtgt ggtcagcgtc   6180
```

-continued

```
ctcaccgtcc tgcaccagga ctggctgaat ggcaaggagt acaagtgcaa ggtctccaac    6240
aaagccctcc cagcccccat cgagaaaacc atctccaaag ccaagggca gccccgagaa     6300 ccacaggtgt acaccctgcc cccatcccgg gaggagatga ccaagaacca ggtcagcctg    6360
acctgcctgg tcaaaggctt ctatcccagc gacatcgccg tggagtggga gagcaatggg    6420
cagccggaga caactacaa gaccacgcct cccgtgctgg actccgacgg ctccttcttc     6480
ctctatagca agctcaccgt ggacaagagc aggtggcagc aggggaacgt cttctcatgc    6540
tccgtgatgc acgaggctct gcacaaccac tacacgcaga agagcctctc cctgtctccc    6600
gggaaatgaa agccgaattc gcccctctcc ctccccccc cctaacgtta ctggccgaag     6660
ccgcttggaa taaggccggt gtgcgtttgt ctatatgtta ttttccacca tattgccgtc    6720
ttttggcaat gtgagggccc ggaaacctgg ccctgtcttc ttgacgagca ttcctagggg    6780
tctttcccct ctcgccaaag gaatgcaagg tctgttgaat gtcgtgaagg aagcagttcc    6840
tctggaagct tcttgaagac aaacaacgtc tgtagcgacc ctttgcaggc agcggaaccc    6900
cccacctggc gacaggtgcc tctgcggcca aaagccacgt gtataagata cacctgcaaa    6960
ggcggcacaa ccccagtgcc acgttgtgag ttggatagtt gtggaaagag tcaaatggct    7020
ctcctcaagc gtattcaaca aggggctgaa ggatgcccag aagtacccc attgtatggg     7080 atctgatctg gggcctcggt gcacatgctt tacatgtgtt tagtcgaggt taaaaaacg     7140 tctaggcccc ccgaaccacg gggacgtggt tttcctttga aaaacgat gataatatgg      7200 cctcctttgt ctctctgctc ctggtaggca tcctattcca tgccacccag gccgacatcc    7260
agctgaccca gagcccaagc agcctgagcg ccagcgtggg tgacagagtg accatcacct    7320
gtaaggccag tcaggatgtg ggtacttctg tagcctggta ccagcagaag ccaggtaagg    7380
ctccaaagct gctgatctac tggacatcca cccggcacac tggtgtgcca agcagattca    7440
gcggtagcgg tagcggtacc gacttcaccT tcaccatcag cagcctccag ccagaggaca    7500
tcgccaccta ctactgccag caatatagcc tctatcggtc gttcggccaa gggaccaagg    7560
tggaaatcaa acgaactgtg gctgcaccat ctgtcttcat cttcccgcca tctgatgagc    7620
agttgaaatc tggaactgcc tctgttgtgt gcctgctgaa taacttctat cccagagagg    7680
ccaaagtaca gtggaaggtg gataacgccc tccaatcggg taactcccag gagagtgtca    7740
cagagcagga cagcaaggac agcacctaca gcctcagcag caccctgacg ctgagcaaag    7800
cagactacga gaaacacaaa gtctacgcct gcgaagtcac ccatcagggc ctgagctcgc    7860
ccgtcacaaa gagcttcaac aggggagagt gttagagatc ccccgggctg caggaattcg    7920
atatcaagct tatcgataat caacctctgg attacaaaat ttgtgaaaga ttgactggta    7980
ttcttaacta tgttgctcct tttacgctat gtggatacgc tgctttaatg cctttgtatc    8040
atgctattgc ttcccgtatg gctttcattt tctcctcctt gtataaatcc tggttgctgt    8100
ctctttatga ggagttgtgg cccgttgtca ggcaacgtgg cgtggtgtgc actgtgtttg    8160
ctgacgcaac ccccactggt tggggcattg ccaccacctg tcagctcctt ccgggacttt    8220
tcgctttccc cctccctatt gccacggcgg aactcatcgc cgcctgcctt gcccgctgct    8280 ggacagggc tcggctgttg ggcactgaca attccgtggt gttgtcgggg aaatcatcgt    8340
cctttccttg gctgctcgcc tgtgttgcca cctggattct gcgcgggacg tccttctgct    8400
acgtcccttc ggccctcaat ccagcggacc ttccttcccg cggcctgctg ccggctctgc    8460
ggcctcttcc gcgtcttcgc cttcgccctc agacgagtcg atctccctt tgggccgcct    8520 ccccgcctga tcgataccgt caacatcgat aaaataaaag attttattta gtctccagaa    8580
```

```
aaaggggga atgaaagacc ccacctgtag gtttggcaag ctagcttaag taacgccatt      8640
ttgcaaggca tggaaaaata cataactgag aatagagaag ttcagatcaa ggtcaggaac      8700
agatggaaca gctgaatatg ggccaaacag gatatctgtg gtaagcagtt cctgccccgg      8760
ctcagggcca agaacagatg gaacagctga atatgggcca acaggatat ctgtggtaag      8820 cagttcctgc cccggctcag ggccaagaac agatggtccc cagatgcggt ccagccctca      8880
gcagtttcta gagaaccatc agatgtttcc agggtgcccc aaggacctga atgaccctg      8940 tgccttattt gaactaacca atcagttcgc ttctcgcttc tgttcgcgcg cttctgctcc      9000
ccgagctcaa taaaagagcc cacaacccct cactcggggc gccagtcctc cgattgactg      9060
agtcgcccgg gtaccgtgt atccaataaa ccctcttgca gttgcatccg acttgtggtc      9120
tcgctgttcc ttgggagggt ctcctctgag tgattgacta cccgtcagcg gggtctttc      9180 att                                                                    9183
```

<210> SEQ ID NO 8
<211> LENGTH: 5711
<212> TYPE: DNA
<213> ORGANISM: Artificial Sequence
<220> FEATURE:
<223> OTHER INFORMATION: Synthetic

<400> SEQUENCE: 8

```
gatcagtcct gggtggtcat tgaaaggact gatgctgaag ttgaagctcc aatactttgg       60
ccacctgatg cgaagaactg actcatgtga taagaccctg atactgggaa agattgaagg      120
caggaggaga agggatgaca gaggatggaa gagttggatg gaatcaccaa ctcgatggac      180
atgagtttga gcaagcttcc aggagttggt aatgggcagg gaagcctggc gtgctgcagt      240
ccatggggtt gcaaagagtt ggacactact gagtgactga actgaactga tagtgtaatc      300
catggtacag aatataggat aaaaagagg aagagtttgc cctgattctg aagagttgta      360
ggatataaaa gtttagaata cctttagttt ggaagtctta aattatttac ttaggatggg      420
tacccactgc aatataagaa atcaggcttt agagactgat gtagagagaa tgagccctgg      480
cataccagaa gctaacagct attggttata gctgttataa ccaatatata accaatatat      540
tggttatata gcatgaagct tgatgccagc aatttgaagg aaccatttag aactagtatc      600
ctaaactcta catgttccag gacactgatc ttaaagctca ggttcagaat cttgttttat      660
aggctctagg tgtatattgt ggggcttccc tggtggctca gatggtaaag tgtctgcctg      720
caatgtgggt gatctggtt cgatccctgg cttgggaaga tcccctggag aaggaaatgg      780
caacccactc tagtactctt acctggaaaa ttccatggac agaggagcct tgtaagctac      840
agtccatggg attgcaaaga gttgaacaca actgagcaac taagcacagc acagtacagt      900
atacacctgt gaggtgaagt gaagtgaagg ttcaatgcag ggtctcctgc attgcagaaa      960
gattctttac catctgagcc accagggaag cccaagaata ctggagtggg tagcctattc     1020
cttctccagg ggatcttccc atcccaggaa ttgaactgga gtctcctgca tttcaggtgg     1080
attcttcacc agctgaacta ccaggtggat actactccaa tattaaagtg cttaaagtcc     1140
agttttccca cctttcccaa aaaggttggg tcactctttt ttaaccttct gtggcctact     1200
ctgaggctgt ctacaagctt atatatttat gaacacattt attgcaagtt gttagtttta     1260
gatttacaat gtggtatctg gctatttagt ggtattggtg gttggggatg gggaggctga     1320
tagcatctca gagggcagct agatactgtc atacacactt ttcaagttct ccattttgt      1380
```

```
gaaatagaaa gtctctggat ctaagttata tgtgattctc agtctctgtg gtcatattct    1440
attctactcc tgaccactca acaaggaacc aagatatcaa gggacacttg ttttgtttca    1500
tgcctgggtt gagtgggcca tgacatatgt tctgggcctt gttacatggc tggattggtt    1560
ggacaagtgc cagctctgat cctgggactg tggcatgtga tgacatacac cccctctcca    1620
cattctgcat gtctctaggg gggaaggggg aagctcggta tagaaccttt attgtatttt    1680
ctgattgcct cacttcttat attgccccca tgccttctt tgttcctcaa gtaaccagag    1740
acagtgcttc ccagaaccaa ccctacaaga aacaaagggc taaacaaagc caaatgggaa    1800
gcaggatcat ggtttgaact ctttctggcc agagaacaat acctgctatg gactagatac    1860
tgggagaggg aaaggaaaag tagggtgaat tatggaagga agctggcagg ctcagcgttt    1920
ctgtcttggc atgaccagtc tctcttcatt ctcttcctag atgtagggct tggtaccaga    1980
gcccctgagg ctttctgcat gaatataaat atatgaaact gagtgatgct tccatttcag    2040
gttcttgggg gcgccgaatt cgagctcggt acccggggat ctcgacggat ccgattactt    2100
actggcaggt gctgggggct tccgagacaa tcgcgaacat ctacaccaca caacaccgcc    2160
tcgaccaggt tgagatatcg gccggggacg cggcggtggt aattacaagc gagatccgat    2220
tacttactgg caggtgctgg gggcttccga gacaatcgcg aacatctaca ccacacaaca    2280
ccgcctcgac cagggtgaga tatcggccgg gacgcggcg gtggtaatta caagcgagat    2340
ctcgagaagc ttgttgggaa ttcaggccat cgatcccgcc gccaccatgg aatggagctg    2400
ggtctttctc ttcttcctgt cagtaactac aggtgtccac tccgacatcc agatgaccca    2460
gtctccagcc tccctatctg catctgtggg agaaactgtc actatcacat gtcgagcaag    2520
tgggaatatt cacaattatt tagcatggta tcagcagaaa cagggaaaat ctcctcagct    2580
cctggtctat aatgcaaaaa ccttagcaga tggtgtgcca tcaaggttca gtggcagtgg    2640
atcaggaaca caatattctc tcaagatcaa cagcctgcag cctgaagatt tgggagttta    2700
ttactgtcaa cattttttgga gtactccgtg gacgttcggt ggaggcacca agctggaaat    2760
caaacgggct gatgctgcac caactgtatc catcttccca ccatccagtg agcagttaac    2820
atctggaggt gcctcagtcg tgtgcttctt gaacaacttc taccccaaag acatcaatgt    2880
caagtggaag attgatggca gtgaacgaca aaatggcgtc ctgaacagtt ggactgatca    2940
ggacagcaaa gacagcacct acagcatgag cagcaccctc acattgacca aggacgagta    3000
tgaacgacat aacagctata cctgtgaggc cactcacaag acatcaactt cacccattgt    3060
caagagcttc aacaggaatg agtgttgaaa gcatcgattt cccctgaatt cgccctctc    3120 cctcccccc cctaacgtt actggccgaa gccgcttgga ataaggccgg tgtgcgttg    3180 tctatatgtt attttccacc atattgccgt cttttggcaa tgtgagggcc cggaaacctg    3240
gccctgtctt cttgacgagc attcctaggg gtctttcccc tctcgccaaa ggaatgcaag    3300
gtctgttgaa tgtcgtgaag gaagcagttc ctctggaagc ttcttgaaga caaacaacgt    3360
ctgtagcgac cctttgcagg cagcggaacc ccccacctgg cgacaggtgc ctctgcggcc    3420
aaaagccacg tgtataagat acacctgcaa aggcggcaca ccccagtgc cacgttgtga    3480 gttggatagt tgtggaaaga gtcaaatggc tctcctcaag cgtattcaac aagggctga    3540 aggatgccca gaaggtaccc cattgtatgg gatctgatct ggggcctcgg tgcacatgct    3600
ttacatgtgt ttagtcgagg ttaaaaaaac gtctaggccc cccgaaccac ggggacgtgg    3660
ttttcctttg aaaacacga tgataatatg gcctccttg tctctctgct cctggtaggc    3720
atcctattcc atgccaccca ggccgaggtt cagcttcagc agtctggggc agagcttgtg    3780
```

-continued

| | |
|---|---|
| aagccagggg cctcagtcaa gttgtcctgc acagcttctg gcttcaacat taaagacacc | 3840 |
| tttatgcact gggtgaagca gaggcctgaa cagggcctgg agtggattgg aaggattgat | 3900 |
| cctgcgaatg ggaatactga atatgacccg aagttccagg gcaaggccac tataacagca | 3960 |
| gacacatcct ccaacacagt caacctgcag ctcagcagcc tgacatctga ggacactgcc | 4020 |
| gtctattact gtgctagtgg aggggaactg gggtttcctt actggggcca agggactctg | 4080 |
| gtcactgtct ctgcagccaa aacgacaccc ccatctgtct atccactggc ccctggatct | 4140 |
| gctgcccaaa ctaactccat ggtgaccctg ggatgcctgg tcaagggcta tttccctgag | 4200 |
| ccagtgacag tgacctggaa ctctggatcc ctgtccagcg gtgtgcacac cttcccagct | 4260 |
| gtcctgcagt ttgacctcta cactctgagc agctcagtga ctgtcccctc cagcacctgg | 4320 |
| cccagcgaga ccgtcacctg caacgttgcc cacccggcca gcagcaccaa ggtggacaag | 4380 |
| aaaattgtgc ccagggattg tactagtgga ggtggaggta gccaccatca ccatcaccat | 4440 |
| taatctagag ttaagcggcc gtcgagatct cgacatcgat aatcaacctc tggattacaa | 4500 |
| aatttgtgaa agattgactg gtattcttaa ctatgttgct ccttttacgc tatgtggata | 4560 |
| cgctgcttta atgcctttgt atcatgctat tgcttcccgt atggctttca ttttctcctc | 4620 |
| cttgtataaa tcctggttgc tgtctcttta tgaggagttg tggcccgttg tcaggcaacg | 4680 |
| tggcgtggtg tgcactgtgt tgctgacgc aacccccact ggttgggca ttgccaccac | 4740 |
| ctgtcagctc ctttccggga cttcgcttt ccccctccct attgccacgg cggaactcat | 4800 |
| cgccgcctgc cttgcccgct gctggacagg ggctcggctg ttgggcactg acaattccgt | 4860 |
| ggtgttgtcg gggaaatcat cgtccttttc ttggctgctc gcctgtgttg ccacctggat | 4920 |
| tctgcgcgg acgtccttct gctacgtccc ttcggccctc aatccagcgg accttccttc | 4980 |
| ccgcggcctg ctgccggctc tgcggcctct tccgcgtctt cgccttcgcc ctcagacgag | 5040 |
| tcggatctcc ctttgggccg cctccccgcc tgatcgataa aataaaagat tttatttagt | 5100 |
| ctccagaaaa agggggaat gaaagacccc acctgtaggt ttggcaagct agcttaagta | 5160 |
| acgccatttt gcaaggcatg gaaaaataca taactgagaa tagagaagtt cagatcaagg | 5220 |
| tcaggaacag atggaacagc tgaatatggg ccaaacagga tatctgtggt aagcagttcc | 5280 |
| tgccccggct cagggccaag aacagatgga acagctgaat atgggccaaa caggatatct | 5340 |
| gtggtaagca gttcctgccc cggctcaggg ccaagaacag atggtcccca gatgcggtcc | 5400 |
| agccctcagc agtttctaga gaaccatcag atgtttccag gtgccccaa ggacctgaaa | 5460 |
| tgaccctgtg ccttatttga actaaccaat cagttcgctt ctcgcttctg ttcgcgcgct | 5520 |
| tctgctcccc gagctcaata aaagagccca caacccctca ctcggggcgc cagtcctccg | 5580 |
| attgactgag tcgcccgggt acccgtgtat ccaataaacc ctcttgcagt tgcatccgac | 5640 |
| ttgtggtctc gctgttcctt gggagggtct cctctgagtg attgactacc cgtcagcggg | 5700 |
| ggtctttcat t | 5711 |

<210> SEQ ID NO 9
<211> LENGTH: 5130
<212> TYPE: DNA
<213> ORGANISM: Artificial Sequence
<220> FEATURE:
<223> OTHER INFORMATION: Synthetic

<400> SEQUENCE: 9

| | |
|---|---|
| tttgaaagac cccacccgta ggtggcaagc tagcttaagt aacgccactt tgcaaggcat | 60 |

-continued

```
ggaaaaatac ataactgaga atagaaaagt tcagatcaag gtcaggaaca aagaaacagc      120
tgaataccaa acaggatatc tgtggtaagc ggttcctgcc ccggctcagg gccaagaaca      180
gatgagacag ctgagtgatg ggccaaacag gatatctgtg gtaagcagtt cctgccccgg      240
ctcggggcca agaacagatg gtccccagat gcggtccagc cctcagcagt ttctagtgaa      300
tcatcagatg tttccagggt gccccaagga cctgaaaatg accctgtacc ttatttgaac      360
taaccaatca gttcgcttct cgcttctgtt cgcgcgcttc cgctctccga gctcaataaa      420
agagcccaca acccctcact cggcgcgcca gtcttccgat agactgcgtc gcccgggtac      480
ccgtattccc aataaagcct cttgctgttt gcatccgaat cgtggtctcg ctgttccttg      540
ggagggtctc ctctgagtga ttgactaccc acgacggggg tctttcattt ggggctcgt       600 ccgggatttg gagacccctg cccagggacc accgacccac caccgggagg taagctggcc      660
agcaacttat ctgtgtctgt ccgattgtct agtgtctatg tttgatgtta tgcgcctgcg      720
tctgtactag ttagctaact agctctgtat ctggcggacc cgtggtggaa ctgacgagtt      780
ctgaacaccc ggccgcaacc ctgggagacg tcccagggac tttggggggcc gttttttgtgg    840 cccgacctga ggaagggagt cgatgtgaaa tccgaccccg tcaggatatg tggttctggt      900
aggagacgag aacctaaaac agttcccgcc tccgtctgaa ttttttgcttt cggtttggaa      960 ccgaagccgc gcgtcttgtc tgctgcagcc aagcttgggc tgcaggtcga ggactgggga     1020
ccctgcaccg aacatggaga acacaacatc aggattccta ggaccccctgc tcgtgttaca    1080 ggcgggggttt ttcttgttga caagaatcct cacaatacca cagagtctag actcgtggtg    1140
gacttctctc aattttctag ggggagcacc cacgtgtcct ggccaaaatt cgcagtcccc    1200
aacctccaat cactcaccaa cctcttgtcc tccaatttgt cctggctatc gctggatgtg    1260
tctgcggcgt tttatcatat tcctcttcat cctgctgcta tgcctcatct tcttgttggt    1320
tcttctggac taccaaggta tgttgcccgt ttgtcctcta cttccaggaa catcaactac    1380
cagcacggga ccatgcaaga cctgcacgat tcctgctcaa ggaacctcta tgtttccctc    1440
ttgttgctgt acaaaacctt cggacggaaa ctgcacttgt attcccatcc catcatcctg    1500
ggctttcgca agattcctat gggagtgggc ctcagtccgt ttctcctggc tcagtttact    1560
agtgccattt gttcagtggt tcgtagggct ttcccccact gtttggcttt cagttatatg    1620
gatgatgtgg tattggggggc caagtctgta caacatcttg agtccctttt tacctctatt    1680
accaattttc ttttgtcttt gggtatacat ttaaaccccta ataaaaccaa acgttggggc    1740
tactccctta acttcatggg atatgtaatt ggatgttggg gtactttacc gcaagaacat    1800
attgtactaa aaatcaagca atgttttcga aaactgcctg taaatagacc tattgattgg    1860
aaagtatgtc agagacttgt gggtcttttg ggctttgctg cccctttttac acaatgtggc    1920 tatcctgcct taatgccttt atatgcatgt atacaatcta agcaggcttt cactttctcg    1980
ccaacttaca aggcctttct gtgtaaacaa tatctgaacc tttaccccgt tgcccggcaa    2040
cggtcaggtc tctgccaagt gtttgctgac gcaaccccca ctggatgggg cttggctatc    2100
ggccatagcc gcatgcgcgg acctttgtgg ctcctctgcc gatccatact gcggaactcc    2160
tagcagcttg ttttgctcgc aggcggtctg gagcgaaact tatcggcacc gacaactctg    2220
ttgtcctctc tcggaaatac acctcctttc catggctgct agggtgtgct gccaactgga    2280
tcccctcagg atatagtagt ttcgcttttg catagggagg gggaaatgta gtcttatgca    2340
atacacttgt agtcttgcaa catggtaacg atgagttagc aacatgcctt acaaggagag    2400
aaaaagcacc gtgcatgccg attggtggaa gtaaggtggt acgatcgtgc cttattagga    2460
```

```
aggcaacaga caggtctgac atggattgga cgaaccactg aattccgcat tgcagagata    2520
attgtattta agtgcctagc tcgatacagc aaacgccatt tttgaccatt caccacattg    2580
gtgtgcacct tccaaagctt cacgctgccg caagcactca gggcgcaagg gctgctaaag    2640
gaagcggaac acgtagaaag ccagtccgca gaaacggtgc tgaccccgga tgaatgtcag    2700
ctactgggct atctggacaa gggaaaacgc aagcgcaaag agaaagcagg tagcttgcag    2760
tgggcttaca tggcgatagc tagactgggc ggttttatgg acagcaagcg aaccggaatt    2820
gccagctggg gcgccctctg gtaaggttgg gaagccctgc aaagtaaact ggatggcttt    2880
cttgccgcca aggatctgat ggcgcagggg atcaagatct gatcaagaga caggatgagg    2940
atcgtttcgc atgattgaac aagatggatt gcacgcaggt tctccggccg cttgggtgga    3000
gaggctattc ggctatgact gggcacaaca gacaatcggc tgctctgatg ccgccgtgtt    3060
ccggctgtca gcgcaggggc gcccggttct ttttgtcaag accgacctgt ccggtgccct    3120
gaatgaactg caggacgagg cagcgcggct atcgtggctg gccacgacgg gcgttccttg    3180
cgcagctgtg ctcgacgttg tcactgaagc gggaagggac tggctgctat tgggcgaagt    3240
gccggggcag gatctcctgt catctcacct tgctcctgcc gagaaagtat ccatcatggc    3300
tgatgcaatg cggcggctgc atacgcttga tccggctacc tgcccattcg accaccaagc    3360
gaaacatcgc atcgagcgag cacgtactcg gatggaagcc ggtcttgtcg atcaggatga    3420
tctggacgaa gagcatcagg ggctcgcgcc agccgaactg ttcgccaggc tcaaggcgcg    3480
catgcccgac ggcgaggatc tcgtcgtgac ccatggcgat gcctgcttgc cgaatatcat    3540
ggtggaaaat ggccgctttt ctggattcat cgactgtggc cggctgggtg tggcggaccg    3600
ctatcaggac atagcgttgg ctacccgtga tattgctgaa gagcttggcg gcgaatgggc    3660
tgaccgcttc ctcgtgcttt acggtatcgc cgctcccgat tcgcagcgca tcgccttcta    3720
tcgccttctt gacgagttct tctgagcggg actctgggt tcgaaatgac cgaccaagcg    3780
acgcccaacc tgccatcacg agatttcgat tccaccgccg ccttctatga aggttgggc    3840 ttcggaatcg ttttccggga cgccggctgg atgatcctcc agcgcgggga tctcatgctg    3900
gagttcttcg cccaccccaa ccctggccct attattgggt ggactaacca tgggggaat    3960 tgccgctgga ataggaacag ggactactgc tctaatggcc actcagcaat tccagcagct    4020
ccaagccgca gtacaggatg atctcaggga ggttgaaaaa tcaatctcta acctagaaaa    4080
gtctctcact tccctgtctg aagttgtcct acagaatcga aggggcctag acttgttatt    4140
tctaaaagaa ggagggctgt gtgctgctct aaaagaagaa tgttgcttct atgcggacca    4200
cacaggacta gtgagagaca gcatggccaa attgagagag aggcttaatc agagacagaa    4260
actgtttgag tcaactcaag gatggtttga gggactgttt aacagatccc cttggtttac    4320 cacctttgata tctaccatta tgggacccct cattgtactc ctaatgattt tgctcttcgg    4380
accctgcatt cttaatcgat tagtccaatt tgttaaagac aggatatcag tggtccaggc    4440
tctagttttg actcaacaat atcaccagct gaagcctata gagtacgagc catagataaa    4500
ataaaagatt ttatttagtc tccagaaaaa gggggaatg aaagacccca cctgtaggtt    4560
tggcaagcta gcttaagtaa cgccattttg caaggcatgg aaaatacat aactgagaat    4620 agagaagttc agatcaaggt caggaacaga tggaacagct gaatatgggc caaacaggat    4680
atctgtggta agcagttcct gccccggctc agggccaaga acagatggaa cagctgaata    4740
tgggccaaac aggatatctg tggtaagcag ttcctgcccc ggctcagggc caagaacaga    4800
```

```
tggtcccag atgcggtcca gccctcagca gtttctagag aaccatcaga tgtttccagg    4860 gtgcccaag gacctgaaat gaccctgtgc cttatttgaa ctaaccaatc agttcgcttc    4920
tcgcttctgt tcgcgcgctt ctgctccccg agctcaataa aagagcccac aaccctcac    4980 tcggggcgcc agtcctccga ttgactgagt cgcccgggta cccgtgtatc caataaaccc    5040
tcttgcagtt gcatccgact tgtggtctcg ctgttccttg ggagggtctc ctctgagtga    5100
ttgactaccc gtcagcgggg gtctttcatt                                     5130

<210> SEQ ID NO 10
<211> LENGTH: 4661
<212> TYPE: DNA
<213> ORGANISM: Artificial Sequence
<220> FEATURE:
<223> OTHER INFORMATION: Synthetic

<400> SEQUENCE: 10
gatcagtcct gggtggtcat tgaaaggact gatgctgaag ttgaagctcc aatactttgg      60
ccacctgatg cgaagaactg actcatgtga taagaccctg atactgggaa agattgaagg     120
caggaggaga agggatgaca gaggatggaa gagttggatg gaatcaccaa ctcgatggac     180
atgagtttga gcaagcttcc aggagttggt aatgggcagg gaagcctggc gtgctgcagt     240
ccatggggtt gcaaagagtt ggacactact gagtgactga actgaactga tagtgtaatc     300
catggtacag aatataggat aaaaagagg aagagtttgc cctgattctg aagagttgta     360
ggatataaaa gtttagaata cctttagttt ggaagtctta aattatttac ttaggatggg     420
tacccactgc aatataagaa atcaggcttt agagactgat gtagagagaa tgagccctgg     480
cataccagaa gctaacagct attggttata gctgttataa ccaatatata accaatatat     540
tggttatata gcatgaagct tgatgccagc aatttgaagg aaccatttag aactagtatc     600
ctaaactcta catgttccag gacactgatc ttaaagctca ggttcagaat cttgttttat     660
aggctctagg tgtatattgt ggggcttccc tggtggctca gatggtaaag tgtctgcctg     720
caatgtgggt gatctgggtt cgatccctgg cttgggaaga tccctggag aaggaaatgg     780 caacccactc tagtactctt acctggaaaa ttccatggac agaggagcct tgtaagctac     840
agtccatggg attgcaaaga gttgaacaca actgagcaac taagcacagc acagtacagt     900
atacacctgt gaggtgaagt gaagtgaagg ttcaatgcag ggtctcctgc attgcagaaa     960
gattctttac catctgagcc accagggaag cccaagaata ctggagtggg tagcctattc    1020
cttctccagg ggatcttccc atcccaggaa ttgaactgga gtctcctgca tttcaggtgg    1080
attcttcacc agctgaacta ccaggtggat actactccaa tattaaagtg cttaaagtcc    1140
agttttccca cctttcccaa aaaggttggg tcactctttt ttaaccttct gtggcctact    1200
ctgaggctgt ctacaagctt atatatttat gaacacattt attgcaagtt gttagtttta    1260
gatttacaat gtggtatctg ctatttagt ggtattggtg gttggggatg gggaggctga    1320
tagcatctca gagggcagct agatactgtc atacacactt ttcaagttct ccatttttgt    1380
gaaatagaaa gtctctggat ctaagttata tgtgattctc agtctctgtg gtcatattct    1440
attctactcc tgaccactca acaaggaacc aagatatcaa gggacacttg ttttgtttca    1500
tgcctgggtt gagtgggcca tgacatatgt tctgggcctt gttacatggc tggattggtt    1560
ggacaagtgc cagctctgat cctgggactg tggcatgtga tgacatacac cccctctcca    1620
cattctgcat gtctctaggg gggaaggggg aagctcggta tagaaccttt attgtatttt    1680
ctgattgcct cacttcttat attgcccca tgcccttctt tgttcctcaa gtaaccagag    1740
```

```
acagtgcttc ccagaaccaa ccctacaaga aacaaagggc taaacaaagc caaatgggaa    1800
gcaggatcat ggtttgaact ctttctggcc agagaacaat acctgctatg gactagatac    1860
tgggagaggg aaaggaaaag tagggtgaat tatggaagga agctggcagg ctcagcgttt    1920
ctgtcttggc atgaccagtc tctcttcatt ctcttcctag atgtagggct tggtaccaga    1980
gcccctgagg ctttctgcat gaatataaat atatgaaact gagtgatgct tccatttcag    2040
gttcttgggg gcgccgaatt cgagctcggt acccggggat ctcgagaagc tttaaccatg    2100
gaatggagct gggtctttct cttcttcctg tcagtaacta caggtgtcca ctcccaggtt    2160
cagttgcagc agtctgacgc tgagttggtg aaacctgggg cttcagtgaa gatttcctgc    2220
aaggcttctg gctacacctt cactgaccat gcaattcact gggtgaaaca gaaccctgaa    2280
cagggcctgg aatggattgg atatttttct cccggaaatg atgattttaa atacaatgag    2340
aggttcaagg gcaaggccac actgactgca gacaaatcct ccagcactgc ctacgtgcag    2400
ctcaacagcc tgacatctga ggattctgca gtgtatttct gtacaagatc cctgaatatg    2460
gcctactggg gtcaaggaac ctcagtcacc gtctcctcag gaggcggagg cagcggaggc    2520
ggtggctcgg gaggcggagg ctcggacatt gtgatgtcac agtctccatc ctccctacct    2580
gtgtcagttg gcgagaaggt tactttgagc tgcaagtcca gtcagagcct tttatatagt    2640
ggtaatcaaa agaactactt ggcctggtac cagcagaaac cagggcagtc tcctaaactg    2700
ctgatttact gggcatccgc tagggaatct ggggtccctg atcgcttcac aggcagtgga    2760
tctgggacag atttcactct ctccatcagc agtgtgaaga ctgaagacct ggcagtttat    2820
tactgtcagc agtattatag ctatcccctc acgttcggtg ctgggaccaa gctggtgctg    2880
aaacgggccg ccgagcccaa atctcctgac aaaactcaca catgcccacc gtgcccagca    2940
cctgaactcc tggggggacc gtcagtcttc ctcttccccc caaaacccaa ggacaccctc    3000
atgatctccc ggacccctga ggtcacatgc gtggtggtgg acgtgagcca cgaagaccct    3060
gaggtcaagt tcaactggta cgtggacggc gtggaggtgc ataatgccaa gacaaagccg    3120
cgggaggagc agtacaacag cacgtaccgt gtggtcagcg tcctcaccgt cctgcaccag    3180
gactggctga atggcaagga gtacaagtgc aaggtctcca acaaagccct cccagccccc    3240
atcgagaaaa ccatctccaa agccaaaggg cagccccgag aaccacaggt gtacaccctg    3300
cccccatccc gggatgagct gaccaagaac caggtcagcc tgacctgcct ggtcaaaggc    3360
ttctatccca gcgacatcgc cgtggagtgg gagagcaatg ggcagccgga gaacaactac    3420
aagaccacgc ctcccgtgct ggactccgac ggctccttct tcctctacag caagctcacc    3480
gtggacaaga gcaggtggca gcaggggaac gtcttctcat gctccgtgat gcatgaggct    3540
ctgcacaacc actacacgca gaagagcctc tccctgtctc cgggtaaagg aggcggatca    3600
ggaggtggcg cacctacttc aagttctaca aagaaaacac agctacaact ggagcattta    3660
ctgctggatt tacagatgat tttgaatgga attaataatt acaagaatcc caaactcacc    3720
aggatgctca catttaagtt ttacatgccc aagaaggcca cagaactgaa acatcttcag    3780
tgtctagaag aagaactcaa acctctggag gaagtgctaa atttagctca aagcaaaaac    3840
tttcacttaa gacccaggga cttaatcagc aatatcaacg taatagttct ggaactaaag    3900
ggatctgaaa caacattcat gtgtgaatat gctgatgaga cagcaaccat tgtagaattt    3960
ctgaacagat ggattacctt ttgtcaaagc atcatctcaa cactaacttg aagcttgtta    4020
acatcgataa aataaaagat tttatttagt ctccagaaaa agggggggaat gaaagacccc    4080
```

-continued

| | |
|---|---|
| acctgtaggt ttggcaagct agcttaagta acgccatttt gcaaggcatg gaaaaataca | 4140 |
| taactgagaa tagagaagtt cagatcaagg tcaggaacag atggaacagc tgaatatggg | 4200 |
| ccaaacagga tatctgtggt aagcagttcc tgccccggct cagggccaag aacagatgga | 4260 |
| acagctgaat atgggccaaa caggatatct gtggtaagca gttcctgccc cggctcaggg | 4320 |
| ccaagaacag atggtcccca gatgcggtcc agccctcagc agtttctaga gaaccatcag | 4380 |
| atgtttccag ggtgcccaa ggacctgaaa tgaccctgtg ccttatttga actaaccaat | 4440 |
| cagttcgctt ctcgcttctg ttcgcgcgct tctgctcccc gagctcaata aaagagccca | 4500 |
| caaccctca ctcggggcgc cagtcctccg attgactgag tcgcccgggt acccgtgtat | 4560 |
| ccaataaacc ctcttgcagt tgcatccgac ttgtggtctc gctgttcctt gggagggtct | 4620 |
| cctctgagtg attgactacc cgtcagcggg ggtctttcat t | 4661 |

<210> SEQ ID NO 11
<211> LENGTH: 5691
<212> TYPE: DNA
<213> ORGANISM: Artificial Sequence
<220> FEATURE:
<223> OTHER INFORMATION: Synthetic

<400> SEQUENCE: 11

| | |
|---|---|
| gatcagtcct gggtggtcat tgaaaggact gatgctgaag ttgaagctcc aatactttgg | 60 |
| ccacctgatg cgaagaactg actcatgtga taagaccctg atactgggaa agattgaagg | 120 |
| caggaggaga agggatgaca gaggatggaa gagttggatg gaatcaccaa ctcgatggac | 180 |
| atgagtttga gcaagcttcc aggagttggt aatgggcagg gaagcctggc gtgctgcagt | 240 |
| ccatggggtt gcaaagagtt ggacactact gagtgactga actgaactga tagtgtaatc | 300 |
| catggtacag aatataggat aaaaagagg aagagtttgc cctgattctg aagagttgta | 360 |
| ggatataaaa gtttagaata ccttagtttt ggaagtctta aattatttac ttaggatggg | 420 |
| tacccactgc aatataagaa atcaggcttt agagactgat gtagagagaa tgagccctgg | 480 |
| cataccagaa gctaacagct attggttata gctgttataa ccaatatata accaatatat | 540 |
| tggttatata gcatgaagct tgatgccagc aatttgaagg aaccatttag aactagtatc | 600 |
| ctaaactcta catgttccag gacactgatc ttaaagctca ggttcagaat cttgttttat | 660 |
| aggctctagg tgtatattgt ggggcttccc tggtggctca gatggtaaag tgtctgcctg | 720 |
| caatgtgggt gatctgggtt cgatccctgg cttgggaaga tccctggag aaggaaatgg | 780 |
| caacccactc tagtactctt acctggaaaa ttccatggac agaggagcct tgtaagctac | 840 |
| agtccatggg attgcaaaga gttgaacaca actgagcaac taagcacagc acagtacagt | 900 |
| atacacctgt gaggtgaagt gaagtgaagg ttcaatgcag ggtctcctgc attgcagaaa | 960 |
| gattctttac catctgagcc accagggaag cccaagaata ctggagtggg tagcctattc | 1020 |
| cttctccagg ggatcttccc atcccaggaa ttgaactgga gtctcctgca tttcaggtgg | 1080 |
| attcttcacc agctgaacta ccaggtggat actactccaa tattaaagtg cttaaagtcc | 1140 |
| agttttccca cctttcccaa aaaggttggg tcactctttt ttaaccttct gtggcctact | 1200 |
| ctgaggctgt ctacaagctt atatatttat gaacacattt attgcaagtt gttagtttta | 1260 |
| gatttacaat gtggtatctg gctatttagt ggtattggtg gttggggatg gggaggctga | 1320 |
| tagcatctca gagggcagct agatactgtc atacacactt ttcaagttct ccattttgt | 1380 |
| gaaatagaaa gtctctggat ctaagttata tgtgattctc agtctctgtg gtcatattct | 1440 |
| attctactcc tgaccactca acaaggaacc aagatatcaa gggacacttg ttttgtttca | 1500 |

-continued

```
tgcctgggtt gagtgggcca tgacatatgt tctgggcctt gttacatggc tggattggtt    1560
ggacaagtgc cagctctgat cctgggactg tggcatgtga tgacatacac cccctctcca    1620
cattctgcat gtctctaggg gggaaggggg aagctcggta tagaaccttt attgtatttt    1680
ctgattgcct cacttcttat attgccccca tgcccttctt tgttcctcaa gtaaccagag    1740
acagtgcttc ccagaaccaa ccctacaaga aacaaagggc taaacaaagc caaatgggaa    1800
gcaggatcat ggtttgaact ctttctggcc agagaacaat acctgctatg gactagatac    1860
tgggagaggg aaaggaaaag tagggtgaat tatggaagga agctggcagg ctcagcgttt    1920
ctgtcttggc atgaccagtc tctcttcatt ctcttcctag atgtagggct tggtaccaga    1980
gcccctgagg ctttctgcat gaatataaat atatgaaact gagtgatgct tccatttcag    2040
gttcttgggg gcgccgaatt cgagctcggt acccggggat ctcgacggat ccgattactt    2100
actggcaggt gctgggggct tccgagacaa tcgcgaacat ctacaccaca caacaccgcc    2160
tcgaccaggg tgagatatcg gccggggacg cggcgtggt aattacaagc gagatccgat    2220
tacttactgg caggtgctgg gggcttccga gacaatcgcg aacatctaca ccacacaaca    2280
ccgcctcgac cagggtgaga tatcggccgg ggacgcggcg gtggtaatta caagcgagat    2340
ctcgagttaa cagatctagg cctcctaggt cgacggatcc ccgggaattc ggcgccgcca    2400
ccatgatgtc ctttgtctct ctgctcctgg taggcatcct attccatgcc acccaggccc    2460
aggtccaact gcagcagtct gggcctgagc tggtgaagcc tgggacttca gtgaggatat    2520
cctgcaaggc ttctggctac accttcacaa gctactattt acactgggtg aagcagaggc    2580
ctggacaggg acttgagtgg attgcatgga tttatcctgg aaatgttatt actacgtaca    2640
atgagaagtt caagggcaag gccacactga ctgcagacaa atcctccagc acagcctaca    2700
tgcacctcaa cagcctgacc tctgaggact ctgcggtcta tttctgtgca aggggtgacc    2760
atgatcttga ctactgggc caaggcacca ctctcacagt ctcctcagcc aaaacgacac    2820
ccccatctgt ctatccactg gcccctggat ctgctgccca aactaactcc atggtgaccc    2880
tgggatgcct ggtcaagggc tatttccctg agccagtgac agtgacctgg aactctggat    2940
ccctgtccag cggtgtgcac accttcccag ctgtcctgca gtctgacctc tacactctga    3000
gcagctcagt gactgtcccc tccagcacct ggcccagcga gaccgtcacc tgcaacgttg    3060
cccacccggc cagcagcacc aaggtggaca gaaaattgt gcccagggat tgtactagtg    3120
gaggtggagg tagctaaggg agatctcgac ggatccccgg gaattcgccc ctctccctcc    3180 cccccccta cgttactgg ccgaagccgc ttggaataag gccggtgtgc gtttgtctat    3240
atgttatttt ccaccatatt gccgtctttt ggcaatgtga gggcccggaa acctggccct    3300
gtcttcttga cgagcattcc tagggtctt tcccctctcg ccaaaggaat gcaaggtctg    3360
ttgaatgtcg tgaaggaagc agttcctctg gaagcttctt gaagacaaac aacgtctgta    3420 gcgaccctt gcaggcagcg gaaccccca cctggcgaca ggtgcctctg cggccaaaag    3480
ccacgtgtat aagatacacc tgcaaaggcg gcacaacccc agtgccacgt tgtgagttgg    3540
atagttgtgg aaagagtcaa atggctctcc tcaagcgtat tcaacaaggg gctgaaggat    3600
gcccagaagg tacccccattg tatgggatct gatctgggc ctcggtgcac atgctttaca    3660
tgtgtttagt cgaggttaaa aaacgtcta ggccccccga accacgggga cgtggttttc    3720 cttgaaaaa cacgatgata atatggcctc ctttgtctct ctgctcctgg taggcatcct    3780
attccatgcc acccaggccg acattgtgct gacacaatct ccagcaatca tgtctgcatc    3840
```

| | | | | |
|---|---|---|---|---|
| tccaggggag | aaggtcacca | tgacctgcag | tgccacctca | agtgtaagtt acatacactg | 3900 |
| gtaccagcag | aagtcaggca | cctcccccaa | agatggatt | tatgacacat ccaaactggc | 3960 |
| ttctggagtc | cctgctcgct | tcagtggcag | tgggtctggg | acctctcact ctctcacact | 4020 |
| cagcagcatg | gaggctgaag | atgctgccac | ttattactgc | cagcagtggg gtagttacct | 4080 |
| cacgttcggt | gcggggacca | agctggagct | gaaacgggct | gatgctgcac caactgtatc | 4140 |
| catcttccca | ccatccagtg | agcagttaac | atctggaggt | gcctcagtcg tgtgcttctt | 4200 |
| gaacaacttc | tacccaaag | acatcaatgt | caagtggaag | attgatggca gtgaacgaca | 4260 |
| aaatggcgtc | ctgaacagtt | ggactgatca | ggacagcaaa | gacagcacct acagcatgag | 4320 |
| cagcaccctc | acgttgacca | aggacgagta | tgaacgacat | aacagctata cctgtgaggc | 4380 |
| cactcacaag | acatcaactt | cacccattgt | caagagcttc | aacaggaatg agtgttaata | 4440 |
| ggggagatct | cgacatcgat | aatcaacctc | tggattacaa | aatttgtgaa agattgactg | 4500 |
| gtattcttaa | ctatgttgct | cctttacgc | tatgtggata | cgctgcttta atgcctttgt | 4560 |
| atcatgctat | tgcttcccgt | atggctttca | ttttctcctc | cttgtataaa tcctggttgc | 4620 |
| tgtctcttta | tgaggagttg | tggcccgttg | tcaggcaacg | tggcgtggtg tgcactgtgt | 4680 |
| ttgctgacgc | aacccccact | ggttggggca | ttgccaccac | ctgtcagctc ctttccggga | 4740 |
| ctttcgcttt | cccctccct | attgccacgt | cggaactcat | cgccgcctgc cttgcccgct | 4800 |
| gctggacagg | ggctcggctg | ttgggcactg | acaattccgt | ggtgttgtcg gggaaatcat | 4860 |
| cgtcctttcc | ttggctgctc | gcctgtgttg | ccacctggat | tctgcgcggg acgtccttct | 4920 |
| gctacgtccc | ttcggccctc | aatccagcgg | accttccttc | ccgcggcctg ctgccggctc | 4980 |
| tgcggcctct | tccgcgtctt | cgccttcgcc | ctcagacgag | tcggatctcc ctttgggccg | 5040 |
| cctccccgcc | tgatcgataa | aataaaagat | tttatttagt | ctccagaaaa aggggggaat | 5100 |
| gaaagacccc | acctgtaggt | ttggcaagct | agcttaagta | acgccatttt gcaaggcatg | 5160 |
| gaaaaataca | taactgagaa | tagagaagtt | cagatcaagg | tcaggaacag atggaacagc | 5220 |
| tgaatatggg | ccaaacagga | tatctgtggt | aagcagttcc | tgccccggct cagggccaag | 5280 |
| aacagatgga | acagctgaat | atgggccaaa | caggatatct | gtggtaagca gttcctgccc | 5340 |
| cggctcaggg | ccaagaacag | atggtcccca | gatgcggtcc | agccctcagc agtttctaga | 5400 |
| gaaccatcag | atgtttccag | ggtgccccaa | ggacctgaaa | tgaccctgtg ccttatttga | 5460 |
| actaaccaat | cagttcgctt | ctcgcttctg | ttcgcgcgct | tctgctcccc gagctcaata | 5520 |
| aaagagccca | aaccccctca | ctcggggcgc | cagtcctccg | attgactgag tcgcccgggt | 5580 |
| acccgtgtat | ccaataaacc | ctcttgcagt | tgcatccgac | ttgtggtctc gctgttcctt | 5640 |
| gggagggtct | cctctgagtg | attgactacc | cgtcagcggg | ggtctttcat t | 5691 |

<210> SEQ ID NO 12
<211> LENGTH: 668
<212> TYPE: DNA
<213> ORGANISM: Artificial Sequence
<220> FEATURE:
<223> OTHER INFORMATION: Synthetic

<400> SEQUENCE: 12

| | | | | |
|---|---|---|---|---|
| ggaattcgcc | cctctccctc | cccccccct | aacgttactg | gccgaagccg cttggaataa | 60 |
| ggccggtgtg | cgtttgtcta | tatgttattt | tccaccatat | tgccgtcttt tggcaatgtg | 120 |
| agggcccgga | aacctggccc | tgtcttcttg | acgagcattc | ctaggggtct ttcccctctc | 180 |
| gccaaaggaa | tgcaaggtct | gttgaatgtc | gtgaaggaag | cagttcctct ggaagcttct | 240 |

-continued

```
tgaagacaaa caacgtctgt agcgacccett tgcaggcagc ggaaccccc  acctggcgac    300 aggtgcctct gcggccaaaa gccacgtgta  taagatacac ctgcaaaggc ggcacaaccc    360
cagtgccacg ttgtgagttg gatagttgtg gaaagagtca atggctctc   ctcaagcgta    420 ttcaacaagg ggctgaagga tgcccagaag gtaccccatt gtatgggatc tgatctgggg    480
cctcggtgca catgctttac atgtgtttag tcgaggttaa aaaaacgtct aggccccccg    540
aaccacgggg acgtggtttt cctttgaaaa acacgatgat aatatggcct tgctcatcct    600
tacctgtctt gtggctgttg ctcttgccgg cgccatggga tatctagatc tcgagctcgc    660
gaaagctt                                                              668
```

<210> SEQ ID NO 13
<211> LENGTH: 6255
<212> TYPE: DNA
<213> ORGANISM: Artificial Sequence
<220> FEATURE:
<223> OTHER INFORMATION: Synthetic

<400> SEQUENCE: 13

```
tttgaaagac cccacccgta ggtggcaagc tagcttaagt aacgccactt tgcaaggcat     60
ggaaaaatac ataactgaga atagaaaagt tcagatcaag gtcaggaaca aagaaacagc    120
tgaataccaa acaggatatc tgtggtaagc ggttcctgcc ccggctcagg gccaagaaca    180
gatgagacag ctgagtgatg ggccaaacag gatatctgtg gtaagcagtt cctgccccgg    240
ctcggggcca agaacagatg gtccccagat gcggtccagc cctcagcagt ttctagtgaa    300
tcatcagatg tttccagggt gccccaagga cctgaaaatg accctgtacc ttatttgaac    360
taaccaatca gttcgcttct cgcttctgtt cgcgcgcttc cgctctccga gctcaataaa    420
agagcccaca ccctcact  cggcgcgcca gtcttccgat agactgcgtc gcccgggtac    480
ccgtattccc aataaagcct cttgctgttt gcatccgaat cgtggtctcg ctgttccttg    540
ggagggtctc ctctgagtga ttgactaccc acgacggggg tctttcattt ggggggctcgt    600 ccgggatttg gagaccccctg cccagggacc accgacccac caccgggagg taagctggcc    660
agcaacttat ctgtgtctgt ccgattgtct agtgtctatg tttgatgtta tgcgcctgcg    720
tctgtactag ttagctaact agctctgtat ctggcggacc cgtggtggaa ctgacgagtt    780
ctgaacaccc ggccgcaacc ctgggagacg tcccagggac tttgggggcc gtttttgtgg    840
cccgacctga ggaagggagt cgatgtggaa tccgaccccg tcaggatatg tggttctggt    900
aggagacgag aacctaaaac agttcccgcc tccgtctgaa ttttttgcttt cggtttggaa    960 ccgaagccgc gcgtcttgtc tgctgcagcg ctgcagcatc gttctgtgtt gtctctgtct   1020
gactgtgttt ctgtatttgt ctgaaaatta gggccagact gttaccactc ccttaagttt   1080
gaccttaggt cactggaaag atgtcgagcg gatcgctcac aaccagtcgg tagatgtcaa   1140
gaagagacgt tgggttacct tctgctctgc agaatggcca acctttaacg tcggatggcc   1200
gcgagacggc acctttaacc gagacctcat cacccaggtt aagatcaagg tcttttcacc   1260
tggcccgcat ggacacccag accaggtccc ctacatcgtg acctgggaag ccttggcttt   1320
tgacccccct ccctgggtca agccctttgt acacccctaag cctccgcctc ctcttcctcc   1380
atccgccccg tctctccccc ttgaacctcc tcgttcgacc ccgcctcgat cctcccttta   1440
tccagccctc actccttctc taggcgccgg aattccgatc tgatcaagag acaggatgag   1500
gatcgtttcg catgattgaa caagatggat tgcacgcagg ttctccggcc gcttgggtgg   1560
```

```
agaggctatt cggctatgac tgggcacaac agacaatcgg ctgctctgat gccgccgtgt    1620
tccggctgtc agcgcagggg cgcccggttc tttttgtcaa gaccgacctg tccggtgccc    1680
tgaatgaact gcaggacgag gcagcgcggc tatcgtggct ggccacgacg ggcgttcctt    1740
gcgcagctgt gctcgacgtt gtcactgaag cgggaaggga ctggctgcta ttgggcgaag    1800
tgccggggca ggatctcctg tcatctcacc ttgctcctgc cgagaaagta tccatcatgg    1860
ctgatgcaat gcggcggctg catacgcttg atccggctac ctgcccattc gaccaccaag    1920
cgaaacatcg catcgagcga gcacgtactc ggatggaagc cggtcttgtc gatcaggatg    1980
atctggacga agagcatcag gggctcgcgc cagccgaact gttcgccagg ctcaaggcgc    2040
gcatgcccga cggcgaggat ctcgtcgtga cccatggcga tgcctgcttg ccgaatatca    2100
tggtggaaaa tggccgcttt tctggattca tcgactgtgg ccggctgggt gtggcggacc    2160
gctatcagga catagcgttg gctacccgtg atattgctga agagcttggc ggcgaatggg    2220
ctgaccgctt cctcgtgctt tacggtatcg ccgctcccga ttcgcagcgc atcgccttct    2280
atcgccttct tgacgagttc ttcctgagcgg gactctgggg ttcgaaatga ccgaccaagc    2340
gacgcccaac ctgccatcac gagatttcga ttccaccgcc gccttctatg aaaggttggg    2400
cttcggaatc gttttccggg acgccggctg gatgatcctc cagcgcgggg atctcatgct    2460
ggagttcttc gcccacccog gctcgatcc cctcgcgagt tggttcagct gctgcctgag    2520
gctggacgac ctcgcggagt tctaccggca gtgcaaatcc gtcggcatcc aggaaaccag    2580
cagcggctat ccgcgcatcc atgccccga actgcaggag tggggaggca cgatggccgc    2640
tttggtcgag gcggatccgg ccattagcca tattattcat tggttatata gcataaatca    2700
atattggcta ttggccattg catacgttgt atccatatca taatatgtac atttatattg    2760
gctcatgtcc aacattaccg ccatgttgac attgattatt gactagttat taatagtaat    2820
caattacggg gtcattagtt catagcccat atatggagtt ccgcgttaca aacttacgg    2880 taaatggccc gcctggctga ccgcccaacg acccccgccc attgacgtca ataatgacgt    2940
atgttcccat agtaacgcca atagggactt tccattgacg tcaatgggtg gagtatttac    3000
ggtaaactgc ccacttggca gtacatcaag tgtatcatat gccaagtacg ccccctattg    3060
acgtcaatga cggtaaatgg cccgcctggc attatgccca gtacatgacc ttatgggact    3120
ttcctacttg gcagtacatc tacgtattag tcatcgctat taccatggtg atgcggtttt    3180
ggcagtacat caatgggcgt ggatagcggt ttgactcacg gggatttcca agtctccacc    3240
ccattgacgt caatgggagt ttgttttggc accaaaatca acgggacttt ccaaaatgtc    3300
gtaacaactc cgccccattg acgcaaatgg gcggtaggca tgtacggtgg gaggtctata    3360
taagcagagc tcgtttagtg aaccgtcaga tcgcctggac acgccatcca cgctgttttg    3420
acctccatag aagacaccgg gaccgatcca gcctccgcgg ccccaagctt ctcgacggat    3480 cccccgggaat tcaggccatc gatcccgccg ccaccatgga atggagctgg gtctttctct    3540
tcttcctgtc agtaactaca ggtgtccact ccgacatcca gatgacccag tctccagcct    3600
ccctatctgc atctgtggga gaaactgtca ctatcacatg tcgagcaagt gggaatattc    3660
acaattattt agcatggtat cagcagaaac agggaaaatc tcctcagctc ctggtctata    3720
atgcaaaaac cttagcagat ggtgtgccat caaggttcag tggcagtgga tcaggaacac    3780
aatattctct caagatcaac agcctgcagc ctgaagattt tgggagttat tactgtcaac    3840 attttttggag tactccgtgg acgttcggtg gaggcaccaa gctggaaatc aaacgggctg    3900
atgctgcacc aactgtatcc atcttcccac catccagtga gcagttaaca tctggaggtg    3960
```

```
cctcagtcgt gtgcttcttg aacaacttct accccaaaga catcaatgtc aagtggaaga    4020
ttgatggcag tgaacgacaa aatggcgtcc tgaacagttg gactgatcag gacagcaaag    4080
acagcaccta cagcatgagc agcaccctca cattgaccaa ggacgagtat gaacgacata    4140
acagctatac ctgtgaggcc actcacaaga catcaacttc acccattgtc aagagcttca    4200
acaggaatga gtgttgaaag catcgatttc ccctgaattc gccctctcc ctcccccccc    4260 cctaacgtta ctggccgaag ccgcttggaa taaggccggt gtgcgtttgt ctatatgtta    4320
ttttccacca tattgccgtc ttttggcaat gtgagggccc ggaaacctgg ccctgtcttc    4380
ttgacgagca ttcctagggg tctttcccct ctcgccaaag gaatgcaagg tctgttgaat    4440
gtcgtgaagg aagcagttcc tctggaagct tcttgaagac aaacaacgtc tgtagcgacc    4500 cttttgcaggc agcggaaccc cccacctggc gacaggtgcc tctgcggcca aaagccacgt    4560
gtataagata cacctgcaaa ggcggcacaa ccccagtgcc acgttgtgag ttggatagtt    4620
gtggaaagag tcaaatggct ctcctcaagc gtattcaaca aggggctgaa ggatgcccag    4680
aaggtacccc attgtatggg atctgatctg gggcctcgt gcacatgctt tacatgtgtt    4740
tagtcgaggt taaaaaacg tctaggcccc ccgaaccacg gggacgtggt tttcctttga    4800
aaaacacgat gataatatgg cctcctttgt ctctctgctc ctggtaggca tcctattcca    4860
tgccacccag gccgaggttc agcttcagca gtctggggca gagcttgtga agccaggggc    4920
ctcagtcaag ttgtcctgca cagcttctgg cttcaacatt aaagacacct ttatgcactg    4980
ggtgaagcag aggcctgaac agggcctgga gtggattgga aggattgatc ctgcgaatgg    5040
gaatactgaa tatgacccga agttccaggg caaggccact ataacagcag acacatcctc    5100
caacacagtc aacctgcagc tcagcagcct gacatctgag gacactgccg tctattactg    5160
tgctagtgga gggggaactgg ggtttcctta ctggggccaa gggactctgg tcactgtctc    5220
tgcagccaaa acgacacccc catctgtcta tccactggcc cctggatctg ctgcccaaac    5280
taactccatg gtgaccctgg gatgcctggt caagggctat ttccctgagc cagtgacagt    5340
gacctggaac tctggatccc tgtccagcgg tgtgcacacc ttcccagctg tcctgcagtc    5400
tgacctctac actctgagca gctcagtgac tgtcccctcc agcacctggc ccagcgagac    5460
cgtcacctgc aacgttgccc acccggccag cagcaccaag gtggacaaga aaattgtgcc    5520
cagggattgt actagtggag gtggaggtag ccaccatcac catcaccatt aatctagagt    5580
taagcggccg tcgagatcta ggcctcctag gtcgacatcg ataaaataaa gatttattat    5640
tagtctccag aaaaagggg gaatgaaaga ccccacctgt aggtttggca agctagctta    5700
agtaacgcca ttttgcaagg catggaaaaa tacataactg agaatagaga agttcagatc    5760
aaggtcagga acagatggaa cagctgaata tgggccaaac aggatatctg tggtaagcag    5820
ttcctgcccc ggctcaggcc caagaacaga tggaacagct gaatatgggc caaacaggat    5880
atctgtggta agcagttcct gccccggctc agggccaaga acagatggtc cccagatgcg    5940
gtccagccct cagcagtttc tagagaacca tcagatgttt ccagggtgcc caaggacct    6000 gaaatgaccc tgtgccttat ttgaactaac caatcagttc gcttctcgct tctgttcgcg    6060
cgcttctgct ccccgagctc aataaaaag cccacaaccc ctcactcggg gcgccagtcc    6120
tccgattgac tgagtcgccc gggtacccgt gtatccaata acctcttg cagttgcatc    6180 cgacttgtgg tctcgctgtt ccttgggagg gtctcctctg agtgattgac tacccgtcag    6240
cgggggtctt tcatt                                                     6255
```

<210> SEQ ID NO 14
<211> LENGTH: 43
<212> TYPE: DNA
<213> ORGANISM: Artificial Sequence
<220> FEATURE:
<223> OTHER INFORMATION: Synthetic

<400> SEQUENCE: 14
ctttgaaaaa cacgatgata atatggcctc ctttgtctct ctg                    43

<210> SEQ ID NO 15
<211> LENGTH: 30
<212> TYPE: DNA
<213> ORGANISM: Artificial Sequence
<220> FEATURE:
<223> OTHER INFORMATION: Synthetic

<400> SEQUENCE: 15
ttcgcgagct cgagatctag atatcccatg                                   30

<210> SEQ ID NO 16
<211> LENGTH: 35
<212> TYPE: DNA
<213> ORGANISM: Artificial Sequence
<220> FEATURE:
<223> OTHER INFORMATION: Synthetic

<400> SEQUENCE: 16
ctacaggtgt ccacgtcgac atccagctga cccag                             35

<210> SEQ ID NO 17
<211> LENGTH: 34
<212> TYPE: DNA
<213> ORGANISM: Artificial Sequence
<220> FEATURE:
<223> OTHER INFORMATION: Synthetic

<400> SEQUENCE: 17
ctgcagaata gatctctaac actctcccct gttg                              34

<210> SEQ ID NO 18
<211> LENGTH: 51
<212> TYPE: DNA
<213> ORGANISM: Artificial Sequence
<220> FEATURE:
<223> OTHER INFORMATION: Synthetic

<400> SEQUENCE: 18
cagtgtgatc tcgagaattc aggacctcac catgggatgg agctgtatca t           51

<210> SEQ ID NO 19
<211> LENGTH: 23
<212> TYPE: DNA
<213> ORGANISM: Artificial Sequence
<220> FEATURE:
<223> OTHER INFORMATION: Synthetic

<400> SEQUENCE: 19
aggctgtatt ggtggattcg tct                                          23

<210> SEQ ID NO 20
<211> LENGTH: 41
<212> TYPE: DNA
<213> ORGANISM: Artificial Sequence
<220> FEATURE:
<223> OTHER INFORMATION: Synthetic

<400> SEQUENCE: 20
agcttctcga gttaacagat ctaggcctcc taggtcgaca t           41

<210> SEQ ID NO 21
<211> LENGTH: 39
<212> TYPE: DNA
<213> ORGANISM: Artificial Sequence
<220> FEATURE:
<223> OTHER INFORMATION: Synthetic

<400> SEQUENCE: 21
cgatgtcgac ctaggaggcc tagatctgtt aactcgaga              39

<210> SEQ ID NO 22
<211> LENGTH: 64
<212> TYPE: DNA
<213> ORGANISM: Artificial Sequence
<220> FEATURE:
<223> OTHER INFORMATION: Synthetic

<400> SEQUENCE: 22
cgaggctctg cacaaccact acacgcagaa gagcctctcc ctgtctcccg ggaaatgaaa    60
gccg                                                                64

<210> SEQ ID NO 23
<211> LENGTH: 72
<212> TYPE: DNA
<213> ORGANISM: Artificial Sequence
<220> FEATURE:
<223> OTHER INFORMATION: Synthetic

<400> SEQUENCE: 23
aattcggctt tcatttcccg ggagacaggg agaggctctt ctgcgtgtag tggttgtgca    60
gagcctcgtg ca                                                       72

<210> SEQ ID NO 24
<211> LENGTH: 41
<212> TYPE: DNA
<213> ORGANISM: Artificial Sequence
<220> FEATURE:
<223> OTHER INFORMATION: Synthetic

<400> SEQUENCE: 24
aaagcatatg ttctgggcct tgttacatgg ctggattggt t           41

<210> SEQ ID NO 25
<211> LENGTH: 54
<212> TYPE: DNA
<213> ORGANISM: Artificial Sequence
<220> FEATURE:
<223> OTHER INFORMATION: Synthetic

<400> SEQUENCE: 25
tgaattcggc gcccccaaga acctgaaatg gaagcatcac tcagtttcat atat          54

<210> SEQ ID NO 26
<211> LENGTH: 35
<212> TYPE: DNA
<213> ORGANISM: Artificial Sequence
<220> FEATURE:
<223> OTHER INFORMATION: Synthetic

<400> SEQUENCE: 26

```
ctacaggtgt ccacgtcgac atccagctga cccag                    35
```

<210> SEQ ID NO 27
<211> LENGTH: 34
<212> TYPE: DNA
<213> ORGANISM: Artificial Sequence
<220> FEATURE:
<223> OTHER INFORMATION: Synthetic

<400> SEQUENCE: 27

```
ctgcagaata gatctctaac actctcccct gttg                     34
```

<210> SEQ ID NO 28
<211> LENGTH: 51
<212> TYPE: DNA
<213> ORGANISM: Artificial Sequence
<220> FEATURE:
<223> OTHER INFORMATION: Synthetic

<400> SEQUENCE: 28

```
cagtgtgatc tcgagaattc aggacctcac catgggatgg agctgtatca t    51
```

<210> SEQ ID NO 29
<211> LENGTH: 22
<212> TYPE: DNA
<213> ORGANISM: Artificial Sequence
<220> FEATURE:
<223> OTHER INFORMATION: Synthetic

<400> SEQUENCE: 29

```
gtgtcttcgg gtctcaggct gt                                  22
```

<210> SEQ ID NO 30
<211> LENGTH: 41
<212> TYPE: DNA
<213> ORGANISM: Artificial Sequence
<220> FEATURE:
<223> OTHER INFORMATION: Synthetic

<400> SEQUENCE: 30

```
agcttctcga gttaacagat ctaggcctcc taggtcgaca t              41
```

<210> SEQ ID NO 31
<211> LENGTH: 39
<212> TYPE: DNA
<213> ORGANISM: Artificial Sequence
<220> FEATURE:
<223> OTHER INFORMATION: Synthetic

<400> SEQUENCE: 31

```
cgatgtcgac ctaggaggcc tagatctgtt aactcgaga                39
```

<210> SEQ ID NO 32
<211> LENGTH: 64
<212> TYPE: DNA
<213> ORGANISM: Artificial Sequence
<220> FEATURE:
<223> OTHER INFORMATION: Synthetic

<400> SEQUENCE: 32

```
cgaggctctg cacaaccact acacgcagaa gagcctctcc ctgtctcccg ggaaatgaaa    60
gccg                                                               64
```

<210> SEQ ID NO 33
<211> LENGTH: 72

```
<212> TYPE: DNA
<213> ORGANISM: Artificial Sequence
<220> FEATURE:
<223> OTHER INFORMATION: Synthetic

<400> SEQUENCE: 33
aattcggctt tcatttcccg ggagacaggg agaggctctt ctgcgtgtag tggttgtgca    60
gagcctcgtg ca                                                       72

<210> SEQ ID NO 34
<211> LENGTH: 9511
<212> TYPE: DNA
<213> ORGANISM: Artificial Sequence
<220> FEATURE:
<223> OTHER INFORMATION: Synthetic

<400> SEQUENCE: 34
gaattaattc ataccagatc accgaaaact gtcctccaaa tgtgtccccc tcacactccc    60
aaattcgcgg gcttctgcct cttagaccac tctaccctat tccccacact caccggagcc   120
aaagccgcgg cccttccgtt tctttgcttt tgaaagaccc cacccgtagg tggcaagcta   180
gcttaagtaa cgccactttg caaggcatgg aaaaatacat aactgagaat agaaaagttc   240
agatcaaggt caggaacaaa gaaacagctg aataccaaac aggatatctg tggtaagcgg   300
ttcctgcccc ggctcagggc caagaacaga tgagacagct gagtgatggg ccaaacagga   360
tatctgtggt aagcagttcc tgccccggct cggggccaag aacagatggt ccccagatgc   420
ggtccagccc tcagcagttt ctagtgaatc atcagatgtt tccagggtgc cccaaggacc   480
tgaaaatgac cctgtacctt atttgaacta accaatcagt tcgcttctcg cttctgttcg   540
cgcgcttccg ctctccgagc tcaataaaag agcccacaac ccctcactcg gcgcgccagt   600
cttccgatag actgcgtcgc ccgggtaccc gtattcccaa taaagcctct tgctgtttgc   660
atccgaatcg tggtctcgct gttccttggg agggtctcct ctgagtgatt gactacccac   720
gacgggggtc tttcatttgg gggctcgtcc gggatttgga gaccccctgcc cagggaccac   780 cgacccacca ccgggaggta agctggccag caacttatct gtgtctgtcc gattgtctag   840
tgtctatgtt tgatgttatg cgcctgcgtc tgtactagtt agctaactag ctctgtatct   900
ggcggacccg tggtggaact gacgagttct gaacacccgg ccgcaaccct gggagacgtc   960
ccagggactt tgggggccgt ttttgtggcc cgacctgagg aagggagtcg atgtggaatc  1020 cgacccegtc aggatatgtg gttctggtag gagacgagaa cctaaaacag ttcccgcctc  1080
cgtctgaatt tttgctttcg gtttggaacc gaagccgcgc gtcttgtctg ctgcagcgct  1140
gcagcatcgt tctgtgttgt ctctgtctga ctgtgtttct gtatttgtct gaaaattagg  1200
gccagactgt taccactccc ttaagtttga ccttaggtca ctggaaagat gtcgagcgga  1260
tcgctcacaa ccagtcggta gatgtcaaga agagacgttg ggttaccttc tgctctgcag  1320
aatggccaac ctttaacgtc ggatggccgc gagacggcac ctttaaccga dccctcatca  1380
cccaggttaa gatcaaggtc ttttcacctg gcccgcatgg acaccagac caggtcccct  1440 acatcgtgac ctgggaagcc ttggcttttg accccctcc ctgggtcaag ccctttgtac  1500
accctaagcc tccgcctcct cttctccat ccgcccgtc tctcccctt gaacctcctc  1560 gttcgacccc gcctcgatcc tcctttatc cagccctcac tccttctcta ggcgccggaa  1620
ttccgatctg atcaagagac aggatgaggg agcttgtata tccattttcg gatctgatca  1680
gcacgtgttg acaattaatc atcggcatag tatatcggca tagtataata cgacaaggtg  1740
```

```
aggaactaaa ccatggccaa gcctttgtct caagaagaat ccaccctcat tgaaagagca    1800
acggctacaa tcaacagcat ccccatctct gaagactaca gcgtcgccag cgcagctctc    1860
tctagcgacg gccgcatctt cactggtgtc aatgtatatc attttactgg gggaccttgt    1920
gcagaactcg tggtgctggg cactgctgct gctgcggcag ctggcaacct gacttgtatc    1980
gtcgcgatcg gaaatgagaa caggggcatc ttgagcccct gcggacggtg tcgacaggtg    2040
cttctcgatc tgcatcctgg gatcaaagcg atagtgaagg acagtgatgg acagccgacg    2100
gcagttggga ttcgtgaatt gctgccctct ggttatgtgt gggagggcta agcacttcgt    2160
ggccgaggag caggactgac acgtgctacg agatttcgat tccaccgccg ccttctatga    2220
aaggttgggc ttcggaatcg ttttccggga cgccggctgg atgatcctcc agcgcgggga    2280
tctcatgctg gagttcttcg cccacccaa cttgtttatt gcagcttata atggttacaa     2340
ataaagcaat agcatcacaa atttcacaaa taaagcattt ttttcactgc attctagttg    2400
tggtttgtcc aaactcatca atgtatctta tcatgtctgt acgagttggt tcagctgctg    2460
cctgaggctg gacgacctcg cggagttcta ccggcagtgc aaatccgtcg gcatccagga    2520
aaccagcagc ggctatccgc gcatccatgc ccccgaactg caggagtggg gaggcacgat    2580
ggccgctttg gtcgaggcgg atccggccat tagccatatt attcattggt tatatagcat    2640
aaatcaatat tggctattgg ccattgcata cgttgtatcc atatcataat atgtacattt    2700
atattggctc atgtccaaca ttaccgccat gttgacattg attattgact agttattaat    2760
agtaatcaat tacggggtca ttagttcata gcccatatat ggagttccgc gttacataac    2820
ttacggtaaa tggcccgcct ggctgaccgc ccaacgaccc ccgcccattg acgtcaataa    2880
tgacgtatgt tcccatagta acgccaatag ggactttcca ttgacgtcaa tgggtggagt    2940
atttacggta aactgcccac ttggcagtac atcaagtgta tcatatgcca agtacgcccc    3000
ctattgacgt caatgacggt aaatggcccg cctggcatta tgcccagtac atgaccttat    3060
gggactttcc tacttggcag tacatctacg tattagtcat cgctattacc atggtgatgc    3120
ggttttggca gtacatcaat gggcgtggat agcggtttga ctcacgggga tttccaagtc    3180
tccaccccat tgacgtcaat gggagtttgt tttggcacca aaatcaacgg gactttccaa    3240
aatgtcgtaa caactccgcc ccattgacgc aaatgggcgg taggcatgta cggtgggagg    3300
tctatataag cagagctcgt ttagtgaacc gtcagatcgc ctggagacgc catccacgct    3360
gttttgacct ccatagaaga caccgggacc gatccagcct ccgcggcccc aagcttctcg    3420
agttaacaga tctaggctgg cacgacaggt ttcccgactg gaaagcgggc agtgagcgca    3480
acgcaattaa tgtgagttag ctcactcatt aggcacccca ggctttacac tttatgcttc    3540
cggctcgtat gttgtgtgga attgtgagcg gataacaatt tcacacagga aacagctatg    3600
accatgatta cgccaagctt ggctgcaggt cgacggatcc actagtaacg gccgccagtg    3660
tgctggaatt caccatgggg caacccggga acggcagcgc cttcttgctg cacccaatg     3720 gaagccatgc gccggaccac gacgtcacgc agcaaaggga cgaggtgtgg gtggtgggca    3780
tgggcatcgt catgtctctc atcgtcctgg ccatcgtgtt tggcaatgtg ctggtcatca    3840
cagccattgc caagttcgag cgtctgcaga cggtcaccaa ctacttcatc acaagcttgg    3900
cctgtgctga tctggtcatg gggctagcag tggtgccctt tggggccgcc catattctca    3960
tgaaaatgtg gactttttggc aacttctggt gcgagttctg gacttccatt gatgtgctgt    4020
gcgtcacggc atcgattgag accctgtgcg tgatcgcagt cgaccgctac tttgccatta    4080
ctagtccttt caagtaccag agcctgctga ccaagaataa ggcccgggtg atcattctga    4140
```

```
tggtgtggat tgtgtcaggc cttacctcct tcttgcccat tcagatgcac tggtacaggg    4200
ccacccacca ggaagccatc aactgctatg ccaatgagac ctgctgtgac ttcttcacga    4260
accaagccta tgccattgcc tcttccatcg tgtccttcta cgttcccctg gtgatcatgg    4320
tcttcgtcta ctccagggtc tttcaggagg ccaaaaggca gctccagaag attgacaaat    4380
ctgagggccg cttccatgtc cagaaccttaa gccaggtgga gcaggatggg cggacggggc    4440
atggactccg cagatcttcc aagttctgct tgaaggagca caaagccctc aagacgttag    4500
gcatcatcat gggcactttc accctctgct ggctgcccct tcttcatcgtt aacattgtgc    4560
atgtgatcca ggataacctc atccgtaagg aagtttacat cctcctaaat tggataggct    4620
atgtcaattc tggtttcaat ccccttatct actgccggag cccagatttc aggattgcct    4680
tccaggagct tctgtgcctg cgcaggtctt ctttgaaggc ctatggcaat ggctactcca    4740
gcaacggcaa cacaggggag cagagtggat atcacgtgga acaggagaaa gaaaataaac    4800
tgctgtgtga agacctccca ggcacggaag actttgtggg ccatcaaggt actgtgccta    4860
gcgataacat tgattcacaa gggaggaatt gtagtacaaa tgactcactg ctctcgagaa    4920
tcgaggggcg gcaccaccat catcaccacg tcgacccccgg ggactacaag gatgacgatg    4980
acaagtaagc tttatccatc acactggcgg ccgctcgagc atgcatctag cggccgctcg    5040
aggccggcaa ggccggatcc ccgggaattc gcccctctcc ctcccccccc cctaacgtta    5100
ctggccgaag ccgcttggaa taaggccggt gtgcgtttgt ctatatgtta ttttccacca    5160
tattgccgtc ttttggcaat gtgagggccc ggaaacctgg ccctgtcttc ttgacgagca    5220
ttcctagggg tctttcccct ctcgccaaag gaatgcaagg tctgttgaat gtcgtgaagg    5280
aagcagttcc tctggaagct tcttgaagac aaacaacgtc tgtagcgacc ctttgcaggc    5340
agcggaaccc cccacctggc gacaggtgcc tctgcggcca aaagccacgt gtataagata    5400
cacctgcaaa ggcggcacaa ccccagtgcc acgttgtgag ttggatagtt gtggaaagag    5460
tcaaatggct ctcctcaagc gtattcaaca aggggctgaa ggatgcccag aaggtacccc    5520
attgtatggg atctgatctg gggcctcggt gcacatgctt tacatgtgtt tagtcgaggt    5580
taaaaaaacg tctaggcccc ccgaaccacg gggacgtggt tttcctttga aaaacacgat    5640
gataatatgg cctcctttgt ctctctgctc ctggtaggca tcctattcca tgccacccag    5700
gccgagctca cccagtctcc agactccctg gctgtgtctc tgggcgagag ggccaccatc    5760
aactgcaagt ccagccagag tgttttgtac agctccaaca taagaactaa tttagcttgg    5820
tatcagcaga aaccaggaca gcctcctaag ctgctcattt actgggcatc tacccgggaa    5880
tccggggtcc ctgaccgatt cagtggcagc gggtctggga cagatttcac tctcaccatc    5940
agcagcctgc aggctgaaga tgtggcagtt tattactgtc agcaatatta tagtactcag    6000
acgttcggcc aagggaccaa ggtggaaatc aaacgaactg tggctgcacc atctgtcttc    6060
atcttcccgc catctgatga gcagttgaaa tctggaactg cctctgttgt gtgcctgctg    6120
aataacttct atcccagaga ggccaaagta cagtggaagg tggataacgc cctccaatcg    6180
ggtaactccc aggagagtgt cacagagcag gacagcaagg acagcaccta cagcctcagc    6240
agcaccctga cgctgagcaa agcagactac gagaaacaca aactctacgc ctgcgaagtc    6300
acccatcagg gcctgagatc gcccgtcaca aagagcttca acaaggggag agtgttagtt    6360
ctagataatt aattaggagg agatctcgag ctcgcgaaag cttggcactg gccgtcgttt    6420
tacaacgtcg tgactgggaa aaccctggcg ttacccaact taatcgcctt gcagcacatc    6480
```

```
cccctttcgc cagcctccta ggtcgacatc gataaaataa aagattttat ttagtctcca    6540 gaaaagggg ggaatgaaag accccacctg taggtttggc aagctagctt aagtaacgcc    6600
attttgcaag gcatggaaaa atacataact gagaatagag aagttcagat caaggtcagg    6660
aacagatgga acagctgaat atgggccaaa caggatatct gtggtaagca gttcctgccc    6720
cggctcaggg ccaagaacag atggaacagc tgaatatggg ccaaacagga tatctgtggt    6780
aagcagttcc tgccccggct cagggccaag aacagatggt ccccagatgc ggtccagccc    6840
tcagcagttt ctagagaacc atcagatgtt tccagggtgc cccaaggacc tgaaatgacc    6900
ctgtgcctta tttgaactaa ccaatcagtt cgcttctcgc ttctgttcgc gcgcttctgc    6960
tccccgagct caataaaaga gcccacaacc cctcactcgg ggcgccagtc ctccgattga    7020
ctgagtcgcc cgggtacccg tgtatccaat aaaccctctt gcagttgcat ccgacttgtg    7080
gtctcgctgt tccttgggag ggtctcctct gagtgattga ctacccgtca gcggggggtct    7140 ttcatttggg ggctcgtccg ggatcgggag acccctgccc agggaccacc gacccaccac    7200
cgggaggtaa gctggctgcc tcgcgcgttt cggtgatgac ggtgaaaacc tctgacacat    7260
gcagctcccg gagacggtca cagcttgtct gtaagcggat gccgggagca gacaagcccg    7320
tcagggcgcg tcagcgggtg ttggcgggtg tcggggcgca gccatgaccc agtcacgtag    7380
cgatagcgga gtgtatactg gcttaactat gcggcatcag agcagattgt actgagagtg    7440
caccatatgc ggtgtgaaat accgcacaga tgcgtaagga gaaataccg catcaggcgc    7500 tcttccgctt cctcgctcac tgactcgctg cgctcggtcg ttcggctgcg gcgagcggta    7560
tcagctcact caaaggcggt aatacggtta tccacagaat caggggataa cgcaggaaag    7620
aacatgtgag caaaaggcca gcaaaaggcc aggaaccgta aaaaggccgc gttgctggcg    7680 ttttccata ggctccgccc ccctgacgag catcacaaaa atcgacgctc aagtcagagg    7740
tggcgaaacc cgacaggact ataaagatac caggcgtttc ccctggaag ctccctcgtg    7800 cgctctcctg ttccgaccct gccgcttacc ggatacctgt ccgcctttct cccttcggga    7860
agcgtggcgc tttctcatag ctcacgctgt aggtatctca gttcggtgta ggtcgttcgc    7920
tccaagctgg gctgtgtgca cgaaccccc gttcagcccg accgctgcgc cttatccggt    7980
aactatcgtc ttgagtccaa cccggtaaga cacgacttat cgccactggc agcagccact    8040
ggtaacagga ttagcagagc gaggtatgta ggcggtgcta cagagttctt gaagtggtgg    8100
cctaactacg gctacactag aaggacagta tttggtatct gcgctctgct gaagccagtt    8160
accttcggaa aaagagttgg tagctcttga tccggcaaac aaaccaccgc tggtagcggt    8220
ggtttttttg tttgcaagca gcagattacg cgcagaaaaa aaggatctca agaagatcct    8280
ttgatctttt ctacggggtc tgacgctcag tggaacgaaa actcacgtta agggattttg    8340
gtcatgagat tatcaaaaag gatcttcacc tagatccttt taaattaaaa atgaagtttt    8400
aaatcaatct aaagtatata tgagtaaact tggtctgaca gttaccaatg cttaatcagt    8460
gaggcaccta tctcagcgat ctgtctattt cgttcatcca tagttgcctg actccccgtc    8520
gtgtagataa ctacgatacg ggagggctta ccatctggcc ccagtgctgc aatgataccg    8580
cgagacccac gctcaccggc tccagattta tcagcaataa accagccagc cggaagggcc    8640
gagcgcagaa gtggtcctgc aactttatcc gcctccatcc agtctattaa ttgttgccgg    8700
gaagctagag taagtagttc gccagttaat agtttgcgca acgttgttgc cattgctgca    8760
ggcatcgtgg tgtcacgctc gtcgtttggt atggcttcat tcagctccgg ttcccaacga    8820
tcaaggcgag ttacatgatc cccatgttg tgcaaaaaag cggttagctc cttcggtcct    8880
```

```
ccgatcgttg tcagaagtaa gttggccgca gtgttatcac tcatggttat ggcagcactg      8940
cataattctc ttactgtcat gccatccgta agatgctttt ctgtgactgg tgagtactca      9000
accaagtcat tctgagaata gtgtatgcgg cgaccgagtt gctcttgccc ggcgtcaaca      9060
cgggataata ccgcgccaca tagcagaact ttaaaagtgc tcatcattgg aaaacgttct      9120
tcggggcgaa aactctcaag gatcttaccg ctgttgagat ccagttcgat gtaacccact      9180
cgtgcaccca actgatcttc agcatctttt actttcacca gcgtttctgg gtgagcaaaa      9240
acaggaaggc aaaatgccgc aaaaaaggga ataaggcga cacggaaatg ttgaatactc       9300
atactcttcc tttttcaata ttattgaagc atttatcagg gttattgtct catgagcgga      9360
tacatatttg aatgtattta gaaaaataaa caaatagggg ttccgcgcac atttccccga      9420
aaagtgccac ctgacgtcta agaaaccatt attatcatga cattaaccta taaaaatagg      9480
cgtatcacga ggccctttcg tcttcaagaa t                                     9511

<210> SEQ ID NO 35
<211> LENGTH: 30
<212> TYPE: DNA
<213> ORGANISM: Artificial Sequence
<220> FEATURE:
<223> OTHER INFORMATION: Synthetic

<400> SEQUENCE: 35
gatccactag taacggccgc cagaattcgc                                         30

<210> SEQ ID NO 36
<211> LENGTH: 43
<212> TYPE: DNA
<213> ORGANISM: Artificial Sequence
<220> FEATURE:
<223> OTHER INFORMATION: Synthetic

<400> SEQUENCE: 36
cagagagaca aaggaggcca tattatcatc gtgttttca aag                           43
```